United States Patent
Barrett et al.

(10) Patent No.: US 7,411,001 B2
(45) Date of Patent: *Aug. 12, 2008

(54) OXYGENATED ESTERS OF 4-IODO PHENYLAMINO BENZHYDROXAMIC ACIDS

(75) Inventors: Stephen Douglas Barrett, Hartland, MI (US); Cathlin Marie Biwersi, Lawrenceville, NJ (US); Michael Huai Gu Chen, Ann Arbor, MI (US); Michael David Kaufman, Ypsilanti, MI (US); Haile Tecle, Ann Arbor, MI (US); Joseph Scott Warmus, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 447 days.

This patent is subject to a terminal disclaimer.

(21) Appl. No.: 11/102,307

(22) Filed: Apr. 7, 2005

(65) Prior Publication Data
US 2005/0176820 A1    Aug. 11, 2005

Related U.S. Application Data

(63) Continuation of application No. 10/333,399, filed on Jun. 19, 2003, now Pat. No. 6,960,614.

(51) Int. Cl.
*A61K 31/215* (2006.01)
*C07C 239/00* (2006.01)
(52) U.S. Cl. ..................... 514/507; 560/315
(58) Field of Classification Search ............. 514/507; 560/315
See application file for complete search history.

(56) References Cited

U.S. PATENT DOCUMENTS

| 5,155,110 | A | 10/1992 | Connor et al. |
| 6,469,004 | B1 | 10/2002 | Barrett et al. |
| 6,960,614 | B2 * | 11/2005 | Barrett et al. ............... 514/507 |

FOREIGN PATENT DOCUMENTS

| EP | 0316630 | 5/1989 |
| JP | 2001 55376 | 2/2001 |
| WO | WO 98/37881 | 9/1998 |
| WO | WO 99/01421 | 1/1999 |
| WO | WO 99/01426 | 1/1999 |
| WO | WO 00/34228 | 6/2000 |
| WO | WO 00/35435 | 6/2000 |
| WO | WO 00/37141 | 6/2000 |
| WO | WO 00/40235 | 7/2000 |
| WO | WO 00/40237 | 7/2000 |
| WO | WO 01/05392 | 1/2001 |
| WO | WO 01/47897 | 7/2001 |

OTHER PUBLICATIONS

Bridges et al., 1998, CAS: 129:230537.*
PCT International Search Report PCT/US01/22331.

* cited by examiner

*Primary Examiner*—Rei-Tsang Shiao
(74) *Attorney, Agent, or Firm*—Steven R. Eck; Suzanne Harvey; Lucy X. Yang

(57) ABSTRACT

The present invention relates to oxygenated esters of 4-iodophenylamino benzhydroxamic acid derivatives, pharmaceutical compositions and methods of use thereof. The present invention also relates to crystalline forms of oxygenated esters of 4-iodophenylamino benzhydroxamic acid derivatives, pharmaceutical compositions and methods of use thereof.

21 Claims, 6 Drawing Sheets

OXYGENATED ESTERS OF 4-IODO PHENYLAMINO BENZHYDROXAMIC ACIDS

This application is a continuation of application Ser. No. 10/333,399 filed Jun. 19, 2003, which is a 371 application of PCT/US01/22331 filed Jul. 12, 2001, which claims the benefit of Provisional Patent Application No. 60/219,372, filed Jul. 19, 2000, which are hereby incorporated by reference in their entireties.

FIELD OF THE INVENTION

The present invention relates to oxygenated esters of 4-iodophenylamino benzhydroxamic acid derivatives, pharmaceutical compositions and methods of use thereof. The present invention also relates to crystalline forms of oxygenated esters of 4-iodophenylamino benzhydroxamic acid derivatives, pharmaceutical compositions and methods of use thereof.

BACKGROUND OF THE INVENTION

MAPK/ERK Kinase ("MEK") enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates the MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

It has been found that the compounds of the present invention are inhibitors of MEK and are useful in the treatment of a variety of proliferative disease states, such as conditions related to the hyperactivity of MEK, as well as diseases modulated by the MEK cascade.

SUMMARY OF THE INVENTION

The present invention provides a compound of formula

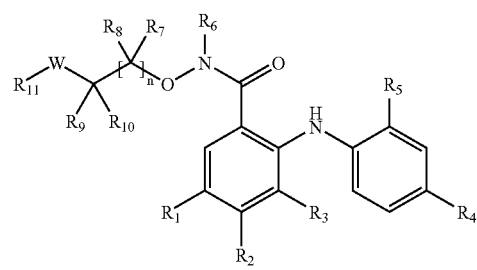

wherein
$R_1$ is hydrogen, halogen, or nitro;
$R_2$ is hydrogen or fluorine;
$R_3$ is hydrogen or fluorine;
$R_4$ is hydrogen, iodine, bromine, chlorine, or fluorine;
$R_5$ is hydrogen, halogen, hydroxy, $C_{1-8}$ alkyl, $C_{1-8}$ alkoxy, trifluoromethyl, or cyano;
n is 1 to 5;
$R_6$, $R_7$, $R_8$, $R_9$, and $R_{10}$ are independently hydrogen, $C_{1-8}$ alkyl, $C_{3-8}$ cycloalkyl, hydroxy, $C_{1-8}$ alkoxy, perhalo($C_{1-3}$) alkyl, hydroxy($C_{1-8}$)alkyl, ($C_{1-5}$)alkoxy($C_{1-8}$)alkyl, [($C_{1-4}$)alkyl]$_2$aminomethyl, ($C_{2-7}$)heterocycle($C_{1-5}$)alkyl, or aryloxy($C_{1-5}$)alkyl, or may be independently joined to complete a 3-10 member cyclic ring optionally containing additional heteroatoms selected from the group consisting of O, S, NH, and N-alkyl, wherein $R_7$ and $R_8$ are independently selected for n>1;
Ra and Rb are independently hydrogen or $C_{1-4}$ alkyl;
W is O or NRa;
$R_{11}$ is hydrogen, $C_{1-8}$ alkyl, $C_{2-6}$ alkenyl, $C_{3-8}$ cycloalkyl, hydroxy($C_{1-8}$)alkyl, ($C_{1-5}$)alkoxy($C_{1-5}$)alkyl, phenyl, $C_{2-7}$ heteroaryl, $(C_{1-8})$alkylcarbonyl, (phenyl)carbonyl, (phenyl)$(C_{1-3}$ alkyl)carbonyl, or trifluoro$(C_{1-6})$alkyl;

wherein the above alkyl, alkoxy, cycloalkyl, heteroaryl, and phenyl groups can be optionally substituted with between 1 and 5 substituents independently selected from the group consisting of hydroxy, amino, monoalkylamino, dialkylamino, halogen, cyano, $(C_{1-3})$alkoxy, COOR, OCORa, CONRaRb, NRaCORb, SO, $SO_2$, $SO_4$, and $SO_2NRaRb$;

and pharmaceutically acceptable salts, $(C_{1-6})$ amides and $(C_{1-6})$ esters thereof;

provided that when $R_{11}$ is phenyl and n is 1, W cannot be O;

further provided that the compound is not

5-Bromo-N-(2-diethylamino-ethoxy)-3,4-difluoro-(4-iodo-2-methyl-phenylamino)-benzamide;

5-Bromo-N-(2-dimethylamino-propoxy)-3,4-difluoro-2-(4-iodo-2-methyl-phenylamino)-benzamide; or 5-Bromo-2-(2-chloro-4-iodo-phenylamino)-N-(2-dimethylamino-ethoxy)-3,4-difluoro-benzamide.

The present invention also provides a compound is of formula

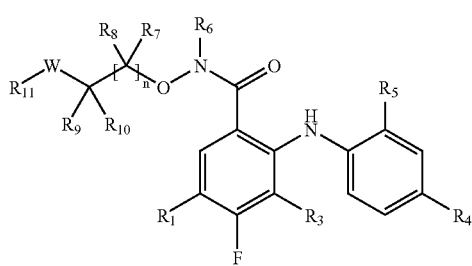

Ia wherein $R_1$ is hydrogen or halogen;

$R_3$ is hydrogen or fluorine;

$R_4$ is hydrogen, iodine, bromine, chlorine, or fluorine;

$R_5$ is hydrogen, halogen, or $C_{1-8}$ alkyl;

n is 1 to 5;

$R_6$, $R_7$, $R_8$, $R_9$, and $R_{10}$ are independently hydrogen, $C_{1-8}$ alkyl, hydroxy, $C_{1-8}$ alkoxy, perhalo$(C_{1-3})$alkyl, $(C_{2-7})$heterocycle$(C_{1-5})$alkyl, or aryloxy$(C_{1-5})$alkyl, or may be independently joined to complete a 3-10 member cyclic ring optionally containing additional heteroatoms selected from the group consisting of O, S, NH, and N-alkyl, wherein $R_7$ and $R_8$ are independently selected for n>1;

Ra and Rb are independently hydrogen or $C_{1-4}$ alkyl;

W is O or NRa;

$R_{11}$ is hydrogen, $C_{1-8}$ alkyl, $C_{2-6}$ alkenyl, $(C_{1-5})$alkoxy$(C_{1-5})$ alkyl, phenyl, $(C_{1-8})$alkylcarbonyl, or trifluoro$(C_{1-6})$alkyl;

wherein the above alkyl, alkoxy, cycloalkyl, heteroaryl, and phenyl groups can be optionally substituted with between 1 and 5 substituents independently selected from the group consisting of hydroxy, amino, monoalkylamino, dialkylamino, halogen, cyano, $(C_{1-3})$alkoxy, COOR, OCORa, CONRaRb, NRaCORb, SO, $SO_2$, $SO_4$, and $SO_2NRaRb$;

and pharmaceutically acceptable salts, $(C_{1-6})$ amides and $(C_{1-6})$ esters thereof;

provided that when $R_{11}$ is phenyl and n is 1, W cannot be O;

further provided that the compound is not

5-Bromo-N-(2-diethylamino-ethoxy)-3,4-difluoro-(4-iodo-2-methyl-phenylamino)-benzamide;

5-Bromo-N-(2-dimethylamino-propoxy)-3,4-difluoro-2-(4-iodo-2-methyl-phenylamino)-benzamide; or 5-Bromo-2-(2-chloro-4-iodo-phenylamino)-N-(2-dimethylamino-ethoxy)-3,4-difluoro-benzamide.

The invention also provides a pharmaceutical composition comprising a compound of formula I or Ia and a pharmaceutically acceptable carrier.

Additionally, the invention provides a method of treating a proliferative disease in a patient in need thereof comprising administering a therapeutically effective amount of a compound of formula I or Ia.

The invention also provides the use of a compound of formula I or Ia for the manufacture of a medicament for the treatment of a proliferative disease.

Furthermore, the invention provides methods of treating cancer, restenosis, psoriasis, autoimmune disease, atherosclerosis, osteoarthritis, rheumatoid arthritis, heart failure, chronic pain, and neuropathic pain in a patient in need thereof comprising administering a therapeutically effective amount of a compound of formula I or Ia.

The invention also provides the use of a compound of formula I or Ia for the manufacture of a medicament for the treatment of cancer, restenosis, psoriasis, autoimmune disease, atherosclerosis, osteoarthritis, rheumatoid arthritis, heart failure, chronic pain, and neuropathic pain.

In addition, the invention provides a method for treating cancer in a patient in need thereof comprising administering a therapeutically effective amount of a compound of formula I or Ia in combination with radiation therapy or at least one chemotherapeutic agent.

In another aspect, the present invention provides a crystalline Form I N-(2,3-Dihydroxy-propoxy)-3,4-difluoro-2-(2-fluoro-4-iodo-phenylamino)-benzamide having an X-ray diffraction powder diffraction containing at least one of the following 2θ values measured using $CuK_\alpha$ radiation: 7.1, 19.2, or 32.1.

The present invention also provides a crystalline Form I N-(2,3-Dihydroxy-propoxy)-3,4-difluoro-2-(2-fluoro-4-iodo-phenylamino)-benzamide having an X-ray diffraction powder diffraction containing the following 2θ values measured using $CuK_\alpha$ radiation: 7.1, 19.2, and 32.1.

Additionally, the present invention provides a crystalline Form I N-(2,3-Dihydroxy-propoxy)-3,4-difluoro-2-(2-fluoro-4-iodo-phenylamino)-benzamide having an X-ray diffraction powder diffraction containing the following 2θ values measured using $CuK_\alpha$ radiation: 7.1, 14.1, 15.3, 15.8, 16.9, 18.1, 19.2, 20.3, 21.4, 22.3, 23.4, 24.5, 25.5, 26.2, 26.8, 27.8, 28.3, 29.5, 32.1, 33.2, 33.6, 40.0, 42.9, and 44.1.

Also provided by the present invention is a crystalline Form II N-(2,3-Dihydroxy-propoxy)-3,4-difluoro-2-(2-fluoro-4-iodo-phenylamino)-benzamide having an X-ray diffraction powder diffraction containing at least one of the following 2θ values measured using $CuK_\alpha$ radiation: 11.6, 12.6 or 24.9.

The present invention also provides a crystalline Form II N-(2,3-Dihydroxy-propoxy)-3,4-difluoro-2-(2-fluoro-4-iodo-phenylamino)-benzamide having an X-ray diffraction powder diffraction containing the following 2θ values measured using $CuK_\alpha$ radiation: 11.6, 12.6 and 24.9.

Additionally, the present invention provides a crystalline Form II N-(2,3-Dihydroxy-propoxy)-3,4-difluoro-2-(2-fluoro-4-iodo-phenylamino)-benzamide having an X-ray diffraction powder diffraction containing the following 2θ values measured using $CuK_\alpha$ radiation: 11.6, 12.6, 15.6, 17.3, 17.9, 20.3, 21.1, 22.1, 24.9, 25.9, 26.7, 27.8, 30.1, 30.9, 33.8, 35.4, 38.2, 39.3, 40.8, 41.6, 43.6, and 47.0.

Additionally, the present invention provides a crystalline Form I N-[(R)-2,3-Dihydroxy-propoxy]-3,4-difluoro-2-(2-fluoro-4-iodo-phenylamino)-benzamide having an X-ray diffraction powder diffraction containing at least one of the following 2θ values measured using CuK$_\alpha$ radiation: 10.6, 13.7, 19.0 or 23.7.

In addition, the present invention provides a crystalline Form I N-[(R)-2,3-Dihydroxy-propoxy]-3,4-difluoro-2-(2-fluoro-4-iodo-phenylamino)-benzamide having an X-ray diffraction powder diffraction containing the following 2θ values measured using CuK$_\alpha$ radiation: 10.6, 13.7, 19.0 and 23.7.

Also provided by the present invention is crystalline Form I N-[(R)-2,3-Dihydroxy-propoxy]-3,4-difluoro-2-(2-fluoro-4-iodo-phenylamino)-benzamide having an X-ray diffraction powder diffraction containing the following 2θ values measured using CuK$_\alpha$ radiation: 10.6, 13.7, 14.6, 17.3, 18.0, 18.2, 98.0, 19.3, 20.1, 21.0, 21.9, 22.4, 23.7, 24.0, 24.9, 26.3, 27.6, 28.0, 30.1, 32.1, 32.3, 32.9, 35.8, and 37.7.

Furthermore, the present invention provides a crystalline Form II N-[(R)-2,3-Dihydroxy-propoxy]-3,4-difluoro-2-(2-fluoro-4-iodo-phenylamino)-benzamide having an X-ray diffraction powder diffraction containing at least one of the following 2θ values measured using CuK$_\alpha$ radiation: 5.5 or 19.6.

The present invention also provides a crystalline Form II N-[(R)-2,3-Dihydroxy-propoxy]-3,4-difluoro-2-(2-fluoro-4-iodo-phenylamino)-benzamide having an X-ray diffraction powder diffraction containing at least one of the following 2θ values measured using CuK$_\alpha$ radiation: 5.5 and 19.6.

Additionally, the present invention provides a crystalline Form II N-[(R)-2,3-Dihydroxy-propoxy]-3,4-difluoro-2-(2-fluoro-4-iodo-phenylamino)-benzamide having an X-ray diffraction powder diffraction containing the following 2θ values measured using CuK$_\alpha$ radiation: 5.5, 10.7, 16.5, 19.6, 22.0, 22.5, 23.6, 24.1, 25.0, 26.2, 27.6, 29.1, 30.5, 31.7, 33.3, and 39.0.

In addition, the present invention provides a crystalline Form I N-[(S)-2,3-Dihydroxy-propoxy]-3,4-difluoro-2-(2-fluoro-4-iodo-phenylamino)-benzamide having an X-ray diffraction powder diffraction containing at least one of the following 2θ values measured using CuK$_\alpha$ radiation: 10.5, 13.7, 19.0, or 23.6.

Also provided by the present invention is crystalline Form I N-[(S)-2,3-Dihydroxy-propoxy]-3,4-difluoro-2-(2-fluoro-4-iodo-phenylamino)-benzamide having an X-ray diffraction powder diffraction containing the following 2θ values measured using CuK$_\alpha$ radiation: 10.5, 13.7, 19.0, and 23.6.

Furthermore, the present invention provides a crystalline Form I N-[(S)-2,3-Dihydroxy-propoxy]-3,4-difluoro-2-(2-fluoro-4-iodo-phenylamino)-benzamide having an X-ray diffraction powder diffraction containing the following 2θ values measured using CuK$_\alpha$ radiation: 10.548, 13.703, 17.887, 18.958, 20.122, 21.950, 22.321, 23.640, 24.803, 26.244, 27.570, 28.000, 29.566, 32.234, 32.769, 35.804, 37.641, 41.402, 41.956, and 44.600.

The present invention also provides a crystalline Form II N-[(S)-2,3-Dihydroxy-propoxy]-3,4-difluoro-2-(2-fluoro-4-iodo-phenylamino)-benzamide having an X-ray diffraction powder diffraction containing at least one of the following 2θ values measured using CuK$_\alpha$ radiation: 5.6 or 19.6.

Additionally, the present invention provides a crystalline Form II N-[(S)-2,3-Dihydroxy-propoxy]-3,4-difluoro-2-(2-fluoro-4-iodo-phenylamino)-benzamide having an X-ray diffraction powder diffraction containing at least one of the following 2θ values measured using CuK$_\alpha$ radiation: 5.6 and 19.6.

In addition, the present invention provides a crystalline Form II N-[(S)-2,3-Dihydroxy-propoxy]-3,4-difluoro-2-(2-fluoro-4-iodo-phenylamino)-benzamide having an X-ray diffraction powder diffraction containing the following 2θ values measured using CuK$_\alpha$ radiation: 5.6, 10.7, 16.5, 19.6, 20.9, 22.0, 23.7, 24.2, 25.0, 26.2, 27.7, 28.0, 29.1, 31.7, 32.8, 33.3, 34.1, 42.0, and 42.3.

BRIEF DESCRIPTION OF THE DRAWINGS

The invention is further described by the following non-limiting examples which refer to the accompanying FIGS. 1 to 6, short particulars of which are given below.

DETAILED DESCRIPTION OF THE INVENTION

Figure 1:
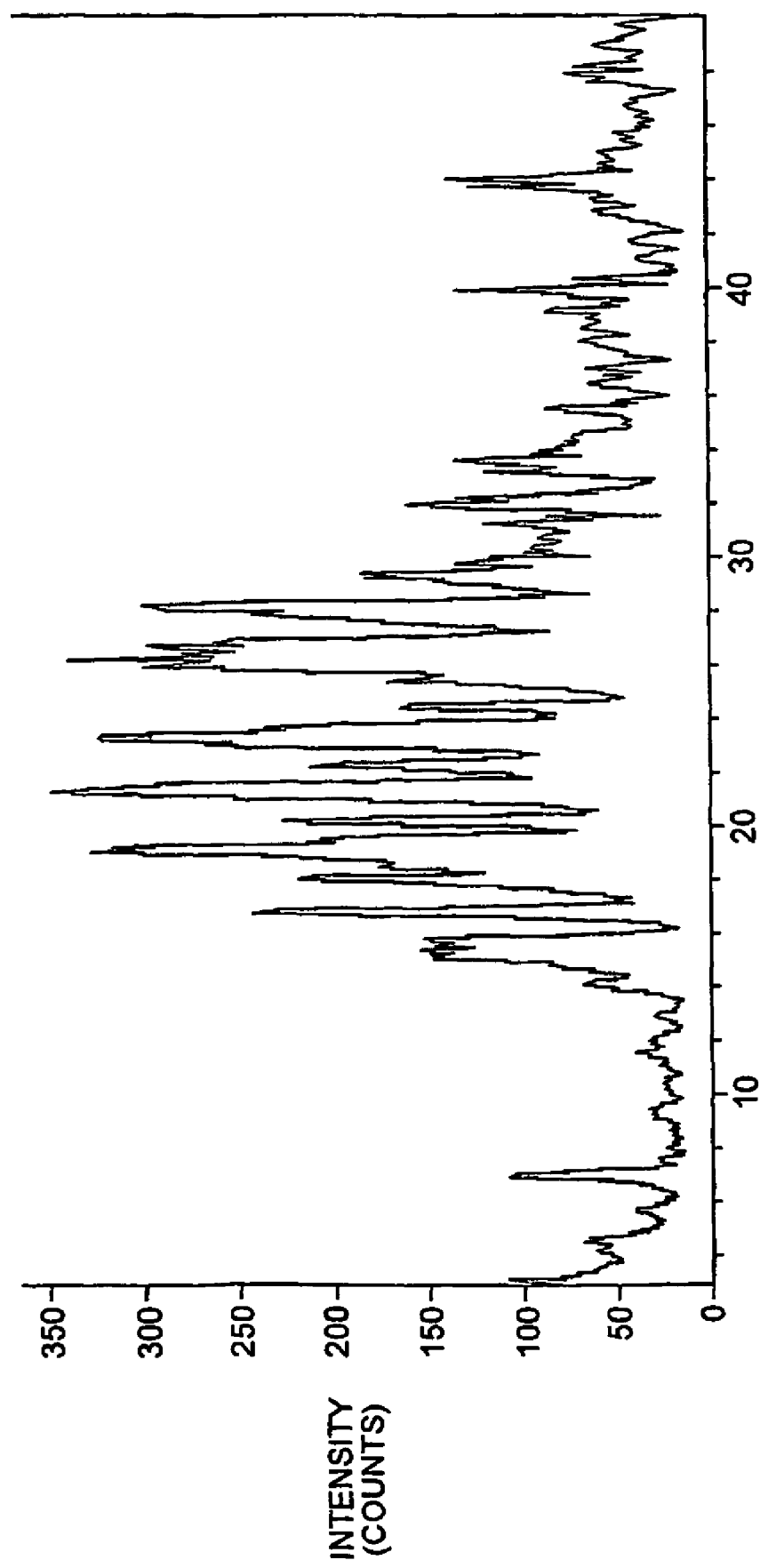
FIG. 1
Diffractogram of Form I N-(2,3-Dihydroxy-propoxy)-3,4-difluoro-2-(2-fluoro-4-iodo-phenylamino)-benzamide (Y-axis=0 to maximum intensity of about 350 counts per second (cps))
Figure 2:
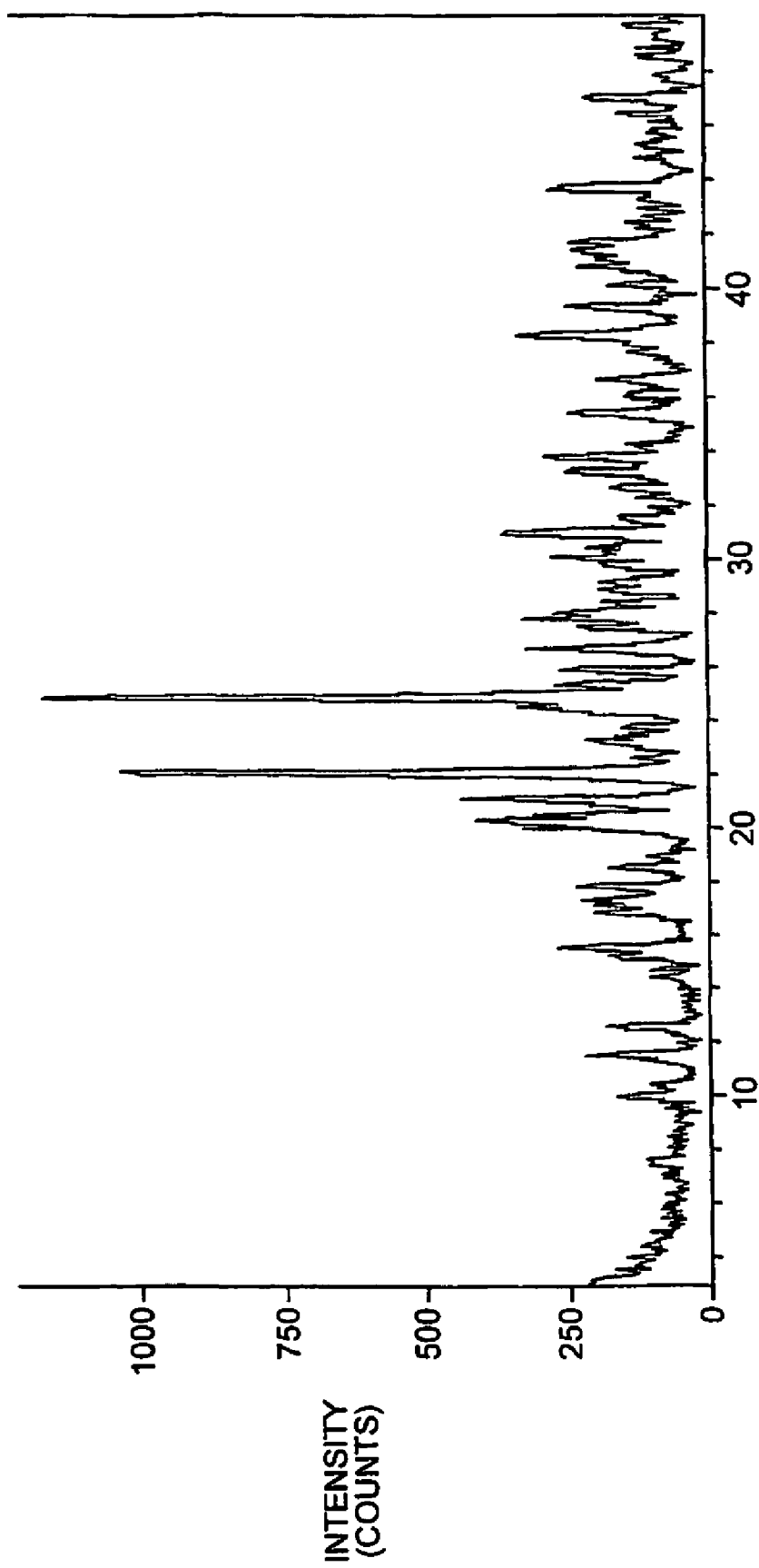
FIG. 2
Diffractogram of Form II N-(2,3-Dihydroxy-propoxy)-3,4-difluoro-2-(2-fluoro-4-iodo-phenylamino)-benzamide (Y-axis=0 to maximum intensity of about 1200 cps)
Figure 3:
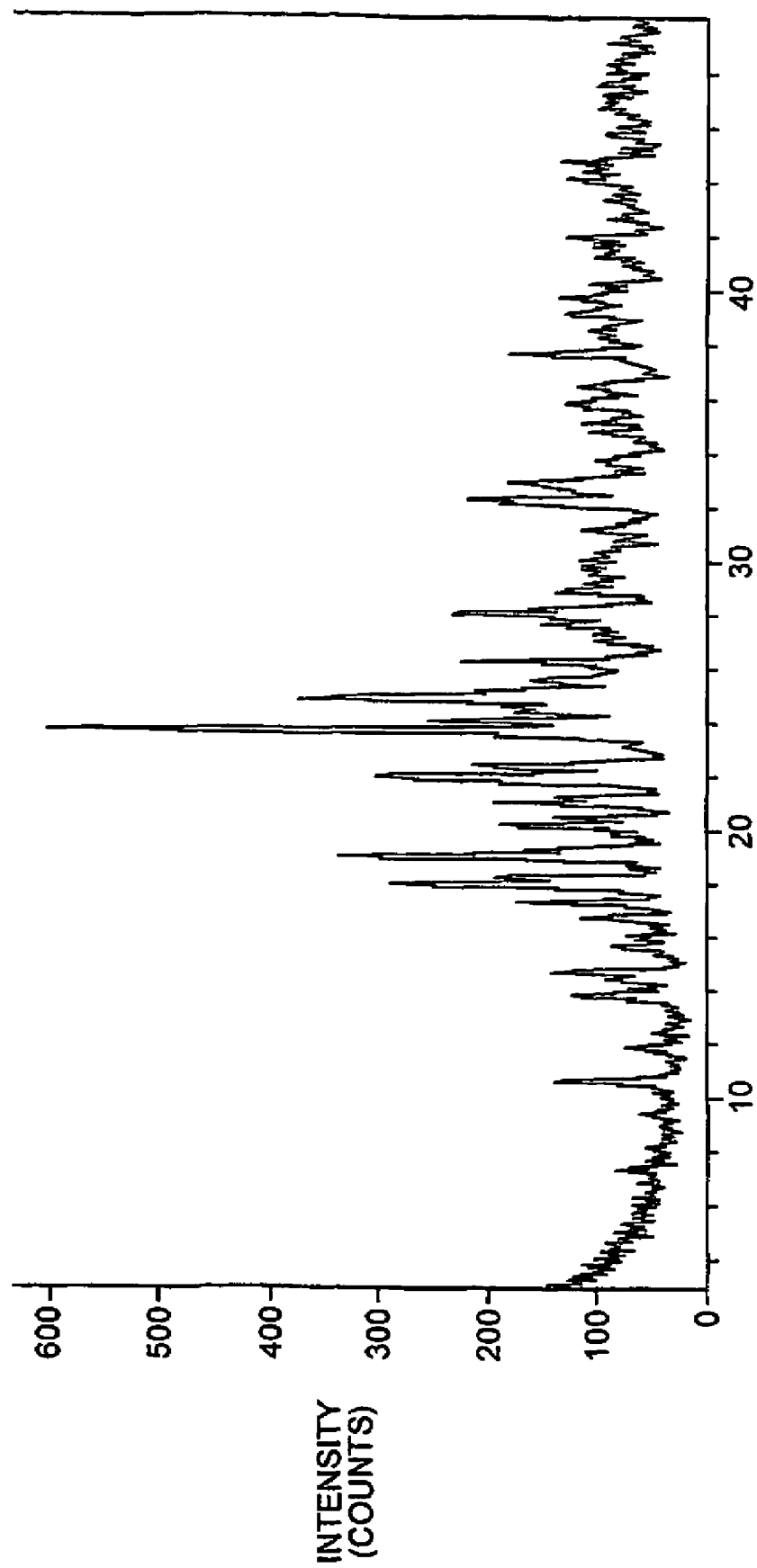
FIG. 3
Diffractogram of Form I N-[(R)-2,3-Dihydroxy-propoxy]-3,4-difluoro-2-(2-fluoro-4-iodo-phenylamino)-benzamide (Y-axis=0 to maximum intensity of about 600 cps).
Figure 4:
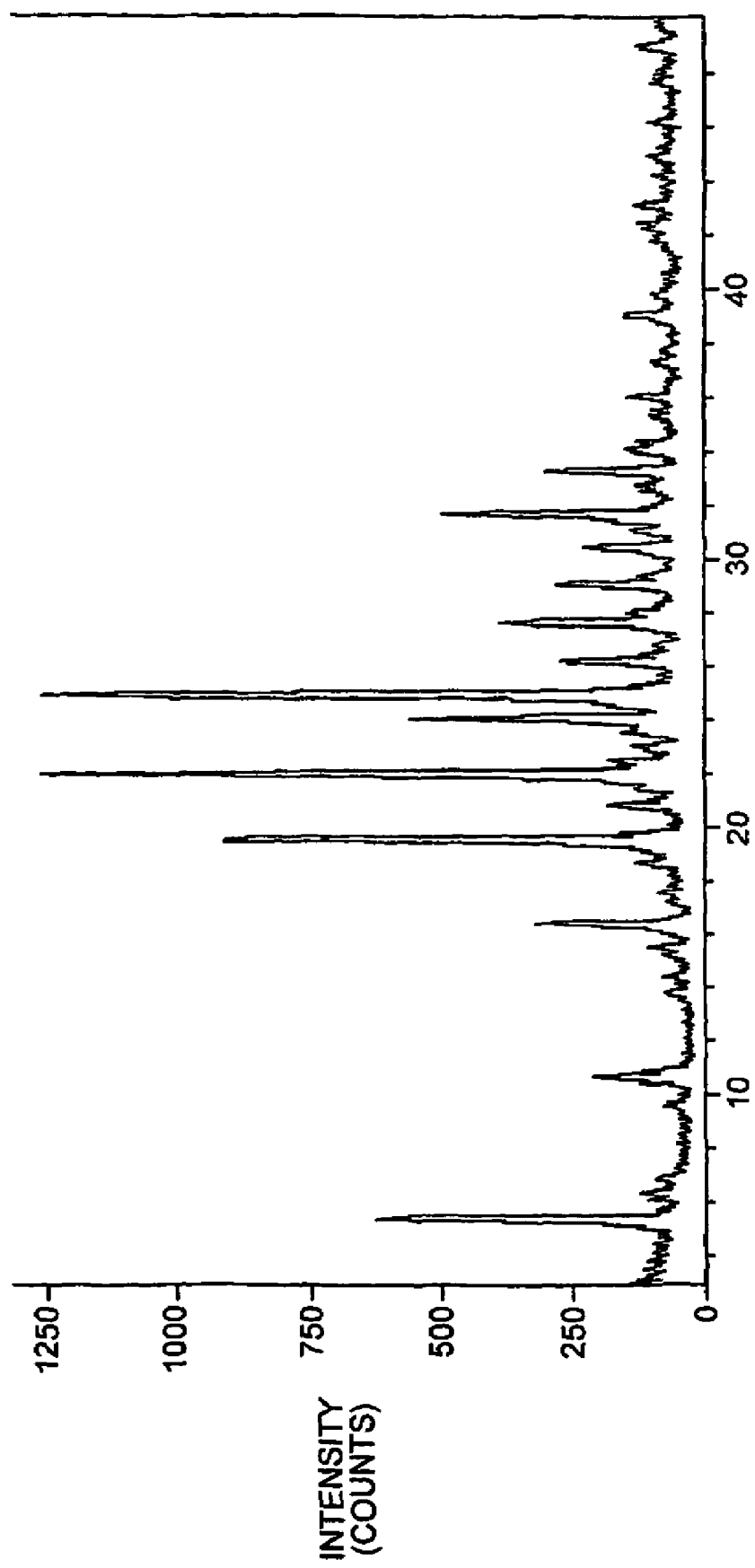
FIG. 4
Diffractogram of Form II N-[(R)-2,3-Dihydroxy-propoxy]-3,4-difluoro-2-(2-fluoro-4-iodo-phenylamino)-benzamide (Y-axis=0 to maximum intensity of about 1250 cps).
Figure 5:
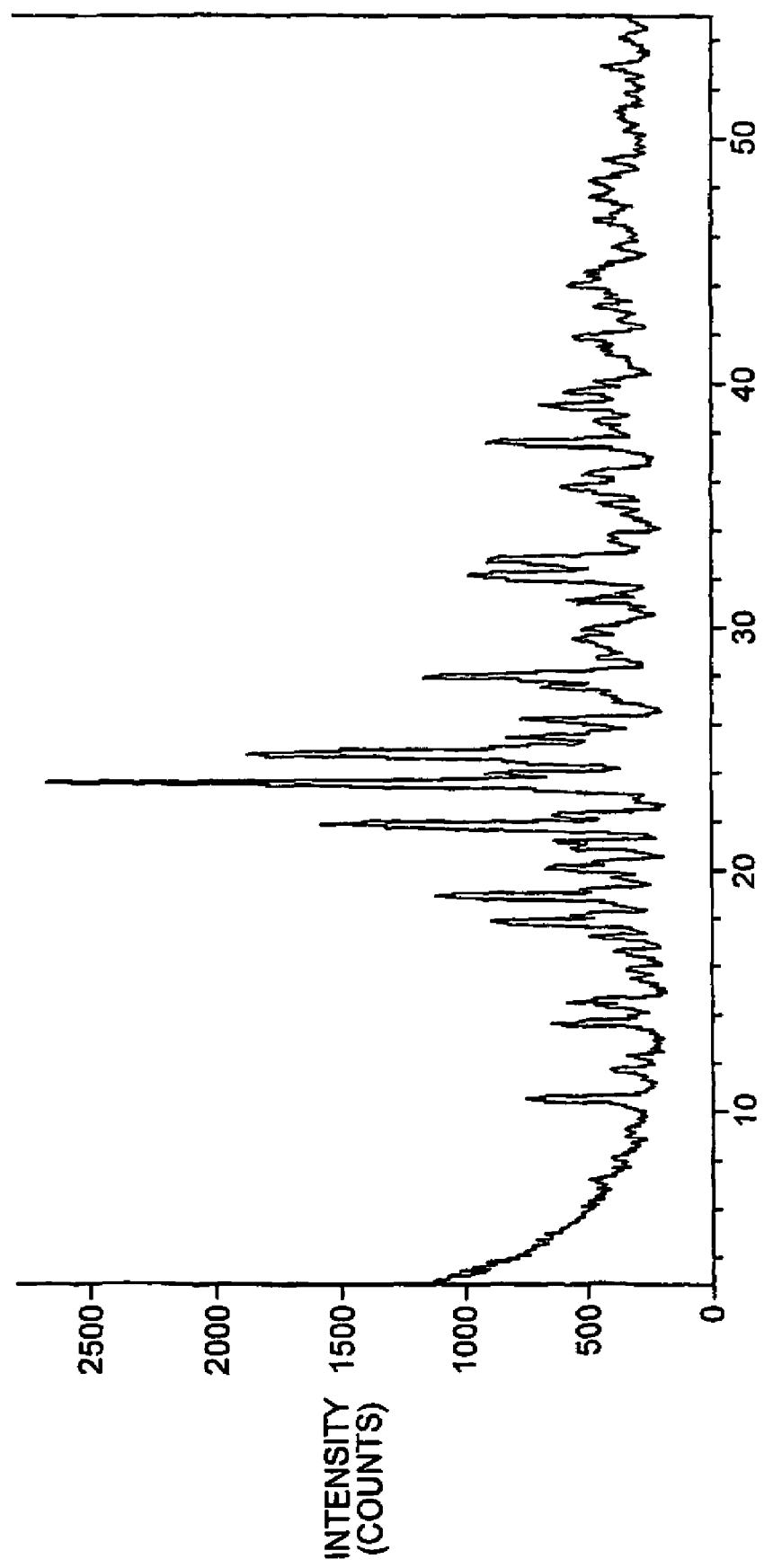
FIG. 5
Diffractogram of Form I N-[(S)-2,3-Dihydroxy-propoxy]-3,4-difluoro-2-(2-fluoro-4-iodo-phenylamino)-benzamide (Y-axis=0 to maximum intensity of about 2600 cps).
Figure 6:
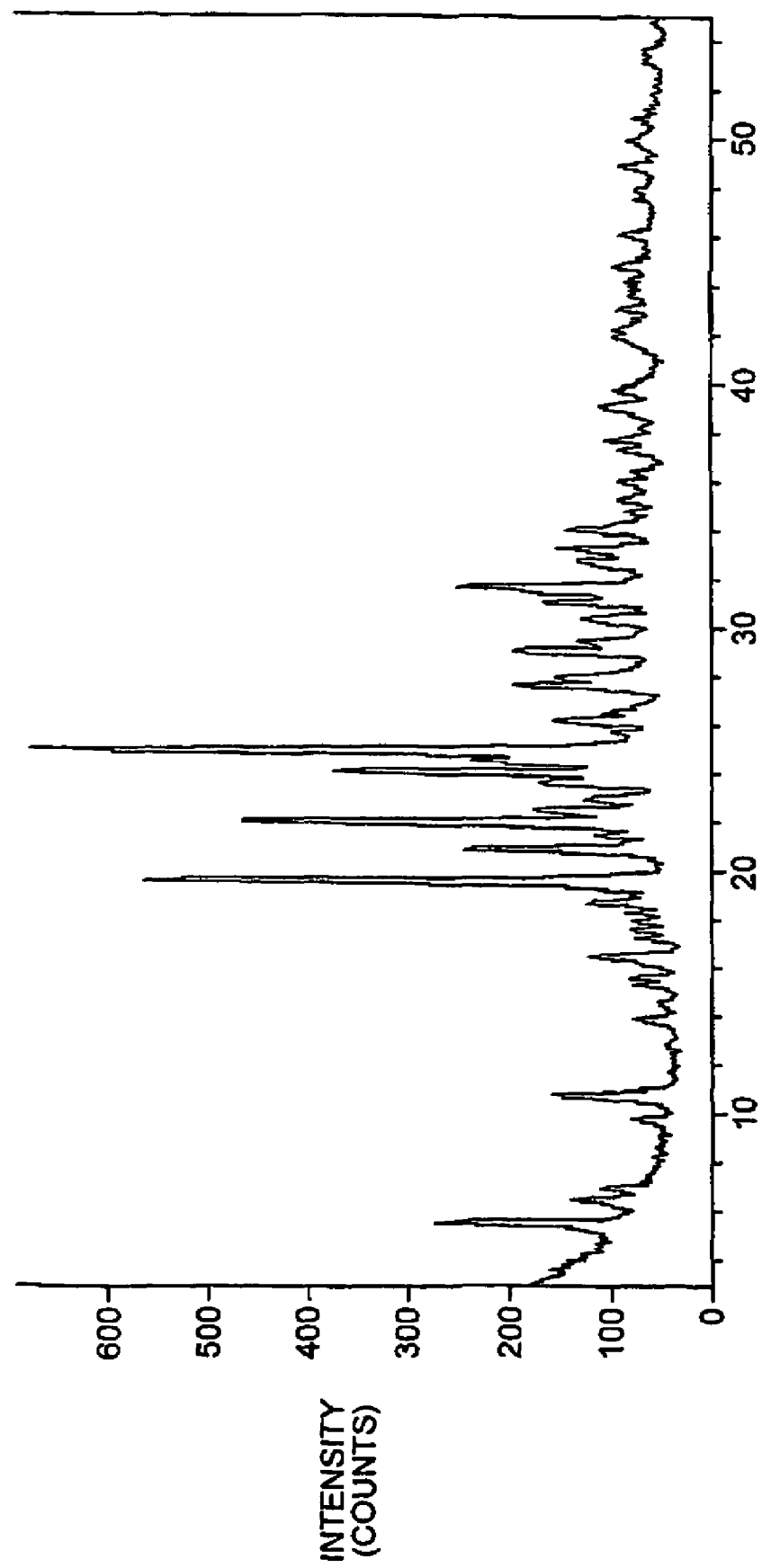
FIG. 6
Diffractogram of Form II N-[(S)-2,3-Dihydroxy-propoxy]-3,4-difluoro-2-(2-fluoro-4-iodo-phenylamino)-benzamide (Y-axis=0 to maximum intensity of about 700 cps).

Certain terms are defined below and by their usage throughout this disclosure.

The terms "halogen" or "halo" in the present invention refer to a fluorine, bromine, chlorine, and iodine atom or fluoro, bromo, chloro, and iodo. The terms fluorine and fluoro, for example, are understood to be equivalent herein.

Alkyl groups, such as "$C_{1-8}$ alkyl", include aliphatic chains (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, n-butyl, isobutyl, t-butyl, pentyl, isopentyl, 2,3-dimethylpropyl, hexyl, 2,3-dimethylhexyl, 1,1-dimethylpentyl, heptyl, octyl, and the like. The term "$C_{1-8}$ alkyl" includes within its definition the terms "$C_{1-6}$ alkyl", "$C_{1-5}$ alkyl", "$C_{1-4}$ alkyl" and "$C_{1-3}$ alkyl".

Alkyl groups can be substituted with 1, 2, 3 or more substituents which are independently selected from halo (fluoro, chloro, bromo, or iodo), cyano, hydroxy, amino, alkoxy, alkylamino, dialkylamino, cycloalkyl, aryl, aryloxy, arylalkyloxy, heterocyclic radical, and (heterocyclic radical)oxy. Specific examples include fluoromethyl, hydroxyethyl, 2,3-dihydroxyethyl, (2- or 3-furanyl)methyl, cyclopropylmethyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, N-pyridinylethyl, diethylaminoethyl, and cyclobutylmethyl.

The term "alkoxy" as used herein refers to a straight or branched alkyl chain attached to an oxygen atom. The term "$C_{1-8}$ alkoxy" as used herein refers to a straight or branched alkyl chain having from one to eight carbon atoms attached to an oxygen atom. Typical $C_{1-8}$ alkoxy groups include methoxy, ethoxy, propoxy, isopropoxy, butoxy, t-butoxy, pentoxy and the like. The term "$C_{1-8}$ alkoxy" includes within its definition the terms "$C_{1-6}$ alkoxy" and "$C_{1-4}$ alkoxy".

Alkenyl groups are analogous to alkyl groups, but have at least one double bond (two adjacent $sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof; like alkyl groups, unsaturated groups may be straight chain or branched, and they may be substituted as described both above for alkyl groups and throughout the disclosure by example. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl. In formula I, the term "alkenyl" includes $C_{2-6}$ alkenyl or $C_{2-4}$ alkenyl.

Cycloalkyl groups, such as $C_{3-10}$ cycloalkyl, refer to a saturated hydrocarbon ring structure containing from 3 to 10 atoms. Typical $C_{3-10}$ cycloalkyl groups include cyclopropyl, cyclobutyl, cyclopentyl, cyclohexyl, cycloheptyl, cyclooctyl, and the like.

The term "aryl" means an unsubstituted aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl). The aryl group can be optionally substituted with between 1 and 5 substituents independently selected from the group consisting of hydroxy, amino, monoalkylamino, dialkylamino, halogen, cyano, ($C_{1-3}$) alkoxy, COOR, OCORa, CONRaRb, NRaCORb, SO, $SO_2$, $SO_4$, and $SO_2$NraRb, where Ra and Rb are independently hydrogen or $C_{1-4}$ alkyl.

The term "aryloxy" as used herein refers to an aryl group attached to an oxygen atom.

As used herein, the terms "heterocycle", "$C_{2-7}$ heterocycle", "$C_{2-9}$ heterocycle", or "$C_{2-7}$ heteroaryl" in the present invention refers to a stable 5-, 6-, or 7-membered monocyclic or 7- to 10-membered bicyclic heterocyclic ring which is saturated or unsaturated, and consists of carbon atoms and from one to four heteroatoms selected from the group consisting of nitrogen, oxygen, or sulfur. The heterocyclic ring may be attached at any heteroatom or carbon atom which affords a stable structure.

Heterocyclic radicals, which include but are not limited to heteroaryls, include: furyl, (is)oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their nonaromatic counterparts. Further examples of heterocyclic radicals include thienyl, piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, octahydrobenzofuranyl, (iso)quinolinyl, naphthyridinyl, benzimidazolyl, and benzoxazolyl.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to formula (I), therefore, substituted alkyls include, but are not limited to, hydroxyalkyl, alkoxyalkyl, aminoalkyl, nitroalkyl, haloalkyl, cyanoalkyl, alkylalkyl (branched alkyls, such as methylpentyl), (cycloalkyl)alkyl, phenylalkyl, alkylaminoalkyl, dialkylaminoalkyl, arylalkyl, aryloxyalkyl, arylalkyloxyalkyl, (heterocyclic radical)alkyl, and (heterocyclic radical)oxyalkyl. Formula I thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alkylaryl)alkyl, (haloaryl)alkyl, (hydroxyaryl)alkynyl, and so forth. $R_6$, $R_7$, $R_8$, $R_9$, and $R_{10}$ include hydroxy($C_{1-8}$)alkyl, ($C_{1-5}$)alkoxy($C_{1-15}$)alkyl, aminoalkyl, (e.g., [($C_{1-4}$)alkyl]$_2$aminomethyl), perhalo($C_{1-3}$) alkyl (e.g., trifluoromethyl or trifluoroethyl), ($C_{2-7}$)heterocycle($C_{1-5}$)alkyl, and aryloxy($C_{1-5}$)alkyl. Similarly, $R_{10}$ includes hydroxy($C_{1-8}$)alkyl, ($C_{1-5}$)alkoxy($C_{1-5}$)alkyl and trifluoro($C_{1-6}$)alkyl.

Representative examples of the independent union of $R_6$, $R_7$, $R_8$, $R_9$, and $R_{10}$ to complete a 3-10 member cyclic ring optionally containing additional heteroatoms selected from O, S, NH, or N-alkyl are demonstrated in the fragments shown below.

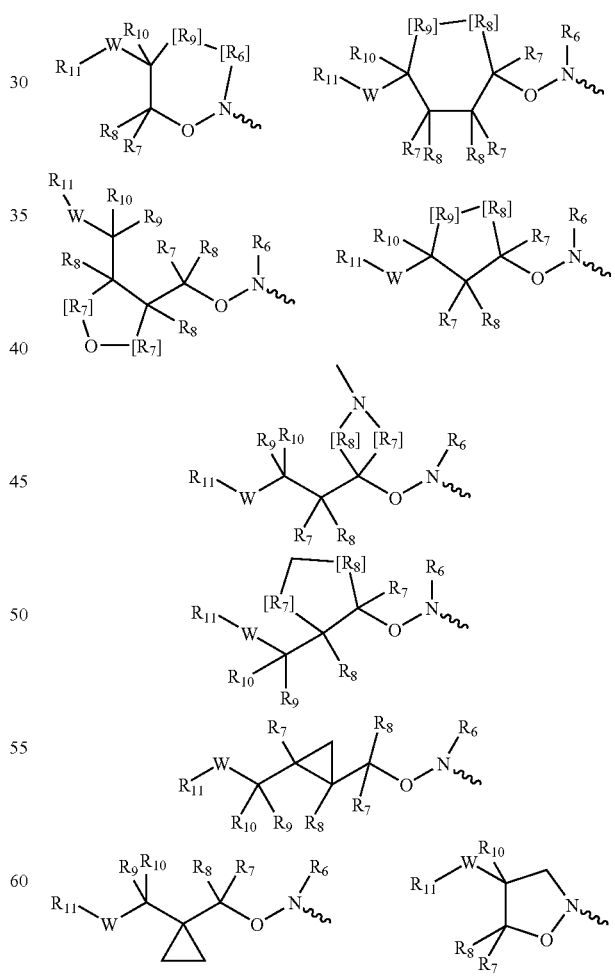

Representative examples of formula I where $R_7$ and $R_8$ are independently selected for n>1 are illustrated in the fragments shown below. The fragments below also show that where n>1, $R_7$ and $R_8$ are independently selected for each $(CR_7R_8)$ unit.

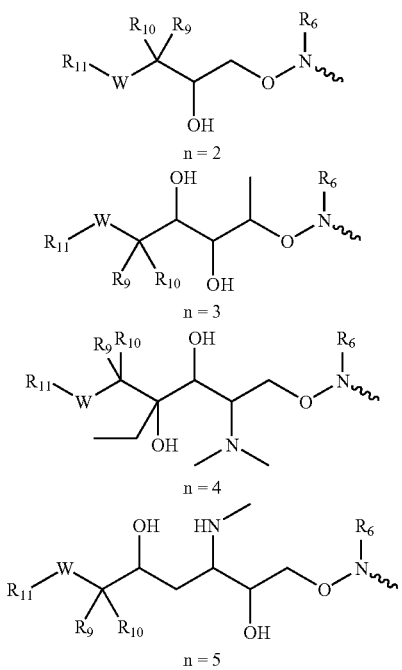

The present invention includes the hydrates and the pharmaceutically acceptable salts and solvates of the compounds defined by formula I. The compounds of this invention can possess a sufficiently basic functional group, and accordingly react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science*, 66, 2-19 (1977), which are know to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Example of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymateate, mandelate, mesylate, nicotinate, isonicotinate, cinnamate, hippurate, nitrate, stearate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydrozybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, hemi-tartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartarate, and the like. A preferred pharmaceutically acceptable salt is hydrochloride.

It should be recognized that the particular counterion forming a part of any salt of this inventions is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to each of two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of enantiomers.

The enantiomers of compounds of the present invention can be resolved by one of ordinary skill in the art using standard techniques well-known in the art, such as those described by J. Jacques, et al., "Enantiomers, Racemates, and Resolutions", John Wiley and Sons, Inc. 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The compounds of formula I can be prepared by techniques and procedures readily available to one of ordinary skill in the art, for example by following the procedures as set forth in the following Schemes. These schemes are not intended to limit the scope of the invention in any way. All substituents, unless otherwise indicated, are previously defined. The reagents and starting materials are readily available to one of ordinary skill in the art.

The compounds of formula I are generally obtained by the union of 2-(arylamino)-benzoic acids (1) with alkoxyamines (2) by the action of a peptide coupling agent in the presence of a base, as shown in Scheme 1. Preferred coupling agents include diphenylphoshinic chloride (DPP-Cl), benzotriazolyl-oxy-tripyrolidinophosphonium hexafluorophosphate (PyBOP), benzotriazol-1-yloxy-tris(dimethylamino)phosphonium hexafluorophosphate (BOP), N,N'-dicyclohexylcarbodiimide (DCC), 1-ethyl-3-(3-dimethylaminopropyl)carbodiimide hydrochloride (EDCI), or 1,1'-carbonyldimidazole (CDI). Preferred bases include diisopropylethylamine, triethylamine, 4-methylmorpholine, or pyridine or a substituted pyridine, for example, 4-dimethyaminopyridine or 2,6-dimethylpyridine. Preferred solvents are polar aprotic solvents such as dichloromethane, tetrahydrofuran, or dimethylformamide. The reactions are generally carried out at a temperature between about −78° C. to about 25° C., and are normally complete within about 2 hours to about 5 days. The product amides can be isolated by removing the solvent, for example by evaporation under reduced pressure, and further purified, if desired, by standard methods such as chromatography, crystallization, or distillation.

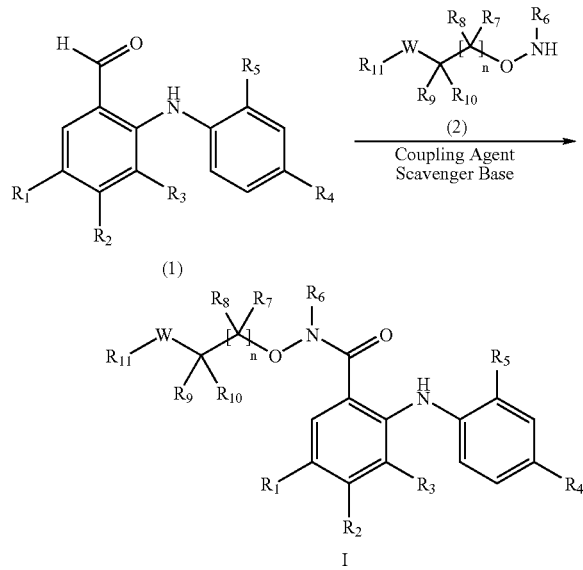

Scheme 1: General Preparation of Benzamides from Benzoic Acids

Alternately, disclosed compounds are also generally prepared as shown in Scheme 2 by the contact of alkoxyamine (2) with "activated" benzoic acid derivatives (3), wherein the activating group "X" completes an acid halide, anhydride, mixed anhydride, or an activated ester, such as a pentafluorophenyl ester, nitrophenyl ester or thioester. Preferred bases include diisopropylethylamine, triethylamine, 4-methylmorpholine, imidazole, pyridine or a substituted pyridine, for example, 4-dimethyaminopyridine or 2,6-dimethylpyridine. Preferred solvents are polar aprotic solvents such as dichloromethane, tetrahydrofuran, or dimethylformamide. These synthetic strategies, which are suitable for both conventional or combinatorial (parallel synthesis) synthetic methods are further exemplified in examples below.

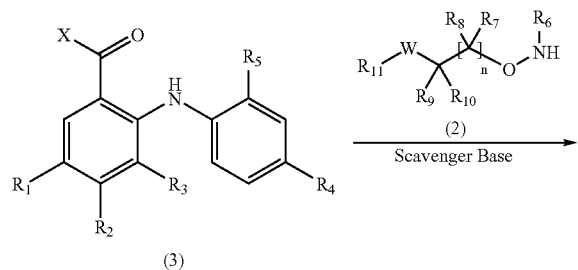

Scheme 2: General Preparation of Benzamides from "Activated" Benzoic Acid Derivatives

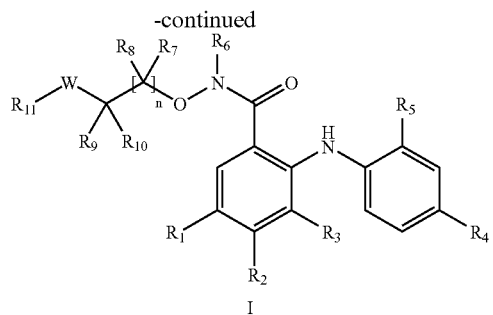

Preferred combinatorial methods are outlined in Scheme 3, wherein the compounds of formula I are obtained by the reaction of an excess of pentafluorophenyl esters (4) with alkoxyamines (2) in the presence of polymer supported (PS) 4-methylmorpholine (5) in dimethylformamide with mechanical shaking. After a reaction period of about 16 to 72 hours, polymer supported amine (6) is added with dichloromethane. After an additional several hours of mechanical agitation, targets I are obtained by filtration, solvent evaporation and chromatograhic purification.

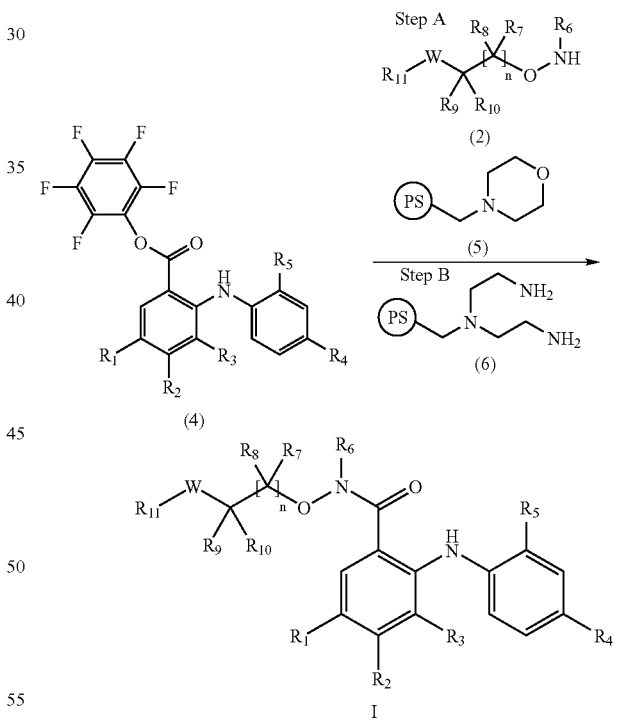

Scheme 3: General Combinatorial Preparation of Benzamides from Benzoic Acid Pentafluorophenyl Esters For the preparation of compounds of formula I wherein $R_{11}$=hydrogen, preferred synthetic modes may utilize a reagent of formula (2), wherein $R_6$, $R_7$, $R_8$, $R_9$, $R_{10}$ are defined as for formula I, above, and $R_{11}$ is a standard hydroxyl (W=O) or amino (W=NRa) protecting group. In such instances, general schemes 1-3, above may be modified to include a standard removal of the said protecting group. Suitable protecting groups include, but are not limited to, vinyl ethers, silyl ethers, acetals, acetonides, and carbamates. Examples of such modifications are outlined below.

As illustrated in Scheme 4, preferred compounds of formula IIa may be obtained by the reaction of benzoic acids (1) with vinyl ether (7), a peptide coupling agent (for example, PyBOP) and a base (for example, diisopropylethylamine) to afford vinyl ether amide (8). Further treatment of vinyl ether (8) with acid affords the compounds of formula IIa.

Scheme 4: Representative Preparation of Hydroxylated Benzamides Using a Vinyl Ether as a Hydroxyl Protecting Group

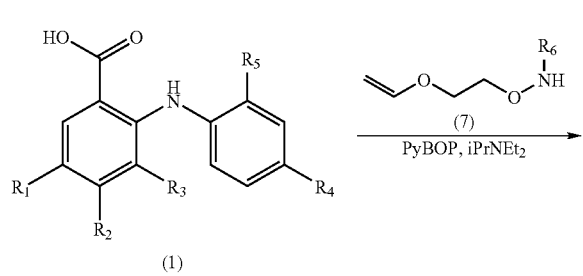

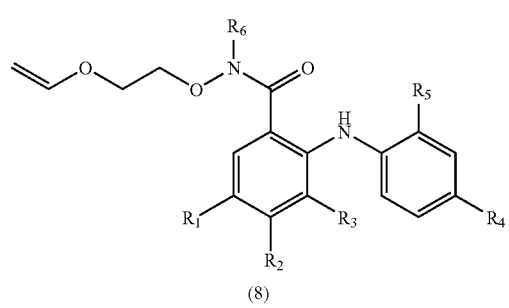

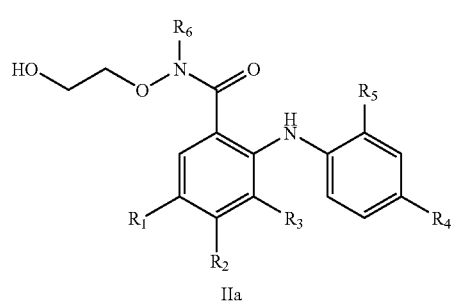

As shown below in Scheme 5, preferred compounds of formula IIb may also be obtained by the reaction of benzoic acids (1) with a suitable protecting group, such as tert-butyldimethylsilyl ether (9), in the presence a peptide coupling agent (for example, PyBOP) and a tertiary amine base (for example, diisopropylethylamine) to afford tert-butyldimethylsilyl ether amide (10). Further treatment of silyl ether (10) with acid in a protic solvent affords the compounds of formula IIb.

Scheme 5: Representative Preparation of Hydroxylated Benzamides Using a Silyl Ether as a Hydroxyl Protecting Group

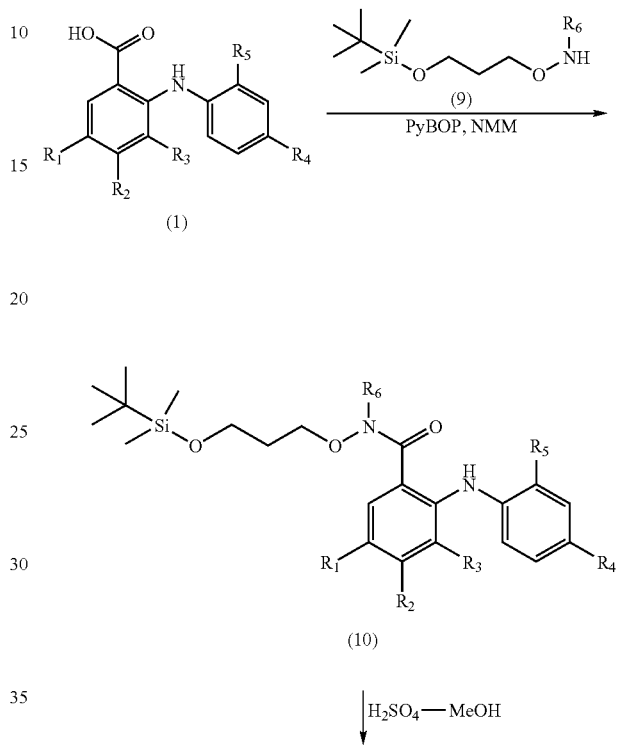

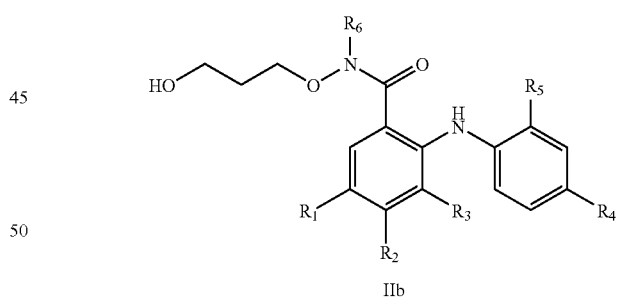

Preferred compounds of formula IVa can be prepared by similar methods, as illustrated in Scheme 6. For example, treatment of benzoic acids (1) with carbamate (11) in the presence of a peptide coupling agent, for example diphenylphosphinic chloride (DPP-Cl), in the presence of a tertiary amine base, for example 4-methylmorpholine (NMM) affords carbamate amide (12). Subsequent treatment of (12) with a suitable acid, for example trifluoracetic acid or hydrogen chloride, gives rise to the amines of general formula IVa, Scheme 6: Representative Preparation of Amino-Substituted Benzamides Using a tert-Butyl Carbamate as an Amino Protecting Group

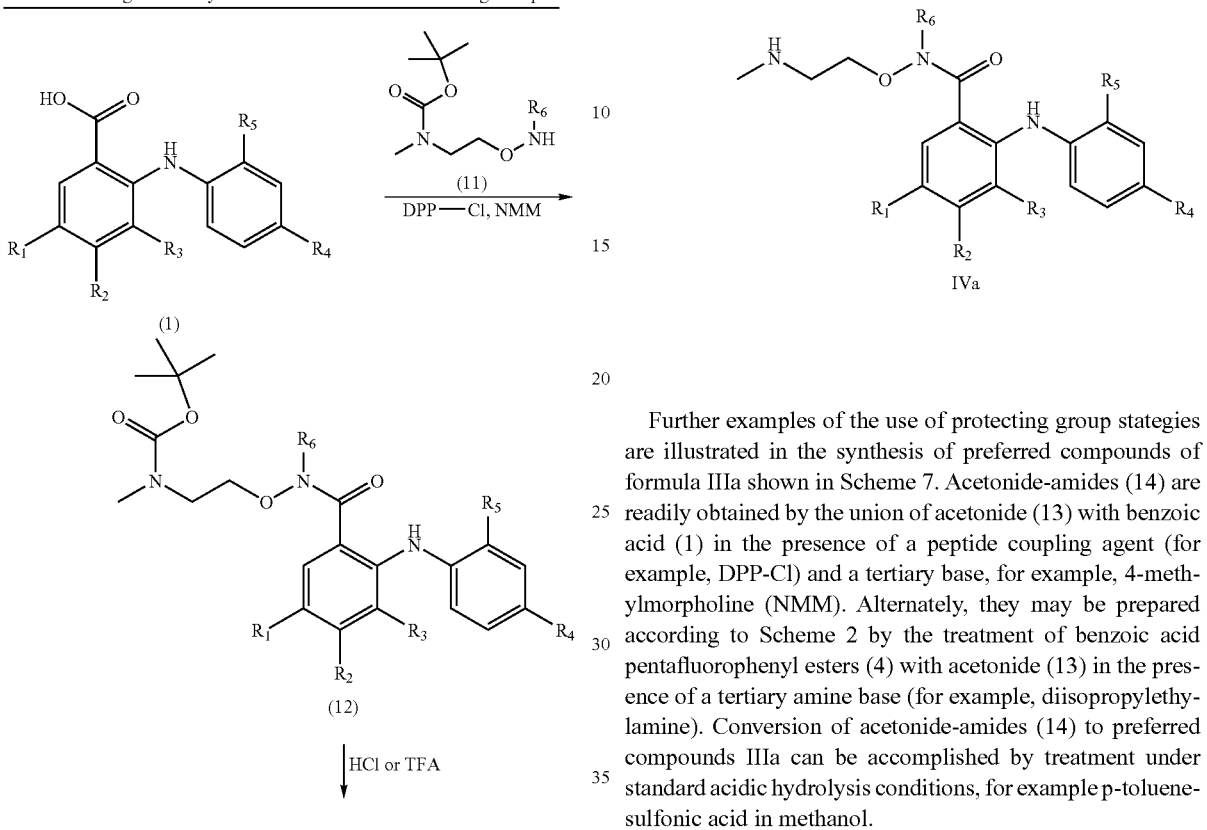

Further examples of the use of protecting group stategies are illustrated in the synthesis of preferred compounds of formula IIIa shown in Scheme 7. Acetonide-amides (14) are readily obtained by the union of acetonide (13) with benzoic acid (1) in the presence of a peptide coupling agent (for example, DPP-Cl) and a tertiary base, for example, 4-methylmorpholine (NMM). Alternately, they may be prepared according to Scheme 2 by the treatment of benzoic acid pentafluorophenyl esters (4) with acetonide (13) in the presence of a tertiary amine base (for example, diisopropylethylamine). Conversion of acetonide-amides (14) to preferred compounds IIIa can be accomplished by treatment under standard acidic hydrolysis conditions, for example p-toluenesulfonic acid in methanol.

Scheme 7: Representative Preparation of Dihydroxylated Benzamides Using an Acetonide as a Diol Protecting Group

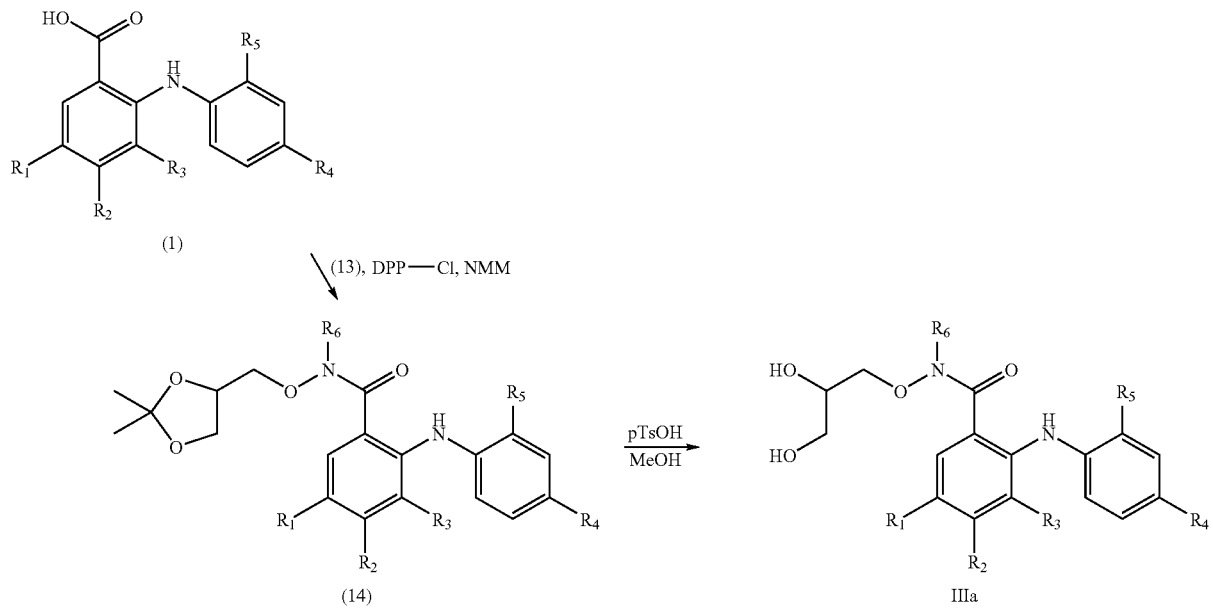

-continued

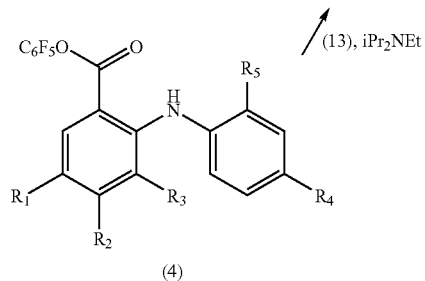

(4)

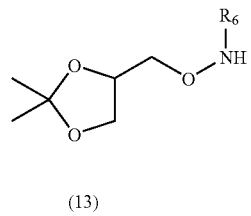

(13)

The compounds of formula I can also be prepared by the modification of other compounds of formula I. For example, compounds of formula I, where $R_6$=H (15) may be converted to compounds of formula I, where $R_6$=alkyl (16) by treatment with alkylating agents (for example, iodomethane) in the presence of a base (for example, potassium carbonate). Alternately, compounds of formula I, where $R_{11}$=H (17) may be converted to compounds of formula I, where $R_{11}$=alkylcarbonyl (18) by treatment with an acid chloride (for example, acetyl chloride) and a base, such as triethylamine. Additionally, a compound of formula I, where $R_4$=H (19) can be prepared from a compound of formula I, where $R_4$=Iodo (20). Illustrations of these examples are found in Schemes 8-10.

Scheme 8: Representative Preparation of Tertiary Benzamides by N-Alkylation

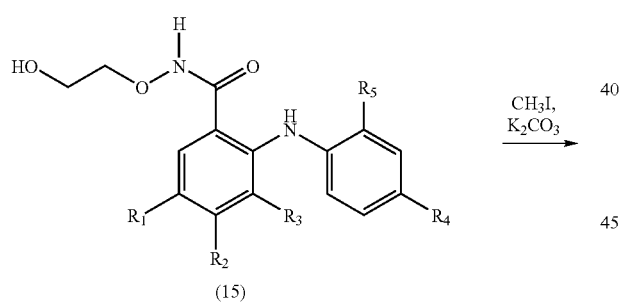

(15)

(16)

Scheme 9: Representative Preparation of Acetates by Acetylation

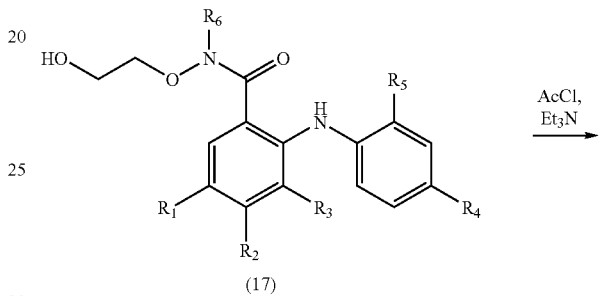

(17)

(18)

Scheme 10: Representative Hydrogenolysis of Aryl Iodides

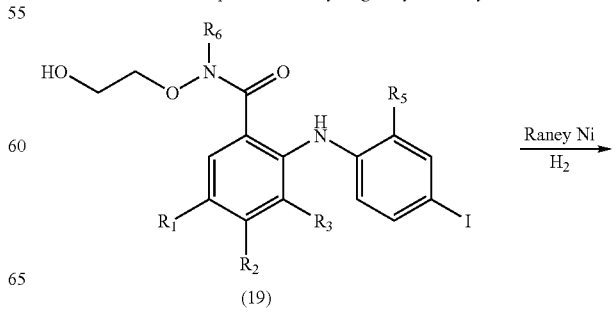

(19)

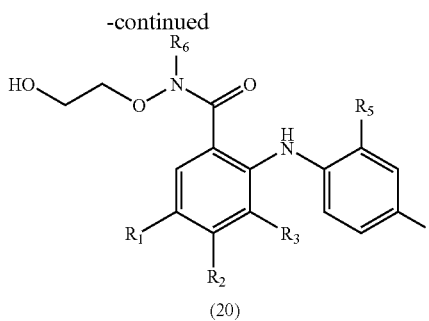

(20)

Specific compounds provided by the invention include:
Chloro-4-iodo-phenylamino)-3,4-difluoro-N-(2-hydroxy-3-phenoxy-propoxy)-benzamide
2-(2-Chloro-4-iodo-phenylamino)-3,4-difluoro-N-(2-hydroxy-butoxy)-benzamide
2-(2-Chloro-4-iodo-phenylamino)-3,4-difluoro-N-(2-hydroxy-1-methyl-ethoxy)-benzamide
2-(2-Chloro-4-iodo-phenylamino)-3,4-difluoro-N-(2-methoxy-ethoxy)-benzamide
2-(2-Chloro-4-iodo-phenylamino)-3,4-difluoro-N-(2-hydroxy-3-morpholin-4-yl-propoxy)-benzamide
2-(2-Chloro-4-iodo-phenylamino)-3,4-difluoro-N-(2-hydroxy-propoxy)-benzamide
2-(2-Chloro-4-iodo-phenylamino)-3,4,5-trifluoro-N-(2-hydroxy-3-phenoxy-propoxy)-benzamide
2-(2-Chloro-4-iodo-phenyl amino)-3,4,5-trifluoro-N-(2-hydroxy-butoxy)-benzamide
2-(2-Chloro-4-iodo-phenylamino)-3,4,5-trifluoro-N-(2-hydroxy-1-methyl-ethoxy)-benzamide
2-(2-Chloro-4-iodo-phenylamino)-3,4,5-trifluoro-N-(2-methoxy-ethoxy)-benzamide
2-(2-Chloro-4-iodo-phenylamino)-3,4,5-trifluoro-N-(2-hydroxy-3-morpholin-4-yl-propoxy)-benzamide
2-(2-Chloro-4-iodo-phenylamino)-3,4,5-trifluoro-N-(2-hydroxy-propoxy)-benzamide
2-(2-Chloro-4-iodo-phenylamino)-3,4,5-trifluoro-N-(3-hydroxy-2,2-dimethyl-propoxy)-benzamide
2-(2-Chloro-4-iodo-phenylamino)-3,4,5-trifluoro-N-(2-hydroxy-2-methyl-propoxy)-benzamide
3,4,5-Trifluoro-N-(2-hydroxy-3-phenoxy-propoxy)-2-(4-iodo-2-methyl-phenylamino)-benzamide
3,4,5-Trifluoro-N-(2-hydroxy-butoxy)-2-(4-iodo-2-methyl-phenylamino)-benzamide
3,4,5-Trifluoro-N-(2-hydroxy-1-methyl-ethoxy)-2-(4-iodo-2-methyl-phenylamino)-benzamide
3,4,5-Trifluoro-2-(4-iodo-2-methyl-phenylamino)-N-(2-methoxy-ethoxy)-benzamide
3,4,5-Trifluoro-N-(2-hydroxy-3-morpholin-4-yl-propoxy)-2-(4-iodo-2-methyl-phenylamino)-benzamide
3,4,5-Trifluoro-N-(2-hydroxy-propoxy)-2-(4-iodo-2-methyl-phenylamino)-benzamide
3,4,5-Trifluoro-N-(3-hydroxy-2,2-dimethyl-propoxy)-2-(4-iodo-2-methyl-phenylamino)-benzamide
3,4,5-Trifluoro-N-(2-hydroxy-2-methyl-propoxy)-2-(4-iodo-2-methyl-phenylamino)-benzamide
5-Bromo-2-(2-chloro-4-iodo-phenylamino)-3,4-difluoro-N-(2-hydroxy-3-phenoxy-propoxy)-benzamide
5-Bromo-2-(2-chloro-4-iodo-phenylamino)-3,4-difluoro-N-(2-hydroxy-butoxy)-benzamide
5-Bromo-2-(2-chloro-4-iodo-phenylamino)-3,4-difluoro-N-(2-hydroxy-1-methyl-ethoxy)-benzamide
5-Bromo-2-(2-chloro-4-iodo-phenylamino)-3,4-difluoro-N-(2-methoxy-ethoxy)-benzamide
5-Bromo-2-(2-chloro-4-iodo-phenylamino)-3,4-difluoro-N-(2-hydroxy-3-morpholin-4-yl-propoxy)-benzamide
5-Bromo-2-(2-chloro-4-iodo-phenylamino)-3,4-difluoro-N-(2-hydroxy-propoxy)-benzamide
5-Bromo-2-(2-chloro-4-iodo-phenyl amino)-3,4-difluoro-N-(2-hydroxy-2-methyl-propoxy)-benzamide
5-Bromo-3,4-difluoro-N-(2-hydroxy-3-phenoxy-propoxy)-2-(4-iodo-2-methyl-phenylamino)-benzamide
5-Bromo-3,4-difluoro-N-(2-hydroxy-butoxy)-2-(4-iodo-2-methyl-phenylamino)-benzamide
5-Bromo-3,4-difluoro-N-(2-hydroxy-1-methyl-ethoxy)-2-(4-iodo-2-methyl-phenylamino)-benzamide
5-Bromo-3,4-difluoro-2-(4-iodo-2-methyl-phenylamino)-N-(2-methoxy-ethoxy)-benzamide
5-Bromo-3,4-difluoro-N-(2-hydroxy-3-morpholin-4-yl-propoxy)-2-(4-iodo-2-methyl-phenylamino)-benzamide
5-Bromo-3,4-difluoro-N-(2-hydroxy-propoxy)-2-(4-iodo-2-methyl-phenylamino)-benzamide
5-Bromo-3,4-difluoro-N-(2-hydroxy-2-methyl-propoxy)-2-(4-iodo-2-methyl-phenylamino)-benzamide
3,4-Difluoro-N-(2-hydroxy-3-phenoxy-propoxy)-2-(4-iodo-2-methyl-phenylamino)-benzamide
3,4-Difluoro-N-(2-hydroxy-butoxy)-2-(4-iodo-2-methyl-phenylamino)-benzamide
3,4-Difluoro-N-(2-hydroxy-1-methyl-ethoxy)-2-(4-iodo-2-methyl-phenylamino)-benzamide
3,4-Difluoro-2-(4-iodo-2-methyl-phenylamino)-N-(2-methoxy-ethoxy)-benzamide
3,4-Difluoro-N-(2-hydroxy-3-morpholin-4-yl-propoxy)-2-(4-iodo-2-methyl-phenylamino)-benzamide
3,4-Difluoro-N-(2-hydroxy-propoxy)-2-(4-iodo-2-methyl-phenylamino)-benzamide
3,4-Difluoro-N-(3-hydroxy-2,2-dimethyl-propoxy)-2-(4-iodo-2-methyl-phenylamino)-benzamide
3,4-Difluoro-N-(2-hydroxy-2-methyl-propoxy)-2-(4-iodo-2-methyl-phenylamino)-benzamide
5-Chloro-2-(2-chloro-4-iodo-phenylamino)-3,4-difluoro-N-(2-hydroxy-3-phenoxy-propoxy)-benzamide
5-Chloro-2-(2-chloro-4-iodo-phenylamino)-3,4-difluoro-N-(2-hydroxy-butoxy)-benzamide
5-Chloro-2-(2-chloro-4-iodo-phenylamino)-3,4-difluoro-N-(2-hydroxy-1-methyl-ethoxy)-benzamide
5-Chloro-2-(2-chloro-4-iodo-phenylamino)-3,4-difluoro-N-(2-methoxy-ethoxy)-benzamide
5-Chloro-2-(2-chloro-4-iodo-phenylamino)-3,4-difluoro-N-(2-hydroxy-3-morpholin-4-yl-propoxy)-benzamide
5-Chloro-2-(2-chloro-4-iodo-phenylamino)-3,4-difluoro-N-(2-hydroxy-propoxy)-benzamide
5-Chloro-2-(2-chloro-4-iodo-phenylamino)-3,4-difluoro-N-(3-hydroxy-2,2-dimethyl-propoxy)-benzamide
5-Chloro-2-(2-chloro-4-iodo-phenylamino)-3,4-difluoro-N-(2-hydroxy-2-methyl-propoxy)-benzamide
5-Chloro-3,4-difluoro-N-(2-hydroxy-3-phenoxy-propoxy)-2-(4-iodo-2-methyl-phenylamino)-benzamide
5-Chloro-3,4-difluoro-N-(2-hydroxy-butoxy)-2-(4-iodo-2-methyl-phenylamino)-benzamide
5-Chloro-3,4-difluoro-N-(2-hydroxy-1-methyl-ethoxy)-2-(4-iodo-2-methyl-phenylamino)-benzamide
5-Chloro-3,4-difluoro-2-(4-iodo-2-methyl-phenylamino)-N-(2-methoxy-ethoxy)-benzamide
5-Chloro-3,4-difluoro-N-(2-hydroxy-3-morpholin-4-yl-propoxy)-2-(4-iodo-2-methyl-phenylamino)-benzamide
5-Chloro-3,4-difluoro-N-(2-hydroxy-propoxy)-2-(4-iodo-2-methyl-phenylamino)-benzamide 5-Chloro-3,4-difluoro-N-(3-hydroxy-2,2-dimethyl-propoxy)-2-(4-iodo-2-methyl-phenylamino)-benzamide
5-Chloro-3,4-difluoro-N-(2-hydroxy-2-methyl-propoxy)-2-(4-iodo-2-methyl-phenylamino)-benzamide
5-Bromo-2-(2-chloro-4-iodo-phenylamino)-3,4-difluoro-N-(3-hydroxy-propoxy)-benzamide
2-(2-Chloro-4-iodo-phenylamino)-3,4-difluoro-N-(3-hydroxy-propoxy)-benzamide
3,4,5-Trifluoro-N-(3-hydroxy-propoxy)-2-(4-iodo-2-methyl-phenylamino)-benzamide
2-(2-Chloro-4-iodo-phenylamino)-3,4,5-trifluoro-N-(3-hydroxy-propoxy)-benzamide
5-Bromo-3,4-difluoro-N-(3-hydroxy-propoxy)-2-(4-iodo-2-methyl-phenylamino)-benzamide
3,4-Difluoro-N-(3-hydroxy-propoxy)-2-(4-iodo-2-methyl-phenylamino)-benzamide
3,4-Difluoro-2-(4-iodo-2-methyl-phenylamino)-N-[2-(2-methoxy-ethoxy)-ethoxy]-benzamide
3,4,5-Trifluoro-2-(4-iodo-2-methyl-phenylamino)-N-[2-(2-methoxy-ethoxy)-ethoxy]-benzamide
5-Bromo-3,4-difluoro-2-(4-iodo-2-methyl-phenylamino)-N-[2-(2-methoxy-ethoxy)-ethoxy]-benzamide
2-(2-Chloro-4-iodo-phenylamino)-3,4-difluoro-N-[2-(2-methoxy-ethoxy)-ethoxy]-benzamide
2-(2-Chloro-4-iodo-phenylamino)-3,4,5-trifluoro-N-[2-(2-methoxy-ethoxy)-ethoxy]-benzamide
5-Bromo-2-(2-chloro-4-iodo-phenylamino)-3,4-difluoro-N-[2-(2-methoxy-ethoxy)-ethoxy]-benzamide Additionally, the claims provide for the following compounds:
5-Bromo-2-(2-chloro-4-iodo-phenylamino)-3,4-difluoro-N-(2-hydroxy-ethoxy)-benzamide,
5-Chloro-2-(2-chloro-4-iodo-phenylamino)-3,4-difluoro-N-(2-hydroxy-ethoxy)-benzamide,
2-(2-Chloro-4-iodo-phenylamino)-3,4,5-trifluoro-N-(2-hydroxy-ethoxy)-benzamide,
5-Bromo-3,4-difluoro-N-(2-hydroxy-ethoxy)-2-(4-iodo-2-methyl-phenylamino)-benzamide,
5-Chloro-3,4-difluoro-N-(2-hydroxy-ethoxy)-2-(4-iodo-2-methyl-phenylamino)-benzamide,
5-Chloro-2-(2-chloro-4-iodo-phenylamino)-3,4-difluoro-N-(2-hydroxy-propoxy)-benzamide,
5-Chloro-3,4-difluoro-N-(2-hydroxy-propoxy)-2-(4-iodo-2-methyl-phenylamino)-benzamide,
2-(2-Chloro-4-iodo-phenylamino)-3,4-difluoro-N-(3-hydroxy-2,2-dimethyl-propoxy)-benzamide,
5-Bromo-2-(2-chloro-4-iodo-phenylamino)-3,4-difluoro-N-(3-hydroxy-2,2-dimethyl-propoxy)-benzamide,
5-Bromo-3,4-difluoro-N-(3-hydroxy-2,2-dimethyl-propoxy)-2-(4-iodo-2-methyl-phenylamino)-benzamide,
2-(2-Chloro-4-iodo-phenylamino)-3,4-difluoro-N-(2-hydroxy-2-methyl-propoxy)-benzamide,
5-Chloro-2-(2-chloro-4-iodo-phenylamino)-N-(2,3-dihydroxy-propoxy)-3,4-difluoro-benzamide,
5-Chloro-N-(2,3-dihydroxy-propoxy)-3,4-difluoro-2-(4-iodo-2-methyl-phenylamino)-benzamide,
5-Chloro-2-(2-chloro-4-iodo-phenylamino)-N-(3,4-dihydroxy-butoxy)-3,4-difluoro-benzamide,
5-Chloro-N-(3,4-dihydroxy-butoxy)-3,4-difluoro-2-(4-iodo-2-methyl-phenylamino)-benzamide,
5-Chloro-2-(2-chloro-4-iodo-phenylamino)-3,4-difluoro-N-[2-(2-methoxy-ethoxy)-ethoxy]-benzamide,
5-Chloro-3,4-difluoro-2-(4-iodo-2-methyl-phenylamino)-N-[2-(2-methoxy-ethoxy)-ethoxy]-benzamide.

Additional Compounds described by the invention include:
4-Fluoro-N-(2-hydroxy-ethoxy)-2-(4-iodo-2-methyl-phenylamino)-benzamide
4-Fluoro-N-(3-hydroxy-propoxy)-2-(4-iodo-2-methyl-phenylamino)-benzamide
4-Fluoro-2-(4-iodo-2-methyl-phenylamino)-N-[2-(2-methoxy-ethoxy)-ethoxy]-benzamide
4-Fluoro-N-(2-hydroxy-butoxy)-2-(4-iodo-2-methyl-phenylamino)-benzamide
4-Fluoro-N-(2-hydroxy-propoxy)-2-(4-iodo-2-methyl-phenylamino)-benzamide
4-Fluoro-N-(2-hydroxy-2-methyl-propoxy)-2-(4-iodo-2-methyl-phenylamino)-benzamide
4-Fluoro-N-(2-hydroxy-1-methyl-ethoxy)-2-(4-iodo-2-methyl-phenylamino)-benzamide
4-Fluoro-2-(4-iodo-2-methyl-phenylamino)-N-(2-methoxy-ethoxy)-benzamide
N-(3,4-Dihydroxy-butoxy)-4-fluoro-2-(4-iodo-2-methyl-phenylamino)-benzamide
N-(2,3-Dihydroxy-propoxy)-4-fluoro-2-(4-iodo-2-methyl-phenylamino)-benzamide
4-Fluoro-N-(2-hydroxy-3-morpholin-4-yl-propoxy)-2-(4-iodo-2-methyl-phenylamino)-benzamide
4-Fluoro-N-(2-hydroxy-3-phenoxy-propoxy)-2-(4-iodo-2-methyl-phenylamino)-benzamide
4-Fluoro-N-(3-hydroxy-2,2-dimethyl-propoxy)-2-(4-iodo-2-methyl-phenylamino)-benzamide
2-(2-Chloro-4-iodo-phenylamino)-4-fluoro-N-(2-hydroxy-ethoxy)-benzamide
2-(2-Chloro-4-iodo-phenylamino)-4-fluoro-N-(3-hydroxy-propoxy)-benzamide
2-(2-Chloro-4-iodo-phenylamino)-4-fluoro-N-[2-(2-methoxy-ethoxy)-ethoxy]-benzamide
2-(2-Chloro-4-iodo-phenylamino)-4-fluoro-N-(2-hydroxy-butoxy)-benzamide
2-(2-Chloro-4-iodo-phenylamino)-4-fluoro-N-(2-hydroxy-propoxy)-benzamide
2-(2-Chloro-4-iodo-phenylamino)-4-fluoro-N-(2-hydroxy-2-methyl-propoxy)-benzamide
2-(2-Chloro-4-iodo-phenylamino)-4-fluoro-N-(2-hydroxy-1-methyl-ethoxy)-benzamide
2-(2-Chloro-4-iodo-phenylamino)-4-fluoro-N-(2-methoxy-ethoxy)-benzamide
2-(2-Chloro-4-iodo-phenylamino)-N-(3,4-dihydroxy-butoxy)-4-fluoro-benzamide
2-(2-Chloro-4-iodo-phenylamino)-N-(2,3-dihydroxy-propoxy)-4-fluoro-benzamide
2-(2-Chloro-4-iodo-phenylamino)-4-fluoro-N-(2-hydroxy-3-morpholin-4-yl-propoxy)-benzamide
2-(2-Chloro-4-iodo-phenylamino)-4-fluoro-N-(2-hydroxy-3-phenoxy-propoxy)-benzamide
2-(2-Chloro-4-iodo-phenylamino)-4-fluoro-N-(3-hydroxy-2,2-dimethyl-propoxy)-benzamide
4-Fluoro-2-(2-fluoro-4-iodo-phenylamino)-N-(2-hydroxy-ethoxy)-benzamide
4-Fluoro-2-(2-fluoro-4-iodo-phenylamino)-N-(3-hydroxy-propoxy)-benzamide
4-Fluoro-2-(2-fluoro-4-iodo-phenylamino)-N-[2-(2-methoxy-ethoxy)-ethoxy]-benzamide
4-Fluoro-2-(2-fluoro-4-iodo-phenylamino)-N-(2-hydroxy-butoxy)-benzamide
4-Fluoro-2-(2-fluoro-4-iodo-phenylamino)-N-(2-hydroxy-propoxy)-benzamide
4-Fluoro-2-(2-fluoro-4-iodo-phenylamino)-N-(2-hydroxy-2-methyl-propoxy)-benzamide 4-Fluoro-2-(2-fluoro-4-iodo-phenylamino)-N-(2-hydroxy-1-methyl-ethoxy)-benzamide
4-Fluoro-2-(2-fluoro-4-iodo-phenylamino)-N-(2-methoxy-ethoxy)-benzamide
N-(3,4-Dihydroxy-butoxy)-4-fluoro-2-(2-fluoro-4-iodo-phenylamino)-benzamide
N-(2,3-Dihydroxy-propoxy)-4-fluoro-2-(2-fluoro-4-iodo-phenylamino)-benzamide
4-Fluoro-2-(2-fluoro-4-iodo-phenylamino)-N-(2-hydroxy-3-morpholin-4-yl-propoxy)-benzamide
4-Fluoro-2-(2-fluoro-4-iodo-phenylamino)-N-(2-hydroxy-3-phenoxy-propoxy)-benzamide
4-Fluoro-2-(2-fluoro-4-iodo-phenylamino)-N-(3-hydroxy-2,2-dimethyl-propoxy)-benzamide
4,5-Difluoro-N-(2-hydroxy-ethoxy)-2-(4-iodo-2-methyl-phenylamino)-benzamide
4,5-Difluoro-N-(3-hydroxy-propoxy)-2-(4-iodo-2-methyl-phenylamino)-benzamide
4,5-Difluoro-2-(4-iodo-2-methyl-phenylamino)-N-[2-(2-methoxy-ethoxy)-ethoxy]-benzamide
4,5-Difluoro-N-(2-hydroxy-butoxy)-2-(4-iodo-2-methyl-phenylamino)-benzamide
4,5-Difluoro-N-(2-hydroxy-propoxy)-2-(4-iodo-2-methyl-phenylamino)-benzamide
4,5-Difluoro-N-(2-hydroxy-1-methyl-propoxy)-2-(4-iodo-2-methyl-phenylamino)-benzamide
4,5-Difluoro-N-(2-hydroxy-1-methyl-ethoxy)-2-(4-iodo-2-methyl-phenylamino)-benzamide
4,5-Difluoro-2-(4-iodo-2-methyl-phenylamino)-N-(2-methoxy-ethoxy)-benzamide
N-(3,4-Dihydroxy-butoxy)-4,5-difluoro-2-(4-iodo-2-methyl-phenylamino)-benzamide
N-(2,3-Dihydroxy-propoxy)-4,5-difluoro-2-(4-iodo-2-methyl-phenylamino)-benzamide
4,5-Difluoro-N-(2-hydroxy-3-morpholin-4-yl-propoxy)-2-(4-iodo-2-methyl-phenylamino)-benzamide
4,5-Difluoro-N-(2-hydroxy-3-phenoxy-propoxy)-2-(4-iodo-2-methyl-phenylamino)-benzamide
4,5-Difluoro-N-(3-hydroxy-2,2-dimethyl-propoxy)-2-(4-iodo-2-methyl-phenylamino)-benzamide
2-(2-Chloro-4-iodo-phenyl amino)-4,5-difluoro-N-(2-hydroxy-ethoxy)-benzamide
2-(2-Chloro-4-iodo-phenylamino)-4,5-difluoro-N-(3-hydroxy-propoxy)-benzamide
2-(2-Chloro-4-iodo-phenylamino)-4,5-difluoro-N-[2-(2-methoxy-ethoxy)-ethoxy]-benzamide
2-(2-Chloro-4-iodo-phenylamino)-4,5-difluoro-N-(2-hydroxy-butoxy)-benzamide
2-(2-Chloro-4-iodo-phenylamino)-4,5-difluoro-N-(2-hydroxy-propoxy)-benzamide
2-(2-Chloro-4-iodo-phenylamino)-4,5-difluoro-N-(2-hydroxy-2-methyl-propoxy)-benzamide
2-(2-Chloro-4-iodo-phenylamino)-4,5-difluoro-N-(2-hydroxy-1-methyl-ethoxy)-benzamide
2-(2-Chloro-4-iodo-phenylamino)-4,5-difluoro-N-(2-methoxy-ethoxy)-benzamide
2-(2-Chloro-4-iodo-phenylamino)-N-(3,4-dihydroxy-butoxy)-4,5-difluoro-benzamide
2-(2-Chloro-4-iodo-phenylamino)-N-(2,3-dihydroxy-propoxy)-4,5-difluoro-benzamide
2-(2-Chloro-4-iodo-phenylamino)-4,5-difluoro-N-(2-hydroxy-3-morpholin-4-yl-propoxy)-benzamide
2-(2-Chloro-4-iodo-phenylamino)-4,5-difluoro-N-(2-hydroxy-3-phenoxy-propoxy)-benzamide
2-(2-Chloro-4-iodo-phenylamino)-4,5-difluoro-N-(3-hydroxy-2,2-dimethyl-propoxy)-benzamide
4,5-Difluoro-2-(2-fluoro-4-iodo-phenylamino)-N-(2-hydroxy-ethoxy)-benzamide
4,5-Difluoro-2-(2-fluoro-4-iodo-phenylamino)-N-(3-hydroxy-propoxy)-benzamide
4,5-Difluoro-2-(2-fluoro-4-iodo-phenylamino)-N-[2-(2-methoxy-ethoxy)-ethoxy]-benzamide
4,5-Difluoro-2-(2-fluoro-4-iodo-phenylamino)-N-(2-hydroxy-butoxy)-benzamide
4,5-Difluoro-2-(2-fluoro-4-iodo-phenylamino)-N-(2-hydroxy-propoxy)-benzamide
4,5-Difluoro-2-(2-fluoro-4-iodo-phenylamino)-N-(2-hydroxy-2-methyl-propoxy)-benzamide
4,5-Difluoro-2-(2-fluoro-4-iodo-phenylamino)-N-(2-hydroxy-1-methyl-ethoxy)-benzamide
4,5-Difluoro-2-(2-fluoro-4-iodo-phenylamino)-N-(2-methoxy-ethoxy)-benzamide
N-(3,4-Dihydroxy-butoxy)-4,5-difluoro-2-(2-fluoro-4-iodo-phenylamino)-benzamide
N-(2,3-Dihydroxy-propoxy)-4,5-difluoro-2-(2-fluoro-4-iodo-phenylamino)-benzamide
4,5-Difluoro-2-(2-fluoro-4-iodo-phenylamino)-N-(2-hydroxy-3-morpholin-4-yl-propoxy)-benzamide
4,5-Difluoro-2-(2-fluoro-4-iodo-phenylamino)-N-(2-hydroxy-3-phenoxy-propoxy)-benzamide
4,5-Difluoro-2-(2-fluoro-4-iodo-phenylamino)-N-(3-hydroxy-2,2-dimethyl-propoxy)-benzamide
5-Chloro-4-fluoro-N-(2-hydroxy-ethoxy)-2-(4-iodo-2-methyl-phenylamino)-benzamide
5-Chloro-4-fluoro-N-(3-hydroxy-propoxy)-2-(4-iodo-2-methyl-phenylamino)-benzamide
5-Chloro-4-fluoro-2-(4-iodo-2-methyl-phenylamino)-N-[2-(2-methoxy-ethoxy)-ethoxy]-benzamide
5-Chloro-4-fluoro-N-(2-hydroxy-butoxy)-2-(4-iodo-2-methyl-phenylamino)-benzamide
5-Chloro-4-fluoro-N-(2-hydroxy-propoxy)-2-(4-iodo-2-methyl-phenylamino)-benzamide
5-Chloro-4-fluoro-N-(2-hydroxy-2-methyl-propoxy)-2-(4-iodo-2-methyl-phenylamino)-benzamide
5-Chloro-4-fluoro-N-(2-hydroxy-1-methyl-ethoxy)-2-(4-iodo-2-methyl-phenylamino)-benzamide
5-Chloro-4-fluoro-2-(4-iodo-2-methyl-phenylamino)-N-(2-methoxy-ethoxy)-benzamide
5-Chloro-N-(3,4-dihydroxy-butoxy)-4-fluoro-2-(4-iodo-2-methyl-phenylamino)-benzamide
5-Chloro-N-(2,3-dihydroxy-propoxy)-4-fluoro-2-(4-iodo-2-methyl-phenylamino)-benzamide
5-Chloro-4-fluoro-N-(2-hydroxy-3-morpholin-4-yl-propoxy)-2-(4-iodo-2-methyl-phenylamino)-benzamide
5-Chloro-4-fluoro-N-(2-hydroxy-3-phenoxy-prop oxy)-2-(4-iodo-2-methyl-phenylamino)-benzamide
5-Chloro-4-fluoro-N-(3-hydroxy-2,2-dimethyl-propoxy)-2-(4-iodo-2-methyl-phenylamino)-benzamide
5-Chloro-2-(2-chloro-4-iodo-phenylamino)-4-fluoro-N-(2-hydroxy-ethoxy)-benzamide
5-Chloro-2-(2-chloro-4-iodo-phenylamino)-4-fluoro-N-(3-hydroxy-propoxy)-benzamide
5-Chloro-2-(2-chloro-4-iodo-phenylamino)-4-fluoro-N-[2-(2-methoxy-ethoxy)-ethoxy]-benzamide
5-Chloro-2-(2-chloro-4-iodo-phenylamino)-4-fluoro-N-(2-hydroxy-butoxy)-benzamide
5-Chloro-2-(2-chloro-4-iodo-phenylamino)-4-fluoro-N-(2-hydroxy-propoxy)-benzamide
5-Chloro-2-(2-chloro-4-iodo-phenylamino)-4-fluoro-N-(2-hydroxy-2-methyl-propoxy)-benzamide
5-Chloro-2-(2-chloro-4-iodo-phenylamino)$_4$-fluoro-N-(2-hydroxy-1-methyl-ethoxy)-benzamide 5-Chloro-2-(2-chloro-4-iodo-phenylamino)-4-fluoro-N-(2-methoxy-ethoxy)-benzamide
5-Chloro-2-(2-chloro-4-iodo-phenylamino)-N-(3,4-dihydroxy-butoxy)-4-fluoro-benzamide
5-Chloro-2-(2-chloro-4-iodo-phenylamino)-N-(2,3-dihydroxy-propoxy)-4-fluoro-benzamide
5-Chloro-2-(2-chloro-4-iodo-phenylamino)-4-fluoro-N-(2-hydroxy-3-morpholin-4-yl-propoxy)-benzamide
5-Chloro-2-(2-chloro-4-iodo-phenylamino)-4-fluoro-N-(2-hydroxy-3-phenoxy-propoxy)-benzamide
5-Chloro-2-(2-chloro-4-iodo-phenylamino)-4-fluoro-N-(3-hydroxy-2,2-dimethyl-propoxy)-benzamide
5-Chloro-4-fluoro-2-(2-fluoro-4-iodo-phenylamino)-N-(2-hydroxy-ethoxy)-benzamide
5-Chloro-4-fluoro-2-(2-fluoro-4-iodo-phenylamino)-N-(3-hydroxy-propoxy)-benzamide
5-Chloro-4-fluoro-2-(2-fluoro-4-iodo-phenyl amino)-N-[2-(2-methoxy-ethoxy)-ethoxy]-benzamide
5-Chloro-4-fluoro-2-(2-fluoro-4-iodo-phenylamino)-N-(2-hydroxy-butoxy)-benzamide
5-Chloro-4-fluoro-2-(2-fluoro-4-iodo-phenylamino)-N-(2-hydroxy-propoxy)-benzamide
5-Chloro-4-fluoro-2-(2-fluoro-4-iodo-phenyl amino)-N-(2-hydroxy-2-methyl-propoxy)-benzamide
5-Chloro-4-fluoro-2-(2-fluoro-4-iodo-phenylamino)-N-(2-hydroxy-1-methyl-ethoxy)-benzamide
5-Chloro-4-fluoro-2-(2-fluoro-4-iodo-phenylamino)-N-(2-methoxy-ethoxy)-benzamide
5-Chloro-N-(3,4-dihydroxy-butoxy)-4-fluoro-2-(2-fluoro-4-iodo-phenylamino)-benzamide
5-Chloro-N-(2,3-dihydroxy-propoxy)-4-fluoro-2-(2-fluoro-4-iodo-phenylamino)-benzamide
5-Chloro-4-fluoro-2-(2-fluoro-4-iodo-phenylamino)-N-(2-hydroxy-3-morpholin-4-yl-propoxy)-benzamide
5-Chloro-4-fluoro-2-(2-fluoro-4-iodo-phenylamino)-N-(2-hydroxy-3-phenoxy-propoxy)-benzamide
5-Chloro-4-fluoro-2-(2-fluoro-4-iodo-phenylamino)-N-(3-hydroxy-2,2-dimethyl-propoxy)-benzamide
5-Bromo-4-fluoro-N-(2-hydroxy-ethoxy)-2-(4-iodo-2-methyl-phenylamino)-benzamide
5-Bromo-4-fluoro-N-(3-hydroxy-propoxy)-2-(4-iodo-2-methyl-phenylamino)-benzamide
5-Bromo-4-fluoro-2-(4-iodo-2-methyl-phenylamino)-N-[2-(2-methoxy-ethoxy)-ethoxy]-benzamide
5-Bromo-4-fluoro-N-(2-hydroxy-butoxy)-2-(4-iodo-2-methyl-phenylamino)-benzamide
5-Bromo-4-fluoro-N-(2-hydroxy-propoxy)-2-(4-iodo-2-methyl-phenylamino)-benzamide
5-Bromo-4-fluoro-N-(2-hydroxy-2-methyl-propoxy)-2-(4-iodo-2-methyl-phenylamino)-benzamide
5-Bromo-4-fluoro-N-(2-hydroxy-1-methyl-ethoxy)-2-(4-iodo-2-methyl-phenylamino)-benzamide
5-Bromo-4-fluoro-2-(4-iodo-2-methyl-phenylamino)-N-(2-methoxy-ethoxy)-benzamide
5-Bromo-N-(3,4-dihydroxy-butoxy)-4-fluoro-2-(4-iodo-2-methyl-phenylamino)-benzamide
5-Bromo-N-(2,3-dihydroxy-propoxy)-4-fluoro-2-(4-iodo-2-methyl-phenylamino)-benzamide
5-Bromo-4-fluoro-N-(2-hydroxy-3-morpholin-4-yl-propoxy)-2-(4-iodo-2-methyl-phenylamino)-benzamide
5-Bromo-4-fluoro-N-(2-hydroxy-3-phenoxy-propoxy)-2-(4-iodo-2-methyl-phenylamino)-benzamide
5-Bromo-4-fluoro-N-(3-hydroxy-2,2-dimethyl-propoxy)-2-(4-iodo-2-methyl-phenylamino)-benzamide
5-Bromo-2-(2-chloro-4-iodo-phenylamino)-4-fluoro-N-(2-hydroxy-ethoxy)-benzamide
5-Bromo-2-(2-chloro-4-iodo-phenylamino)-4-fluoro-N-(3-hydroxy-propoxy)-benzamide
5-Bromo-2-(2-chloro-4-iodo-phenylamino)-4-fluoro-N-[2-(2-methoxy-ethoxy)-ethoxy]-benzamide
5-Bromo-2-(2-chloro-4-iodo-phenylamino)-4-fluoro-N-(2-hydroxy-butoxy)-benzamide
5-Bromo-2-(2-chloro-4-iodo-phenylamino)-4-fluoro-N-(2-hydroxy-propoxy)-benzamide
5-Bromo-2-(2-chloro-4-iodo-phenylamino)-4-fluoro-N-(2-hydroxy-2-methyl-propoxy)-benzamide
5-Bromo-2-(2-chloro-4-iodo-phenylamino)-4-fluoro-N-(2-hydroxy-1-methyl-ethoxy)-benzamide
5-Bromo-2-(2-chloro-4-iodo-phenylamino)-4-fluoro-N-(2-methoxy-ethoxy)-benzamide
5-Bromo-2-(2-chloro-4-iodo-phenylamino)-N-(3,4-dihydroxy-butoxy)-4-fluoro-benzamide
5-Bromo-2-(2-chloro-4-iodo-phenylamino)-N-(2,3-dihydroxy-propoxy)-4-fluoro-benzamide
5-Bromo-2-(2-chloro-4-iodo-phenylamino)-4-fluoro-N-(2-hydroxy-3-morpholin-4-yl-propoxy)-benzamide
5-Bromo-2-(2-chloro-4-iodo-phenylamino)-4-fluoro-N-(2-hydroxy-3-phenoxy-propoxy)-benzamide
5-Bromo-2-(2-chloro-4-iodo-phenylamino)-4-fluoro-N-(3-hydroxy-2,2-dimethyl-propoxy)-benzamide
5-Bromo-4-fluoro-2-(2-fluoro-4-iodo-phenylamino)-N-(2-hydroxy-ethoxy)-benzamide
5-Bromo-4-fluoro-2-(2-fluoro-4-iodo-phenylamino)-N-(3-hydroxy-propoxy)-benzamide
5-Bromo-4-fluoro-2-(2-fluoro-4-iodo-phenylamino)-N-[2-(2-methoxy-ethoxy)-ethoxy]-benzamide
5-Bromo-4-fluoro-2-(2-fluoro-4-iodo-phenylamino)-N-(2-hydroxy-butoxy)-benzamide
5-Bromo-4-fluoro-2-(2-fluoro-4-iodo-phenylamino)-N-(2-hydroxy-propoxy)-benzamide
5-Bromo-4-fluoro-2-(2-fluoro-4-iodo-phenylamino)-N-(2-hydroxy-2-methyl-propoxy)-benzamide
5-Bromo-4-fluoro-2-(2-fluoro-4-iodo-phenylamino)-N-(2-hydroxy 1-methyl-ethoxy)-benzamide
5-Bromo-4-fluoro-2-(2-fluoro-4-iodo-phenylamino)-N-(2-methoxy-ethoxy)-benzamide
5-Bromo-N-(3,4-dihydroxy-butoxy)-4-fluoro-2-(2-fluoro-4-iodo-phenylamino)-benzamide
5-Bromo-N-(2,3-dihydroxy-propoxy)-4-fluoro-2-(2-fluoro-4-iodo-phenylamino)-benzamide
5-Bromo-4-fluoro-2-(2-fluoro-4-iodo-phenylamino)-N-(2-hydroxy-3-morpholin-4-yl-propoxy)-benzamide
5-Bromo-4-fluoro-2-(2-fluoro-4-iodo-phenylamino)-N-(2-hydroxy-3-phenoxy-propoxy)-benzamide
5-Bromo-4-fluoro-2-(2-fluoro-4-iodo-phenylamino)-N-(3-hydroxy-2,2-dimethyl-propoxy)-benzamide
3,4-Difluoro-2-(2-fluoro-4-iodo-phenylamino)-N-(2-hydroxy-ethoxy)-benzamide
3,4-Difluoro-2-(2-fluoro-4-iodo-phenylamino)-N-(3-hydroxy-propoxy)-benzamide
3,4-Difluoro-2-(2-fluoro-4-iodo-phenylamino)-N-[2-(2-methoxy-ethoxy)-ethoxy]-benzamide
3,4-Difluoro-2-(2-fluoro-4-iodo-phenylamino)-N-(2-hydroxy-butoxy)-benzamide
3,4-Difluoro-2-(2-fluoro-4-iodo-phenylamino)-N-(2-hydroxy-propoxy)-benzamide
3,4-Difluoro-2-(2-fluoro-4-iodo-phenylamino)-N-(2-hydroxy-2-methyl-propoxy)-benzamide
3,4-Difluoro-2-(2-fluoro-4-iodo-phenylamino)-N-(2-hydroxy-1-methyl-ethoxy)-benzamide
3,4-Difluoro-2-(2-fluoro-4-iodo-phenylamino)-N-(2-methoxy-ethoxy)-benzamide N-(3,4-Dihydroxy-butoxy)-3,4-difluoro-2-(2-fluoro-4-iodo-phenylamino)-benzamide
N-(2,3-Dihydroxy-propoxy)-3,4-difluoro-2-(2-fluoro-4-iodo-phenylamino)-benzamide
3,4-Difluoro-2-(2-fluoro-4-iodo-phenylamino)-N-(2-hydroxy-3-morpholin-4-yl-propoxy)-benzamide
3,4-Difluoro-2-(2-fluoro-4-iodo-phenylamino)-N-(2-hydroxy-3-phenoxy-propoxy)-benzamide
3,4-Difluoro-2-(2-fluoro-4-iodo-phenylamino)-N-(3-hydroxy-2,2-dimethyl-propoxy)-benzamide
3,4,5-Trifluoro-2-(2-fluoro-4-iodo-phenylamino)-N-(2-hydroxy-ethoxy)-benzamide
3,4,5-Trifluoro-2-(2-fluoro-4-iodo-phenylamino)-N-(3-hydroxy-propoxy)-benzamide
3,4,5-Trifluoro-2-(2-fluoro-4-iodo-phenylamino)-N-[2-(2-methoxy-ethoxy)-ethoxy]-benzamide
3,4,5-Trifluoro-2-(2-fluoro-4-iodo-phenylamino)-N-(2-hydroxy-butoxy)-benzamide
3,4,5-Trifluoro-2-(2-fluoro-4-iodo-phenylamino)-N-(2-hydroxy-propoxy)-benzamide
3,4,5-Trifluoro-2-(2-fluoro-4-iodo-phenylamino)-N-(2-hydroxy-2-methyl-propoxy)-benzamide
3,4,5-Trifluoro-2-(2-fluoro-4-iodo-phenylamino)-N-(2-hydroxy-1-methyl-ethoxy)-benzamide
3,4,5-Trifluoro-2-(2-fluoro-4-iodo-phenylamino)-N-(2-methoxy-ethoxy)-benzamide
N-(3,4-Dihydroxy-butoxy)-3,4,5-trifluoro-2-(2-fluoro-4-iodo-phenylamino)-benzamide
N-(2,3-Dihydroxy-propoxy)-3,4,5-trifluoro-2-(2-fluoro-4-iodo-phenylamino)-benzamide
3,4,5-Trifluoro-2-(2-fluoro-4-iodo-phenylamino)-N-(2-hydroxy-3-morpholin-4-yl-propoxy)-benzamide
3,4,5-Trifluoro-2-(2-fluoro-4-iodo-phenylamino)-N-(2-hydroxy-3-phenoxy-propoxy)-benzamide
3,4,5-Trifluoro-2-(2-fluoro-4-iodo-phenylamino)-N-(3-hydroxy-2,2-dimethyl-propoxy)-benzamide
5-Chloro-3,4-difluoro-2-(2-fluoro-4-iodo-phenylamino)-N-(2-hydroxy-ethoxy)-benzamide
5-Chloro-3,4-difluoro-2-(2-fluoro-4-iodo-phenylamino)-N-(3-hydroxy-propoxy)-benzamide
5-Chloro-3,4-difluoro-2-(2-fluoro-4-iodo-phenylamino)-N-[2-(2-methoxy-ethoxy)-ethoxy]-benzamide
5-Chloro-3,4-difluoro-2-(2-fluoro-4-iodo-phenylamino)-N-(2-hydroxy-butoxy)-benzamide
5-Chloro-3,4-difluoro-2-(2-fluoro-4-iodo-phenylamino)-N-(2-hydroxy-propoxy)-benzamide
5-Chloro-3,4-difluoro-2-(2-fluoro-4-iodo-phenylamino)-N-(2-hydroxy-2-methyl-propoxy)-benzamide
5-Chloro-3,4-difluoro-2-(2-fluoro-4-iodo-phenylamino)-N-(2-hydroxy-1-methyl-ethoxy)-benzamide
5-Chloro-3,4-difluoro-2-(2-fluoro-4-iodo-phenylamino)-N-(2-methoxy-ethoxy)-benzamide
5-Chloro-N-(3,4-dihydroxy-butoxy)-3,4-difluoro-2-(2-fluoro-4-iodo-phenylamino)-benzamide
5-Chloro-N-(2,3-dihydroxy-propoxy)-3,4-difluoro-2-(2-fluoro-4-iodo-phenylamino)-benzamide
5-Chloro-3,4-difluoro-2-(2-fluoro-4-iodo-phenylamino)-N-(2-hydroxy-3-morpholin-4-yl-propoxy)-benzamide
5-Chloro-3,4-difluoro-2-(2-fluoro-4-iodo-phenylamino)-N-(2-hydroxy-3-phenoxy-propoxy)-benzamide
5-Chloro-3,4-difluoro-2-(2-fluoro-4-iodo-phenylamino)-N-(3-hydroxy-2,2-dimethyl-propoxy)-benzamide
5-Bromo-3,4-difluoro-2-(2-fluoro-4-iodo-phenylamino)-N-(2-hydroxy-ethoxy)-benzamide
5-Bromo-3,4-difluoro-2-(2-fluoro-4-iodo-phenylamino)-N-(3-hydroxy-propoxy)-benzamide
5-Bromo-3,4-difluoro-2-(2-fluoro-4-iodo-phenylamino)-N-[2-(2-methoxy-ethoxy)-ethoxy]-benzamide
5-Bromo-3,4-difluoro-2-(2-fluoro-4-iodo-phenylamino)-N-(2-hydroxy-butoxy)-benzamide
5-Bromo-3,4-difluoro-2-(2-fluoro-4-iodo-phenylamino)-N-(2-hydroxy-propoxy)-benzamide
5-Bromo-3,4-difluoro-2-(2-fluoro-4-iodo-phenylamino)-N-(2-hydroxy-2-methyl-propoxy)-benzamide
5-Bromo-3,4-difluoro-2-(2-fluoro-4-iodo-phenylamino)-N-(2-hydroxy-1-methyl-ethoxy)-benzamide
5-Bromo-3,4-difluoro-2-(2-fluoro-4-iodo-phenylamino)-N-(2-methoxy-ethoxy)-benzamide
5-Bromo-N-(3,4-dihydroxy-butoxy)-3,4-difluoro-2-(2-fluoro-4-iodo-phenylamino)-benzamide
5-Bromo-N-(2,3-dihydroxy-propoxy)-3,4-difluoro-2-(2-fluoro-4-iodo-phenylamino)-benzamide
5-Bromo-3,4-difluoro-2-(2-fluoro-4-iodo-phenylamino)-N-(2-hydroxy-3-morpholin-4-yl-propoxy)-benzamide
5-Bromo-3,4-difluoro-2-(2-fluoro-4-iodo-phenylamino)-N-(2-hydroxy-3-phenoxy-propoxy)-benzamide
5-Bromo-3,4-difluoro-2-(2-fluoro-4-iodo-phenylamino)-N-(3-hydroxy-2,2-dimethyl-propoxy)-benzamide
2-(2-Chloro-4-iodo-phenylamino)-3,4-difluoro-N-(2-hydroxy-3-methoxy-propoxy)-benzamide
2-(2-Chloro-4-iodo-phenylamino)-3,4-difluoro-N-(2-hydroxy-pentyloxy)-benzamide
2-(2-Chloro-4-iodo-phenylamino)-3,4-difluoro-N-(3,3,3-trifluoro-2-hydroxy-propoxy)-benzamide
2-(2-Chloro-4-iodo-phenylamino)-3,4-difluoro-N-(2-hydroxy-3-methyl-butoxy)-benzamide
2-(2-Chloro-4-iodo-phenylamino)-3,4-difluoro-N-(2-hydroxy-4-methyl-pentyloxy)-benzamide
2-(2-Chloro-4-iodo-phenylamino)-3,4-difluoro-N-(1-hydroxy-cyclopropylmethoxy)-benzamide
2-(2-Chloro-4-iodo-phenylamino)-3,4-difluoro-N-(1-hydroxy-cyclobutylmethoxy)-benzamide
2-(2-Chloro-4-iodo-phenylamino)-3,4-difluoro-N-(1-hydroxymethyl-propoxy)-benzamide
2-(2-Chloro-4-iodo-phenylamino)-3,4-difluoro-N-(2-hydroxy-1,1-dimethyl-ethoxy)-benzamide
2-(2-Chloro-4-iodo-phenylamino)-3,4-difluoro-N-(1-hydroxymethyl-cyclopropyl)-benzamide
2-(2-Chloro-4-iodo-phenylamino)-N-(2-ethoxy-ethoxy)-3,4-difluoro-benzamide
2-(2-Chloro-4-iodo-phenylamino)-3,4-difluoro-N-(3-hydroxy-2-methoxy-propoxy)-benzamide
2-(2-Chloro-4-iodo-phenylamino)-3,4-difluoro-N-(3-hydroxy-pentyloxy)-benzamide
2-(2-Chloro-4-iodo-phenylamino)-3,4-difluoro-N-(3-hydroxy-butoxy)-benzamide
2-(2-Chloro-4-iodo-phenyl amino)-3,4-difluoro-N-(3-hydroxy-3-methyl-butoxy)-benzamide
2-(2-Chloro-4-iodo-phenylamino)-3,4-difluoro-N-[2-(1-hydroxy-cyclopropyl)-ethoxy]-benzamide
2-(2-Chloro-4-iodo-phenylamino)-3,4-difluoro-N-(1-hydroxymethyl-cyclopropylmethoxy)-benzamide
2-(2-Chloro-4-iodo-phenylamino)-3,4-difluoro-N-(2-hydroxymethyl-cyclopropylmethoxy)-benzamide
2-(2-Chloro-4-iodo-phenylamino)-3,4-difluoro-N-(3-hydroxy-1,1-dimethyl-propoxy)-benzamide
2-(2-Chloro-4-iodo-phenylamino)-3,4-difluoro-N-(3-hydroxy-1-methyl-propoxy)-benzamide
2-(2-Chloro-4-iodo-phenylamino)-N-(2,3-dihydroxy-1,1-dimethyl-propoxy)-3,4-difluoro-benzamide
2-(2-Chloro-4-iodo-phenylamino)-3,4,5-trifluoro-N-(2-hydroxy-3-methoxy-propoxy)-benzamide 2-(2-Chloro-4-iodo-phenylamino)-3,4,5-trifluoro-N-(2-hydroxy-pentyloxy)-benzamide
2-(2-Chloro-4-iodo-phenylamino)-3,4,5-trifluoro-N-(3,3,3-trifluoro-2-hydroxy-propoxy)-benzamide
2-(2-Chloro-4-iodo-phenylamino)-3,4,5-trifluoro-N-(2-hydroxy-3-methyl-butoxy)-benzamide
2-(2-Chloro-4-iodo-phenylamino)-3,4,5-trifluoro-N-(2-hydroxy-4-methyl-pentyloxy)-benzamide
2-(2-Chloro-4-iodo-phenylamino)-3,4,5-trifluoro-N-(1-hydroxy-cyclopropylmethoxy)-benzamide
2-(2-Chloro-4-iodo-phenylamino)-3,4,5-trifluoro-N-(1-hydroxy-cyclobutylmethoxy)-benzamide
2-(2-Chloro-4-iodo-phenylamino)-3,4,5-trifluoro-N-(1-hydroxymethyl-propoxy)-benzamide
2-(2-Chloro-4-iodo-phenylamino)-3,4,5-trifluoro-N-(2-hydroxy-1,1-dimethyl-ethoxy)-benzamide
2-(2-Chloro-4-iodo-phenylamino)-3,4,5-trifluoro-N-(1-hydroxymethyl-cyclopropoxy)-benzamide
2-(2-Chloro-4-iodo-phenylamino)-N-(2-ethoxy-ethoxy)-3,4,5-trifluoro-benzamide
2-(2-Chloro-4-iodo-phenylamino)-3,4,5-trifluoro-N-(3-hydroxy-2-methoxy-propoxy)-benzamide
2-(2-Chloro-4-iodo-phenylamino)-3,4,5-trifluoro-N-(3-hydroxy-pentyloxy)-benzamide
2-(2-Chloro-4-iodo-phenylamino)-3,4,5-trifluoro-N-(3-hydroxy-butoxy)-benzamide
2-(2-Chloro-4-iodo-phenylamino)-3,4,5-trifluoro-N-(3-hydroxy-3-methyl-butoxy)-benzamide
2-(2-Chloro-4-iodo-phenylamino)-3,4,5-trifluoro-N-[2-(1-hydroxy-cyclopropyl)-ethoxy]-benzamide
2-(2-Chloro-4-iodo-phenylamino)-3,4,5-trifluoro-N-(1-hydroxymethyl-cyclopropylmethoxy)-benzamide
2-(2-Chloro-4-iodo-phenylamino)-3,4,5-trifluoro-N-(2-hydroxymethyl-cyclopropylmethoxy)-benzamide
2-(2-Chloro-4-iodo-phenylamino)-3,4,5-trifluoro-N-(3-hydroxy-1,1-dimethyl-propoxy)-benzamide
2-(2-Chloro-4-iodo-phenylamino)-3,4,5-trifluoro-N-(3-hydroxy-1-methyl-propoxy)-benzamide
2-(2-Chloro-4-iodo-phenylamino)-N-(2,3-dihydroxy-1,1-dimethyl-propoxy)-3,4,5-trifluoro-benzamide
5-Chloro-2-(2-chloro-4-iodo-phenylamino)-3,4-difluoro-N-(2-hydroxy-3-methoxy-propoxy)-benzamide
5-Chloro-2-(2-chloro-4-iodo-phenylamino)-3,4-difluoro-N-(2-hydroxy-pentyloxy)-benzamide
5-Chloro-2-(2-chloro-4-iodo-phenylamino)-3,4-difluoro-N-(3,3,3-trifluoro-2-hydroxy-propoxy)-benzamide
5-Chloro-2-(2-chloro-4-iodo-phenylamino)-3,4-difluoro-N-(2-hydroxy-3-methyl-butoxy)-benzamide
5-Chloro-2-(2-chloro-4-iodo-phenylamino)-3,4-difluoro-N-(2-hydroxy-4-methyl-pentyloxy)-benzamide
5-Chloro-2-(2-chloro-4-iodo-phenylamino)-3,4-difluoro-N-(1-hydroxy-cyclopropylmethoxy)-benzamide
5-Chloro-2-(2-chloro-4-iodo-phenylamino)-3,4-difluoro-N-(1-hydroxy-cyclobutylmethoxy)-benzamide
5-Chloro-2-(2-chloro-4-iodo-phenylamino)-3,4-difluoro-N-(1-hydroxymethyl-propoxy)-benzamide
5-Chloro-2-(2-chloro-4-iodo-phenylamino)-3,4-difluoro-N-(2-hydroxy-1,1-dimethyl-ethoxy)-benzamide
5-Chloro-2-(2-chloro-4-iodo-phenylamino)-3,4-difluoro-N-(1-hydroxymethyl-cyclopropoxy)-benzamide
5-Chloro-2-(2-chloro-4-iodo-phenylamino)-N-(2-ethoxy-ethoxy)-3,4-difluoro-benzamide
5-Chloro-2-(2-chloro-4-iodo-phenylamino)-3,4-difluoro-N-(3-hydroxy-2-methoxy-propoxy)-benzamide
5-Chloro-2-(2-chloro-4-iodo-phenylamino)-3,4-difluoro-N-(3-hydroxy-pentyloxy)-benzamide
5-Chloro-2-(2-chloro-4-iodo-phenylamino)-3,4-difluoro-N-(3-hydroxy-butoxy)-benzamide
5-Chloro-2-(2-chloro-4-iodo-phenylamino)-3,4-difluoro-N-(3-hydroxy-3-methyl-butoxy)-benzamide
5-Chloro-2-(2-chloro-4-iodo-phenylamino)-3,4-difluoro-N-[2-(1-hydroxy-cyclopropyl)-ethoxy]-benzamide
5-Chloro-2-(2-chloro-4-iodo-phenylamino)-3,4-difluoro-N-(1-hydroxymethyl-cyclopropylmethoxy)-benzamide
5-Chloro-2-(2-chloro-4-iodo-phenylamino)-3,4-difluoro-N-(2-hydroxymethyl-cyclopropylmethoxy)-benzamide
5-Chloro-2-(2-chloro-4-iodo-phenylamino)-3,4-difluoro-N-(3-hydroxy-1,1-dimethyl-propoxy)-benzamide
5-Chloro-2-(2-chloro-4-iodo-phenylamino)-3,4-difluoro-N-(3-hydroxy-1-methyl-propoxy)-benzamide
5-Chloro-2-(2-chloro-4-iodo-phenylamino)-N-(2,3-dihydroxy-1,1-dimethyl-propoxy)-3,4-difluoro-benzamide
5-Bromo-2-(2-chloro-4-iodo-phenylamino)-3,4-difluoro-N-(2-hydroxy-3-methoxy-propoxy)-benzamide
5-Bromo-2-(2-chloro-4-iodo-phenylamino)-3,4-difluoro-N-(2-hydroxy-pentyloxy)-benzamide
5-Bromo-2-(2-chloro-4-iodo-phenylamino)-3,4-difluoro-N-(3,3,3-trifluoro-2-hydroxy-propoxy)-benzamide
5-Bromo-2-(2-chloro-4-iodo-phenylamino)-3,4-difluoro-N-(2-hydroxy-3-methyl-butoxy)-benzamide
5-Bromo-2-(2-chloro-4-iodo-phenylamino)-3,4-difluoro-N-(2-hydroxy-4-methyl-pentyloxy)-benzamide
5-Bromo-2-(2-chloro-4-iodo-phenyl amino)-3,4-difluoro-N-(1-hydroxy-cyclopropylmethoxy)-benzamide
5-Bromo-2-(2-chloro-4-iodo-phenylamino)-3,4-difluoro-N-(1-hydroxy-cyclobutylmethoxy)-benzamide
5-Bromo-2-(2-chloro-4-iodo-phenylamino)-3,4-difluoro-N-(1-hydroxymethyl-propoxy)-benzamide
5-Bromo-2-(2-chloro-4-iodo-phenylamino)-3,4-difluoro-N-(2-hydroxy-1,1-dimethyl-ethoxy)-benzamide
5-Bromo-2-(2-chloro-4-iodo-phenylamino)-3,4-difluoro-N-(1-hydroxymethyl-cyclopropoxy)-benzamide
5-Bromo-2-(2-chloro-4-iodo-phenylamino)-N-(2-ethoxy-ethoxy)-3,4-difluoro-benzamide
5-Bromo-2-(2-chloro-4-iodo-phenylamino)-3,4-difluoro-N-(3-hydroxy-2-methoxy-propoxy)-benzamide
5-Bromo-2-(2-chloro-4-iodo-phenylamino)-3,4-difluoro-N-(3-hydroxy-pentyloxy)-benzamide
5-Bromo-2-(2-chloro-4-iodo-phenylamino)-3,4-difluoro-N-(3-hydroxy-butoxy)-benzamide
5-Bromo-2-(2-chloro-4-iodo-phenylamino)-3,4-difluoro-N-(3-hydroxy-3-methyl-butoxy)-benzamide
5-Bromo-2-(2-chloro-4-iodo-phenylamino)-3,4-difluoro-N-[2-(1-hydroxy-cyclopropyl)-ethoxy]-benzamide
5-Bromo-2-(2-chloro-4-iodo-phenylamino)-3,4-difluoro-N-(1-hydroxymethyl-cyclopropylmethoxy)-benzamide
5-Bromo-2-(2-chloro-4-iodo-phenylamino)-3,4-difluoro-N-(2-hydroxymethyl-cyclopropylmethoxy)-benzamide
5-Bromo-2-(2-chloro-4-iodo-phenylamino)-3,4-difluoro-N-(3-hydroxy-1,1-dimethyl-propoxy)-benzamide
5-Bromo-2-(2-chloro-4-iodo-phenylamino)-3,4-difluoro-N-(3-hydroxy-1-methyl-propoxy)-benzamide
5-Bromo-2-(2-chloro-4-iodo-phenylamino)-N-(2,3-dihydroxy-1,1-dimethyl-propoxy)-3,4-difluoro-benzamide
3,4-Difluoro-N-(2-hydroxy-3-methoxy-propoxy)-2-(4-iodo-2-methyl-phenylamino)-benzamide
3,4-Difluoro-N-(2-hydroxy-pentyloxy)-2-(4-iodo-2-methyl-phenylamino)-benzamide
3,4-Difluoro-2-(4-iodo-2-methyl-phenylamino)-N-(3,3,3-trifluoro-2-hydroxy-propoxy)-benzamide
3,4-Difluoro-N-(2-hydroxy-3-methyl-butoxy)-2-(4-iodo-2-methyl-phenylamino)-benzamide 3,4-Difluoro-N-(2-hydroxy-4-methyl-pentyloxy)-2-(4-iodo-2-methyl-phenylamino)-benzamide
3,4-Difluoro-N-(1-hydroxy-cyclopropylmethoxy)-2-(4-iodo-2-methyl-phenylamino)-benzamide
3,4-Difluoro-N-(1-hydroxy-cyclobutylmethoxy)-2-(4-iodo-2-methyl-phenylamino)-benzamide
3,4-Difluoro-N-(1-hydroxymethyl-propoxy)-2-(4-iodo-2-methyl-phenylamino)-benzamide
3,4-Difluoro-N-(2-hydroxy-1,1-dimethyl-ethoxy)-2-(4-iodo-2-methyl-phenylamino)-benzamide
3,4-Difluoro-N-(1-hydroxymethyl-cyclopropoxy)-2-(4-iodo-2-methyl-phenylamino)-benzamide
N-(2-Ethoxy-ethoxy)-3,4-difluoro-2-(4-iodo-2-methyl-phenylamino)-benzamide
3,4-Difluoro-N-(3-hydroxy-2-methoxy-propoxy)-2-(4-iodo-2-methyl-phenylamino)-benzamide
3,4-Difluoro-N-(3-hydroxy-pentyloxy)-2-(4-iodo-2-methyl-phenylamino)-benzamide
3,4-Difluoro-N-(3-hydroxy-butoxy)-2-(4-iodo-2-methyl-phenylamino)-benzamide
3,4-Difluoro-N-(3-hydroxy-3-methyl-butoxy)-2-(4-iodo-2-methyl-phenylamino)-benzamide
3,4-Difluoro-N-[2-(1-hydroxy-cyclopropyl)-ethoxy]-2-(4-iodo-2-methyl-phenylamino)-benzamide
3,4-Difluoro-N-(1-hydroxymethyl-cyclopropylmethoxy)-2-(4-iodo-2-methyl-phenylamino)-benzamide
3,4-Difluoro-N-(2-hydroxymethyl-cyclopropylmethoxy)-2-(4-iodo-2-methyl-phenylamino)-benzamide
3,4-Difluoro-N-(3-hydroxy-1,1-dimethyl-propoxy)-2-(4-iodo-2-methyl-phenylamino)-benzamide
3,4-Difluoro-N-(3-hydroxy-1-methyl-propoxy)-2-(4-iodo-2-methyl-phenylamino)-benzamide
N-(2,3-Dihydroxy-1,1-dimethyl-propoxy)-3,4-difluoro-2-(4-iodo-2-methyl-phenylamino)-benzamide
3,4,5-Trifluoro-N-(2-hydroxy-3-methoxy-propoxy)-2-(4-iodo-2-methyl-phenylamino)-benzamide
3,4,5-Trifluoro-N-(2-hydroxy-pentyloxy)-2-(4-iodo-2-methyl-phenylamino)-benzamide
3,4,5-Trifluoro-2-(4-iodo-2-methyl-phenylamino)-N-(3,3,3-trifluoro-2-hydroxy-propoxy)-benzamide
3,4,5-Trifluoro-N-(2-hydroxy-3-methyl-butoxy)-2-(4-iodo-2-methyl-phenylamino)-benzamide
3,4,5-Trifluoro-N-(2-hydroxy-4-methyl-pentyloxy)-2-(4-iodo-2-methyl-phenylamino)-benzamide
3,4,5-Trifluoro-N-(1-hydroxy-cyclopropylmethoxy)-2-(4-iodo-2-methyl-phenylamino)-benzamide
3,4,5-Trifluoro-N-(1-hydroxy-cyclobutylmethoxy)-2-(4-iodo-2-methyl-phenylamino)-benzamide
3,4,5-Trifluoro-N-(1-hydroxymethyl-propoxy)-2-(4-iodo-2-methyl-phenylamino)-benzamide
3,4,5-Trifluoro-N-(2-hydroxy-1,1-dimethyl-ethoxy)-2-(4-iodo-2-methyl-phenylamino)-benzamide
3,4,5-Trifluoro-N-(1-hydroxymethyl-cyclopropoxy)-2-(4-iodo-2-methyl-phenylamino)-benzamide
N-(2-Ethoxy-ethoxy)-3,4,5-trifluoro-2-(4-iodo-2-methyl-phenylamino)-benzamide
3,4,5-Trifluoro-N-(3-hydroxy-2-methoxy-propoxy)-2-(4-iodo-2-methyl-phenylamino)-benzamide
3,4,5-Trifluoro-N-(3-hydroxy-pentyloxy)-2-(4-iodo-2-methyl-phenylamino)-benzamide
3,4,5-Trifluoro-N-(3-hydroxy-butoxy)-2-(4-iodo-2-methyl-phenylamino)-benzamide
3,4,5-Trifluoro-N-(3-hydroxy-3-methyl-butoxy)-2-(4-iodo-2-methyl-phenylamino)-benzamide
3,4,5-Trifluoro-N-[2-(1-hydroxy-cyclopropyl)-ethoxy]-2-(4-iodo-2-methyl-phenylamino)-benzamide
3,4,5-Trifluoro-N-(1-hydroxymethyl-cyclopropylmethoxy)-2-(4-iodo-2-methyl-phenylamino)-benzamide
3,4,5-Trifluoro-N-(2-hydroxymethyl-cyclopropylmethoxy)-2-(4-iodo-2-methyl-phenylamino)-benzamide
3,4,5-Trifluoro-N-(3-hydroxy-1,1-dimethyl-propoxy)-2-(4-iodo-2-methyl-phenylamino)-benzamide
3,4,5-Trifluoro-N-(3-hydroxy-1-methyl-propoxy)-2-(4-iodo-2-methyl-phenylamino)-benzamide
N-(2,3-Dihydroxy-1,1-dimethyl-propoxy)-3,4,5-trifluoro-2-(4-iodo-2-methyl-phenylamino)-benzamide
5-Chloro-3,4-difluoro-N-(2-hydroxy-3-methoxy-propoxy)-2-(4-iodo-2-methyl-phenylamino)-benzamide
5-Chloro-3,4-difluoro-N-(2-hydroxy-pentyloxy)-2-(4-iodo-2-methyl-phenylamino)-benzamide
5-Chloro-3,4-difluoro-2-(4-iodo-2-methyl-phenylamino)-N-(3,3,3-trifluoro-2-hydroxy-propoxy)-benzamide
5-Chloro-3,4-difluoro-N-(2-hydroxy-3-methyl-butoxy)-2-(4-iodo-2-methyl-phenylamino)-benzamide
5-Chloro-3,4-difluoro-N-(2-hydroxy-4-methyl-pentyloxy)-2-(4-iodo-2-methyl-phenylamino)-benzamide
5-Chloro-3,4-difluoro-N-(1-hydroxy-cyclopropylmethoxy)-2-(4-iodo-2-methyl-phenylamino)-benzamide
5-Chloro-3,4-difluoro-N-(1-hydroxy-cyclobutylmethoxy)-2-(4-iodo-2-methyl-phenylamino)-benzamide
5-Chloro-3,4-difluoro-N-(1-hydroxymethyl-propoxy)-2-(4-iodo-2-methyl-phenylamino)-benzamide
5-Chloro-3,4-difluoro-N-(2-hydroxy-1,1-dimethyl-ethoxy)-2-(4-iodo-2-methyl-phenylamino)-benzamide
5-Chloro-3,4-difluoro-N-(1-hydroxymethyl-cyclopropoxy)-2-(4-iodo-2-methyl-phenylamino)-benzamide
5-Chloro-N-(2-ethoxy-ethoxy)-3,4-difluoro-2-(4-iodo-2-methyl-phenylamino)-benzamide
5-Chloro-3,4-difluoro-N-(3-hydroxy-2-methoxy-propoxy)-2-(4-iodo-2-methyl-phenylamino)-benzamide
5-Chloro-3,4-difluoro-N-(3-hydroxy-pentyloxy)-2-(4-iodo-2-methyl-phenylamino)-benzamide
5-Chloro-3,4-difluoro-N-(3-hydroxy-butoxy)-2-(4-iodo-2-methyl-phenylamino)-benzamide
5-Chloro-3,4-difluoro-N-(3-hydroxy-3-methyl-butoxy)-2-(4-iodo-2-methyl-phenylamino)-benzamide
5-Chloro-3,4-difluoro-N-[2-(1-hydroxy-cyclopropyl)-ethoxy]-2-(4-iodo-2-methyl-phenylamino)-benzamide
5-Chloro-3,4-difluoro-N-(1-hydroxymethyl-cyclopropylmethoxy)-2-(4-iodo-2-methyl-phenylamino)-benzamide
5-Chloro-3,4-difluoro-N-(2-hydroxymethyl-cyclopropylmethoxy)-2-(4-iodo-2-methyl-phenylamino)-benzamide
5-Chloro-3,4-difluoro-N-(3-hydroxy-1,1-dimethyl-propoxy)-2-(4-iodo-2-methyl-phenylamino)-benzamide
5-Chloro-3,4-difluoro-N-(3-hydroxy-1-methyl-propoxy)-2-(4-iodo-2-methyl-phenylamino)-benzamide
5-Chloro-N-(2,3-dihydroxy-1,1-dimethyl-propoxy)-3,4-difluoro-2-(4-iodo-2-methyl-phenylamino)-benzamide
5-Bromo-3,4-difluoro-N-(2-hydroxy-3-methoxy-propoxy)-2-(4-iodo-2-methyl-phenylamino)-benzamide
5-Bromo-3,4-difluoro-N-(2-hydroxy-pentyloxy)-2-(4-iodo-2-methyl-phenylamino)-benzamide
5-Bromo-3,4-difluoro-2-(4-iodo-2-methyl-phenylamino)-N-(3,3,3-trifluoro-2-hydroxy-propoxy)-benzamide
5-Bromo-3,4-difluoro-N-(2-hydroxy-3-methyl-butoxy)-2-(4-iodo-2-methyl-phenylamino)-benzamide
5-Bromo-3,4-difluoro-N-(2-hydroxy-4-methyl-pentyloxy)-2-(4-iodo-2-methyl-phenylamino)-benzamide
5-Bromo-3,4-difluoro-N-(1-hydroxy-cyclopropylmethoxy)-2-(4-iodo-2-methyl-phenylamino)-benzamide
5-Bromo-3,4-difluoro-N-(1-hydroxy-cyclobutylmethoxy)-2-(4-iodo-2-methyl-phenylamino)-benzamide 5-Bromo-3,4-difluoro-N-(1-hydroxymethyl-propoxy)-2-(4-iodo-2-methyl-phenylamino)-benzamide
5-Bromo-3,4-difluoro-N-(2-hydroxy-1,1-dimethyl-ethoxy)-2-(4-iodo-2-methyl-phenylamino)-benzamide
5-Bromo-3,4-difluoro-N-(1-hydroxymethyl-cyclopropoxy)-2-(4-iodo-2-methyl-phenylamino)-benzamide
5-Bromo-N-(2-ethoxy-ethoxy)-3,4-difluoro-2-(4-iodo-2-methyl-phenylamino)-benzamide
5-Bromo-3,4-difluoro-N-(3-hydroxy-2-methoxy-propoxy)-2-(4-iodo-2-methyl-phenylamino)-benzamide
5-Bromo-3,4-difluoro-N-(3-hydroxy-pentyloxy)-2-(4-iodo-2-methyl-phenylamino)-benzamide
5-Bromo-3,4-difluoro-N-(3-hydroxy-butoxy)-2-(4-iodo-2-methyl-phenylamino)-benzamide
5-Bromo-3,4-difluoro-N-(3-hydroxy-3-methyl-butoxy)-2-(4-iodo-2-methyl-phenylamino)-benzamide
5-Bromo-3,4-difluoro-N-[2-(1-hydroxy-cyclopropyl)-ethoxy]-2-(4-iodo-2-methyl-phenylamino)-benzamide
5-Bromo-3,4-difluoro-N-(1-hydroxymethyl-cyclopropyl-methoxy)-2-(4-iodo-2-methyl-phenylamino)-benzamide
5-Bromo-3,4-difluoro-N-(2-hydroxymethyl-cyclopropyl-methoxy)-2-(4-iodo-2-methyl-phenylamino)-benzamide
5-Bromo-3,4-difluoro-N-(3-hydroxy-1,1-dimethyl-propoxy)-2-(4-iodo-2-methyl-phenylamino)-benzamide
5-Bromo-3,4-difluoro-N-(3-hydroxy-1-methyl-propoxy)-2-(4-iodo-2-methyl-phenylamino)-benzamide
5-Bromo-N-(2,3-dihydroxy-1,1-dimethyl-propoxy)-3,4-difluoro-2-(4-iodo-2-methyl-phenylamino)-benzamide
4-Fluoro-N-(2-hydroxy-3-methoxy-propoxy)-2-(4-iodo-2-methyl-phenylamino)-benzamide
4-Fluoro-N-(2-hydroxy-pentyloxy)-2-(4-iodo-2-methyl-phenylamino)-benzamide
4-Fluoro-2-(4-iodo-2-methyl-phenylamino)-N-(3,3,3-trifluoro-2-hydroxy-propoxy)-benzamide
4-Fluoro-N-(2-hydroxy-3-methyl-butoxy)-2-(4-iodo-2-methyl-phenylamino)-benzamide
4-Fluoro-N-(2-hydroxy-4-methyl-pentyloxy)-2-(4-iodo-2-methyl-phenylamino)-benzamide
4-Fluoro-N-(1-hydroxy-cyclopropylmethoxy)-2-(4-iodo-2-methyl-phenylamino)-benzamide
4-Fluoro-N-(1-hydroxy-cyclobutylmethoxy)-2-(4-iodo-2-methyl-phenylamino)-benzamide
4-Fluoro-N-(1-hydroxymethyl-propoxy)-2-(4-iodo-2-methyl-phenylamino)-benzamide
4-Fluoro-N-(2-hydroxy-1,1-dimethyl-ethoxy)-2-(4-iodo-2-methyl-phenylamino)-benzamide
4-Fluoro-N-(1-hydroxymethyl-cyclopropoxy)-2-(4-iodo-2-methyl-phenylamino)-benzamide
N-(2-Ethoxy-ethoxy)-4-fluoro-2-(4-iodo-2-methyl-phenylamino)-benzamide
4-Fluoro-N-(3-hydroxy-2-methoxy-propoxy)-2-(4-iodo-2-methyl-phenylamino)-benzamide
4-Fluoro-N-(3-hydroxy-pentyloxy)-2-(4-iodo-2-methyl-phenylamino)-benzamide
4-Fluoro-N-(3-hydroxy-butoxy)-2-(4-iodo-2-methyl-phenylamino)-benzamide
4-Fluoro-N-(3-hydroxy-3-methyl-butoxy)-2-(4-iodo-2-methyl-phenylamino)-benzamide
4-Fluoro-N-[2-(1-hydroxy-cyclopropyl)-ethoxy]-2-(4-iodo-2-methyl-phenylamino)-benzamide
4-Fluoro-N-(1-hydroxymethyl-cyclopropylmethoxy)-2-(4-iodo-2-methyl-phenylamino)-benzamide
4-Fluoro-N-(2-hydroxymethyl-cyclopropylmethoxy)-2-(4-iodo-2-methyl-phenylamino)-benzamide
4-Fluoro-N-(3-hydroxy-1,1-dimethyl-propoxy)-2-(4-iodo-2-methyl-phenylamino)-benzamide
4-Fluoro-N-(3-hydroxy-1-methyl-propoxy)-2-(4-iodo-2-methyl-phenylamino)-benzamide
N-(2,3-Dihydroxy-1,1-dimethyl-propoxy)-4-fluoro-2-(4-iodo-2-methyl-phenylamino)-benzamide
2-(2-Chloro-4-iodo-phenylamino)-4-fluoro-N-(2-hydroxy-3-methoxy-propoxy)-benzamide
2-(2-Chloro-4-iodo-phenylamino)-4-fluoro-N-(2-hydroxy-pentyloxy)-benzamide
2-(2-Chloro-4-iodo-phenylamino)-4-fluoro-N-(3,3,3-trifluoro-2-hydroxy-propoxy)-benzamide
2-(2-Chloro-4-iodo-phenylamino)-4-fluoro-N-(2-hydroxy-3-methyl-butoxy)-benzamide
2-(2-Chloro-4-iodo-phenylamino)-4-fluoro-N-(2-hydroxy-4-methyl-pentyloxy)-benzamide
2-(2-Chloro-4-iodo-phenylamino)-4-fluoro-N-(1-hydroxy-cyclopropylmethoxy)-benzamide
2-(2-Chloro-4-iodo-phenylamino)-4-fluoro-N-(1-hydroxy-cyclobutylmethoxy)-benzamide
2-(2-Chloro-4-iodo-phenylamino)-4-fluoro-N-(1-hydroxymethyl-propoxy)-benzamide
2-(2-Chloro-4-iodo-phenylamino)-4-fluoro-N-(2-hydroxy-1,1-dimethyl-ethoxy)-benzamide
2-(2-Chloro-4-iodo-phenylamino)-4-fluoro-N-(1-hydroxymethyl-cyclopropoxy)-benzamide
2-(2-Chloro-4-iodo-phenylamino)-N-(2-ethoxy-ethoxy)-4-fluoro-benzamide
2-(2-Chloro-4-iodo-phenylamino)-4-fluoro-N-(3-hydroxy-2-methoxy-propoxy)-benzamide
2-(2-Chloro-4-iodo-phenylamino)-4-fluoro-N-(3-hydroxy-pentyloxy)-benzamide
2-(2-Chloro-4-iodo-phenylamino)-4-fluoro-N-(3-hydroxy-butoxy)-benzamide
2-(2-Chloro-4-iodo-phenylamino)-4-fluoro-N-(3-hydroxy-3-methyl-butoxy)-benzamide
2-(2-Chloro-4-iodo-phenylamino)-4-fluoro-N-[2-(1-hydroxy-cyclopropyl)-ethoxy]-benzamide
2-(2-Chloro-4-iodo-phenylamino)-4-fluoro-N-(1-hydroxymethyl-cyclopropylmethoxy)-benzamide
2-(2-Chloro-4-iodo-phenylamino)-4-fluoro-N-(2-hydroxymethyl-cyclopropylmethoxy)-benzamide
2-(2-Chloro-4-iodo-phenylamino)-4-fluoro-N-(3-hydroxy-1,1-dimethyl-propoxy)-benzamide
2-(2-Chloro-4-iodo-phenylamino)-4-fluoro-N-(3-hydroxy-1-methyl-propoxy)-benzamide
2-(2-Chloro-4-iodo-phenylamino)-N-(2,3-dihydroxy-1,1-dimethyl-propoxy)-4-fluoro-benzamide
4-Fluoro-2-(2-fluoro-4-iodo-phenylamino)-N-(2-hydroxy-3-methoxy-propoxy)-benzamide
4-Fluoro-2-(2-fluoro-4-iodo-phenylamino)-N-(2-hydroxy-pentyloxy)-benzamide
4-Fluoro-2-(2-fluoro-4-iodo-phenylamino)-N-(3,3,3-trifluoro-2-hydroxy-propoxy)-benzamide
4-Fluoro-2-(2-fluoro-4-iodo-phenylamino)-N-(2-hydroxy-3-methyl-butoxy)-benzamide
4-Fluoro-2-(2-fluoro-4-iodo-phenylamino)-N-(2-hydroxy-4-methyl-pentyloxy)-benzamide
4-Fluoro-2-(2-fluoro-4-iodo-phenylamino)-N-(1-hydroxy-cyclopropylmethoxy)-benzamide
4-Fluoro-2-(2-fluoro-4-iodo-phenylamino)-N-(1-hydroxy-cyclobutylmethoxy)-benzamide
4-Fluoro-2-(2-fluoro-4-iodo-phenylamino)-N-(1-hydroxymethyl-propoxy)-benzamide
4-Fluoro-2-(2-fluoro-4-iodo-phenylamino)-N-(2-hydroxy-1,1-dimethyl-ethoxy)-benzamide
4-Fluoro-2-(2-fluoro-4-iodo-phenylamino)-N-(1-hydroxymethyl-cyclopropoxy)-benzamide N-(2-Ethoxy-ethoxy)-4-fluoro-2-(2-fluoro-4-iodo-phenylamino)-benzamide
4-Fluoro-2-(2-fluoro-4-iodo-phenylamino)-N-(3-hydroxy-2-methoxy-propoxy)-benzamide
4-Fluoro-2-(2-fluoro-4-iodo-phenylamino)-N-(3-hydroxy-pentyloxy)-benzamide
4-Fluoro-2-(2-fluoro-4-iodo-phenylamino)-N-(3-hydroxy-butoxy)-benzamide
4-Fluoro-2-(2-fluoro-4-iodo-phenylamino)-N-(3-hydroxy-3-methyl-butoxy)-benzamide
4-Fluoro-2-(2-fluoro-4-iodo-phenylamino)-N-[2-(1-hydroxy-cyclopropyl)-ethoxy]-benzamide
4-Fluoro-2-(2-fluoro-4-iodo-phenylamino)-N-(1-hydroxymethyl-cyclopropylmethoxy)-benzamide
4-Fluoro-2-(2-fluoro-4-iodo-phenylamino)-N-(2-hydroxymethyl-cyclopropylmethoxy)-benzamide
4-Fluoro-2-(2-fluoro-4-iodo-phenylamino)-N-(3-hydroxy-1,1-dimethyl-propoxy)-benzamide
4-Fluoro-2-(2-fluoro-4-iodo-phenylamino)-N-(3-hydroxy-1-methyl-propoxy)-benzamide
N-(2,3-Dihydroxy-1,1-dimethyl-propoxy)-4-fluoro-2-(2-fluoro-4-iodo-phenylamino)-benzamide
4,5-Difluoro-N-(2-hydroxy-3-methoxy-propoxy)-2-(4-iodo-2-methyl-phenylamino)-benzamide
4,5-Difluoro-N-(2-hydroxy-pentyloxy)-2-(4-iodo-2-methyl-phenylamino)-benzamide
4,5-Difluoro-2-(4-iodo-2-methyl-phenylamino)-N-(3,3,3-trifluoro-2-hydroxy-propoxy)-benzamide
4,5-Difluoro-N-(2-hydroxy-3-methyl-butoxy)-2-(4-iodo-2-methyl-phenylamino)-benzamide
4,5-Difluoro-N-(2-hydroxy-4-methyl-pentyloxy)-2-(4-iodo-2-methyl-phenylamino)-benzamide
4,5-Difluoro-N-(1-hydroxy-cyclopropylmethoxy)-2-(4-iodo-2-methyl-phenylamino)-benzamide
4,5-Difluoro-N-(1-hydroxy-cyclobutylmethoxy)-2-(4-iodo-2-methyl-phenylamino)-benzamide
4,5-Difluoro-N-(1-hydroxymethyl-propoxy)-2-(4-iodo-2-methyl-phenylamino)-benzamide
4,5-Difluoro-N-(2-hydroxy-1,1-dimethyl-ethoxy)-2-(4-iodo-2-methyl-phenylamino)-benzamide
4,5-Difluoro-N-(1-hydroxymethyl-cyclopropoxy)-2-(4-iodo-2-methyl-phenylamino)-benzamide
N-(2-Ethoxy-ethoxy)-4,5-difluoro-2-(4-iodo-2-methyl-phenylamino)-benzamide
4,5-Difluoro-N-(3-hydroxy-2-methoxy-propoxy)-2-(4-iodo-2-methyl-phenylamino)-benzamide
4,5-Difluoro-N-(3-hydroxy-pentyloxy)-2-(4-iodo-2-methyl-phenylamino)-benzamide
4,5-Difluoro-N-(3-hydroxy-butoxy)-2-(4-iodo-2-methyl-phenylamino)-benzamide
4,5-Difluoro-N-(3-hydroxy-3-methyl-butoxy)-2-(4-iodo-2-methyl-phenylamino)-benzamide
4,5-Difluoro-N-[2-(1-hydroxy-cyclopropyl)-ethoxy]-2-(4-iodo-2-methyl-phenylamino)-benzamide
4,5-Difluoro-N-(1-hydroxymethyl-cyclopropylmethoxy)-2-(4-iodo-2-methyl-phenylamino)-benzamide
4,5-Difluoro-N-(2-hydroxymethyl-cyclopropylmethoxy)-2-(4-iodo-2-methyl-phenylamino)-benzamide
4,5-Difluoro-N-(3-hydroxy-1,1-dimethyl-propoxy)-2-(4-iodo-2-methyl-phenylamino)-benzamide
4,5-Difluoro-N-(3-hydroxy-1-methyl-propoxy)-2-(4-iodo-2-methyl-phenylamino)-benzamide
N-(2,3-Dihydroxy-1,1-dimethyl-propoxy)-4,5-difluoro-2-(4-iodo-2-methyl-phenylamino)-benzamide
2-(2-Chloro-4-iodo-phenylamino)-4,5-difluoro-N-(2-hydroxy-3-methoxy-propoxy)-benzamide
2-(2-Chloro-4-iodo-phenylamino)-4,5-difluoro-N-(2-hydroxy-pentyloxy)-benzamide
2-(2-Chloro-4-iodo-phenylamino)-4,5-difluoro-N-(3,3,3-trifluoro-2-hydroxy-propoxy)-benzamide
2-(2-Chloro-4-iodo-phenylamino)-4,5-difluoro-N-(2-hydroxy-3-methyl-butoxy)-benzamide
2-(2-Chloro-4-iodo-phenylamino)-4,5-difluoro-N-(2-hydroxy-4-methyl-pentyloxy)-benzamide
2-(2-Chloro-4-iodo-phenylamino)-4,5-difluoro-N-(1-hydroxy-cyclopropylmethoxy)-benzamide
2-(2-Chloro-4-iodo-phenylamino)-4,5-difluoro-N-(1-hydroxy-cyclobutylmethoxy)-benzamide
2-(2-Chloro-4-iodo-phenylamino)-4,5-difluoro-N-(1-hydroxymethyl-propoxy)-benzamide
2-(2-Chloro-4-iodo-phenylamino)-4,5-difluoro-N-(2-hydroxy-1,1-dimethyl-ethoxy)-benzamide
2-(2-Chloro-4-iodo-phenylamino)-4,5-difluoro-N-(1-hydroxymethyl-cyclopropoxy)-benzamide
2-(2-Chloro-4-iodo-phenylamino)-N-(2-ethoxy-ethoxy)-4,5-difluoro-benzamide
2-(2-Chloro-4-iodo-phenylamino)-4,5-difluoro-N-(3-hydroxy-2-methoxy-propoxy)-benzamide
2-(2-Chloro-4-iodo-phenylamino)-4,5-difluoro-N-(3-hydroxy-pentyloxy)-benzamide
2-(2-Chloro-4-iodo-phenylamino)-4,5-difluoro-N-(3-hydroxy-butoxy)-benzamide
2-(2-Chloro-4-iodo-phenylamino)-4,5-difluoro-N-(3-hydroxy-3-methyl-butoxy)-benzamide
2-(2-Chloro-4-iodo-phenylamino)-4,5-difluoro-N-[2-(1-hydroxy-cyclopropyl)-ethoxy]-benzamide
2-(2-Chloro-4-iodo-phenylamino)-4,5-difluoro-N-(1-hydroxymethyl-cyclopropylmethoxy)-benzamide
2-(2-Chloro-4-iodo-phenylamino)-4,5-difluoro-N-(2-hydroxymethyl-cyclopropylmethoxy)-benzamide
2-(2-Chloro-4-iodo-phenylamino)-4,5-difluoro-N-(3-hydroxy-1,1-dimethyl-propoxy)-benzamide
2-(2-Chloro-4-iodo-phenylamino)-4,5-difluoro-N-(3-hydroxy-1-methyl-propoxy)-benzamide
2-(2-Chloro-4-iodo-phenylamino)-N-(2,3-dihydroxy-1,1-dimethyl-propoxy)-4,5-difluoro-benzamide
4,5-Difluoro-2-(2-fluoro-4-iodo-phenylamino)-N-(2-hydroxy-3-methoxy-propoxy)-benzamide
4,5-Difluoro-2-(2-fluoro-4-iodo-phenylamino)-N-(2-hydroxy-pentyloxy)-benzamide
4,5-Difluoro-2-(2-fluoro-4-iodo-phenylamino)-N-(3,3,3-trifluoro-2-hydroxy-propoxy)-benzamide
4,5-Difluoro-2-(2-fluoro-4-iodo-phenylamino)-N-(2-hydroxy-3-methyl-butoxy)-benzamide
4,5-Difluoro-2-(2-fluoro-4-iodo-phenylamino)-N-(2-hydroxy-4-methyl-pentyloxy)-benzamide
4,5-Difluoro-2-(2-fluoro-4-iodo-phenylamino)-N-(1-hydroxy-cyclopropylmethoxy)-benzamide
4,5-Difluoro-2-(2-fluoro-4-iodo-phenylamino)-N-(1-hydroxy-cyclobutylmethoxy)-benzamide
4,5-Difluoro-2-(2-fluoro-4-iodo-phenylamino)-N-(1-hydroxymethyl-propoxy)-benzamide
4,5-Difluoro-2-(2-fluoro-4-iodo-phenylamino)-N-(2-hydroxy-1,1-dimethyl-ethoxy)-benzamide
4,5-Difluoro-2-(2-fluoro-4-iodo-phenylamino)-N-(1-hydroxymethyl-cyclopropoxy)-benzamide
N-(2-Ethoxy-ethoxy)-4,5-difluoro-2-(2-fluoro-4-iodo-phenylamino)-benzamide
4,5-Difluoro-2-(2-fluoro-4-iodo-phenylamino)-N-(3-hydroxy-2-methoxy-propoxy)-benzamide
4,5-Difluoro-2-(2-fluoro-4-iodo-phenylamino)-N-(3-hydroxy-pentyloxy)-benzamide 4,5-Difluoro-2-(2-fluoro-4-iodo-phenylamino)-N-(3-hydroxy-butoxy)-benzamide
4,5-Difluoro-2-(2-fluoro-4-iodo-phenylamino)-N-(3-hydroxy-3-methyl-butoxy)-benzamide
4,5-Difluoro-2-(2-fluoro-4-iodo-phenylamino)-N-[2-(1-hydroxy-cyclopropyl)-ethoxy]-benzamide
4,5-Difluoro-2-(2-fluoro-4-iodo-phenylamino)-N-(1-hydroxymethyl-cyclopropylmethoxy)-benzamide
4,5-Difluoro-2-(2-fluoro-4-iodo-phenylamino)-N-(2-hydroxymethyl-cyclopropylmethoxy)-benzamide
4,5-Difluoro-2-(2-fluoro-4-iodo-phenylamino)-N-(3-hydroxy-1,1-dimethyl-propoxy)-benzamide
4,5-Difluoro-2-(2-fluoro-4-iodo-phenylamino)-N-(3-hydroxy-1-methyl-propoxy)-benzamide
N-(2,3-Dihydroxy-1,1-dimethyl-propoxy)-4,5-difluoro-2-(2-fluoro-4-iodo-phenylamino)-benzamide
5-Chloro-4-fluoro-N-(2-hydroxy-3-methoxy-propoxy)-2-(4-iodo-2-methyl-phenylamino)-benzamide
5-Chloro-4-fluoro-N-(2-hydroxy-pentyloxy)-2-(4-iodo-2-methyl-phenylamino)-benzamide
5-Chloro-4-fluoro-2-(4-iodo-2-methyl-phenylamino)-N-(3,3,3-trifluoro-2-hydroxy-propoxy)-benzamide
5-Chloro-4-fluoro-N-(2-hydroxy-3-methyl-butoxy)-2-(4-iodo-2-methyl-phenylamino)-benzamide
5-Chloro-4-fluoro-N-(2-hydroxy-4-methyl-pentyloxy)-2-(4-iodo-2-methyl-phenylamino)-benzamide
5-Chloro-4-fluoro-N-(1-hydroxy-cyclopropylmethoxy)-2-(4-iodo-2-methyl-phenylamino)-benzamide
5-Chloro-4-fluoro-N-(1-hydroxy-cyclobutylmethoxy)-2-(4-iodo-2-methyl-phenylamino)-benzamide
5-Chloro-4-fluoro-N-(1-hydroxymethyl-propoxy)-2-(4-iodo-2-methyl-phenylamino)-benzamide
5-Chloro-4-fluoro-N-(2-hydroxy-1,1-dimethyl-ethoxy)-2-(4-iodo-2-methyl-phenylamino)-benzamide
5-Chloro-4-fluoro-N-(1-hydroxymethyl-cyclopropoxy)-2-(4-iodo-2-methyl-phenylamino)-benzamide
5-Chloro-N-(2-ethoxy-ethoxy)-4-fluoro-2-(4-iodo-2-methyl-phenylamino)-benzamide
5-Chloro-4-fluoro-N-(3-hydroxy-2-methoxy-propoxy)-2-(4-iodo-2-methyl-phenylamino)-benzamide
5-Chloro-4-fluoro-N-(3-hydroxy-pentyloxy)-2-(4-iodo-2-methyl-phenylamino)-benzamide
5-Chloro-4-fluoro-N-(3-hydroxy-butoxy)-2-(4-iodo-2-methyl-phenylamino)-benzamide
5-Chloro-4-fluoro-N-(3-hydroxy-3-methyl-butoxy)-2-(4-iodo-2-methyl-phenylamino)-benzamide
5-Chloro-4-fluoro-N-[2-(1-hydroxy-cyclopropyl)-ethoxy]-2-(4-iodo-2-methyl-phenylamino)-benzamide
5-Chloro-4-fluoro-N-(1-hydroxymethyl-cyclopropylmethoxy)-2-(4-iodo-2-methyl-phenylamino)-benzamide
5-Chloro-4-fluoro-N-(2-hydroxymethyl-cyclopropylmethoxy)-2-(4-iodo-2-methyl-phenylamino)-benzamide
5-Chloro-4-fluoro-N-(3-hydroxy-1,1-dimethyl-propoxy)-2-(4-iodo-2-methyl-phenylamino)-benzamide
5-Chloro-4-fluoro-N-(3-hydroxy-1-methyl-propoxy)-2-(4-iodo-2-methyl-phenylamino)-benzamide
5-Chloro-N-(2,3-dihydroxy-1,1-dimethyl-propoxy)-4-fluoro-2-(4-iodo-2-methyl-phenylamino)-benzamide
5-Chloro-2-(2-chloro-4-iodo-phenylamino)-4-fluoro-N-(2-hydroxy-3-methoxy-propoxy)-benzamide
5-Chloro-2-(2-chloro-4-iodo-phenylamino)-4-fluoro-N-(2-hydroxy-pentyloxy)-benzamide
5-Chloro-2-(2-chloro-4-iodo-phenyl amino)-4-fluoro-N-(3,3,33-trifluoro-2-hydroxy-propoxy)-benzamide
5-Chloro-2-(2-chloro-4-iodo-phenylamino)-4-fluoro-N-(2-hydroxy-3-methyl-butoxy)-benzamide
5-Chloro-2-(2-chloro-4-iodo-phenylamino)-4-fluoro-N-(2-hydroxy-4-methyl-pentyloxy)-benzamide
5-Chloro-2-(2-chloro-4-iodo-phenylamino)-4-fluoro-N-(1-hydroxy-cyclopropylmethoxy)-benzamide
5-Chloro-2-(2-chloro-4-iodo-phenylamino)-4-fluoro-N-(1-hydroxy-cyclobutylmethoxy)-benzamide
5-Chloro-2-(2-chloro-4-iodo-phenylamino)-4-fluoro-N-(1-hydroxymethyl-propoxy)-benzamide
5-Chloro-2-(2-chloro-4-iodo-phenylamino)-4-fluoro-N-(2-hydroxy-1,1-dimethyl-ethoxy)-benzamide
5-Chloro-2-(2-chloro-4-iodo-phenylamino)-4-fluoro-N-(1-hydroxymethyl-cyclopropoxy)-benzamide
5-Chloro-2-(2-chloro-4-iodo-phenylamino)-N-(2-ethoxy-ethoxy)-4-fluoro-benzamide
5-Chloro-2-(2-chloro-4-iodo-phenylamino)-4-fluoro-N-(3-hydroxy-2-methoxy-propoxy)-benzamide
5-Chloro-2-(2-chloro-4-iodo-phenylamino)$_4$-fluoro-N-(3-hydroxy-pentyloxy)-benzamide
5-Chloro-2-(2-chloro-4-iodo-phenylamino)-4-fluoro-N-(3-hydroxy-butoxy)-benzamide
5-Chloro-2-(2-chloro-4-iodo-phenylamino)-4-fluoro-N-(3-hydroxy-3-methyl-butoxy)-benzamide
5-Chloro-2-(2-chloro-4-iodo-phenylamino)-4-fluoro-N-[2-(1-hydroxy-cyclopropyl)-ethoxy]-benzamide
5-Chloro-2-(2-chloro-4-iodo-phenylamino)-4-fluoro-N-(1-hydroxymethyl-cyclopropylmethoxy)-benzamide
5-Chloro-2-(2-chloro-4-iodo-phenylamino)-4-fluoro-N-(2-hydroxymethyl-cyclopropylmethoxy)-benzamide
5-Chloro-2-(2-chloro-4-iodo-phenylamino)-4-fluoro-N-(3-hydroxy-1,1-dimethyl-propoxy)-benzamide
5-Chloro-2-(2-chloro-4-iodo-phenylamino)-4-fluoro-N-(3-hydroxy-1-methyl-propoxy)-benzamide
5-Chloro-2-(2-chloro-4-iodo-phenylamino)-N-(2,3-dihydroxy-1,1-dimethyl-propoxy)-4-fluoro-benzamide
5-Chloro-4-fluoro-2-(2-fluoro-4-iodo-phenylamino)-N-(2-hydroxy-3-methoxy-propoxy)-benzamide
5-Chloro-4-fluoro-2-(2-fluoro-4-iodo-phenylamino)-N-(2-hydroxy-pentyloxy)-benzamide
5-Chloro-4-fluoro-2-(2-fluoro-4-iodo-phenylamino)-N-(3,3,3-trifluoro-2-hydroxy-propoxy)-benzamide
5-Chloro-4-fluoro-2-(2-fluoro-4-iodo-phenylamino)-N-(2-hydroxy-3-methyl-butoxy)-benzamide
5-Chloro-4-fluoro-2-(2-fluoro-4-iodo-phenylamino)-N-(2-hydroxy-4-methyl-pentyloxy)-benzamide
5-Chloro-4-fluoro-2-(2-fluoro-4-iodo-phenylamino)-N-(1-hydroxy-cyclopropylmethoxy)-benzamide
5-Chloro-4-fluoro-2-(2-fluoro-4-iodo-phenylamino)-N-(1-hydroxy-cyclobutylmethoxy)-benzamide
5-Chloro-4-fluoro-2-(2-fluoro-4-iodo-phenylamino)-N-(1-hydroxymethyl-propoxy)-benzamide
5-Chloro-4-fluoro-2-(2-fluoro-4-iodo-phenylamino)-N-(2-hydroxy-1,1-dimethyl-ethoxy)-benzamide
5-Chloro-4-fluoro-2-(2-fluoro-4-iodo-phenylamino)-N-(1-hydroxymethyl-cyclopropoxy)-benzamide
5-Chloro-N-(2-ethoxy-ethoxy)$_4$-fluoro-2-(2-fluoro-4-iodo-phenylamino)-benzamide
5-Chloro-4-fluoro-2-(2-fluoro-4-iodo-phenylamino)-N-(3-hydroxy-2-methoxy-propoxy)-benzamide
5-Chloro-4-fluoro-2-(2-fluoro-4-iodo-phenylamino)-N-(3-hydroxy-pentyloxy)-benzamide
5-Chloro-4-fluoro-2-(2-fluoro-4-iodo-phenylamino)-N-(3-hydroxy-butoxy)-benzamide
5-Chloro-4-fluoro-2-(2-fluoro-4-iodo-phenylamino)-N-(3-hydroxy-3-methyl-butoxy)-benzamide
5-Chloro-4-fluoro-2-(2-fluoro-4-iodo-phenylamino)-N-[2-(1-hydroxy-cyclopropyl)-ethoxy]-benzamide 5-Chloro-4-fluoro-2-(2-fluoro-4-iodo-phenylamino)-N-(1-hydroxymethyl-cyclopropylmethoxy)-benzamide
5-Chloro-4-fluoro-2-(2-fluoro-4-iodo-phenylamino)-N-(2-hydroxymethyl-cyclopropylmethoxy)-benzamide
5-Chloro-4-fluoro-2-(2-fluoro-4-iodo-phenylamino)-N-(3-hydroxy-1,1-dimethyl-propoxy)-benzamide
5-Chloro-4-fluoro-2-(2-fluoro-4-iodo-phenylamino)-N-(3-hydroxy-1-methyl-propoxy)-benzamide
5-Chloro-N-(2,3-dihydroxy-1,1-dimethyl-propoxy)-4-fluoro-2-(2-fluoro-4-iodo-phenylamino)-benzamide
5-Bromo-4-fluoro-N-(2-hydroxy-3-methoxy-propoxy)-2-(4-iodo-2-methyl-phenylamino)-benzamide
5-Bromo-4-fluoro-N-(2-hydroxy-pentyloxy)-2-(4-iodo-2-methyl-phenylamino)-benzamide
5-Bromo-4-fluoro-2-(4-iodo-2-methyl-phenylamino)-N-(3,3,3-trifluoro-2-hydroxy-propoxy)-benzamide
5-Bromo-4-fluoro-N-(2-hydroxy-3-methyl-butoxy)-2-(4-iodo-2-methyl-phenylamino)-benzamide
5-Bromo-4-fluoro-N-(2-hydroxy-4-methyl-pentyloxy)-2-(4-iodo-2-methyl-phenylamino)-benzamide
5-Bromo-4-fluoro-N-(1-hydroxy-cyclopropylmethoxy)-2-(4-iodo-2-methyl-phenylamino)-benzamide
5-Bromo-4-fluoro-N-(1-hydroxy-cyclobutylmethoxy)-2-(4-iodo-2-methyl-phenylamino)-benzamide
5-Bromo-4-fluoro-N-(1-hydroxymethyl-propoxy)-2-(4-iodo-2-methyl-phenylamino)-benzamide
5-Bromo-4-fluoro-N-(2-hydroxy-1,1-dimethyl-ethoxy)-2-(4-iodo-2-methyl-phenylamino)-benzamide
5-Bromo-4-fluoro-N-(1-hydroxymethyl-cyclopropoxy)-2-(4-iodo-2-methyl-phenylamino)-benzamide
5-Bromo-N-(2-ethoxy-ethoxy)-4-fluoro-2-(4-iodo-2-methyl-phenylamino)-benzamide
5-Bromo-4-fluoro-N-(3-hydroxy-2-methoxy-propoxy)-2-(4-iodo-2-methyl-phenylamino)-benzamide
5-Bromo-4-fluoro-N-(3-hydroxy-pentyloxy)-2-(4-iodo-2-methyl-phenylamino)-benzamide
5-Bromo-4-fluoro-N-(3-hydroxy-butoxy)-2-(4-iodo-2-methyl-phenylamino)-benzamide
5-Bromo-4-fluoro-N-(3-hydroxy-3-methyl-butoxy)-2-(4-iodo-2-methyl-phenylamino)-benzamide
5-Bromo-4-fluoro-N-[2-(1-hydroxy-cyclopropyl)-ethoxy]-2-(4-iodo-2-methyl-phenylamino)-benzamide
5-Bromo-4-fluoro-N-(1-hydroxymethyl-cyclopropylmethoxy)-2-(4-iodo-2-methyl-phenylamino)-benzamide
5-Bromo-4-fluoro-N-(2-hydroxymethyl-cyclopropylmethoxy)-2-(4-iodo-2-methyl-phenylamino)-benzamide
5-Bromo-4-fluoro-N-(3-hydroxy-1,1-dimethyl-propoxy)-2-(4-iodo-2-methyl-phenylamino)-benzamide
5-Bromo-4-fluoro-N-(3-hydroxy-1-methyl-propoxy)-2-(4-iodo-2-methyl-phenylamino)-benzamide
5-Bromo-N-(2,3-dihydroxy-1,1-dimethyl-propoxy)-4-fluoro-2-(4-iodo-2-methyl-phenylamino)-benzamide
5-Bromo-2-(2-chloro-4-iodo-phenylamino)-4-fluoro-N-(2-hydroxy-3-methoxy-propoxy)-benzamide
5-Bromo-2-(2-chloro-4-iodo-phenylamino)-4-fluoro-N-(2-hydroxy-pentyloxy)-benzamide
5-Bromo-2-(2-chloro-4-iodo-phenylamino)-4-fluoro-N-(3,3,3-trifluoro-2-hydroxy-propoxy)-benzamide
5-Bromo-2-(2-chloro-4-iodo-phenylamino)-4-fluoro-N-(2-hydroxy-3-methyl-butoxy)-benzamide
5-Bromo-2-(2-chloro-4-iodo-phenylamino)-4-fluoro-N-(2-hydroxy-4-methyl-pentyloxy)-benzamide
5-Bromo-2-(2-chloro-4-iodo-phenylamino)-4-fluoro-N-(1-hydroxy-cyclopropylmethoxy)-benzamide
5-Bromo-2-(2-chloro-4-iodo-phenylamino)4-fluoro-N-(1-hydroxy-cyclobutylmethoxy)-benzamide
5-Bromo-2-(2-chloro-4-iodo-phenylamino)-4-fluoro-N-(1-hydroxymethyl-propoxy)-benzamide
5-Bromo-2-(2-chloro-4-iodo-phenylamino)-4-fluoro-N-(2-hydroxy-1,1-dimethyl-ethoxy)-benzamide
5-Bromo-2-(2-chloro-4-iodo-phenylamino)-4-fluoro-N-(1-hydroxymethyl-cyclopropoxy)-benzamide
5-Bromo-2-(2-chloro-4-iodo-phenylamino)-N-(2-ethoxy-ethoxy)-4-fluoro-benzamide
5-Bromo-2-(2-chloro-4-iodo-phenylamino)-4-fluoro-N-(3-hydroxy-2-methoxy-propoxy)-benzamide
5-Bromo-2-(2-chloro-4-iodo-phenylamino)-4-fluoro-N-(3-hydroxy-pentyloxy)-benzamide
5-Bromo-2-(2-chloro-4-iodo-phenylamino)-4-fluoro-N-(3-hydroxy-butoxy)-benzamide
5-Bromo-2-(2-chloro-4-iodo-phenylamino)-4-fluoro-N-(3-hydroxy-3-methyl-butoxy)-benzamide
5-Bromo-2-(2-chloro-4-iodo-phenylamino)-4-fluoro-N-[2-(1-hydroxy-cyclopropyl)-ethoxy]-benzamide
5-Bromo-2-(2-chloro-4-iodo-phenylamino)-4-fluoro-N-(1-hydroxymethyl-cyclopropylmethoxy)-benzamide
5-Bromo-2-(2-chloro-4-iodo-phenyl amino)-4-fluoro-N-(2-hydroxymethyl-cyclopropylmethoxy)-benzamide
5-Bromo-2-(2-chloro-4-iodo-phenylamino)-4-fluoro-N-(3-hydroxy-1,1-dimethyl-propoxy)-benzamide
5-Bromo-2-(2-chloro-4-iodo-phenylamino)-4-fluoro-N-(3-hydroxy-1-methyl-propoxy)-benzamide
5-Bromo-2-(2-chloro-4-iodo-phenylamino)-N-(2,3-dihydroxy-1,1-dimethyl-propoxy)-4-fluoro-benzamide
5-Bromo-4-fluoro-2-(2-fluoro-4-iodo-phenylamino)-N-(2-hydroxy-3-methoxy-propoxy)-benzamide
5-Bromo-4-fluoro-2-(2-fluoro-4-iodo-phenylamino)-N-(2-hydroxy-pentyloxy)-benzamide
5-Bromo-4-fluoro-2-(2-fluoro-4-iodo-phenylamino)-N-(3,3,3-trifluoro-2-hydroxy-propoxy)-benzamide
5-Bromo-4-fluoro-2-(2-fluoro-4-iodo-phenylamino)-N-(2-hydroxy-3-methyl-butoxy)-benzamide
5-Bromo-4-fluoro-2-(2-fluoro-4-iodo-phenylamino)-N-(2-hydroxy-4-methyl-pentyloxy)-benzamide
5-Bromo-4-fluoro-2-(2-fluoro-4-iodo-phenylamino)-N-(1-hydroxy-cyclopropylmethoxy)-benzamide
5-Bromo-4-fluoro-2-(2-fluoro-4-iodo-phenylamino)-N-(1-hydroxy-cyclobutylmethoxy)-benzamide
5-Bromo-4-fluoro-2-(2-fluoro-4-iodo-phenylamino)-N-(1-hydroxymethyl-propoxy)-benzamide
5-Bromo-4-fluoro-2-(2-fluoro-4-iodo-phenylamino)-N-(2-hydroxy-1,1-dimethyl-ethoxy)-benzamide
5-Bromo-4-fluoro-2-(2-fluoro-4-iodo-phenylamino)-N-(1-hydroxymethyl-cyclopropoxy)-benzamide
5-Bromo-N-(2-ethoxy-ethoxy)-4-fluoro-2-(2-fluoro-4-iodo-phenylamino)-benzamide
5-Bromo-4-fluoro-2-(2-fluoro-4-iodo-phenylamino)-N-(3-hydroxy-2-methoxy-propoxy)-benzamide
5-Bromo-4-fluoro-2-(2-fluoro-4-iodo-phenylamino)-N-(3-hydroxy-pentyloxy)-benzamide
5-Bromo-4-fluoro-2-(2-fluoro-4-iodo-phenylamino)-N-(3-hydroxy-butoxy)-benzamide
5-Bromo-4-fluoro-2-(2-fluoro-4-iodo-phenylamino)-N-(3-hydroxy-3-methyl-butoxy)-benzamide
5-Bromo-4-fluoro-2-(2-fluoro-4-iodo-phenylamino)-N-[2-(1-hydroxy-cyclopropyl)-ethoxy]-benzamide
5-Bromo-4-fluoro-2-(2-fluoro-4-iodo-phenylamino)-N-(1-hydroxymethyl-cyclopropylmethoxy)-benzamide
5-Bromo-4-fluoro-2-(2-fluoro-4-iodo-phenylamino)-N-(2-hydroxymethyl-cyclopropylmethoxy)-benzamide
5-Bromo-4-fluoro-2-(2-fluoro-4-iodo-phenylamino)-N-(3-hydroxy-1,1-dimethyl-propoxy)-benzamide 5-Bromo-4-fluoro-2-(2-fluoro-4-iodo-phenylamino)-N-(3-hydroxy-1-methyl-propoxy)-benzamide
5-Bromo-N-(2,3-dihydroxy-1,1-dimethyl-propoxy)-4-fluoro-2-(2-fluoro-4-iodo-phenylamino)-benzamide
3,4-Difluoro-2-(2-fluoro-4-iodo-phenylamino)-N-(2-hydroxy-3-methoxy-propoxy)-benzamide
3,4-Difluoro-2-(2-fluoro-4-iodo-phenylamino)-N-(2-hydroxy-pentyloxy)-benzamide
3,4-Difluoro-2-(2-fluoro-4-iodo-phenylamino)-N-(3,3,3-trifluoro-2-hydroxy-propoxy)-benzamide
3,4-Difluoro-2-(2-fluoro-4-iodo-phenylamino)-N-(2-hydroxy-3-methyl-butoxy)-benzamide
3,4-Difluoro-2-(2-fluoro-4-iodo-phenylamino)-N-(2-hydroxy-4-methyl-pentyloxy)-benzamide
3,4-Difluoro-2-(2-fluoro-4-iodo-phenylamino)-N-(1-hydroxy-cyclopropylmethoxy)-benzamide
3,4-Difluoro-2-(2-fluoro-4-iodo-phenylamino)-N-(1-hydroxy-cyclobutylmethoxy)-benzamide
3,4-Difluoro-2-(2-fluoro-4-iodo-phenylamino)-N-(1-hydroxymethyl-propoxy)-benzamide
3,4-Difluoro-2-(2-fluoro-4-iodo-phenylamino)-N-(2-hydroxy-1,1-dimethyl-ethoxy)-benzamide
3,4-Difluoro-2-(2-fluoro-4-iodo-phenylamino)-N-(1-hydroxymethyl-cyclopropoxy)-benzamide
N-(2-Ethoxy-ethoxy)-3,4-difluoro-2-(2-fluoro-4-iodo-phenylamino)-benzamide
3,4-Difluoro-2-(2-fluoro-4-iodo-phenylamino)-N-(3-hydroxy-2-methoxy-propoxy)-benzamide
3,4-Difluoro-2-(2-fluoro-4-iodo-phenylamino)-N-(3-hydroxy-pentyloxy)-benzamide
3,4-Difluoro-2-(2-fluoro-4-iodo-phenylamino)-N-(3-hydroxy-butoxy)-benzamide
3,4-Difluoro-2-(2-fluoro-4-iodo-phenylamino)-N-(3-hydroxy-3-methyl-butoxy)-benzamide
3,4-Difluoro-2-(2-fluoro-4-iodo-phenylamino)-N-[2-(1-hydroxy-cyclopropyl)-ethoxy]-benzamide
3,4-Difluoro-2-(2-fluoro-4-iodo-phenylamino)-N-(1-hydroxymethyl-cyclopropylmethoxy)-benzamide
3,4-Difluoro-2-(2-fluoro-4-iodo-phenylamino)-N-(2-hydroxymethyl-cyclopropylmethoxy)-benzamide
3,4-Difluoro-2-(2-fluoro-4-iodo-phenylamino)-N-(3-hydroxy-1,1-dimethyl-propoxy)-benzamide
3,4-Difluoro-2-(2-fluoro-4-iodo-phenylamino)-N-(3-hydroxy-1-methyl-propoxy)-benzamide
N-(2,3-Dihydroxy-1,1-dimethyl-propoxy)-3,4-difluoro-2-(2-fluoro-4-iodo-phenylamino)-benzamide
3,4,5-Trifluoro-2-(2-fluoro-4-iodo-phenylamino)-N-(2-hydroxy-3-methoxy-propoxy)-benzamide
3,4,5-Trifluoro-2-(2-fluoro-4-iodo-phenylamino)-N-(2-hydroxy-pentyloxy)-benzamide
3,4,5-Trifluoro-2-(2-fluoro-4-iodo-phenylamino)-N-(3,3,3-trifluoro-2-hydroxy-propoxy)-benzamide
3,4,5-Trifluoro-2-(2-fluoro-4-iodo-phenylamino)-N-(2-hydroxy-3-methyl-butoxy)-benzamide
3,4,5-Trifluoro-2-(2-fluoro-4-iodo-phenylamino)-N-(2-hydroxy-4-methyl-pentyloxy)-benzamide
3,4,5-Trifluoro-2-(2-fluoro-4-iodo-phenylamino)-N-(1-hydroxy-cyclopropylmethoxy)-benzamide
3,4,5-Trifluoro-2-(2-fluoro-4-iodo-phenylamino)-N-(1-hydroxy-cyclobutylmethoxy)-benzamide
3,4,5-Trifluoro-2-(2-fluoro-4-iodo-phenylamino)-N-(1-hydroxymethyl-propoxy)-benzamide
3,4,5-Trifluoro-2-(2-fluoro-4-iodo-phenylamino)-N-(2-hydroxy-1,1-dimethyl-ethoxy)-benzamide
3,4,5-Trifluoro-2-(2-fluoro-4-iodo-phenylamino)-N-(1-hydroxymethyl-cyclopropoxy)-benzamide
N-(2-Ethoxy-ethoxy)-3,4,5-trifluoro-2-(2-fluoro-4-iodo-phenylamino)-benzamide
3,4,5-Trifluoro-2-(2-fluoro-4-iodo-phenylamino)-N-(3-hydroxy-2-methoxy-propoxy)-benzamide
3,4,5-Trifluoro-2-(2-fluoro-4-iodo-phenylamino)-N-(3-hydroxy-pentyloxy)-benzamide
3,4,5-Trifluoro-2-(2-fluoro-4-iodo-phenylamino)-N-(3-hydroxy-butoxy)-benzamide
3,4,5-Trifluoro-2-(2-fluoro-4-iodo-phenylamino)-N-(3-hydroxy-3-methyl-butoxy)-benzamide
3,4,5-Trifluoro-2-(2-fluoro-4-iodo-phenylamino)-N-[2-(1-hydroxy-cyclopropyl)-ethoxy]-benzamide
3,4,5-Trifluoro-2-(2-fluoro-4-iodo-phenylamino)-N-(1-hydroxymethyl-cyclopropylmethoxy)-benzamide
3,4,5-Trifluoro-2-(2-fluoro-4-iodo-phenylamino)-N-(2-hydroxymethyl-cyclopropylmethoxy)-benzamide
3,4,5-Trifluoro-2-(2-fluoro-4-iodo-phenylamino)-N-(3-hydroxy-1,1-dimethyl-propoxy)-benzamide
3,4,5-Trifluoro-2-(2-fluoro-4-iodo-phenylamino)-N-(3-hydroxy-1-methyl-propoxy)-benzamide
N-(2,3-Dihydroxy-1,1-dimethyl-propoxy)-3,4,5-trifluoro-2-(2-fluoro-4-iodo-phenylamino)-benzamide
5-Chloro-3,4-difluoro-2-(2-fluoro-4-iodo-phenylamino)-N-(2-hydroxy-3-methoxy-propoxy)-benzamide
5-Chloro-3,4-difluoro-2-(2-fluoro-4-iodo-phenylamino)-N-(2-hydroxy-pentyloxy)-benzamide
5-Chloro-3,4-difluoro-2-(2-fluoro-4-iodo-phenylamino)-N-(3,3,3-trifluoro-2-hydroxy-propoxy)-benzamide
5-Chloro-3,4-difluoro-2-(2-fluoro-4-iodo-phenylamino)-N-(2-hydroxy-3-methyl-butoxy)-benzamide
5-Chloro-3,4-difluoro-2-(2-fluoro-4-iodo-phenylamino)-N-(2-hydroxy-4-methyl-pentyloxy)-benzamide
5-Chloro-3,4-difluoro-2-(2-fluoro-4-iodo-phenylamino)-N-(1-hydroxy-cyclopropylmethoxy)-benzamide
5-Chloro-3,4-difluoro-2-(2-fluoro-4-iodo-phenylamino)-N-(1-hydroxy-cyclobutylmethoxy)-benzamide
5-Chloro-3,4-difluoro-2-(2-fluoro-4-iodo-phenylamino)-N-(1-hydroxymethyl-propoxy)-benzamide
5-Chloro-3,4-difluoro-2-(2-fluoro-4-iodo-phenylamino)-N-(2-hydroxy-1,1-dimethyl-ethoxy)-benzamide
5-Chloro-3,4-difluoro-2-(2-fluoro-4-iodo-phenylamino)-N-(1-hydroxymethyl-cyclopropoxy)-benzamide
5-Chloro-N-(2-ethoxy-ethoxy)-3,4-difluoro-2-(2-fluoro-4-iodo-phenylamino)-benzamide
5-Chloro-3,4-difluoro-2-(2-fluoro-4-iodo-phenylamino)-N-(3-hydroxy-2-methoxy-propoxy)-benzamide
5-Chloro-3,4-difluoro-2-(2-fluoro-4-iodo-phenylamino)-N-(3-hydroxy-pentyloxy)-benzamide
5-Chloro-3,4-difluoro-2-(2-fluoro-4-iodo-phenylamino)-N-(3-hydroxy-butoxy)-benzamide
5-Chloro-3,4-difluoro-2-(2-fluoro-4-iodo-phenylamino)-N-(3-hydroxy-3-methyl-butoxy)-benzamide
5-Chloro-3,4-difluoro-2-(2-fluoro-4-iodo-phenylamino)-N-[2-(1-hydroxy-cyclopropyl)-ethoxy]-benzamide
5-Chloro-3,4-difluoro-2-(2-fluoro-4-iodo-phenylamino)-N-(1-hydroxymethyl-cyclopropylmethoxy)-benzamide
5-Chloro-3,4-difluoro-2-(2-fluoro-4-iodo-phenylamino)-N-(2-hydroxymethyl-cyclopropylmethoxy)-benzamide
5-Chloro-3,4-difluoro-2-(2-fluoro-4-iodo-phenylamino)-N-(3-hydroxy-1,1-dimethyl-propoxy)-benzamide
5-Chloro-3,4-difluoro-2-(2-fluoro-4-iodo-phenylamino)-N-(3-hydroxy-1-methyl-propoxy)-benzamide
5-Chloro-N-(2,3-dihydroxy-1,1-dimethyl-propoxy)-3,4-difluoro-2-(2-fluoro-4-iodo-phenylamino)-benzamide
5-Bromo-3,4-difluoro-2-(2-fluoro-4-iodo-phenylamino)-N-(2-hydroxy-3-methoxy-propoxy)-benzamide 5-Bromo-3,4-difluoro-2-(2-fluoro-4-iodo-phenylamino)-N-(2-hydroxy-pentyloxy)-benzamide 5-Bromo-3,4-difluoro-2-(2-fluoro-4-iodo-phenylamino)-N-(3,3,3-trifluoro-2-hydroxy-propoxy)-benzamide 5-Bromo-3,4-difluoro-2-(2-fluoro-4-iodo-phenylamino)-N-(2-hydroxy-3-methyl-butoxy)-benzamide 5-Bromo-3,4-difluoro-2-(2-fluoro-4-iodo-phenylamino)-N-(2-hydroxy-4-methyl-pentyloxy)-benzamide 5-Bromo-3,4-difluoro-2-(2-fluoro-4-iodo-phenylamino)-N-(1-hydroxy-cyclopropylmethoxy)-benzamide 5-Bromo-3,4-difluoro-2-(2-fluoro-4-iodo-phenylamino)-N-(1-hydroxy-cyclobutylmethoxy)-benzamide 5-Bromo-3,4-difluoro-2-(2-fluoro-4-iodo-phenylamino)-N-(1-hydroxymethyl-propoxy)-benzamide 5-Bromo-3,4-difluoro-2-(2-fluoro-4-iodo-phenylamino)-N-(2-hydroxy-1,1-dimethyl-ethoxy)-benzamide 5-Bromo-3,4-difluoro-2-(2-fluoro-4-iodo-phenylamino)-N-(1-hydroxymethyl-cyclopropoxy)-benzamide 5-Bromo-N-(2-ethoxy-ethoxy)-3,4-difluoro-2-(2-fluoro-4-iodo-phenylamino)-benzamide 5-Bromo-3,4-difluoro-2-(2-fluoro-4-iodo-phenylamino)-N-(3-hydroxy-2-methoxy-propoxy)-benzamide 5-Bromo-3,4-difluoro-2-(2-fluoro-4-iodo-phenylamino)-N-(3-hydroxy-pentyloxy)-benzamide 5-Bromo-3,4-difluoro-2-(2-fluoro-4-iodo-phenylamino)-N-(3-hydroxy-butoxy)-benzamide 5-Bromo-3,4-difluoro-2-(2-fluoro-4-iodo-phenylamino)-N-(3-hydroxy-3-methyl-butoxy)-benzamide 5-Bromo-3,4-difluoro-2-(2-fluoro-4-iodo-phenylamino)-N-[2-(1-hydroxy-cyclopropyl)-ethoxy]-benzamide 5-Bromo-3,4-difluoro-2-(2-fluoro-4-iodo-phenylamino)-N-(1-hydroxymethyl-cyclopropylmethoxy)-benzamide 5-Bromo-3,4-difluoro-2-(2-fluoro-4-iodo-phenylamino)-N-(2-hydroxymethyl-cyclopropylmethoxy)-benzamide 5-Bromo-3,4-difluoro-2-(2-fluoro-4-iodo-phenylamino)-N-(3-hydroxy-1,1-dimethyl-propoxy)-benzamide 5-Bromo-3,4-difluoro-2-(2-fluoro-4-iodo-phenylamino)-N-(3-hydroxy-1-methyl-propoxy)-benzamide, and 5-Bromo-N-(2,3-dihydroxy-1,1-dimethyl-propoxy)-3,4-difluoro-2-(2-fluoro-4-iodo-phenylamino)-benzamide.

Preferred compounds are those of formula I wherein $R_1$ is hydrogen or halogen; and more preferably, hydrogen, F, Br, or Cl; and most preferably, hydrogen; $R_2$ and $R_3$ are fluoro; $R_4$ is hydrogen, iodine, bromine, chlorine, or fluorine; and more preferably hydrogen, iodine, chlorine, or fluorine; and most preferably is iodo; $R_5$ is fluoro, chloro, or methyl; more preferably is fluoro or chloro; and most preferably is fluoro; n is 1 or 2; or combinations thereof. Preferred compounds are selective MEK inhibitors. The most preferred compounds within are those wherein $R_6$, $R_7$, $R_8$, $R_9$, $R_{10}$, and $R_{11}$ are hydrogen, W is oxygen, and n is 1 or 2 and also those wherein, $R_6$, $R_7$, $R_9$, $R_{10}$, and $R_{11}$ are hydrogen, W is oxygen, n is 2, and $R_8(1)$ is hydrogen and $R_8(2)$ is hydroxy. Such compounds have the formulae II and III.

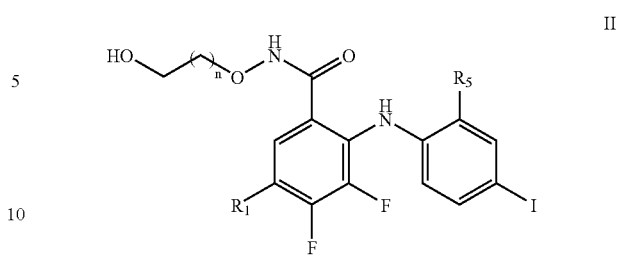

wherein
$R_1$ is hydrogen or halogen;
$R_5$ is fluorine, chlorine, or methyl; and
n is 1 or 2.

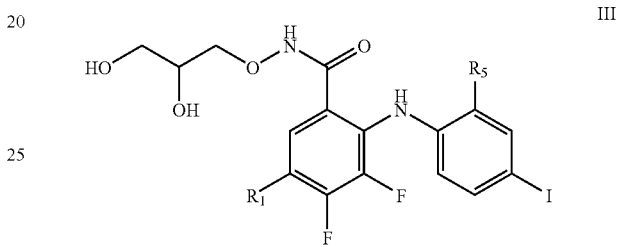

wherein
$R_1$ is hydrogen or halogen; and
$R_5$ is fluorine, chlorine, or methyl.

Other most preferred compounds are those of formula I wherein $R_1$ is hydrogen or halo such as F, Br, or Cl; $R_2$ and $R_3$ are fluoro; $R_4$ is iodo; $R_5$ is fluoro, chloro, or methyl; n is 1; $R_6$, $R_7$, $R_8$, $R_9$, and $R_{10}$ are hydrogen, W is NRa and Ra is H: $R_{11}$ is methyl or phenyl; and pharaceutically accepted salts thereof. These compounds have formulae IV and V.

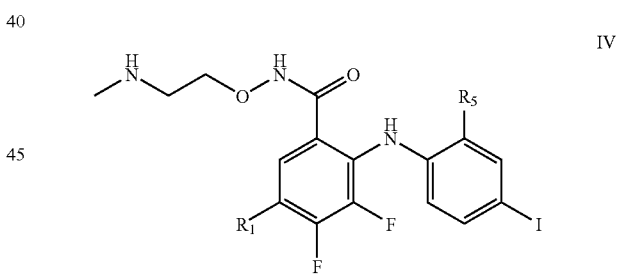

wherein
$R_1$ is hydrogen or halogen; and
$R_5$ is fluorine, chlorine, or methyl.

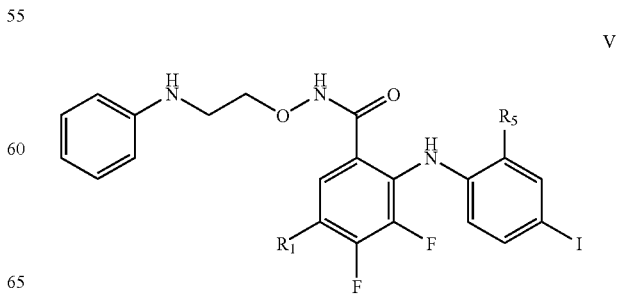

wherein

R₁ is hydrogen or halogen; and

R₅ is fluorine, chlorine, or methyl.

Preferred compounds of the present invention include, but are not limited to the following compounds:

5-Chloro-2-(2-chloro-4-iodo-phenylamino)-N-(2,3-dihydroxy-propoxy)-3,4-difluoro-benzamide;

3,4-Difluoro-2-(2-fluoro-4-iodo-phenylamino)-N-(2-hydroxy-ethoxy)-benzamide;

N-(2,3-Dihydroxy-propoxy)-3,4-difluoro-2-(2-fluoro-4-iodo-phenylamino)-benzamide;

5-Chloro-N-(2,3-dihydroxy-propoxy)-3,4-difluoro-2-(2-fluoro-4-iodo-phenylamino)-benzamide;

5-Chloro-N-((R)-2,3-dihydroxy-propoxy)-3,4-difluoro-2-(2-fluoro-4-iodo-phenylamino)-benzamide;

3,4-Difluoro-2-(2-fluoro-4-iodo-phenylamino)-N-(2-methylamino-ethoxy)-benzamide; hydrochloride;

N-((R)-2,3-Dihydroxy-propoxy)-3,4-difluoro-2-(2-fluoro-4-iodo-phenylamino)-benzamide;

N-((S)-2,3-Dihydroxy-propoxy)-3,4-difluoro-2-(2-fluoro-4-iodo-phenylamino)-benzamide;

5-Chloro-2-(2-chloro-4-iodo-phenylamino)-N-((S)-2,3-dihydroxy-propoxy)-3,4-difluoro-benzamide;

5-Chloro-2-(2-chloro-4-iodo-phenylamino)-N-((R)-2,3-dihydroxy-propoxy)-3,4-difluoro-benzamide;

5-Chloro-N-((S) 2,3-dihydroxy-propoxy)-3,4-difluoro-2-(2-fluoro-4-iodo-phenylamino)-benzamide;

3,4-Difluoro-2-(2-fluoro-4-iodo-phenylamino)-N-(2-hydroxy-1-hydroxymethyl-ethoxy)-benzamide; and 5-Chloro-3,4-difluoro-2-(2-fluoro-4-iodo-phenylamino)-N-(2-hydroxy-1-hydroxymethyl-ethoxy)-benzamide.

In another aspect, the present invention provides Crystalline Form I and Form II of N-(2,3-Dihydroxy-propoxy)-3,4-difluoro-2-(2-fluoro-4-iodo-phenylamino)-benzamide (hereinafter referred to as "Form I of Compound A" and "Form II of Compound A", respectively) or hydrates thereof, Crystalline Form I and Form II of N-[(R)-2,3-Dihydroxy-propoxy]-3,4-difluoro-2-(2-fluoro-4-iodo-phenylamino)-benzamide (hereinafter referred to as "Form I of Compound B" and "Form II of Compound B", respectively) or hydrates thereof, and Crystalline Form I and Form II of N-[(S)-2,3-Dihydroxy-propoxy]-3,4-difluoro-2-(2-fluoro-4-iodo-phenylamino)-benzamide (hereinafter referred to as "Form I of Compound C" and "Form II of Compound C", respectively) or hydrates thereof.

The present invention also provides Crystalline Form I and Form II of Compound A or hydrates thereof, Crystalline Form I and Form II of Compound B or hydrates thereof, and Crystalline Form I or Form II of Compound C or hydrates thereof (hereinafter referred to collectively as "crystal forms" or "crystal forms" of the present invention, unless specified otherwise) which are useful as pharmaceutical agents, to methods for their production and isolation, to pharmaceutical compositions which include these compounds and a pharmaceutically acceptable carrier, and to pharmaceutical methods of treatment. The novel crystalline compounds of the present invention are useful as inhibitors of MEK.

The crystal forms provided by the present invention may be characterized by their X-ray powder diffraction patterns.

Crystalline Form I and Form II of Compound A, Crystalline Form I and Form II of Compound B, and Crystalline Form I and Form II of Compound C were characterized by their X-ray powder diffraction pattern. Thus, the X-ray diffraction patterns of the crystal forms of the present invention were measured on a Rigaku Ultima+diffractometer with CuK$_\alpha$ radiation.

Equipment

Rigaku Ultima+Diffractometer with an IBM-compatible interface equipped with 6 position autosampler, software=RigMeas v2.0 (Rigaku, December 1995) and JADE 3.1 (Materials Data, Inc.).

CuK$_\alpha$ radiation (40 mA, 40 kV, k=1.5419 Å). Slits I and II at 0.50, slit III at 0.30.

Methodology

The silicon standard is run once a week to check the X-ray tube alignment.

Continuous θ/2θ coupled scan: 3.00° to 50.00° in 2θ, scan rate of 1°/min: 1.0 sec/0.04° step.

Sample tapped out of vial and pressed onto zero-background silicon in aluminum holder. Sample width 5 mm.

Samples are stored and run at room temperature.

Samples are being spun at 40 rpm around vertical axis during data collection.

Table 1 lists the X-ray powder diffraction pattern for crystalline Form I of Compound A, expressed in terms of the 2-theta ("2θ"), d-spacings or d(A), and relative intensities by peak area with a relative intensity of >10% measured on a Rigaku Ultima+diffractometer with CuK$_\alpha$ radiation. It should be noted that the computer-generated, unrounded numbers are listed in Table 1.

TABLE 1

| 2-Theta | d(A) | Relative Intensity (>10%) |
|---------|---------|------|
| 7.078   | 12.4779 | 15.2 |
| 14.123  | 6.2659  | 15.4 |
| 15.280  | 5.7939  | 58.7 |
| 15.836  | 5.5917  | 31.4 |
| 16.880  | 5.2481  | 42.2 |
| 18.082  | 4.9019  | 41.4 |
| 19.162  | 4.6280  | 67.4 |
| 20.279  | 4.3754  | 21.1 |
| 21.360  | 4.1565  | 73.6 |
| 22.325  | 3.9789  | 14.4 |
| 23.400  | 3.7984  | 79.3 |
| 24.522  | 3.6271  | 11.0 |
| 25.480  | 3.4929  | 24.6 |
| 26.159  | 3.4037  | 100.0 |
| 26.801  | 3.3237  | 48.9 |
| 27.842  | 3.2017  | 22.8 |
| 28.280  | 3.1531  | 45.4 |
| 29.475  | 3.0280  | 16.0 |
| 32.118  | 2.7845  | 19.7 |
| 33.248  | 2.6924  | 10.6 |
| 33.645  | 2.6615  | 16.3 |
| 40.008  | 2.2517  | 10.6 |
| 42.885  | 2.1071  | 12.1 |
| 44.095  | 2.0520  | 12.8 |

Table 2 lists the X-ray powder diffraction pattern for crystalline Form II of Compound A, expressed in terms of the 2-theta ("2θ"), d-spacings or d(A), and relative intensities by peak area with a relative intensity of >10% measured on a Rigaku Ultima+diffractometer with CuK$_\alpha$ radiation. It should be noted that the computer-generated, unrounded numbers are listed in Table 2.

TABLE 2

| 2-Theta | d(A) | Relative Intensity (>10%) |
|---------|--------|--------|
| 11.582  | 7.6344 | 11.2 * |
| 12.598  | 7.0205 | 13.0 * |
| 15.622  | 5.6678 | 17.1 |
| 17.302  | 5.1211 | 29.3 |

TABLE 2-continued

| 2-Theta | d(A) | Relative Intensity (>10%) |
|---|---|---|
| 17.886 | 4.9551 | 13.3 |
| 20.345 | 4.3614 | 49.8 |
| 21.140 | 4.1991 | 31.0 |
| 22.137 | 4.0123 | 81.7 |
| 24.855 | 3.5793 | 100.0 * |
| 25.885 | 3.4391 | 15.1 |
| 26.699 | 3.3362 | 23.3 |
| 27.842 | 3.2018 | 23.7 |
| 30.059 | 2.9704 | 11.8 |
| 30.948 | 2.8871 | 33.4 |
| 33.799 | 2.6498 | 24.8 |
| 35.399 | 2.5336 | 16.2 |
| 38.242 | 2.3516 | 33.9 |
| 39.282 | 2.2916 | 11.3 |
| 40.755 | 2.2122 | 12.6 |
| 41.641 | 2.1671 | 11.7 |
| 43.570 | 2.0756 | 24.5 |
| 46.958 | 1.9334 | 19.5 |

Table 3 lists the X-ray powder diffraction pattern for crystalline Form I of Compound B, expressed in terms of the 2-theta ("2θ"), d-spacings or d(A), and relative intensities by peak area with a relative intensity of >10% measured on a Rigaku Ultima+diffractometer with CuK$_\alpha$ radiation. It should be noted that the computer-generated, unrounded numbers are listed in Table 3.

TABLE 3

| 2-Theta | d(A) | Relative Intensity (>10%) |
|---|---|---|
| 10.560 | 8.3702 | 14.9 * |
| 13.720 | 6.4488 | 10.3 * |
| 14.619 | 6.0543 | 13.9 |
| 17.258 | 5.1340 | 12.4 |
| 17.958 | 4.9354 | 44.5 |
| 18.219 | 4.8654 | 15.8 |
| 18.998 | 4.6675 | 38.1 * |
| 19.258 | 4.6052 | 12.3 |
| 20.142 | 4.4050 | 17.7 |
| 21.002 | 4.2264 | 18.5 |
| 21.940 | 4.0479 | 53.2 |
| 22.360 | 3.9727 | 19.3 |
| 23.680 | 3.7541 | 100.0 * |
| 24.043 | 3.6983 | 16.9 |
| 24.919 | 3.5702 | 67.3 |
| 26.278 | 3.3886 | 20.1 |
| 27.603 | 3.2289 | 40.6 |
| 28.024 | 3.1813 | 30.7 |
| 30.100 | 2.9665 | 14.6 |
| 32.142 | 2.7825 | 15.8 |
| 32.298 | 2.7694 | 14.6 |
| 32.938 | 2.7171 | 14.7 |
| 35.841 | 2.5034 | 16.3 |
| 37.660 | 2.3865 | 15.6 |

Table 4 lists the X-ray powder diffraction pattern for crystalline Form H of Compound B, expressed in terms of the 2-theta ("2θ"), d-spacings or d(A), and relative intensities by peak area with a relative intensity of >10% measured on a Rigaku Ultima+diffractometer with CuK$_\alpha$ radiation. It should be noted that the computer-generated, unrounded numbers are listed in Table 4.

TABLE 4

| 2-Theta | d(A) | Relative Intensity (>10%) |
|---|---|---|
| 5.482 | 16.1076 | 39.6 * |
| 10.721 | 8.2453 | 20.3 |
| 16.478 | 5.3751 | 21.9 |
| 19.563 | 4.5340 | 73.2 * |
| 22.019 | 4.0334 | 100.0 |
| 22.478 | 3.9521 | 16.1 |
| 23.621 | 3.7634 | 11.1 |
| 24.100 | 3.6896 | 31.9 |
| 24.959 | 3.5647 | 98.2 |
| 26.181 | 3.4010 | 15.1 |
| 27.621 | 3.2269 | 31.7 |
| 29.081 | 3.0681 | 17.7 |
| 30.476 | 2.9307 | 11.4 |
| 31.698 | 2.8204 | 38.9 |
| 33.263 | 2.6913 | 19.4 |
| 39.020 | 2.3064 | 10.2 |

Table 5 lists the X-ray powder diffraction pattern for crystalline Form I of Compound C, expressed in terms of the 2-theta ("2θ"), d-spacings or d(A), and relative intensities by peak area with a relative intensity of >10% measured on a Rigaku Ultima+diffractometer with CuK$_\alpha$ radiation. It should be noted that the computer-generated, unrounded numbers are listed in Table 5.

TABLE 5

| 2-Theta | d(A) | Relative Intensity (>10%) |
|---|---|---|
| 10.548 | 8.3798 | 14.6 * |
| 13.703 | 6.4568 | 11.3 * |
| 17.887 | 4.9549 | 19.9 |
| 18.958 | 4.6772 | 27.3 * |
| 20.122 | 4.4093 | 10.9 |
| 21.950 | 4.0460 | 58.3 |
| 22.321 | 3.9796 | 13.4 |
| 23.640 | 3.7604 | 100.0 * |
| 24.803 | 3.5867 | 66.6 |
| 26.244 | 3.3929 | 12.1 |
| 27.570 | 3.2327 | 21.6 |
| 28.000 | 3.1840 | 31.9 |
| 29.566 | 3.0189 | 23.1 |
| 32.234 | 2.7748 | 18.3 |
| 32.769 | 2.7307 | 16.4 |
| 35.804 | 2.5059 | 13.8 |
| 37.641 | 2.3877 | 16.8 |
| 41.402 | 2.1791 | 14.4 |
| 41.956 | 2.1516 | 10.0 |
| 44.600 | 2.0300 | 13.9 |

Table 6 lists the X-ray powder diffraction pattern for crystalline Form II of Compound C, expressed in terms of the 2-theta ("2θ"), d-spacings or d(A), and relative intensities by peak area with a relative intensity of >10% measured on a Rigaku Ultima+diffractometer with CuK$_\alpha$ radiation. It should be noted that the computer-generated, unrounded numbers are listed in Table 6.

TABLE 6

| 2-Theta | d(A) | Relative Intensity (>10%) |
|---|---|---|
| 5.550 | 15.91107 | 21.8 * |
| 10.763 | 8.2128 | 22.3 |
| 16.485 | 5.3729 | 11.8 |
| 19.636 | 4.5173 | 73.5 * |
| 20.922 | 4.2425 | 20.6 |
| 22.043 | 4.0291 | 54.0 |

TABLE 6-continued

| 2-Theta | d(A) | Relative Intensity (>10%) |
|---|---|---|
| 23.683 | 3.7538 | 18.0 |
| 24.153 | 3.6817 | 52.6 |
| 24.996 | 3.5595 | 100.0 |
| 26.236 | 3.3939 | 11.4 |
| 27.680 | 3.2201 | 25.2 |
| 28.037 | 3.1799 | 22.4 |
| 29.120 | 3.0641 | 21.5 |
| 31.718 | 2.8187 | 36.4 |
| 32.794 | 2.7287 | 13.3 |
| 33.314 | 2.6872 | 10.8 |
| 34.085 | 2.6282 | 13.6 |
| 41.999 | 2.1494 | 14.6 |
| 42.278 | 2.1359 | 10.3 |

The crystal forms of the present invention may exist in anhydrous forms as well as hydrated forms. In general, the hydrated forms, are equivalent to unhydrated forms and are intended to be encompassed within the scope of the present invention.

The present invention provides a process for the preparation of crystalline Form I of Compound A which comprises crystallizing Compound A from a solution in solvents under conditions which yield crystalline Form I of Compound A.

The precise conditions under which crystalline Form I of Compound A is formed may be empirically determined and it is only possible to give a number of methods which have been found to be suitable in practice. The desired Form I may be obtained by suspending the solid in a suitable solvent, such as ethanol and precipitating with water; by dissolving the solid in a minimum amount of a boiling solvent, such as ethanol and adding water to the boiling solvent; and by dissolving the solid in a minimum amount of boiling solvent, such as ethyl acetate, and adding a suitable solvent, such as heptane to the boiling solvent, as is more fully set forth in Example 39A below.

The present invention provides a process for the preparation of crystalline Form II of Compound A which comprises crystallizing Compound A from a solution in solvents under conditions which yield crystalline Form II of Compound A.

The precise conditions under which crystalline Form R of Compound A is formed may be empirically determined and it is only possible to give a number of methods which have been found to be suitable in practice. The desired Form II may be obtained by suspending the solid in a suitable solvent, such as ethyl acetate/hexanes or suspending the solid in a suitable solvent, such as heptane-$CH_2Cl_2$ (1:1), as is more fully set forth in Example 39 below.

The present invention provides a process for the preparation of crystalline Form I of Compound B which comprises crystallizing Compound B from a solution in solvents under conditions which yield crystalline Form I of Compound B.

The precise conditions under which crystalline Form I of Compound B is formed may be empirically determined and it is only possible to give a method which has been found to be suitable in practice. The desired Form I may be obtained by suspending the solid in hexane-AcOEt. A more detailed procedure is set forth in Example 49 below.

The present invention provides a process for the preparation of crystalline Form II of Compound B which comprises crystallizing Compound B from a solution in solvents under conditions which yield crystalline Form II of Compound B.

The precise conditions under which crystalline Form II of Compound B is formed may be empirically determined and it is only possible to give a method which has been found to be suitable in practice. The desired Form II may be obtained by suspending the solid in ethyl acetate and heptane or by suspending the solid in by suspending the solid in hexane-AcOEt, as is more fully set forth in Examples 49 and 49A below.

The present invention provides a process for the preparation of crystalline Form I of Compound C which comprises crystallizing Compound C from a solution in solvents under conditions which yield crystalline Form I of Compound C.

The precise conditions under which crystalline Form I of Compound C is formed may be empirically determined and it is only possible to give a method which has been found to be suitable in practice. The desired Form I may be obtained by suspending the solid in hexane-AcOEt. A more detailed procedure is set forth in Example 50 below.

The present invention provides a process for the preparation of crystalline Form II of Compound C which comprises crystallizing Compound C from a solution in solvents under conditions which yield crystalline Form II of Compound C.

The precise conditions under which crystalline Form H of Compound C is formed may be empirically determined and it is only possible to give a method which has been found to be suitable in practice. The desired Form II may be obtained by suspending the solid in ethyl acetate and heptane, or by suspending the solid in hexane-AcOEt, as is more fully set forth in Examples 50 and 50A below.

As used herein, the term "patient" refers to any warm-blooded animal such as, but not limited to, a human, horse, dog, guinea pig, or mouse. Preferably, the patient is human.

The term "treating" for purposes of the present invention refers to prophylaxis or prevention, amelioration or elimination of a named condition once the condition has been established.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a therapeutically effective amount of a disclosed compound, including crystal forms, or pharmaceutical composition thereof.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and post-therpetic pain, causalgia, diabetic neuropathy, plexus avulsion, neuroma, vasculitis, viral infection, crush injury, constriction injury, tissue injury, limb amputation, post-operative pain, arthritis pain, and nerve injury between the peripheral nervous system and the central nervous system.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H,3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount will be between about 0.1 and about 1000 mg/kg per day, preferably between about 1 and about 300 mg/kg body weight, and daily dosages will be between about 10 and about 5000 mg for an adult subject of normal weight. Commercially available capsules or other formulations (such as liquids and film-coated tablets) of 100 mg, 200 mg, 300 mg, or 400 mg can be administered according to the disclosed methods.

The compounds of the present invention, including crystal forms, are preferably formulated prior to administration. Therefore, another aspect of the present invention is a pharmaceutical composition comprising a compound of formula I and a pharmaceutically acceptable carrier. In making the compositions of the present invention, the active ingredient, such as a compound of formula I, will usually be mixed with a carrier, or diluted by a carrier or enclosed within a carrier. Dosage unit forms or pharmaceutical compositions include tablets, capsules, pills, powders, granules, aqueous and non-aqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption acccelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

The following examples represent typical syntheses of the compounds of the present invention as described generally above. These examples are illustrative only and are not intended to limit the invention in any way. The reagents and starting materials are readily available to one of ordinary skill in the art.

PREPARATION 1

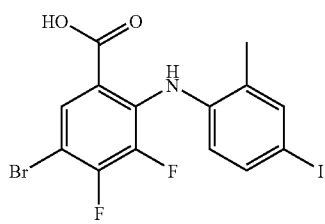

5-Bromo-3,4-difluoro-2-(4-iodo-2-methyl-phenylamino)-benzoic acid

To a stirred solution comprised of 1.88 g (0.00791 mol) of 2-amino-5-iodotoluene in 10 mL of tetrahydrofuran at −78° C. was added 6 mL (0.012 mol) of a 2.0 M lithium diisopropylamide in tetrahydrofuran/heptane/ethylbenzene (Aldrich) solution. The resulting green suspension was stirred vigorously for 10 minutes, after which time a solution of 1.00 g (0.00392 mol) of 5-bromo-2,3,4-trifluorobenzoic acid in 15 mL of tetrahydrofuran was added. The cold bath was subsequently removed, and the reaction mixture stirred for 18 hours. The mixture was concentrated, and the concentrate was treated with 100 mL of dilute (10%) aqueous hydrochloric acid. The resulting suspension was extracted with ether (2×150 mL), and the combined organic extractions were dried (MgSO$_4$) and concentrated in vacuo to give an orange solid. The solid was triturated with boiling dichloromethane, cooled to ambient temperature, and collected by filtration.

The solid was rinsed with dichloromethane, and dried in the vacuum-oven (80° C.) to afford 1.39 g (76%) of a yellow-green powder; mp 259.5-262° C.; $^1$H NMR (400 MHz, DMSO): δ 9.03 (s, 1H), 7.99 (dd, 1H, J=7.5, 1.9 Hz), 7.57 (dd, 1H, J=1.5 Hz), 7.42 (dd, 1H, J=8.4, 1.9 Hz), 6.70 (dd, 1H, J=8.4, 6.0 Hz), 2.24 (s, 3H); $^{19}$F NMR (376 MHz, DMSO): δ −123.40 to −123.47 (m); −139.00 to −139.14 (m); IR (KBr) 1667 (C=O stretch)cm$^{-1}$; MS (CI) M+1=469.

Anal. Calcd/found for $C_{14}H_9BrF_2INO_2$: C, 35.93/36.15; H, 1.94/1.91; N, 2.99/2.70; Br, 17.07/16.40; F, 8.12/8.46; I, 27.11/26.05.

Preparations

Preparations 2 to 25 in Table 7 below were prepared by the general procedure of Example 1.

TABLE 7

| Preparation | Compound | | MP ° C. |
|---|---|---|---|
| 2 | (structure) | 3,4,5-Trifluoro-2-(4-iodo-2-methyl-phenylamino)-benzoic acid | 206-210 |
| 3 | (structure) | 5-Chloro-3,4-difluoro-2-(4-iodo-2-methyl-phenylamino)-benzoic acid | 249-251 |
| 4 | (structure) | 3,4-Difluoro-2-(4-iodo-2-methyl-phenylamino)-benzoic acid | 240.5-244.5 |
| 5 | (structure) | 5-Chloro-2-(2-chloro-4-iodo-phenylamino)-3,4-difluoro-benzoic acid | 293.3-293.6 |
| 6 | (structure) | 2-(2-Chloro-4-iodo-phenylamino)-3,4,5-trifluoro-benzoic acid | 237-239 |
| 7 | (structure) | 5-Bromo-2-(2-chloro-4-iodo-phenylamino)-3,4-difluoro-benzoic acid | 302-304 |

TABLE 7-continued

| | Structure | Name | mp (°C) |
|---|---|---|---|
| 8 | 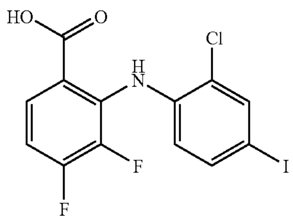 | 2-(2-Chloro-4-iodo-phenylamino)-3,4-difluoro-benzoic acid | 226-228 |
| 9 | 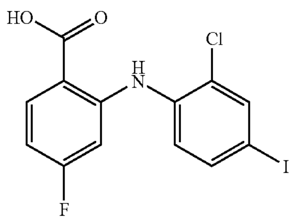 | 2-(2-Chloro-4-iodo-phenylamino)-4-fluoro-benzoic acid | 242-247 |
| 10 | 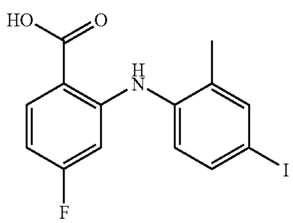 | 4-Fluoro-2-(4-iodo-2-methyl-phenylamino)-benzoic acid | 224-229.5 |
| 11 | 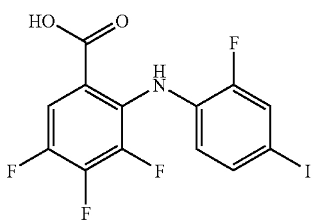 | 3,4,5-Trifluoro-2-(2-fluoro-4-iodo-phenylamino)-benzoic acid | |
| 12 | 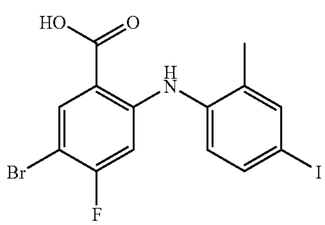 | 5-bromo-4-fluoro-2-(4-iodo-2-methyl-phenylamino)-benzoic acid | |
| 13 | 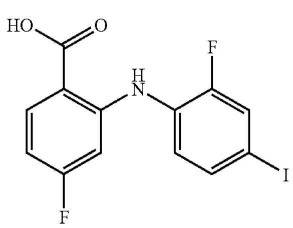 | 4-Fluoro-2-(2-fluoro-4-iodo-phenylamino)-benzoic acid | 215-217 |
| 14 | 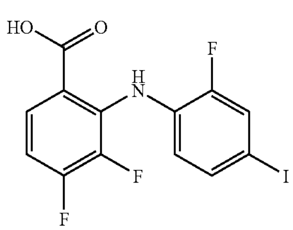 | 3,4-Difluoro-2-(2-fluoro-4-iodo-phenylamino)-benzoic acid | 200-201 |

TABLE 7-continued

| # | Structure | Name | mp (°C) |
|---|---|---|---|
| 15 | 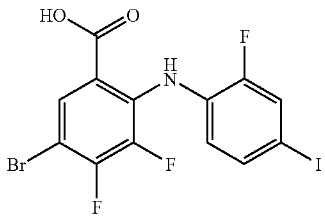 | 5-Bromo-3,4-difluoro-2-(2-fluoro-4-iodo-phenylamino)-benzoic acid | 258–259 |
| 16 | 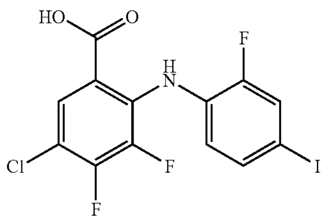 | 5-Chloro-3,4-difluoro-2-(2-fluoro-4-iodo-phenylamino)-benzoic acid | 256–258 |
| 17 | 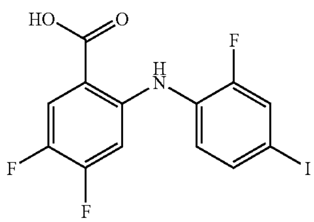 | 4,5-Difluoro-2-(2-fluoro-4-iodo-phenylamino)-benzoic acid | 244–245 |
| 18 | 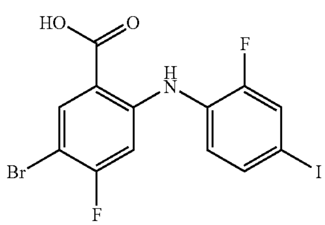 | 5-Bromo-4-fluoro-2-(2-fluoro-4-iodo-phenylamino)-benzoic acid | 296–298 |
| 19 | 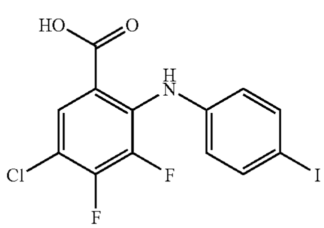 | 5-Chloro-3,4-difluoro-2-(4-iodo-phenylamino)-benzoic acid | 267–269 |
| 20 | 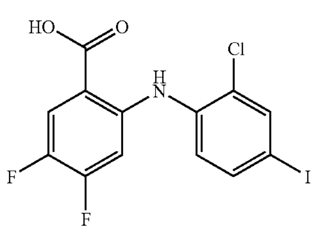 | 2-(2-Chloro-4-iodo-phenylamino)-4,5-difluoro-benzoic acid | 245, dec |
| 21 | 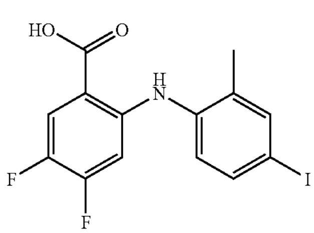 | 4,5-Difluoro-2-(4-iodo-2-methyl-phenylamino)-benzoic acid | 238–239 |

TABLE 7-continued
| | | | |
|---|---|---|---|
| 22 | 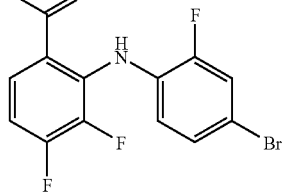 | 2-(4-Bromo-2-fluoro-phenylamino)-3,4-difluoro-benzoic acid | 214.4-214.9 |
| 23 | 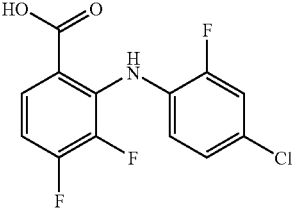 | 2-(4-Chloro-2-fluoro-phenylamino)-3,4-difluoro-benzoic acid | 215.4-215.6 |
| 24 | 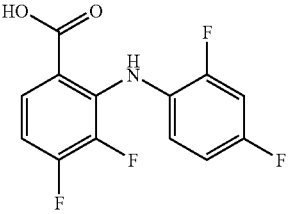 | 2-(2,4-Difluoro-phenylamino)-3,4-difluoro-benzoic acid | 191.8-192.0 |
| 25 | 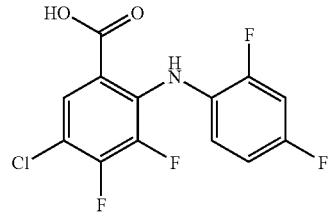 | 5-Chloro-2-(2,4-difluoro-phenylamino)-3,4-difluoro-benzoic acid | 240-240.3 |

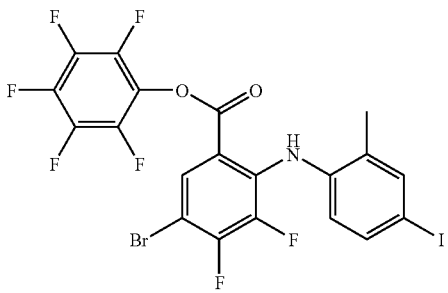

PREPARATION 26

5-Bromo-3,4-difluoro-2-(4-iodo-2-methyl-phenylamino)-benzoic acid pentafluorophenyl ester To a solution of 5-Bromo-3,4-difluoro-2-(4-iodo-2-methyl-phenylamino)-benzoic acid (prepared as described in WO 99/01426) (1.61 g, 3.4 mmol) and pyridine (0.31 mL, 3.83 mmol) in anhydrous dimethylformamide (7 mL) was added pentafluorophenyl trifluoroacetate (0.71 mL, 4.13 mmol). The resultant solution was stirred at ambient temperature for 18 h. The reaction mixture was diluted with ether (100 mL) and washed with water (40 mL), 0.1 M aqueous hydrochloric acid (40 mL), saturated aqueous sodium bicarbonate (40 mL), and saturated brine (40 mL). The organics were dried over anhydrous magnesium sulfate and concentrated under reduced pressure to afford a foam that was purified on silica gel. Elution with hexanes-ethyl acetate (19:1) afforded 5-Bromo-3,4-difluoro-2-(4-iodo-2-methyl-phenylamino)-benzoic acid pentafluorophenyl ester (1.95 g, 89%) as a pale-yellow powder: $^1$H NMR (400 MHz, CDCl$_3$) δ 8.59 (s, 1 H), 8.24 (d, J=5.8 Hz, 1 H), 7.54 (s, 1 H), 7.45 (d, J=8.4 Hz, 1 H), 6.70 (dd, J=8.4, 5.3 Hz, 1 H), 2.26 (s, 3 H).

Preparations 27-46 were prepared by the general procedure of Preparation 26.

PREPARATION 27

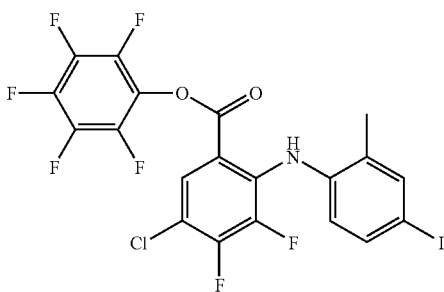

5-Chloro-3,4-difluoro-2-(4-iodo-2-methyl-phenylamino)-benzoic acid pentafluorophenyl ester $^1$H-NMR (400 MHz, CDCl$_3$) δ 8.58 (s, 1 H), 8.12 (dd, J=7.5, 2.0 Hz, 1 H), 7.54 (s, 1 H), 7.46 (dd, J=8.3, 1.5 Hz, 1 H), 6.70 (dd, J=8.3, 5.4 Hz, 1 H), 2.28 (s, 3 H); $^{19}$F-NMR (376 MHz, CDCl$_3$) δ −125.1 (dd, J=17.7, 5.0 Hz, 1 F), −139.1 (d, J=17.7 Hz, 1 F), −152.6 (d, J=17.7 Hz, 2 F), −156.9 (t, J=20.3 Hz, 1 H), −161.9 (t, J=20.2 Hz, 2 H); MS (APCI−)=587.9.

PREPARATION 28

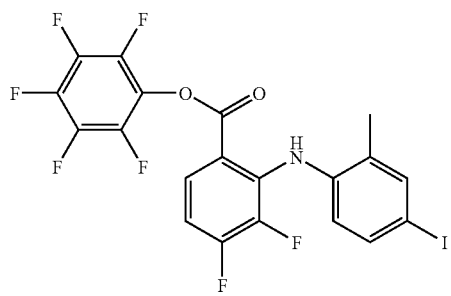

3,4-Difluoro-2-(4-iodo-2-methyl-phenylamino)-benzoic acid pentafluorophenyl ester $^1$H-NMR (400 MHz, CDCl$_3$) δ 8.59 (s, 1 H), 8.04 (dd, J=7.5, 7.0 Hz, 1 H), 7.53 (s, 1 H), 7.45 (d, J=8.4 Hz, 1 H), 6.77 (m, 1 H), 6.70 (dd, J=7.2, 6.9 Hz, 1 H), 2.27 (s, 3 H); MS (APCI−)=554.0

PREPARATION 29

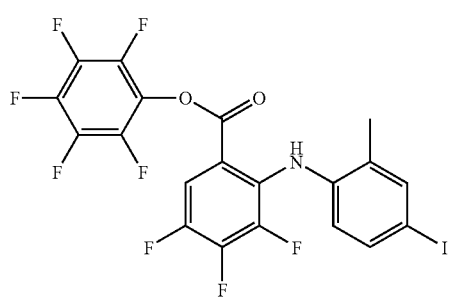

3,4,5-Trifluoro-2-(4-iodo-2-methyl-phenylamino)-benzoic acid pentafluorophenyl ester MP: 108.5–110.6° C.; $^1$H-NMR (400 MHz, CDCl$_3$) δ 8.35 (s, 1H), 7.89 (ddd, J=10.4, 8.0, 2.2 Hz, 1H), 7.53 (s, 1H), 7.44 (dd, J=8.2, 1.9 Hz, 1H), 6.64 (dd, J=8.2, 5.5 Hz, 1H), 2.27 (s, 3H); $^{19}$F-NMR (376 MHz, CDCl$_3$) δ −137.25 (d, J=16.8 Hz, 1F), −144.18 (dd, J=21.4, 10.7 Hz, 1F), −145.55 (td, J=21.4, 7.6 Hz, 1F), −152.31 (d, J=18.3 Hz, 2F), −156.60 (t, J=21.4 Hz, 1F), −161.62 (t, J=18.3 Hz, 2F). Anal. Calcd/found for C$_{20}$H$_8$NO$_2$F$_8$I: C, 41.91/41.52; H, 1.41/1.32; N, 2.44/2.36; F, 26.52/26.34; I, 22.14/22.19.

PREPARATION 30

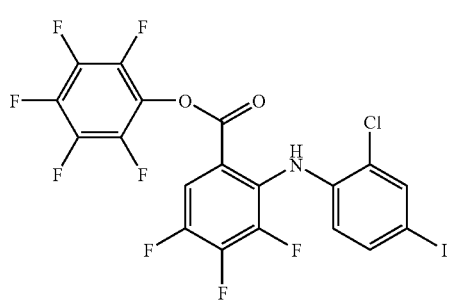

2-(2-Chloro-4-iodo-phenylamino)-3,4,5-trifluoro-benzoic acid pentafluorophenyl ester MP: 98.2-99.2° C.; $^1$H-NMR (400 MHz, CDCl$_3$) δ 8.50 (s, 1H), 7.93 (ddd, J=10.1, 8.0, 2.2 Hz, 1H), 7.70 (d, J=1.7 Hz, 1H), 7.48 (dd, J=8.7, 1.7 Hz, 1H), 6.62 (t, J=7.6 Hz, 1H); $^{19}$F-NMR (376 MHz, CDCl$_3$) δ −134.42 (d, J=18.3 Hz, 1F), −141.59 (dd, J=21.4, 9.2 Hz, 1F), −145.26 (td, J=21.4, 7.6 Hz, 1F), −152.26 (d, J=18.3 Hz, 2F), −156.46 (t, J=21.4 Hz, 1F), −161.53 (t, J=18.3 Hz, 2F). Anal. Calcd/found for C$_{19}$H$_5$NO$_2$F$_8$ClI: C, 38.45/38.39; H, 0.85/0.91; N, 2.36/2.32; Cl, 5.97/6.32; F, 25.60/25.68; I, 21.38/21.32.

PREPARATION 31

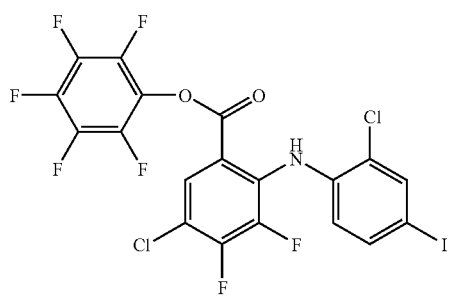

5-Chloro-2-(2-chloro-4-iodo-phenylamino)-3,4-difluoro-benzoic acid pentafluorophenyl ester $^1$H-NMR (400 MHz, CDCl$_3$) δ 8.74 (s, 1 H), 8.15 (dd, J=7.3, 2.0 Hz, 1 H), 7.71 (d, J=2.0 Hz, 1 H), 7.49 (dd, J=8.4, 2.0 Hz, 1 H), 6.68 (dd, J=8.4, 7.1 Hz, 1 H); MS (APCI−)= 607.8.

PREPARATION 32

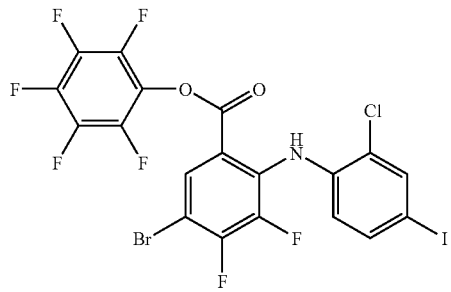

5-Bromo-2-(2-chloro-4-iodo-phenylamino)-3,4-difluoro-benzoic acid pentafluorophenyl ester Yield, 1.99 g (61%); mp. 112-114° C.; $^1$H-NMR (400 MHz, CDCl$_3$) δ 8.75 (s, 1H), 8.28 (dd, J=7.0, 2.2 Hz, 1H), 7.50 (dd, J=8.4, 1.9 Hz, 1H), 7.713 (d, J=1.9 Hz, 1H), 6.68 (dd, J=8.4, 7.0 Hz, 1H); $^{19}$F-NMR (376 MHz, CDCl$_3$) δ −116.43 (dd, J=19.8, 6.1 Hz, 1F), −135.59 (dd, J=18.3, 6.1 Hz, 1F), −152.2 (d, J=16.8 Hz, 2F), −156.47 (t, J=21.4 Hz, 1F), −161.53 (t, J=18.3 Hz, 2F). Anal. Calcd/found for C$_{19}$H$_5$NO$_2$F$_7$BrClI: C, 34.87/34.72; H, 0.77/0.65; N, 2.14/2.07; F, 20.32/20.68; Cl, 5.42/6.06; Br, 12.21/11.67; I, 19.39/19.75.

PREPARATION 33

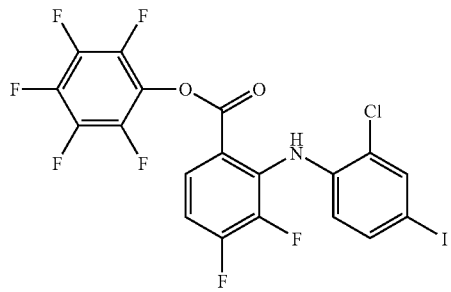

2-(2-Chloro-4-iodo-phenylamino)-3,4-difluoro-benzoic acid pentafluorophenyl ester Yield, 2.15 g (75%); mp. 108.5-110.0° C.; $^1$H-NMR (400 MHz, CDCl$_3$) δ 8.77 (br s, 1H), 8.07 (br s, 1H), 7.69 (br s, 1H), 7.48 (br d, J=7.0 Hz, 1H), 6.91 (br d, J=7.2 Hz, 1H), 6.67 (br s., 1H); $^{19}$F-NMR (376 MHz, CDCl$_3$) δ −123.74 (s, 1F), −139.17 (d, J=16.8 Hz, 1F), −152.35 (d, J=21.4 Hz, 2F), −156.96 (t, J=21.4 Hz, 1F), −161.81 (t, J=21.4 Hz, 2F). Anal. Calcd/found for C₁₉H₆NO₂F₇ClI: C, 39.65/39.32; H, 1.05/0.91; N, 2.43/2.35; F, 23.10/22.85; Cl, 6.16/6.92; I, 22.05/22.50.

PREPARATION 34

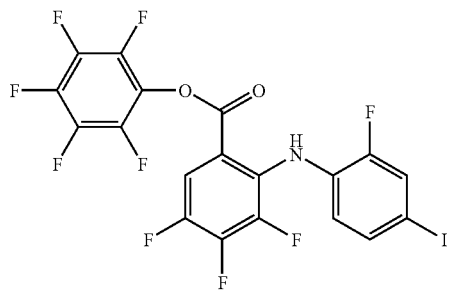

3,4,5-Trifluoro-2-(2-fluoro-4-iodo-phenylamino)-benzoic acid pentafluorophenyl ester $^1$H NMR (400 MHz, CDCl$_3$) δ 8.40 (s, 1H), 7.85-7.91 (m, 1H), 7.35-7.43 (m, 2H), 6.67-6.73 (m, 1H);); MS (APCI−)= 575.9.

PREPARATION 36

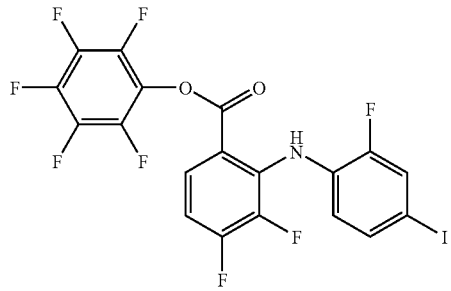

3,4-Difluoro-2-(2-fluoro-4-iodo-phenylamino)-benzoic acid pentafluorophenyl ester $^1$H NMR (400 MHz, CDCl$_3$) δ 8.67 (s, 1 H), 8.04 (ddd, J=9.3, 5.6, 2.2 Hz, 1 H), 7.42 9dd, J=10.0, 1.9 Hz, 1 H), 7.38 (d, J=8.8 Hz, 1 H), 6.84 (td, J=9.1, 6.8 Hz, 1 H), 6.77 (td, J=8.5, 5.1 Hz, 1 H); $^{19}$F NMR (376 MHz, CDCl$_3$) δ −124.3, −125.1, −143.5, −152.6, −157.3, −162.1; MS (APCI−)= 557.9.

PREPARATION 35

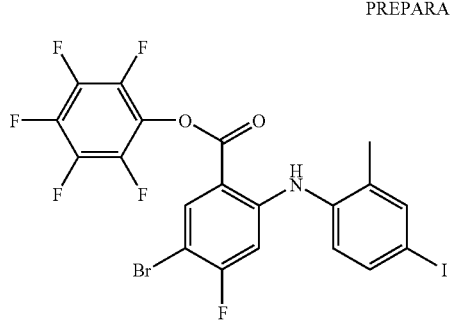

5-Bromo-4-fluoro-2-(4-iodo-2-methylphenylamino)-benzoic acid pentafluorophenyl ester $^1$H-NMR (400 MHz, acetone-d$_6$) δ 9.04 (br. s., 1H), 8.44 (d, 1H, J=7.81 Hz), 7.74 (d, 1H, J=1.22 Hz), 7.64 (dd, 1H, J=8.31, 1.96 Hz), 7.19 (d, 1H, 8.3 Hz), 6.67 (d, 1H, J=11.48 Hz), 2.22 (s, 3H). $^{19}$F-NMR (376 MHz, acetone-d$_6$) δ −97.1 (t), −155.0 (t), −160.2 (t), −165.1 (t). MS (APCI−) 415.8 m/z, 429.9 m/z, 447.9 m/z, 615.8 m/z.

PREPARATION 37

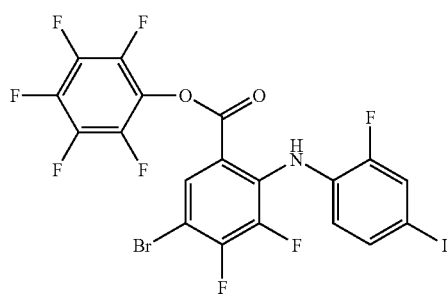

5-Bromo-3,4-difluoro-2-(2-fluoro-4-iodo-phenylamino)-benzoic acid pentafluorophenyl ester $^1$H NMR (400 MHz, acetone-d$_6$) δ 8.60 (s, 1 H), 8.39 (ddd, J=7.1, 2.3, 0.7 Hz, 1 H), 7.58 (dd, J=10.5, 1.7 Hz, 1 H), 7.49 (dt, J=7.5, 1.5 Hz, 1 H), 7.06 (td, J=8.5, 4.4 Hz, 1 H); $^{19}$F NMR (376 MHz, acetone-d$_6$) δ −120.5, −127.1, −141.5, −154.7, −159.8, −164.8; MS (APCI−)=635.8, 637.8.

(APCI−) 355.9 m/z, 391.9 m/z, 558.0 m/z. Anal. Calcd for C$_{14}$H$_{10}$F$_2$INO$_2$: C, 40.81; H, 1.08; N, 2.50. Found: C, 40.92; H, 1.00; N, 2.32.

PREPARATION 38

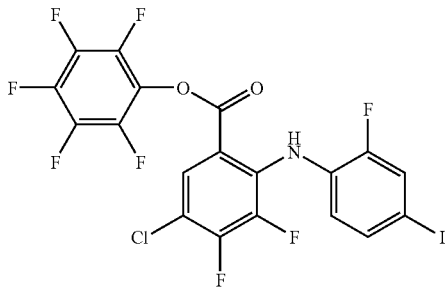

5-Chloro-3,4-difluoro-2-(2-fluoro-4-iodo-phenylamino)-benzoic acid pentafluorophenyl ester $^1$H NMR (400 MHz, CDCl$_3$) δ 8.62 (s, 1 H), 8.10 (dd, J=7.5, 2.3 Hz, 1 H), 7.44 (dd, J=10.0, 1.7 Hz, 1 H), 7.41 (dd, J=8.4, 1.1 Hz, 1 H), 6.76 (td, J=8.3, 4.6 Hz, 1 H); $^{19}$F NMR (376 MHz, CDCl$_3$) δ −124.6, −124.9, −140.3, −152.5, −156.8, −161.9; MS (APCI−)=591.8, 593.8.

PREPARATION 39

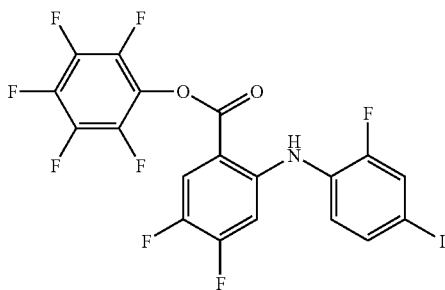

4,5-Difluoro-2-(2-fluoro-4-iodo-phenylamino)-benzoic acid pentafluorophenyl ester $^1$H-NMR (400 MHz, acetone-d$_6$) δ 8.99 (br. s.), 8.17 (dd, 1H, J=10.99, 8.79 Hz), 7.69 (dd, 1H, J=10.0, 1.95 Hz), 7.63 (m, 1H), 7.38 (t, 1H, J=8.55 Hz), 7.04 (qd, 1H, J=6.84, 1.47 Hz). $^{19}$F-NMR (376 MHz, acetone-d$_6$) δ −123.0 (t), −125.7 (p), −150.8 (m), −155.1 (d), −160.1 (t), −165.0 (t). MS

PREPARATION 40

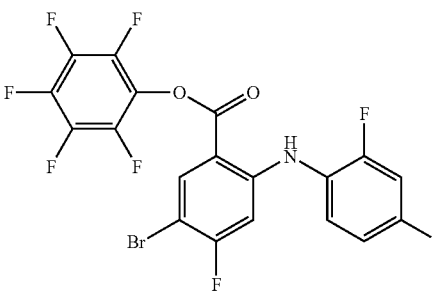

5-Bromo-4-fluoro-2-(2-fluoro-4-iodo-phenylamino)-benzoic acid pentafluorophenyl ester $^1$H-NMR (400 MHz, acetone-d$_6$) δ 9.11 (br. s.), 8.2 (dd, 1H, J=11.24, 8.79 Hz), 7.9 (d, 1H, J=1.95 Hz), 7.73 (dd, 1H, J=8.55, 2.2 Hz), 7.45 (d, 1H, J=8.55 Hz), 7.17 (dd, 1H, J=13.18, 6.83 Hz). $^{19}$F-NMR (376 MHz, acetone-d$_6$) δ −96.8, −122.4, −155.0, −160.0, −165.0. MS (APCI−) 415.8 m/z (d), 453.8 m/z (d), 617.8 m/z (d). Anal. Calcd for C$_{13}$H$_7$BrF$_2$INO$_2$: C, 34.39; H, 0.98; N, 2.26. Found: C, 36.61; H, 0.99; N, 2.09.

PREPARATION 41

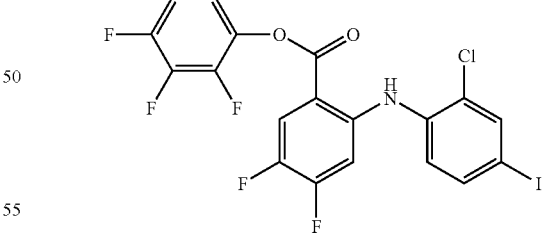

2-(2-Chloro-4-iodo-phenylamino)-4,5-difluoro-benzoic acid pentafluorophenyl ester $^1$H-NMR (400 MHz, acetone-d$_6$) δ 9.11 (br. s.), 8.2 (dd, 1H, J=11.24, 8.79 Hz), 7.9 (d, 1H, J=1.95 Hz), 7.73 (dd, 1H, J=8.55, 2.2 Hz), 7.45 (d, 1H, J=8.55 Hz), 7.17 (dd, 1H, J=13.18, 6.83 Hz). $^{19}$F-NMR (376 MHz, acetone-d$_6$) δ −125.5 (p), −150.1 (m), −155.1 (d), −160.0 (t), −164.9 (t). MS (APCI−) 355.9 m/z, 389.9 m/z, 407.9 m/z, 573.9 m/z.

J=10.1 Hz); −126.7 (m), −145.3 (d, J=20.2 Hz), −153.3 (d, J=20.2 Hz), −157.8 (t, J=22.7 Hz), −162.9 (t, J=21.5 Hz); MS (APCI−)=510.0/512.0.

PREPARATION 42

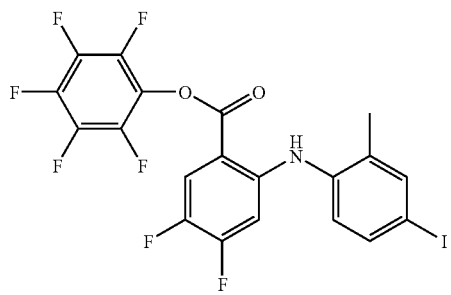

PREPARATION 44

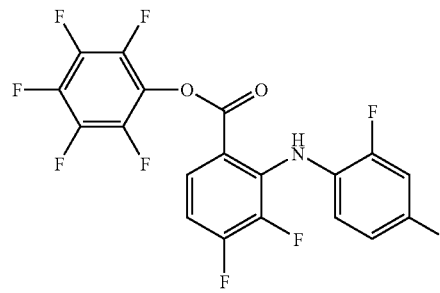

4,5-Difluoro-2-(4-iodo-2-methyl-phenylamino)-benzoic acid pentafluorophenyl ester $^1$H-NMR (400 MHz, acetone-$d_6$) δ 8.92 (br. s.), 8.14 (dd, 1H, J=11.23, 8.79 Hz), 7.75 (d, 1H, J=1.46 Hz), 7.64 (dd, 1H, J=8.31, 2.2 Hz), 7.2 (d, 1H J=8.31 Hz), 6.76 (dd, 1H, J=13.19, 6.84 Hz), 2.24 (s, 3H). $^{19}$F-NMR (376 MHz, acetone-$d_6$) δ −125.78 (p), −152.41 (m), −155.1 (d), −160.2 (t), −165.0 (t). MS (APCI−): 355.9 m/z, 369.9 m/z, 386.9 m/z (d), 554.0 m/z.

2-(4-Chloro-2-fluoro-phenylamino)-3,4-difluoro-benzoic acid pentafluorophenyl ester m.p. 99.0-99.4° C.; $^1$H NMR (400 MHz, DMSO-$d_6$) δ 8.59 (s, 1 H), 8.07 (ddd, J=9.0, 5.8, 2.0 Hz, 1 H), 7.45 (dd, J=11.2, 2.2 Hz, 1 H), 7.30 (dt, J=7.3, 9.2 Hz, 1 H), 7.19-7.08 (m, 2 H); $^{19}$F NMR (376 MHz, DMSO-$d_6$) δ −125.6 (t, J=10.1 Hz), −126.7 (m, 1 H), −145.6 (d, J=15.2 Hz), −153.3 (d, J=20.2 Hz); −157.7 (t, J=22.8 Hz), −162.8 (t, J=20.2 Hz); MS (APCI−)=466.0.

PREPARATION 43

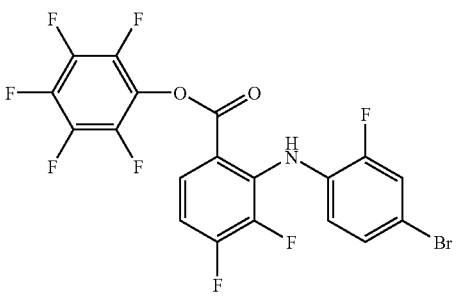

PREPARATION 45

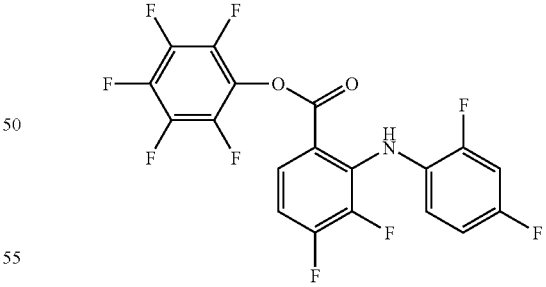

2-(2,4-Difluoro-phenylamino)-3,4-difluoro-benzoic acid pentafluorophenyl ester $^1$H NMR (400 MHz, DMSO-$d_6$) δ 8.58 (s, 1 H), 8.07 (ddd, J=9.0, 5.9, 2.0 Hz, 1 H), 7.34-7.12 (cm, 3 H), 7.01 (m, 1 H); $^{19}$F NMR (376 MHz, DMSO-$d_6$) δ −116.9 (s), −122.6 (t, J=10.1 Hz), −126.7 (m), −147.9 (d, J=20.2 Hz), −153.5 (d, J=20.2 Hz), −157.7 (t, J=22.8 Hz), −162.8 (t, J=20.2 Hz); MS (APCI−)=450.0.

2-(4-Bromo-2-fluoro-phenylamino)-3,4-difluoro-benzoic acid pentafluorophenyl ester m.p. 100.9-101.5° C.; $^1$H NMR (400 MHz, DMSO-$d_6$) δ 8.56 (s, 1 H), 8.07 (ddd, J=9.3, 5.9, 2.0 Hz, 1 H), 7.54 (dd, J=11.0, 2.2 Hz, 1 H), 7.35-7.22 (cm, 2 H), 7.04 (td, J=8.9, 2.0 Hz, 1 H); $^{19}$F-NMR (376 MHz, DMSO-$d_6$) δ −125.8 (t,

PREPARATION 46

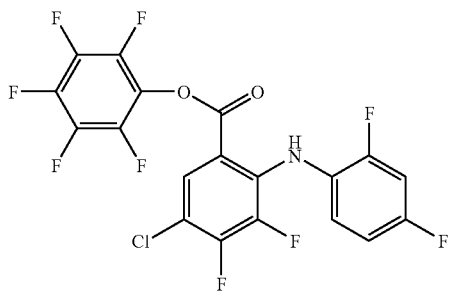

5-Chloro-2-(2,4-difluoro-phenylamino)-3,4-difluoro-benzoic acid pentafluorophenyl ester m.p. 92.5-93.2° C.; $^1$H NMR (400 MHz, DMSO-d$_6$) δ 8.62 (s, 1 H), 8.21 (dd, J=7.7, 2.1 Hz, 1 H), 7.34-7.24 (m, 2 H), 7.02 (m, 1 H); $^{19}$F NMR (376 MHz, DMSO-d$_6$) δ −116.7(m), −122.4 (m), −128.1 (dd, J=20.2, 7.6 Hz), −143.4 (d, J=17.7 Hz), −153.2 (d, J=20.2 Hz), −157.4 (t, J=22.7 Hz), −162.8 (t, J=20.2 Hz); MS (APCI−)=483.9.

PREPARATION 47

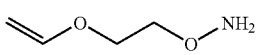

O-(2-Vinyloxy-ethyl)-hydroxylamine

Part A: Synthesis of 2-(2-Vinyloxy-ethoxy)-isoindole-1,3-dione

Ethylene glycol vinyl ether (9.88 g, 112 mmol), triphenylphosphine (29.4 g, 112 mmol), and N-hydroxyphthalimide (18.22 g, 111.7 mmol) were combined in 300 mL of anhydrous tetrahydrofuran and cooled to 0° C. (ice bath). Diethylazodicarboxylate (18.0 mL, 114 mmol) was added dropwise over 15 min and the resultant reaction mixture was allowed to warm to ambient temperature over 18 h. The reaction mixture was concentrated to a paste and the solids were filtered and washed with chloroform. The filtrate was further concentrated and filtered again, washing the solids with chloroform. The remaining chloroform solution was concentrated to an oil. The oil was dissolved in absolute ethanol (75 mL). Scratching with a glass rod induced crystallization. The crystals were collected and recrystallized from hot ethanol to afford colorless needles of 2-(2-vinyloxy-ethoxy)-isoindole-1,3-dione (13.8 g, 53% yield): $^1$H NMR (400 MHz, CDCl$_3$) δ 7.85 (m, 2 H), 7.75 (m, 2 H), 6.46 (dd, J=14.3, 6.7 Hz, 1 H), 4.45 (m, 2H), 4.16 (dd, J=14.4, 2.2 Hz), 4.02 (m 3 H).

Part B: Synthesis of O-(2-Vinyloxy-ethyl)-hydroxylamine 2-(2-vinyloxy-ethoxy)-isoindole-1,3-dione (13.8 g, 59.2 mmol) was dissolved in dichloromethane (45 mL). Methylhydrazine (3.2 mL, 60 mmol) was added dropwise and the resultant solution was stirred 30 min at ambient temperature. The resultant suspension was diluted with diethyl ether (150 mL) and was filtered. The filtrate was concentrated in vacuo. The residual oil was distilled (bp 60-65° C. @ 20 mm Hg) to afford the amine as a colorless liquid (4.6 g, 75% yield): $^1$H NMR (400 MHz, CDCl$_3$) δ 6.49 (dd, J=14.3, 6.7 Hz, 1 H), 5.59 (br s, J=2 H), 4.19 (dd, J=14.3, 2.2 Hz, 1 H), 4.01 (dd, J=6.8, 2.2 Hz, 1 H), 3.90-3.83 (m, 4 H); $^{13}$C NMR (100 MHz, CDCl$_3$) δ 151.7, 86.8, 73.7, 66.0.

Preparations 48-51 were prepared by the general procedure of preparation 47, part A.

PREPARATION 48

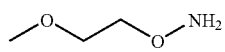

O-(2-Methoxy-ethyl)-hydroxylamine $^1$H NMR (400 MHz, CDCl$_3$) δ 5.21 (br s, 2 H), 3.82 (m, 2 H), 3.54 (m, 2 H), 3.37 (s, 3 H).

PREPARATION 49

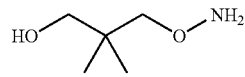

3-Aminooxy-2,2-dimethyl-propan-1-ol

BP 148° C. @ 20 mm Hg; $^1$H NMR (400 MHz, CDCl$_3$) δ 3.50 (s, 2H), 3.37 (s, 2H), 0.86 (s, 6H).

PREPARATION 50

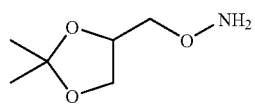

O-(2,2-Dimethyl-[1,3]dioxolan-4-ylmethyl)-hydroxylamine $^1$H NMR (400 MHz; CDCl$_3$) δ 5.50 (bs, 1 H), 4.32 (m, 1 H), 4.04 (t, J=6.81 Hz, 1 H), 3.72 (m, 2 H), 3.67 (m, 1 H), 1.41 (s, 3 H), 1.34 (s, 3 H); MS(APCI+)=148.

PREPARATION 51

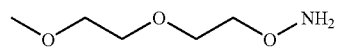

O-[2-(2-Methoxy-ethoxy)-ethyl]-hydroxylamine

BP 95-100° C. @ 20 mm Hg; $^1$H NMR (400 MHz, DMSO-d$_6$) δ 5.96 (br s, 2 H), 3.62 (t, J=4.3 Hz, 2 Hz), 3.55-3.47 (m, 4 H), 3.42 (m, 2 H) 3.24 (s, 3 H); MS (APCI+)=136.1.

PREPARATION 52

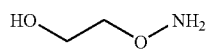

2-Aminooxy-ethanol

2-Aminooxy-ethanol was prepared by the literature procedure: Dhanak, D.; Reese, C. B. J. Chem. Soc., Perkin Trans. 1 1987, 2829.

PREPARATION 53

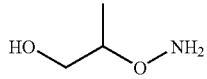

2-Aminooxy-propan-1-ol

2-Aminooxy-propan-1-ol was prepared according to the literature procedure (Cannon, J. G; Mulligan, P. J.; Garst, J. E.; Long, J. P.; Heintz, S. *J. Med. Chem.* 1973, 16, 287). $^1$H NMR (400 MHz, CDCl$_3$) δ 5.41 (br s, 2 H), 3.77 (m, 1 H), 3.58 (dd, J=11.7, 2.8 Hz, 1 H), 3.52 (dd, J=11.7, 6.9 Hz, 1 H), 1.02 (d, J=6.4 Hz, 3 H).

PREPARATION 54

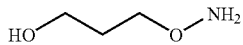

3-Aminooxy-propan-1-ol

3-Aminooxy-propan-1-ol was prepared by the literature procedure (Ludwig, B. J.; Reisner, D. B.; Meyer, M.; Powell, L. S.; Simet, L.; Stiefel, F. J. *J. Med. Chem.* 1970, 13, 60). $^1$H NMR (400 MHz, CDCl$_3$) δ 3.84 (t, J=5.8 Hz, 2 H), 3.74 (t, J=5.8 Hz, 2 H), 1.85 (quintet, J=5.8 Hz, 2 H).

PREPARATION 55

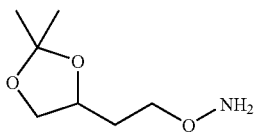

O-(2,2-Dimethyl-[1,3]dioxolan-4-ylethyl)-hydroxylamine

To a vigorously stirring suspension of 1,2,4-butanetriol (5.8 g, 54.6 mmol) in dichloromethane (20 mL) was added 2,2-dimethoxypropane (6.8 mL, 54.6 mmol) and catalytic p-toluenesulfonic acid. After 5 minutes, the solution became homogenous and was allowed to stir for an additional 30 minutes. The reaction mixture was then concentrated in vacuo to afford (2,2-Dimethyl-[1,3]dioxolan-4-yl)-ethanol (7.72 g, 96.7%). To a stirring solution of (2,2-Dimethyl-[1,3]dioxolan-4-yl)-ethanol (6.95 g, 47.5 mmol), triphenylphosphine (12.5 g, 47.5 mmol) and N-hydroxyphthalimide in freshly distilled tetrahydrofuran (200 mL) at 0° C. was slowly added (over 20 minutes) diethylazodicarboxylate. The dark red solution was allowed to stir for 2 hours at 0° C. and then allowed to warm to room temperature while stirring for 17 hours. The yellow solution was concentrated in vacuo and dissolved in chloroform (100 mL). The solids were filtered and filtrate concentrated. This filtration was repeated twice. The remaining yellow oil was purified on silica gel eluting with hexanes-ethyl acetate (4:1) to afford 2-[2-(2,2-Dimethyl-[1,3]dioxolan-4-yl)-ethoxy]-isoindole-1,3-dione (8.1 g, 58.7%). To a stirring solution of 2-[2-(2,2-Dimethyl-[1,3] dioxolan-4-yl)-ethoxy]-isoindole-1,3-dione (0.86 g, 2.95 mmol) in dichloromethane (10 mL) at 0° C. was added methylhydrazine (0.16 mL, 2.95 mmol). The resultant solution was allowed to warm to room temperature and stirred for 3 days. The resulting suspension was diluted with diethyl ether (20 mL) and filtered. The filtrate concentrated in vacuo to afford O-(2,2-dimethyl-[1,3]dioxolan-4-ylethyl)-hydroxylamine (0.36 g, 75.3%): $^1$H-NMR (400 MHz; CDCl$_3$) δ 4.18 (quint, 1H, J=5.9), 4.07 (dd, 1H, J=5.9, 7.8), 3.86 (t, 2H, J=6.2), 3.56 (t, 1H, J=7.6), 1.89 (m, 2H), 1.36 (s, 3H), 1.20 (s, 3H); MS(APCI+)=162.

PREPARATION 56

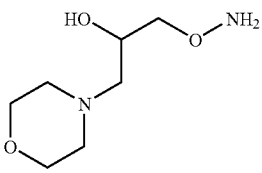

1-Aminooxy-3-morpholin-4-yl-propan-2-ol

Step A. Synthesis of 2-(2-hydroxy-3-morpholin-4-yl-propoxy)-isoindole-1,3-dione: Triethylamine (15.0 mL, 108 mmol) was added to a solution of N-hydroxyphthalimide (17.1 g, 105 mmol) and 4-Oxiranylmethyl-morpholine (14.3 g, 100 mmol) in anhydrous dimethylformamide (200 mL). The resultant deep red-colored reaction mixture was heated to 85° C. for 18 h. After removal of the solvent in vacuo, the residue was diluted with ethyl acetate (200 mL) and washed with water (3×100 mL) and brine (2×75 mL). The organics were dried over anhydrous magnesium sulfate and concentrated in vacuo. The residue was chromatographed on silica gel (chloroform-methanol, 19:1) to afford 2-(2-Hydroxy-3-morpholin-4-yl-propoxy)-isoindole-1,3-dione (7.96 g, 25% yield): $^1$H NMR (400 MHz, CDCl$_3$) δ 7.84 (m, 2 H), 7.77 (m, 2 H), 4.26 (dd, J=10.8, 3.4 Hz, 1 H), 4.18-4.10 (m, 2 H), 3.72 (m, 4 H), 2.70-2.47 (m, 6 H); MS (APCI+)=307.2.

Step B. Synthesis of 1-aminooxy-3-morpholin-4-yl-propan-2-ol: A solution of 2-(2-hydroxy-3-morpholin-4-yl-propoxy)-isoindole-1,3-dione (7.96 g, 26.0 mmol) in dichloromethane (50 mL) was chilled to 0° C. and treated with methylhydrazine (1.45 mL, 27.3 mmol). The reaction mixture was stirred 5 min at 0° C. and 2 h at ambient temperature. Ether (200 mL) was added, the heterogenous solution was filtered, and the collected precipitate was washed with ether (300 mL). The ethereal solutions were concentrated in vacuo, and the residue was chromatographed on silica gel. Elution with chloroform-methanol (4:1) afforded 1-aminooxy-3-morpholin-4-yl-propan-2-ol (3.21 g, 70% yield) as a colorless solid. Recrystallization (ether-dichloromethane) afforded colorless needles: mp 83-85° C.; $^1$H NMR (400 MHz, DMSO-d$_6$) δ 5.96 (br s, 2 H), 4.56 (d, J=4.4 Hz, 1 H), 3.81 (m, 1 H), 3.53 (apparent t, J=4.6 Hz, 4 H), 3.50-3.38 (m, 2 H), 2.41-2.30 (m, 4 H), 2.29-2.17 (m, 2 H). Anal. Calcd/found for C$_7$H$_{16}$N$_2$O$_3$: C, 47.71/47.54; H, 9.15/9.23; N, 15.90/15.65.

Preparations 57-62 were prepared by the general procedure of Preparation 56.

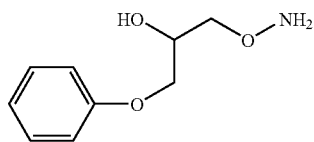

PREPARATION 57

1-Aminooxy-3-phenoxy-propan-2-ol m.p. 67.5° C.; $^1$H NMR (400 MHz, DMSO-d$_6$) δ 7.27 (m, 2H), 6.91 (m, 3 H), 6.06 (s, 2 H), 5.07 (d, J=3.7 Hz, 1 H), 4.02 (m, 1 H), 3.92 (dd, J=10.0, 4.3 Hz, 1 H), 3.84 (dd, J=10.0, 6.1 Hz, 1H), 3.59 (m, 2 H); MS (APCI+)=183.0.

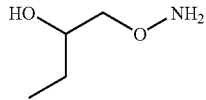

PREPARATION 58

1-Aminooxy-butan-2-ol $^1$H NMR (400 MHz, CDCl$_3$) δ 5.49 (br s, 2 H), 3.78 (m, 1 H), 3.65 (dd, J=11.2, 2.4 Hz, 1 H), 3.54-3.45 (m, 2 H), 1.42 (m, 2 H), 0.91 (t, J=7.6 hz, 3 H); MS (APCI+)=105.9.

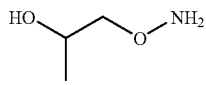

PREPARATION 59

1-Aminooxy-propan-2-ol

BP 85-87° C. @ 20 mm Hg; $^1$H NMR (400 MHz, DMSO-d$_6$) δ 5.96 (br s, 2 H), 4.58 (d, J=3.9 Hz, 1 H), 3.80 (m, 1 H), 3.41-3.28 (m, 2 H), 0.99 (d, J=6.4 Hz, 3 H).

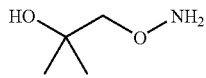

PREPARATION 60

1-Aminooxy-2-methyl-propan-2-ol $^1$H NMR (400 MHz, CDCl$_3$) δ 4.84 (br s, 2 H), 3.50 (s, 2 H), 1.15 (s, 6 H).

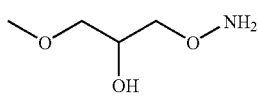

PREPARATION 61

1-Aminooxy-3-methoxy-propan-2-ol $^1$H NMR (400 MHz; DMSO-d$_6$) δ 5.95 (2H, br, NH$_2$), 4.76 (1H, br, —OH), 3.72-3.78(1H, m), 3.36-3.46 (2H, m), 3.19-3.26 (2H, m), 3.19 (3H, s); MS (APCI+)=121.9.

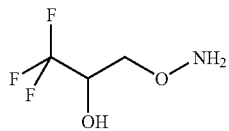

PREPARATION 62

1-Aminooxy-4,4,4-trifluoro-butan-2-ol $^1$H NMR (400 MHz; CDCl$_3$) δ 5.40 (2H, br, NH$_2$), 3.60-4.10 (3H, m); MS (APCI+)=145.9.

PREPARATION 63 trans-(2-Aminooxymethyl-cyclopropyl)-methanol

Step A: To a suspension of lithium aluminum hydride (7.6 g, 0.3 mol) in tetrahydrofuran (150 ml) at 0° C. was added diethyl trans-1,2-cyclopropanedicarboxylate (18.6 g, 0.1 mol) dropwise over a period of 15 minutes. The resultant reaction mixture was removed from the cooling bath and heated at reflux for 20 h. The reaction mixture was cooled to 0° C. and quenched cautiously with water (7.7 mL), 10% aqueous sodium hydroxide (7.7 mL), and water (23 mL). The resultant solids were filtered and the filtrate was dried over sodium sulfate and concentrated under reduced pressure. The residual oil was distilled under reduced pressure to afford trans 2-hydroxymethyl-cyclopropyl)-methanol (7.5 g, 73% yield) as a colorless liquid: b.p. 142-144° C. @ 20 mm Hg.

Step B: A solution of trans 2-hydroxymethyl-cyclopropyl)-methanol (7.5 g, 73 mmol), triphenylphosphine (19.3 g, 73 mmol), N-hydroxyphthalimide (73 mmol) in anhydrous tetrahydrofuran (200 mL) was chilled to 0° C. and treated with diethyl azodicarboxylate. The resulting mixture was allowed to warm naturally to room temperature and stirred overnight. The reaction mixture was concentrated to about ⅛ volume and filtered. The filtered precipitate was washed with ether and the combined washings and filtrate were concentrated in vacuo. The crude product was dissolved in dichloromethane. Methylhydrazine (73 mmol) was added and the reaction mixture was stirred overnight at ambient temperature. The resultant precipitate was removed by filtration. Concentration of the filtrate afforded additional precipitate which was also removed by filtration. The final filtrate was concentrated and distilled under reduced pressure to afford trans-(2-aminooxymethyl-cyclopropyl)-methanol (3.84 g, 45% yield) as a colorless oil: bp 183° C. @ 20 mm Hg; $^1$H NMR (400 MHz; CDCl$_3$) δ 3.80 (br, NH$_2$), 3.50-3.70 (2H, m), 3.30-3.42 (2H, m), 0.95-1.15 (2H, m), 0.40-0.60 (2H, m); MS (APCI+)= 117.9

PREPARATION 64

(1-Aminooxymethyl-cyclopropyl)-methanol

Step A: Diethyl 1,1-cyclopropanedicarboxylate (25 g, 0.13 mol) was added dropwise over 1 h to a stirring suspension of lithium aluminum hydride in tetrahydrofuran (150 mL) at 0° C. After addition was complete, the reaction mixture was heated at reflux for additional 18 h. The mixture was cooled to 0° C. and sequentially treated with water (10 g), then 10% aqueous sodium hydroxide (10 g) and water (30 g). The mixture was filtered, and the filtrate was dried over potassium carbonate and concentrated under reduced pressure. Distillation provided (1-hydroxymethyl-cyclopropyl)-methanol (8.8 g, 66% yield) as a colorless viscous oil: $^1$H NMR (400 MHz; CDCl$_3$) δ 3.57 (4H, s), 3.26 (2H, s), 0.48 (4H, s).

Step B: (1-Hydroxymethyl-cyclopropyl)-methanol (4.08 g, 0.04 mol), N-hydroxyphthalimide (6.53 g, 0.04 mol) and triphenylphosphine (10.50 g, 0.04 mol) were combined in anhydrous tetrahydrofuran (100 mL) and stirred at 0° C. for 1.5 hours. Diethyl azodicarboxylate (6.97 g, 0.04 mol) was added at 0° C. and the reaction mixture was stirred at room temperature overnight. Repeated concentration of the reaction mixture from chloroform and filtration of the resulting precipitate (triphenylphosphine oxide) afforded the crude product which was further purified by silica gel chromatography. Elution with hexane/ethyl acetate (3:2) provided 2-(1-Hydroxymethyl-cyclopropylmethoxy)-isoindole-1,3-dione (5.63 g, 57% yield) as a white solid: $^1$H NMR (400 MHz; CDCl$_3$) δ 7.82-7.85 (2H, m), 7.74-7.78 (2H, m), 4.19 (2H, s), 3.72 (2H, s), 0.63 (4H, s)

Step C: To a stirring solution of 2-(1-Hydroxymethyl-cyclopropylmethoxy)-isoindole-1,3-dione (5.63 g, 22.8 mmol) in dichloromethane (60 ml) at 0° C. was added methylhydrazine (1.1 g, 23.8). The reaction mixture was stirred at room temperature overnight, filtered and concentrated under reduced pressure. Distillation afforded pure 1-Aminooxymethyl-cyclopropyl)-methanol (2.9 g, 71% yield) as a colorless oil: bp 140° C. @ 20 mm Hg; $^1$H NMR (400 MHz; CDCl$_3$) δ 4.00 (br s, NH$_2$), 3.61 (2H, s), 3.43 (2H, s), 0.49 (4H, s); MS (APCI+)=117.9.

PREPARATION 65

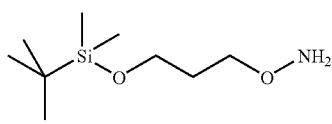

O-[3-(tert-Butyl-dimethyl-silanyloxy)-propyl]-hydroxylamine

Step A: Diisopropylethylamine (43 mL, 246 mmol) was added to a stirring solution of N-hydroxphthalimide (20.6 g, 123 mmol) in dimethylformamide (95 mL). After 5 minutes, 3-bromopropanol (11.5 mL, 127 mmol) was added and the reaction mixture was heated to 80° C. for 18 h. The cooled solution was diluted with ethyl acetate (700 mL) and was washed with water (4×500 mL) and saturated brine (2×500 mL), dried over sodium sulfate and concentrated to an oil that solidified on standing to afford 2-(3-hydroxy-propoxy)-isoindole-1,3-dione (17.5 g, 65% yield) as a tan-colored solid: $^1$H NMR (400 MHz, CDCl$_3$) δ 7.81 (m, 2H), 7.74 (m, 2H), 4.36 (t, 2H, J=5.6 Hz), 3.92 (t, 2H, J=5.9 Hz), 1.98 (quintet, 2H, J=5.9 Hz).

Step B: To a solution of 2-(3-hydroxy-propoxy)-isoindole-1,3-dione (17.5 g, 79.1 mmol) and imidazole (5.92 g, 86.1 mmol) in dichloromethane (200 mL) was added tert-butyldimethylsilyl chloride (13.2 g, 86.1 mmol). After 30 min, the reaction was transferred to a separatory funnel and shaken with dilute aqueous hydrochloric acid (400 mL). The organic layer was washed with saturated aqueous sodium bicarbonate, dried over magnesium sulfate and concentrated in vacuo to afford 2-[3-(tert-Butyl-dimethyl-silanyloxy)-propoxy]-isoindole-1,3-dione (26.3 g, 99% yield) as a viscous liquid: $^1$H NMR (400 MHz, CDCl$_3$) δ 7.76 (m, 2H), 7.67 (m, 2H), 4.25 (t, 2H, J=5.9 Hz), 3.77 (t, 2H, J=6.0 Hz), 1.91 (quintet, 2H, J=6.1 Hz), 0.82 (s, 9H), 0.00 (s, 6H).

Step C: A solution of 2-[3-(tert-butyl-dimethyl-silanyloxy)-propoxy]-isoindole-1,3-dione (26.3 g, 78.3 mmol) in dichloromethane (120 mL) was cooled to 0° C. and treated with methylhydrazine (16.1 g, 78.3 mmol). The reaction mixture was stirred for 30 min at 0° C. and filtered. The filtrate was concentrated under reduced pressure, redissolved in ether, and refrigerated (4° C.) overnight. The resultant crytalline material was removed by filtration and the filtrate was concentrated under reduced pressure to afford O-[3-(tert-butyl-dimethyl-silanyloxy)-propyl]-hydroxylamine (15.95 g, 99% yield) as a colorless oil: $^1$H NMR (400 MHz, CDCl$_3$) δ 4.69 (br s, 2 H), 3.74 (t, J=6.3 Hz, 2 H), 3.67 (t, J=6.3 Hz, 2 H), 1.78 (quintet, J=6.3 Hz, 2 H), 0.88 (s, 9 H), 0.00 (s, 6 H); MS (APCI+)=206.1. Anal. Calcd./Found for C$_9$H$_{23}$NO$_2$Si: C, 52.64/52.22; H, 11.29/10.94; N, 6.82/6.46.

PREPARATION 66

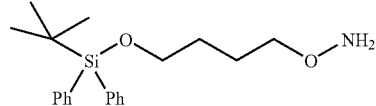

O-[4-(tert-butyl-diphenyl-silanyloxy)-butyl]-hydroxylamine

Step A: To a solution of 1,4-butanediol (5 g, 55 mol) in dichlormethane (10 mL) containing diisopropylethylamine (10 mL) was added tert-butylchlorodiphenylsilane (5 mL, 18 mmol) dropwise under N$_2$ atmosphere at 18° C. over 2 h. The resultant solution was stirred at room temperature for 4 hours and concentrated under reduced pressure. Purification by column chromatography with hexane/ethyl acetate (1/1) gave 4-(tert-butyl-diphenyl-silanyloxy)-butan-1-ol (10.2 g, 85% yield) as colorless oil: $^1$H NMR (400 MHz, CDCl$_3$) δ 7.62-7.71 (4H, m); 7.32-7.43 (6H, m), 3.63-3.69 (4H, m), 1.83 (1H, br s), 1.59-1.71 (4H, m), 1.03 (9H, s).

Step B: 4-(tert-Butyl-diphenyl-silanyloxy)-butan-1-ol (10.0 g, 30.5 mmol), triphenylphosphine (8.0 g, 30 mmol), and N-hydroxyphthalimide (4.97 g, 30.5 mmol) were combined in anhydrous tetrahydrofuran (200 ml) att 0° C. and the resultant solution was stirred at 0° C. for 1 hour. Diethyl azodicarboxylate (5.31 g, 30.5 mmol) was added at 0° C., and the reaction mixture was allowed to gradually warm to room temperature and stirred overnight. The reaction mixture was concentrated under reduced pressure and the residue was dissolved in chloroform. Precipitation ensued, and the white solid was removed by filtration. The filtrate was concentrated and purified with column chromatography (hexane/ethyl acetate (3/1)) to afford 2-[4-(tert-butyl-diphenyl-silanyloxy)-butoxy]-isoindole-1,3-dione (11.06 g, 77% yield) as colorless crystals: $^1$H NMR (400 MHz, DMSO-d$_6$) δ 7.84 (4H, s), 7.59 (4H, dd, J=7.6, 1.0 Hz), 7.39-7.43 (6H, m), 4.13 (2H, t, J=6.4 Hz), 3.68 (2H, t, J=5.8 Hz), 1.67-1.78 (4H, m), 0.95 (9H, s).

Step C: A solution of 2-[4-(tert-butyl-diphenyl-silanyloxy)-butoxy]-isoindole-1,3-dione (11.1 g, 23.4 mmol) in dichloromethane (100 ml) was treated with methylhydrazine. The reaction mixture was stirred overnight and was filtered. The filtrate was concentrated and purified by column chromatography [hexane/ethyl acetate (3.5/1)] to afford O-[4-(tert-butyl-diphenyl-silanyloxy)-butyl]-hydroxylamine (7.2 g, 90% yield) as a colorless oil: $^1$H NMR (400 MHz, CDCl$_3$) δ 7.62-7.66(4H, m), 7.33-7.42 (6H, m), 3.64-3.68(4H), 1.54-1.70 (4H, m), 1.02 (9H, s); MS (APCI+)=344.2.

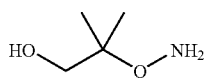

PREPARATION 67

2-Aminooxy-2-methyl-propan-1-ol

Step A: To a stirring solution of t-butyl-N-hydroxycarbamate (2.38 g, 17.87 mmol) in absolute ethanol (50 mL) is added potassium hydroxide (1.2 g, 21.45 mmol) and ethyl-2-bromoisobutyrate (3.15 mL, 21.45 mmol). The reaction mixture was heated at reflux for 17 hours. The solids were filtered off and filtrate concentrated. The afforded residue was partitioned between diethyl ether and water. The aqueous layers were extracted twice with ether. The organic layers were collected and dried over Na$_2$SO$_4$, filtered and concentrated in vacuo, affording 2-Boc-aminooxy-2-methyl-propionic acid ethyl ester as a clear oil (4.2 g, 95%): $^1$H NMR (400 MHz; CDCl$_3$) δ 7.34 (bs, 1H), 4.16 (q, 2H, J=13.9, 6.6), 1.45 (s, 6H), 1.42 (s, 9H), 1.16 (t, 3H, J=7.1); MS (APCI–)=246.0.

Step B: 2-Boc-aminooxy-2-methyl-propionic acid ethyl ester (2.54 g, 10.27 mmol) was dissolved in freshly distilled THF (100 mL), cooled to 0° C. and charged with 2.0 M lithium borohydride solution (10.3 mL, 20.54 mmol) in THF. The ice bath was removed and reaction was heated to reflux. After 17 hours, the reaction was cooled to 0° C. and quenched with methanol and concentrated in vacuo. The afforded residue was partitioned between ethyl acetate and 1M sodium hydroxide solution. The organic layers were washed twice with 1M sodium hydroxide solution, twice with saturated sodium chloride solution, collected and dried over Na$_2$SO$_4$, filtered and concentrated in vacuo, affording 2-Boc-aminooxy-2-methyl-propan-1-ol (1.50 g, 71%) as a white solid: $^1$H NMR (400 MHz; CDCl$_3$) δ 6.84 (bs, 1H), 3.37 (s, 2H), 1.45 (s, 9H), 1.18 (s, 6H); MS (APCI–)=204.0.

STEP C: 2-Boc-aminooxy-2-methyl-propan-1-ol (0.21 g, 1.02 mmol) was dissolved in methanol (5 mL) and charged with anhydrous hydrogen chloride gas for 1 minute. After stirring for 1 hour, the reaction mixture was concentrated in vacuo and to the resulting residue was added diethylether, affording white solids. The solids were washed several times with diethylether and dried in vacuo to afford 2-aminooxy-2-methyl-propan-1-ol as the hydrogen chloride salt (0.091 g, 63%). $^1$H NMR (400 MHz; CDCl$_3$) δ 3.61 (s, 2H), 1.16 (s, 6H); MS (APCI+)=105.9.

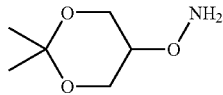

PREPARATION 68

O-(2,2-Dimethyl-[1,3]dioxan-5-yl)-hydroxylamine

Step A: 2,2-Dimethyl-[1,3]dioxan-5-ol was prepared as described previously (Forbes, D. C. et. al.; *Synthesis;* 1998, 6, 879-882). $^1$H NMR (400 MHz; DMSO-d$_6$) δ 4.91 (d, 1H, J=5.1), 3.70-3.75 (m, 2H), 3.41-3.46 (m, 3H), 1.30 (s, 3H), 1.24 (s, 3H); MS (APCI+)=132.9.

Step B: To a stirring solution of 2,2-dimethyl-[1,3]dioxan-5-ol (1.50 g, 11.35 mmol), N-hydroxyphthalimide (1.85 g, 11.35 mmol) and triphenylphosphine (2.98 g, 11.35 mmol) in anhydrous tetrahydrofuran (30 mL) at 0° C. was added diethyl azodicarboxylate (2.3 mL, 14.75 mmol). The resultant solution was allowed to warm to room temperature. After stirring for 3 hours, the mixture was concentrated in vacuo and charged with chloroform affording white solids. The solids were filtered off and filtrate was collected and concentrated. The residue was purified via silica column chromatography (4:1 hexanes/ethyl acetate) affording 2-(2,2-dimethyl-[1,3]dioxan-5-yloxy)-isoindole-1,3-dione as clear crystals (1.74 g, 55% over 2 steps): $^1$H NMR (400 MHz; DMSO-d$_6$) δ 7.83 (s, 4H), 4.11-4.12 (m, 1H), 4.04-4.09 (m, 2H), 3.92-3.96 (m, 2H), 1.32 (s, 3H), 1.25 (s, 3H); MS (APCI+)=278.0.

Step C: To a stirring solution of 2-(2,2-dimethyl-[1,3]dioxan-5-yloxy)-isoindole-1,3-dione (1.72 g, 6.20 mmol) in dichloromethane (15 mL) at 0° C. under nitrogen was added methylhydrazine (0.36 mL, 6.82 mmol) and allowed to warm to room temperature. After stirring for two hours the reaction mixture was concentrated in vacuo and charged with diethylether. The solids were filtered off and the filtrate was collected and concentrated to afford O-(2,2-dimethyl-[1,3]dioxan-5-yl)-hydroxylamine as a yellow oil (0.97 g, 100%). $^1$H NMR (400 MHz; DMSO-d$_6$) δ 5.98 (bs, 2H), 3.84-3.87 (m, 2H), 3.66-3.68 (m, 2H), 3.30-3.35 (m, 1H), 1.29 (s, 3H), 1.22 (s, 3H); MS (APCI+)=147.9.

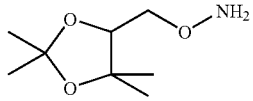

PREPARATION 69

O-(2,2,5,5-Tetramethyl-[1,3]dioxolan-4-ylmethyl)-hydroxylamine

Step A: To a stirring solution of N-hydroxyphthalimide (Aldrich, 1.63 g, 10.0 mmol) in anhydrous ethanol (50 mL) was added 1-bromo-3-methyl-but-2-ene (Aldrich, 1.4 mL, 12.0 mmol) and potassium hydroxide (0.67 g, 12.0 mmol). After the reaction was allowed to stir at 50° C. for 4 hours, it was concentrated in vacuo and then dissolved in ethyl acetate and partitioned with water. The organic layer was washed twice with water, twice with saturated sodium chloride solution, collected and dried over Na$_2$SO$_4$, filtered and concentrated in vacuo, affording a white solid. The collected solid was purified via silica column in 10% methanol in dichloromethane to afford 2-(3-methyl-but-2-enyloxy)-isoindole- 1,3-dione (0.53 g, 23%): $^1$H NMR (400 MHz; DMSO-$d_6$) δ 7.81 (s, 4H), 5.38 (t, 1H, J=1.5), 4.57 (d, 2H, J=7.6). 1.67 (s, 3H), 1.62 (s, 3H); MS (APCI+)=232.0.

Step B: 2-(3-Methyl-but-2-enyloxy)-isoindole-1,3-dione was dissolved in a t-butanol/THF/H$_2$O solution (10 mL/3 mL/1 mL) and charged with N-methylmorpholine N-oxide (0.085 g, 0.73 mmol) and a catalytic amount of potassium osmate dihydrate. After stirring for 17 hours the reaction was diluted with a saturated solution of sodium metabisulfate and partitioned with ethyl acetate. The organic layer was washed twice with saturated solution of sodium metabisulfate, twice with saturated sodium chloride solution, collected and dried over Na$_2$SO$_4$, filtered and concentrated in vacuo affording 2-(2,3-dihydroxy-3-methyl-butoxy)-isoindole-1,3-dione as a clear oil, which was charged with dichloromethane (10 mL), 2,2-dimethoxypropane (0.12 mL, 0.75 mmol) and a catalytic amount of p-toluenesulfonic acid. After stirring for 17 hours, the reaction was concentrated in vacuo, and partitioned between ethyl acetate and water. The organic layer was washed twice with water, once with saturated sodium chloride solution, collected and dried over Na$_2$SO$_4$, filtered and concentrated in vacuo, affording 2-(2,2,5,5-tetramethyl-[1,3]dioxolan-4-ylmethoxy)-isoindole-1,3-dione as a light brown solid (0.158 g, 77.1%): $^1$H NMR (400 MHz; DMSO-$d_6$) δ 7.82 s, (4H), 4.12-4.26 (m, 2H), 4.04-4.07 (m, 1H), 1.22 (s, 9H), 1.17 (s, 3H), 0.97 s(3H).

Step C: 2-(2,2,5,5-tetramethyl-[1,3]dioxolan-4-ylmethoxy)-isoindole-1,3-dione (0.158 g, 0.52 mmol) was dissolved in dichloromethane (3 mL), cooled to 0° C., and charged with methylhydrazine (30 μL, 0.57 mmol). The ice bath was removed and the reaction was allowed to stir at ambient temperature for 1 hour. The reaction mixture was diluted with diethylether and the solids were filtered off and filtrate concentrated in vacuo to afford O-(2,2,5,5-tetramethyl-[1,3]dioxolan-4-ylmethyl)-hydroxylamine as a yellow oil (0.042 g, 46%). $^1$H NMR (400 MHz; DMSO-$d_6$) δ 6.06 (bs, 2H), 3.84-3.87 (m, 1H), 3.50-3.59 (m, 2H), 1.26 (s, 3H), 1.19 (s, 3H), 1.16 (s, 3H), 0.94 (s, 3H); MS (APCI+)=176.9.

PREPARATION 70

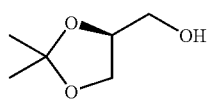

(S)-(+)-(2,2-Dimethyl-[1,3]dioxolan-4-yl)-methanol

Step A: To a stirring suspension of D-Mannitol (1.82 g, 10.0 mmol) in tetrahydrofuran (21 mL) and dimethylformamide (9 mL) was added p-toluenesulfonic acid monohydrate (0.02 g, 0.1 mmol) at ambient temperature, followed by 2,2-dimethoxypropane (2.8 ml, 0.023 mole). The reaction mixture was stirred for 18 h at room temperature, then additional 2,2-dimethoxypropane (0.3 ml, 2.4 mmol) was added. The suspension was heated to 40-45° C., and stirred for 2 hrs. Sodium bicarbonate (1.8 g, 0.016 mol) was added to neutralize the acid and the mixture was stirred for 30 minutes. The excess Na$_2$CO$_3$ was filtered and washed with tetrahydrofuran (5 ml). The filtrate was concentrated. To the remaining light yellow oil was added toluene (15 mL) and the mixture was stirred at 3-5° C. until a light-yellow gelatinous solid formed. The solid was filtered and washed with hexane (2×5 mL). The product was dried in a vacuum oven for 18 h to give 1,2:5,6-Di-O-isopropylidene-D-mannitol (1.24 g, 47.3%) as an off-white solid, mp 110-113° C.

Step B: To a solution of 1,2:5,6-di-O-isopropylidene-D-mannitol (50 g, 0.191 mol) in water (700 mL), was added solid sodium bicarbonate (20 g). The resultant solution was stirred until all the solid dissolved, and then cooled in an ice-water bath. Solid sodium periodate (81.5 g, 0.381 mol) was slowly added to the solution portionwise. Gas evolution observed. The white mixture was stirred at ambient temperature for 2 hrs. Solid sodium chloride (30 g) was added, and the mixture was stirred for 15 min. The white solid was filtered. The filtrate was cooled in an ice-water bath. Solid sodium borohydride was added slowly. Gas bubble evolved. The mixture was warmed to ambient temperature, and stirred overnight. The milky mixture turned to a clear solution. The aqueous solution was extracted with dichloromethane (3×). The organic solution was washed with brine, and dried over magnesium sulfate. The solvent was removed in vacuo to give (S)-(+)-(2,2-Dimethyl-[1,3]dioxolan-4-yl)-methanol as a colorless oil, which was dried under high vacuum at ambient temperature overnight, 34.82 g (60%); MS (APCI+)=133 (M$^+$+1).

PREPARATION 71

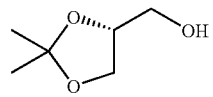

(R)-(+)-(2,2-Dimethyl-[1,3]dioxolan-4-yl)-methanol

Step A: To a solution of L-ascorbic acid (83.9 g, 0.477 mole) in water (600 mL) was added Pd/C (10%, 8.3 g). The mixture was subjected to hydrogenation in a Parr hydrogenator at 48 psi, 18° C. for 62 hrs. The reaction mixture was filtered and the filtrate was concentrated in vacuo to afford L-gulonic γ-lactone (81.0 g, 96%) as an off-white solid, after drying at 50° C. in a vacuum oven for 18 hrs: m.p. 182-184° C.

Step B: L-Gulonic γ-lactone (25.0 g, 140.3 mmol) was dissolved in mixture of tetrahydrofuran (140 mL) and dimethylformamide (200 mL). p-Toluenesulfonic acid monohydrate (2.67 g, 14.0 mmol) was added and the reaction mixture was cooled to 0-5° C. in an ice-water bath. 2,2-dimethoxypropane (22.4 mL, 182.4 mmol) was added dropwise and the reaction mixture was stirred at ambient temperature for 18 hours. The mixture was neutralized with solid sodium carbonate (24.0 g), and stirred for 1 hour. The solid was filtered and washed with tetrahydrofuran. The THF was removed under vacuo, and DMF by distillation under high vacuum. The resulting orange solid was triturated with toluene (300 mL), filtered, washed with toluene (20 mL), and dried in a vacuum oven at 40° C. for 3 days, to yield 5,6-Isopropylidene-L-gulonic Acid γ-lactone (28.9 g, 94%) as a pale orange solid: mp 155-158° C.; MS(APCI+)=219.0 (M$^+$+1).

Step C: To a stirring suspension of 5,6-O-isopropylidene-L-gulono-1,4-lactone (15.16 g, 69.5 mmol) in water (0.3 L) was added solid sodium periodate in small portions at 3-5° C. The pH of the mixture was adjusted to 5.5 with 1N aqueous sodium hydroxide. The suspension was stirred for 2 hrs at ambient temperature, then saturated with sodium chloride (20.0 g) and filtered. To the filtrate, at 3-5° C., was added sodium borohydride (10.5 g, 0.278 mol) in small portions. The reaction mixture was stirred for 18 h at ambient temperature. Acetone (100 mL) was added to destroy the excess of sodium borohydride, and the stirring was continued for 30 minutes. The acetone was removed under reduced pressure and the aqueous residue was extracted with dichloromethane (3×300 mL) and EtOAc (3×300 mL). The combined organic layers were dried over magnesium sulfate, filtered, and evaporated to give (R)-(+)-(2,2-Dimethyl-[1,3]dioxolan-4-yl)-methanol (5.07 g, 55.7%) as a colorless clear liquid: MS(APCI+)=132.9 (M++1).

PREPARATION 72

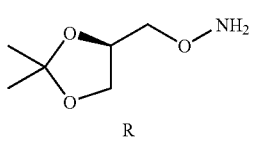 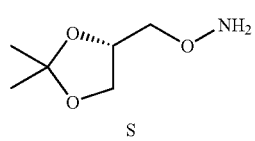

R          S

Preparation of (R)-O-(2,2-dimethyl-[1,3]dioxolan-4-ylmethyl)-hydroxylamine and (S)-O-(2,2-dimethyl-[1,3]dioxolan-4-ylmethyl)-hydroxylamine (R)-O-(2,2-dimethyl-[1,3]dioxolan-4-ylmethyl)-hydroxylamine and (S)-O-(2,2-dimethyl-[1,3]dioxolan-4-ylmethyl)-hydroxylamine were prepared from (S)-(+)-(2,2-dimethyl-[1,3]dioxolan-4-yl)-methanol and (R)-(−)-(2,2-dimethyl-[1,3]dioxolan-4-yl)-methanol respectively by the following procedure:

Step A: A 3-L round-bottomed flask equipped with mechanical stirrer and additional funnel was charged with N-hydroxyphthalimide (68.0 g, 0.416 mol) and tetrahydrofuran (1.2 L) under nitrogen atmosphere. To this solution was added triphenylphosphine (109.2 g, 0.416 mol) and (R)- or (S)-(2,2-dimethyl-[1,3]dioxolan-4-yl)-methanol (55.0 g, 0.416 mol). The mixture was cooled to 3-5° C. and diethyl azodicarboxylate (85.2 mL, 0.541 mol) was added dropwise, while keeping the inner temperature below 15° C. The reaction mixture was warmed to ambient temperature, and stirred for 18 hrs. The tetrahydrofuran was evaporated under reduced pressure. To the remaining orange solid was added dichloromethane (0.5 L) and the mixture was stirred for 1 h. The white solid (Ph$_3$PO) was filtered and washed with dichloromethane (0.1 L). The solvent was removed and ethanol (0.5 L) was added to the resulting solid. The mixture was stirred for 2 h at 3-5° C. The white solid was filtered, washed with a small amount of cold EtOH and dried in vacuum oven at 40° C. to give (S)- or (R)-2-(2,2-Dimethyl-[1,3]dioxolan-4-ylmethoxy)-isoindole-1,3-dione (112.5 g, 97%) as a white solid: $^1$H NMR (CDCl$_3$): δ 1.33 (s, 3H), 1.99 (s, 3H), 3.96 (m, 1H), 4.15 (m, 2H), 4.30 (m, 1H), 4.48 (m, 1H), 7.59 (m, 2H), 7.84 (m, 2H); MS (APCI+)=278 (M++1).

Step B: To a stirring solution of (S)- or (R)-2-(2,2-Dimethyl-[1,3]dioxolan-4-ylmethoxy)-isoindole-1,3-dione (74.9 g, 0.27 mol) in dichloromethane (480 mL) at 3-5° C. was added methylhydrazine (15.8 mL, 0.29 mole) dropwise. The color of the suspension turned from yellow to white. The cooling bath was removed and the mixture was stirred for 2 hrs at ambient temperature. The resulting suspension was concentrated on a rotary evaporator. To the white solid was added ether (0.5 L) and the resulting mixture was stirred for 1.5 h at ambient temperature. The white precipitate was filtered and washed with ether (0.2 L). The filtrate was concentrated on rotary evaporator to give (S)- or (R)-O-(2,2-dimethyl-[1,3]dioxolan-4-ylmethyl)-hydroxylamine (39.0 g, 98.3%): $^1$H NMR (CDCl$_3$): δ 1.35 (s, 3H), 1.42 (s, 3H), 3.73 (m, 3H), 4.05 (m, 1H), 4.33 (m, 1H), 5.39 (m, 2H); MS (APCI+)=148.1 (M++1)

PREPARATION 73

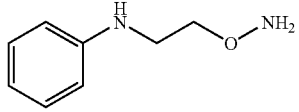

O-(2-Phenylamino-ethyl)-hydroxylamine: hydrochloride

O-(2-Phenylamino-ethyl)-hydroxylamine was prepared from 2-Phenylamino-ethanol by the general procedure of Preparation 48 and was isolated as the hydrochloride salt by precipitation from etheral hydrogen chloride. $^1$H NMR (DMSO-d$_6$): δ 7.12 (t, J=7.7 Hz, 2 H), 6.72-6.61 (m, 3 H), 4.16 (t, J=5.4 Hz, 2 H), 3.35 (t, J=5.4 Hz, 2 H); MS (APCI+) =153.1 (M++1).

PREPARATION 74

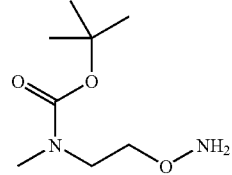

(2-Aminooxy-ethyl)-methyl-carbamic acid tert-butyl ester

Step A: (2-Hydroxy-ethyl)-methyl-carbamic acid tert-butyl ester was prepared as previously described: Mewshaw, R. E.; et. al. *J. Med. Chem.* 1999, 42, 2007.

Step B: Diethylazodicarboxylate was added dropwise over 45 min to a stirring solution of (2-hydroxy-ethyl)-methyl-carbamic acid tert-butyl ester (7.10 g, 40.5 mmol), N-hydroxyphthalimide (7.17 g, 44.0 mmol) and triphenylphosphine (11.5 g, 43.8 mmol) in tetrahydrofuran (150 mL). The resultant reaction mixture was stirred 22 h at ambient temperature and was concentrated in vacuo to a thick oil. Chloroform (200 mL) was added and the resultant solution was chilled to affect crystallization of diethyl 1,2-hydrazaine dicarboxylate. The precipitate was filtered and the filtrate was concentrated and further diluted with hexanes. A single crystal of triphenylphosphine oxide was added. The resultant crystals of triphenylphoshine oxide were removed by filtration and the filtrate was concentrated in vacuo and chromatographed on silica gel to afford [2-(1,3-dioxo-1,3-dihydro-isoindol-2-yloxy)-ethyl]-methyl-carbamic acid tert-butyl ester (12.8 g, 98% yield) as a colorless oil: $^1$H NMR (400 MHz, DMSO-d$_6$) δ 7.86 (bs, 4 H), 8.55 (bs, H), 4.24 (t, J=5.5 Hz, 2 H), 3.50 br t, J=5.4 Hz, 2 H), 2.92 and 2.88 (br s, 3 H), 1.39 and 1.36 (br s, 9 H).

Step C: A solution of [2-(1,3-dioxo-1,3-dihydro-isoindol-2-yloxy)-ethyl]-methyl-carbamic acid tert-butyl ester (4.50 g, 14.0 mmol) in dichloromethane (40 mL) was treated with methylhydrazine (0.78 mL, 14.7 mmol) and the reaction mixture was stirred 6 h at ambient temperature. Diethyl ether (80 mL) was added and the heterogeneous solution was allowed to stand overnight. The precipitate was removed by filtration and was washed with ether (80 mL). The filtrate was further concentrated and the resultant precipitate was filtered and the second filtrate concentrated to afford (2-Aminooxy-ethyl)-methyl-carbamic acid tert-butyl ester (2.83 g) as a viscous oil: ¹H NMR (400 MHz, CDCl₃) δ 3.73 (t, J=5.2 Hz, 2 H), 5.45 (br s, NH₂), 3.46 and 3.42 (br s, 2 H), 2.86 br s, 3 H), 1.25 (br s, 9 H); MS (APCI+)=191.1.

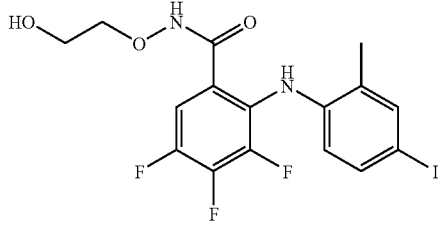

EXAMPLE 1

3,4,5-Trifluoro-N-(2-hydroxy-ethoxy)-2-(4-iodo-2-methyl-phenylamino)-benzamide

Step A: To a solution comprised of 2-(4-iodo-2-methyl-phenylamino)-3,4,5-trifluoro-benzoic acid (3.60 g, 8.84 mmol), O-(2-vinyloxyethyl)hydroxylamine (1.09 g, 10.5 mol) and diisopropylethylamine (2.80 mL, 16.0 mmol) in dichloromethane (50 mL) was added benzotriazole-1-yl-oxy-tris-pyrrolidino-phosphonium-hexafluorophosphate (5.26 g, 10.1 mmol). The resultant solution was stirred 90 min at ambient temperature. The reaction mixture was diluted with ether (100 mL) and washed with water (3×50 mL) and saturated brine (50 mL). The organics were dried over anhydrous magnesium sulfate and concentrated in vacuo. The residue was purified by silica gel chromatography to afford 2-(4-iodo-2-methyl-phenylamino)-3,4,5-trifluoro-N-(2-vinyloxyethoxy)benzamide (3.17 g, 73%) as a pale-yellow foam.

Step B: A solution of 2-(4-iodo-2-methyl-phenylamino)-3,4,5-trifluoro-N-(2-vinyloxyethoxy)-benzamide (3.00 g, 6.09 mmol) in ethanol (80 mL) was treated with 1 M aqueous hydrochloric acid (16 mL, 16 mol). The resultant solution was stirred for 2.5 h at ambient temperature. Water (50 mL) was added and the slurry was filtered. The solids were washed with ethanol-water (1:1, 150 mL) and recrystallized from methanol-acetone to afford N-(2-hydroxyethoxy)-2-(4-iodo-2-methyl-phenylamino)-3,4,5-trifluoro-benzamide (2.12 g, 75%): m.p. 205-207° C. (dec); ¹H NMR (400 MHz, DMSO-d₆) δ 11.85 (br s, 1 H), 8.13 (s, 1 H), 7.54 (dd, J=8.9, 8.7 Hz, 1 H), 7.47 (d, J=1.0 Hz, 1 H), 7.32 9d, J=8.5 Hz, 1 H), 6.41 (dd, J=8.1, 5.0 Hz, 1 H), 4.69 (br s, 1 H), 3.79 (br s, 2 H), 3.52 (br s, 2 H), 2.20 (s, 3 H); MS (APCI+)=467.1; MS (APCI-)= 465.1; Anal. Calcd/found for C₁₆H₁₄F₃IN₂O₃: C, 41.22/41.28; H, 3.03/2.91; N, 6.01/5.79.

Examples 2-11 were prepared by the general procedure of Example 1.

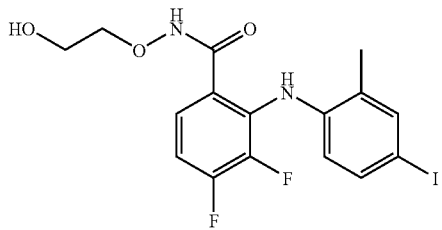

EXAMPLE 2

3,4-Difluoro-N-(2-hydroxy-ethoxy)-2-(4-iodo-2-methyl-phenylamino)-benzamide

MP 181-183° C.; ¹H NMR (400 MHz, DMSO-d₆) δ 11.87 (s, 1 H), 8.50 (s, 1 H), 7.49 (s, 1H), 7.40 (dd, 7.3, 6.6 Hz, 1 H), 7.35 (dd, J=8.3, 1.7 Hz, 1 H), 7.16 (dt, J=7.3, 9.3 Hz, 1 H), 6.46 (dd, J=8.5, 5.6 Hz, 1 H), 4.70 (br s, 1H), 3.81 (br s, 2 H), 3.54 (br s, 2 H), 2.21 (s, 3 H); MS (APCI+)=449.1; MS (APCI-)=447.1; Anal. Calcd/found for C₁₆H₁₅F₂IN₂O₃: C, 42.88/42.94; H, 3.37/3.39; N, 6.25/6.05.

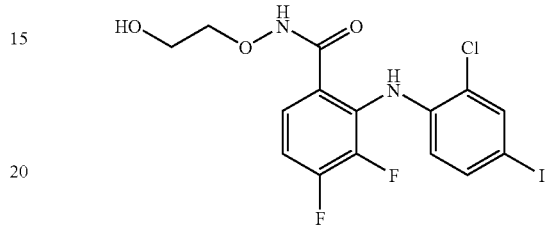

EXAMPLE 3

2-(2-Chloro-4-iodo-phenylamino)-3,4-difluoro-N-(2-hydroxy-ethoxy)-benzamide

Method A: By the general procedure of Example 1: m.p. 173-175° C.; ¹H NMR (400 MHz, DMSO-d₆) δ 11.93 (br s, 1 H), 8.85 (br s, 1 H), 7.76 (d, J=1.7 Hz, 1 H), 7.48 (dd, J=8.6, 1.7 Hz, 1 H), 7.44 (dd, J=8.5, 6.2 Hz, 1 H), 7.25 (dt, J=8.5, 9.3 Hz, 1 H), 6.58 (dd, J=8.5, 6.4 Hz, 1 H), 4.70 (br s, 1 H), 3.86 (br s, 2 H), 3.56 (br d, J=3.9 Hz, 2 H); MS (APCI+)=469.0; MS (APCI-)=467.0; Anal. Calcd/found for C₁₅H₁₂ClF₂IN₂O₃: C, 38.45/38.60; H, 2.58/2.53; N, 5.98/5.91; F, 8.11/8.08; I, 27.08/27.43.

Method B: To a solution of 2-(2-chloro-4-iodo-phenylamino)-3,4-difluoro-benzoic acid pentafluorophenyl ester (10.0 g, 17.4 mmol) in anhydrous dimethylformamide (36 mL) was added 2-(aminooxy)-ethanol (1.6 g, 20.8 mmol) and N,N-diisopropylethylamine (6.0 mL, 34.8 mmol). The resultant solution was stirred at ambient temperature for 16 h. The reaction mixture was concentrated to 20% volume then diluted with ethyl acetate (360 mL). The resultant solution was washed with water (6×60 mL) and brine (2×60 mL). The organics were dried over anhydrous magnesium sulfate and concentrated under reduced pressure to afford a white solid that was purified on silica gel. Elution with ethyl acetate-methanol (9:1) afforded 2-(2-chloro-4-iodo-phenylamino)-3,4-difluoro-N-(2-hydroxy-ethoxy)-benzamide (7.31 g, 90%) as a white solid. Recrystallization from methanol afforded analytically pure material, identical in all respects to the material prepared by method A.

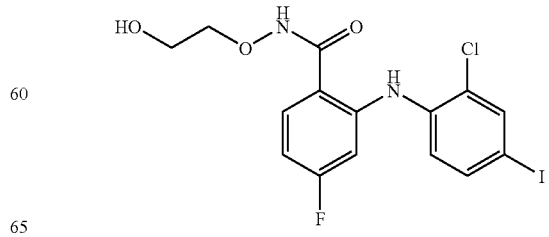

EXAMPLE 4

2-(2-Chloro-4-iodo-phenylamino)-4-fluoro-N-(2-hydroxy-ethoxy)-benzamide $^1$H NMR (400 MHz, DMSO-d$_6$) δ 11.88 (br s, 1 H), 9.81 (s, 1 H), 7.85 (d, J=2.0 Hz, 1 H), 7.64 (m, 1 H), 7.60 (dd, J=8.5, 1.9 Hz, 1 H), 7.31 (d, J=8.3 Hz, 1 H), 7.00 (dd, J=11.7, 2.5 Hz, 1H), 6.75 (td, J=8.5, 2.5 Hz, 1 H), 4.73 br s, 1 H), 3.90 (t, J=4.6 Hz, 2 H), 3.60 (br t, J=4.2 Hz, 2 H); MS (APCI+)=451.0; MS (APCI−)=449.0; Anal. Calcd/found for C$_{15}$H$_{13}$ClF$_1$IN$_2$O$_3$: C, 39.98/40.07; H, 2.91/2.83; N, 6.22/6.11.

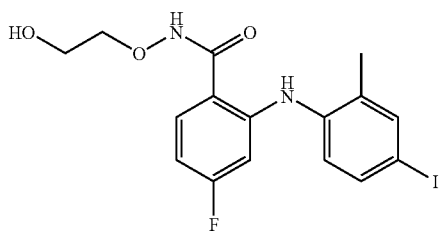

EXAMPLE 5

4-Fluoro-N-(2-hydroxy-ethoxy)-2-(4-iodo-2-methyl-phenylamino)-benzamide $^1$H NMR (400 MHz, CDCl$_3$) δ 9.16 (br s, 1 H), 8.67 (s, 1 H), 7.60 (d, J=1.7 Hz, 1 H), 7.51 (dd, J=8.4, 1.7 Hz, 1 H), 7.37 (dd, J=7.8, 6.6 Hz, 1 H), 7.02 (d, 8.3 Hz, 1 H), 6.59 (dd, J=12.2, 2.4 Hz, 1 H), 6.41 (m, 1 H), 4.08 (t, J=4.2 Hz, 2 H), 3.80 (t, J=4.2 Hz, 2 H), 2.22 (s, 3 H); MS (APCI+)=431.0; MS (APCI−)=429.0.

EXAMPLE 6

2-(2-Chloro-4-iodo-phenylamino)-3,4,5-trifluoro-N-(2-hydroxy-ethoxy)-benzamide Yield: 96%; m.p. 183-184.5° C.; $^1$H-NMR (400 MHz; DMSO-d$_6$) δ 8.46 (s, 1H), 7.73 (d, 1H, J=1.7 Hz), 7.58 (m, 1H), 7.44 (dd, 1H, J=8.5, 2.0 Hz), 6.54 (dd, 1H, J=8.5, 5.4 Hz), 4.70 (broad s, 1H), 3.84 (m, 2H), 3.54 (s, 2H); $^{19}$F-NMR (376 MHz; DMSO-d$_6$) δ −137.03 (d, 1F, J=20.2 Hz), −141.04 (s, 1F), −154.73 (s, 1F); MS (APCI$^+$) 486.9 (M+1, 100); MS (APCI$^-$) 484.9 (M−1, 50), 424.9 (100); IR (KBr) 3337 (O—H stretch), 1652 (C=O stretch), 1502 cm$^{-1}$. Anal. Calcd./found for C$_{15}$H$_{11}$ClF$_3$IN$_2$O$_3$: C, 37.02/37.16; H, 2.28/2.29; N, 5.76/5.49.

EXAMPLE 7

5-Chloro-3,4-difluoro-N-(2-hydroxy-ethoxy)-2-(4-iodo-phenylamino)-benzamide

Yield: 21%; m.p. 174-176° C.; $^1$H-NMR (400 MHz; DMSO-d$_6$) δ 11.72 (s, 1H), 8.47 (s, 1H), 7.53 (d, 1H, J=7.1 Hz), AB[7.43 (d, 2H, J=8.3 Hz), 6.63 (d, 2H, J=7.6 Hz)], 4.67 (s, 1H), 3.74 (s, 2H), 3.49 (s, 2H); $^{19}$F-NMR (376 MHz; DMSO-d$_6$) δ −134.59 (s, 1F), −139.07 (d, 1F, J=17.7 Hz); MS (APCI$^+$) 469.0 (M+1,100); MS (APCI$^-$) 467.0 (M−1, 40), 406.9 (100); IR (KBr) 1636 cm$^{-1}$ (C=O stretch). Anal. Calcd./found for C$_{15}$H$_{12}$ClF$_2$IN$_2$O$_3$: C, 38.45/38.61; H, 2.58/2.43; N, 5.98/5.94.

EXAMPLE 8

4-Fluoro-2-(2-fluoro-4-iodo-phenylamino)-N-(2-hydroxy-ethoxy)-benzamide

Yield: 96%; m.p. 117-119° C.; $^1$H-NMR (400 MHz; DMSO-d$_6$) δ 11.83 (s, 1H), 9.62 (s, 1H), 7.69 (d, 1H, J=10.5 Hz), 7.60 (m, 1H), 7.49 (d, 1H, J=8.6 Hz), 7.27 (m, 1H), 6.84 (d, 1H, J=111.2 Hz), 6.70 (m, 1H), 4.73 (broad s, 1H), 3.90 (m, 2H), 3.60 (m, 2H); $^{19}$F-NMR (376 MHz; DMSO-d$_6$) δ −106.74 (s, 1F), −124.58 (s, 1F); MS (APCI$^+$) 435.0 (M+1, 100); MS (APCI$^-$)433.0 (M−1, 82), 373.0 (100); IR (KBr) 1638 (C=O stretch), 1597 cm$^{-1}$. Anal. Calcd./found for C$_{15}$H$_{13}$F$_2$IN$_2$O$_3$: C, 41.49/41.52; H, 3.02/2.97; N, 6.45/6.18.

EXAMPLE 9

3,4-Difluoro-2-(2-fluoro-4-iodo-phenylamino)-N-(2-hydroxy-ethoxy)-benzamide

Method A: By the general procedure of example 32. Yield: 54%; m.p. 155-156° C.; $^1$H-NMR (400 MHz; DMSO-d$_6$) δ 11.83 (s, 1H), 8.69 (s, 1H), 7.56 (dd, 1H, J=11.0, 1.5 Hz), 7.36 (m, 2H), 7.19 (m, 1H), 6.65 (m, 1H), 3.82 (s, 2H), 3.55 (s, 2H); $^{19}$F-NMR (376 MHz; DMSO-d$_6$) δ −128.18 (s, 1F), −133.11 (s, 1F), −144.16 (s, 1F); MS (APCI$^+$) 453.0 (M+1, 100); MS (APCI$^-$) 451.0 (M−1, 100); IR (KBr) 3349 (O—H stretch), 1641 (C=O stretch), 1610 cm$^{-1}$.

Anal. Calcd./found for C$_{15}$H$_{12}$F$_3$IN$_2$O$_3$: C, 39.84/39.99; H, 2.67/2.81; N, 6.20/6.20.

EXAMPLE 10

5-Chloro-3,4-difluoro-2-(2-fluoro-4-iodo-phenylamino)-N-(2-hydroxy-ethoxy)-benzamide Yield: 96%; m.p. 180-180.5° C.; $^1$H-NMR (400 MHz; DMSO-d$_6$) δ 11.89 (s, 1H), 8.68 (s, 1H), 7.59 (m, 2H), 7.34 (d, 1H, J=8.8 Hz), 6.72 (m, 1H), 4.70 (broad s, 1H), 3.82 (m, 2H), 3.55 (s, 2H); $^{19}$F-NMR (376 MHz; DMSO-d$_6$) δ −127.72 (s, 1F), −134.13 (s, 1F), −140.35 (d, 1F, J=17.7 Hz); MS (APCI$^+$) 487.0 (M+1,100); MS (APCI$^-$) 484.9 (M−1, 63), 424.9 (100); IR (KBr) 3333 (O—H stretch), 1643 (C=O stretch), 1609, 1490 cm$^{-1}$. Anal. Calcd./found for C$_{15}$H$_{11}$ClF$_3$IN$_2$O$_3$: C, 37.02/37.30; H, 2.28/2.23; N, 5.76/5.69.

EXAMPLE 11

5-Bromo-3,4-difluoro-2-(2-fluoro-4-iodo-phenylamino)-N-(2-hydroxy-ethoxy)-benzamide Yield: 100%; m.p. 189-190° C.; $^1$H-NMR (400 MHz; DMSO-d$_6$) 811.89 (s, 1H), 8.70 (s, 1H), 7.69 (d, 1H, J=6.1 Hz), 7.57 (d, 1H, J=10.7 Hz), 7.34 (d, 1H, J=7.8 Hz), 6.73 (m, 1H), 4.70 (broad s, 1H), 3.81 (s, 2H), 3.54 (s, 2H); $^{19}$F-NMR (376 MHz; DMSO-d$_6$) δ −126.43 (s, 1F), −127.65 (s, 1F), −140.20 (d, 1F, J=17.7 Hz); MS (APCI$^+$) 533.0 (95), 531.0 (M+1, 100); MS (APCI$^-$) 531.0 (40), 529.0 (M−1, 42), 470.9 (95), 468.9 (100); IR (KBr) 3341 (O—H stretch), 1647 (C=O stretch), 1606, 1509, 1484 cm$^{-1}$. Anal. Calcd./found for C$_{15}$H$_{11}$BrF$_3$IN$_2$O$_3$: C, 33.93/33.89; H, 2.09/2.02; N, 5.27/5.13.

EXAMPLE 12

4,5-Difluoro-N-(2-hydroxy-ethoxy)-2-(4-iodo-2-methyl-phenylamino)-benzamide

To a solution of 4,5-difluoro-2-(2-fluoro-4-iodo-phenylamino)-benzoic acid pentafluorophenyl ester (2.96 g, 0.533 mmol) in dimethylformamide at rt was added diisopropylethylamine (0.184 mL, 1.1 mmol). After the reaction stirred overnight, the reaction mixture was concentrated to about half volume. The solution was diluted with ether (30 mL) then washed with water (4×10 mL) and brine (10 mL). The ether layer was dried over magnesium sulfate and the resultant mixture was filtered. The filtrate solvent was removed in vacuo to obtain an oily solid. The oily solid was purified by flash chromatography (35 g silica gel), eluting with a gradient of ethyl acetate in hexanes. The solvent was removed in vacuo to obtain a solid which was dried on a vacuum pump overnight. Recrystallization from hexanes-acetone afforded 4,5-difluoro-N-(2-hydroxy-ethoxy)-2-(4-iodo-2-methyl-phenylamino)-benzamide as a solid (0.107 g, 45% yield): m.p. 151.2-152.5 C; $^1$H-NMR (400 MHz, $(CD_3)_2CO$) δ 9.22 (br. S, 1H), 7.63 (m, 2H), 7.53 (dd, 1H, J=8.3, 1.95 Hz), 7.14 (d, 1H, J=8.3 Hz), 6.41 (m, 1H), 4.03 (t, 2H, J=4.4 Hz), 3.69 (t, 2H, J=4.88 Hz), 2.23 (s, 3H); $^{19}$F-NMR (376 MHz, $(CD_3)_2CO$) δ −132.75, −152.61; MS 478.9 m/z (APCI+); 476.9 m/z (APCI−). Anal. Calcd. for $C_{16}H_{15}F_2IN_2O_3$: C, 42.88; H, 3.39; N, 6.25. Found: C, 42.79; H, 3.19; N, 6.02.

Examples 13 to 20 were prepared by the general procedure of Example 12.

EXAMPLE 13

5-Bromo-3,4-difluoro-N-(2-hydroxy-ethoxy)-2-(4-iodo-2-methyl-phenylamino)-benzamide m.p. 208.2-209.6 C; $^1$H-NMR (400 MHz, $(CD_3)_2CO$) δ 8.62 (br. S, 1H), 7.79 (dd, 1H, J=7.08, 1.47 Hz), 7.55 (s, 1H), 7.42 (d, 1H, J=8.79 Hz), 6.65 (dd, 1H, J=8.30, 5.86 Hz), 4.02 (t, 2H, J=4.64 Hz), 3.67 (t, 2H, J=4.64 Hz), 2.32 (s, 3H); $^{19}$F-NMR (376 MHz, $(CD_3)_2CO$) δ −126.85, −139.3 (d, J=15.16 Hz).

Anal. Calcd. for $C_{16}H_{14}BrF_2IN_2O_3$: C, 36.46; H, 2.68; N, 5.31; F, 7.21; Br, 15.16; I, 24.08. Found: C, 36.67; H, 2.62; N, 5.23; F, 7.23; Br, 15.32; I, 23.3.

EXAMPLE 14

5-Bromo-2-(2-chloro-4-iodo-phenylamino)-3,4-difluoro-N-(2-hydroxy-ethoxy)-benzamide m.p. 190.2-200.2 C; $^1$H-NMR (400 MHz, $(CD_3)_2CO$) δ 11.11 (br s, 1H), 8.92 (br. s., 1H), 7.84 (dd, 1H, J=6.84, 2.2 Hz), 7.76 (d, 1H, J=1.95 Hz), 7.54 (dd, 1H, J=8.54, 6.59 Hz), 6.77 (dd, 1H, J=8.54, 6.59 Hz), 4.40 (t, 2H, J=4.39 Hz), 3.69 (t, 2H, J=4.89 Hz). $^{19}$F-NMR (376 MHz, $(CD_3)_2CO$) δ −126.16, −137.47 (d, J=17.69 Hz); MS 546.9 m/z, 548.9 m/z (AP+); 544.9 m/z, 546.9 m/z (AP−). Anal. Calcd. for $C_{15}H_{11}BrClF_2IN_2O_3$: C, 32.91; H, 2.03; N, 5.12; F, 6.94; Br, 14.58; I, 23.18. Found: C, 32.94; H, 1.95; H, 5.30; F, 6.87; Br, 14.79; I, 22.91.

EXAMPLE 15

5-Chloro-3,4-difluoro-N-(2-hydroxy-ethoxy)-2-(4-iodo-2-methyl-phenylamino)-benzamide m.p. 199.1-200.8 C; $^1$H-NMR (400 MHz, $(CD_3)_2CO$) δ 8.57 (br. S, 1H), 7.68 (dd, 1H, J=7.32, 2.2 Hz), 7.55 (s, 1H), 7.41 (dd, 1H, J=8.3, 1.71 Hz), 6.64 (dd, 1H, J=8.3, 5.86), 4.02 (t, 2H, J=4.63 Hz), 3.67 (t, 2H, J=4.88 Hz), 2.32 (s, 3H). $^{19}$F-NMR (376 MHz, $(CD_3)_2CO$) δ −134.75, −139.56 (t, J=15.17 Hz); MS 483.0 m/z (AP+); 481.0 m/z (AP−). Anal. Calcd. for $C_{16}H_{14}ClF_2IN_2O_3$: C, 39.82; H, 2.92; N, 5.8; F, 7.87; Cl, 7.35; I, 26.29. Found: C, 39.91; H, 2.92; N, 6.0; F, 7.91; Cl, 7.39; I, 27.06.

EXAMPLE 16

5-Bromo-4-fluoro-N-(2-hydroxy-ethoxy)-2-(4-iodo-2-methyl-phenylamino)-benzamide m.p. 154.4-156.4; $^1$H-NMR (400 MHz, $(CD_3)_2CO$) δ 9.42 (br. s, 1H), 7.86 (d, 1H, J=7.57 Hz), 7.66 (d, 1H, J=1.46 Hz), 7.56 (dd, 1H, J=8.3, 2.2 Hz), 7.16 (d, 1H, J=8.55 Hz), 6.8 (dd, 1H, J=11.72, 6.59 Hz), 4.04 (t, 2H, J=7.9, 4.4 Hz), 3.69 (t, 2H, J=6.84, 4.64 Hz), 2.23 (s, 3H). $^{19}$F-NMR (376 MHz, $(CD_3)_2$CO) δ −103.3; MS 508.9 m/z, 510.9 m/z (AP+); 506.9 m/z, 508.9 m/z (AP−). Anal. Calcd. for $C_{16}H_{15}BrFIN_2O_3$: C, 37.75; H, 2.97; N, 5.50. Found: C, 37.68; H, 2.7; N, 5.31.

EXAMPLE 17

2-(2-Chloro-4-iodo-phenylamino)-4,5-difluoro-N-(2-hydroxy-ethoxy)-benzamide $^1$H-NMR (400 MHz, $(CD_3)_2CO$) δ 11.01 (br. s, 1H), 9.53 (br. s, 1H), 7.79 (br. s, 1H), 7.67 (br. s, 1H), 7.59 (br. d, 1H, J=7.82 Hz), 7.32 (d, 1H, J=8.55 Hz), 7.26 (br. s, 1H), 4.03 (br. s, 2H), 3.7 (br. s, 2H); $^{19}$F-NMR (376 MHz, $(CD_3)_2CO$) δ −132.54, −149.93; MS 469.0 (AP+); 467.0 (AP−).

EXAMPLE 18

4,5-Difluoro-2-(2-fluoro-4-iodo-phenylamino)-N-(2-hydroxy-ethoxy)-benzamide m.p. 189.6-190.6 C; $^1$H-NMR (400 MHz, $(CD_3)_2CO$) δ 11.00 (br s, 1H), 9.39 (br. s, 1H), 7.65 (dd, 1H, J=11.23, 8.79 Hz), 7.59 (dd, 1H, J=10.26, 1.96 Hz), 7.51 (m, 1H), 7.31 (t, 1H, J=8.8 Hz), 7.13 (m, 1H), 4.02 (t, 2H, J=4.64 Hz), 3.69 (t, 2H, J=4.89 Hz); $^{19}$F-NMR (376 MHz, $(CD_3)_2CO$) δ − 125.9 (d, J=50.55 Hz), −132.74, −151.05; MS 453.0 m/z (AP+); 451.0 m/z (AP−).

Anal. Calcd. for $C_{15}H_{12}F_3IN_2O_3$: C, 39.84; H, 2.67; N, 6.20. Found: C, 40.22; H, 2.62; N, 6.03.

EXAMPLE 19

5-Bromo-4-fluoro-2-(2-fluoro-4-iodo-phenylamino)-N-(2-hydroxy-ethoxy)-benzamide m.p. 173-175 C; $^1$H-NMR (400 MHz, $(CD_3)_2CO$) δ 9.59 (br. s.), 7.89 (d, 1H, J=7.57 Hz), 7.62 (dd, 1H, J=10.26, 1.95 Hz), 7.55 (m, 1H), 7.34 (t, 1H, J=8.64 Hz), 7.03 (d, 1H, J=11.48 Hz), 4.04 (d, 2H, J=4.39 Hz), 3.70 (d, 2H, J=4.64 Hz); $^{19}$F-NMR (376 MHz, $(CD_3)_2CO$) δ −103.07, −124.7 (d, J=53.1 Hz); MS 512.8 m/z, 514.8 m/z (AP+); 510.9 m/z, 512.9 m/z (AP−). Anal. Calcd. for $C_{15}H_{12}BrF_2IN_2O_3 \cdot 0.17$ $C_4H_8O_2 \cdot 0.13$ $C_6H_{14}$: C, 36.66; H, 2.84 N, 5.19. Found: C, 36.65; H, 2.57; N, 5.16.

EXAMPLE 20

5-Chloro-2-(2-chloro-4-iodo-phenylamino)-3,4-difluoro-N-(2-hydroxy-ethoxy)-benzamide m.p.=178-181° C.; $^1$NMR (400 MHz; DMSO-d$_6$) δ 12.00 (s, 1H), 8.80 (s, 1H), 7.76 (s, 1H), 7.66 (d, 1H, J=7.1), 7.47 (d, 1H, J=8.5), 6.66 (t, 1H, J=7.6), 4.70 (bs, 1H), 3.85 (m, 2H), 3.56 (m, 2H); MS(APCI+)=502.9/504.9. Anal. calcd/found for C$_{15}$H$_{11}$Cl$_2$F$_2$IN$_2$O$_3$: C, 35.81/35.69; H, 2.20/2.25; N, 5.57/5.22; F, 7.55/7.72.

Examples 21-24 and 26-27 were prepared by the general method of Example 38.

EXAMPLE 21

3,4,5-Trifluoro-2-(2-fluoro-4-iodo-phenylamino)-N-(2-hydroxy-ethoxy)-benzamide m.p.=185-187° C.; $^1$H NMR (400 MHz, DMSO-d$_6$) δ 11.79 (s, 1H), 8.32 (s, 1H), 7.53 (m, 2H), 7.30 (d, 1H, J=8.5), 6.60-6.55 (m, 1H), 4.69 (bs, 1H), 3.80 (bs, 2H), 3.50 (bs, 2H); MS(APCI+)=471.0. Anal. calcd/found for C$_{15}$H$_{11}$F$_4$IN$_2$O$_3$: C, 38.32/38.38; H, 2.36/2.15; N, 5.96/5.76; F, 16.16/15.87.

EXAMPLE 22

2-(4-Bromo-2-fluoro-phenylamino)-3,4-difluoro-N-(2-hydroxy-ethoxy)-benzamide m.p. 146.1-146.4° C.; $^1$H NMR (400 MHz, DMSO-d$_6$) δ 11.82 (1H, s), 8.71 (1H, s), 7.47 (1H, dd, J=11.1 Hz, 2.1 Hz), 7.30-7.40 (1H, m), 7.15-7.20 (2H, m), 6.76-6.81 (1H, m), 4.69 (1H, br s), 3.80 (2H, t, J<4.0 Hz), 3.52 (2H, t, J<4.0 Hz). Anal. Calcd/Found for C$_{15}$H$_{12}$F$_3$BrN$_2$O$_3$: C, 44.47/44.58; H, 2.99/2.88; N, 6.91/6.72; F, 14.07/14.01; Br, 19.72/19.60.

EXAMPLE 23

2-(4-Bromo-2-fluoro-phenylamino)-4,5-difluoro-N-(2-hydroxy-ethoxy)-benzamide m.p. 190.8-192.5° C.; $^1$H NMR (400 MHz, Acetone-d$_6$) δ 9.40 (br s, 1H), 7.67 (1H, dd, J=11.48 Hz, 8.79 Hz), 7.48 (2H, m), 7.37 (1H, m), 7.12 (1H, m), 4.05 (2H, t, J=4.64 Hz), 3.71 (2H, t, J=4.64 Hz). Anal Calcd/Found C$_{15}$H$_{12}$BrF$_3$N$_2$O$_3$: C, 44.47/45.55; H, 2.99/2.98; N, 6.91/6.29.

EXAMPLE 24

2-(4-Chloro-2-fluoro-phenylamino)-3,4-difluoro-N-(2-hydroxy-ethoxy)-benzamide m.p. 142.1-142.5° C.; $^1$H NMR (400 MHz, DMSO-d$_6$) δ 11.83 (1H, s), 8.72 (1H, s), 7.36-7.39 (2H, m), 7.16 (1H, dd, J=16.5 Hz, 9.4 Hz), 7.07 (1H, dd, J=8.5 Hz, 1.3 Hz), 6.82-6.88 (1H, m), 4.69 (1H, br s), 3.80 (2H, t, J=4.6 Hz), 3.52 (2H, t, J=4.6 Hz). Anal Calcd/Found for C$_{15}$H$_{12}$ClF$_3$N$_2$O$_3$: C, 49.95/50.18; H, 3.35/3.21; N, 7.77/7.70; F, 15.80/15.70; Cl 9.83/9.94.

EXAMPLE 25

3,4-Difluoro-2-(2-fluoro-phenylamino)-N-(2-hydroxy-ethoxy)-benzamide

Prepared from 3,4-difluoro-2-(2-fluoro-4-iodo-phenylamino)-N-(2-hydroxy-ethoxy)-benzamide by the general method of Example 86. m.p. 129.6-130.4° C.; $^1$H NMR (400 MHz, DMSO-d$_6$) δ 11.85 (1H, s), 8.72 (1H, s), 7.36-7.39 (1H, m), 6.82-7.18 (5H, m), 4.69 (1H, br s), 3.82 (2H, t, J=4.7 Hz), 3.53 (2H, t, J=4.7 Hz). Anal Calcd/Found for C$_{15}$H$_{13}$F$_3$N$_2$O$_3$: C, 55.22/55.16; H, 4.02/3.97; N, 8.59/8.51; F, 17.47/17.15.

EXAMPLE 26

5-Chloro-2-(2,4-difluoro-phenylamino)-3,4-difluoro-N-(2-hydroxy-ethoxy)-benzamide m.p. 161.6-162.4° C.; $^1$H NMR (400 MHz, DMSO-d$_6$) δ 11.89 (1H, s), 8.69 (1H, s), 7.56 (1H, dd, J=7.5 Hz, 1.9 Hz), 7.21-7.27 (1H, m), 6.94-7.06 (1H, m), 6.89-6.92 (1H, m), 4.69 (1H, br s), 3.81 (2H, t, J=4.6 Hz), 3.53 (2H, t, J=4.6 Hz). Anal Calcd/Found for C$_{15}$H$_{12}$ClF$_4$N$_2$O$_3$: C, 47.57/47.74; H, 2.93/2.83; N, 7.40/7.31; F, 20.07/19.76; Cl, 9.36/9.39.

EXAMPLE 27

2-(2,4-Difluoro-phenylamino)-3,4-difluoro-N-(2-hydroxy-ethoxy)-benzamide m.p. 141.1-141.6° C.; $^1$H NMR (400 MHz, DMSO-d$_6$) δ 11.84 (1H, s), 8.73 (1H, s); 7.34-7.37 (1H, m), 7.11-7.27 (1H, m), 7.04-7.09 (1H, m), 6.89-6.99 (2H, m), 4.70 (1H, br s), 3.82 (2H, t, J=4.9 Hz), 3.53 (2H, t, J=4.8 Hz). Anal Calcd/Found for C$_{15}$H$_{12}$F$_4$N$_2$O$_3$: C, 52.33/52.34; H, 3.51/3.39; N 8.14/8.01; F, 22.07/21.93.

EXAMPLE 28

4-Fluoro-N-(3-hydroxy-propoxy)-2-(4-iodo-2-methyl-phenylamino)-benzamide

Step A: To a mixture of 4-fluoro-2-(4-iodo-2-methyl-phenylamino)benzoic acid (3.32 g, 8.95 mmol) in dichloromethane at ambient temperature was added diisopropylethylamine (2.82 mL, 16.2 mmol). To the resultant solution was added O-[3-(tert-butyl-dimethyl-silanyloxy)-propyl]-hydroxylamine (2.19 g, 10.65 mmol) and PyBOP. After 1.5 h of stirring, the solution was diluted with ether (100 mL) and was washed with water (3×50 mL) and brine (50 mL), dried over magnesium sulfate and filtered, and concentrated in vacuo to obtain a gum. Chromatographed the gum using a gradient of 100% hexanes to 30% ethyl acetate in hexanes over 45 min. The solvent of the combined fractions was removed in vacuo to obtain a yellow gum. The gum was dried on a vacuum pump for c.a. 18 h which afforded N-[3-(tert-Butyl-dimethyl-silanyloxy)-propoxy]-4-fluoro-2-(4-iodo-2-methyl-phenylamino)-benzamide as a solid. (4.06 g, 81% yield). $^1$H-NMR (400 MHz, CDCl$_3$) δ 9.3 (br. s., 1H), 9.0 (br. s., 1H), 7.58 (s, 1H), 7.49 (dd, 1H, J=8.3, 1.95 Hz)), 7.36 (br. t., 1H, =5.71 Hz), 7.05 (d, 1H, J=8.3 Hz), 6.65 (dd, 1H, J=11.96, 2.44 Hz), 6.4 (br. t., J=7.1 Hz), 4.14 (t, 2H, J=5.61 Hz), 3.812 (t, 2H, J=5.62 Hz), 2.28 (s, 3H), 1.94 (p, 2H, J=5.86 Hz), 0.9 (s, 9H), 0.08 (s, 6H). $^{19}$F-NMR (376 MHz, CDCl$_3$) δ –105.25. MS (AP+) 559.2 m/z, (AP–) 557.1 m/z.

Step B: To a solution of N-[3-(tert-Butyl-dimethyl-silanyloxy)-propoxy]-4-fluoro-2-(4-iodo-2-methyl-phenylamino)- benzamide (4.0 g, 7.27 mmol) in methanol (5 mL) at ambient temperature was added 5 M $H_2SO_4$ in methanol (0.073 mL, 0.364 mmol). After 1 h of stirring, to the reaction was added additional 5 M $H_2SO_4$ in methanol (0.035 mL, 0.182 mmol). After 2 h of stirring, the reaction was adjusted to pH 7 using saturated $NaHCO_3$ (aq) (c.a. 1.5 mL), followed by addition of water (35 mL). The aqueous layer was extracted with ethyl acetate (1×20 mL, 2×10 mL). The extracts were combined, washed with brine, and dried over magnesium sulfate. The resultant mixture was filtered, and the filtrate solvent was removed in vacuo to obtain an oil that was dried on a vacuum pump over the weekend. The oil was purified by flash chromatography, eluted with a gradient of 100% hexanes to 100% ethyl acetate in 50 min. The solvent was removed in vacuo of combined fractions to obtain a solid which was dried on a vacuum pump for c.a. 6 h. Recrystalized solid in a mixture of hexanes and ethyl acetate to afford 4-fluoro-N-(3-hydroxy-propoxy)-2-(4-iodo-2-methyl-phenylamino)-benzamide as a solid (2.4 g, 74% yield): m.p. 120.8-122.4 C; $^1$H-NMR (400 MHz, $(CD_3)_2CO$) δ 10.91 (br s, 1H), 9.59 (br. S, 1H), 9.68 (m, 2H), 7.57 (d, 1H, J=8.54 Hz), 7.18 (d, 1H, J=8.34 Hz), 6.72 (m, 1H); 6.53 (m, 1H); 4.12 (t, 2H, J=6.11 Hz), 3.71 (t, 2H, J=5.86 Hz), 2.26 (s, 3H), 1.86 (m, 2H); $^{19}$F-NMR (376 MHz, $(CD_3)_2CO$) δ −108.14; MS 445.1 m/z (AP+), 443.1 m/z (AP−). Anal. Calcd. for $C_{17}H_{18}FIN_2O_3$: C, 45.96; H, 4.08; N, 6.31; F, 4.28; I, 28.57. Found: C, 45.78; H, 3.88; N, 6.14; F, 4.30; I, 28.27.

Examples 29-33 were prepared by the general procedure of example 28.

EXAMPLE 29

5-Chloro-3,4-difluoro-N-(3-hydroxy-propoxy)-2-(4-iodo-2-methyl-phenylamino)-benzamide m.p. 155.2-156.6 C; $^1$H-NMR (400 MHz, $(CD_3)_2CO$) δ 10.98 (br s, 1H), 8.70 (br. S, 1H), 7.66 (dd, 1H, J=7.33, 1.95 Hz), 7.55 (s, 1H), 7.42 (dd, 1H, J=8.54, 1.95 Hz), 6.64 (dd, 1H, J=8.55, 6.11 Hz), 4.08 (t, 2H, J=6.11 Hz), 3.67 (t, 2H, J=6.10 Hz), 2.32 (s, 3H), 1.83 (m, 2H); $^{19}$F-NMR (376 MHz, $(CD_3)_2CO$) δ −135.0, −139.63 (d, J=17.67 Hz); MS 497.1 m/z (AP+); 495.1 m/z (AP−). Anal. Calcd. for $C_{17}H_{16}ClF_2IN_2O_3$: C, 41.11; H, 3.25; N, 5.64; F, 7.65; Cl, 7.14; I, 25.55. Found: C, 41.09; H, 3.07; N, 5.46; F, 7.63; Cl, 7.24; I, 25.57.

EXAMPLE 30

2-(2-Chloro-4-iodo-phenylamino)-4-fluoro-N-(3-hydroxy-propoxy)-benzamide m.p. 158.8-160.8 C; $^1$H-NMR (400 MHz, $(CD_3)_2CO$) δ 10.90 (br s, 1H), 9.93 (br. S, 1H), 7.84 (d, 1H, J=1.95 Hz), 7.72. (dd, 1H, J=8.55, 1.96 Hz), 7.65 (dd, 1H, J=8.55, 1.96 Hz), 7.39 (d, 1H, J=8.54 Hz), 7.05 (dd, 1H, J=11.72, 2.44 Hz), 6.67 (td, 1H, J=8.55, 2.69 Hz), 4.13 (t, 2H, J=6.34 Hz), 3.71 (t, 2H, J=6.10 Hz), 1.86 (m, 2H). $^{19}$F-NMR (376 MHz, $(CD_3)_2$ CO) δ −108.0; MS 465.1 m/z (AP+), 463.1 m/z (AP−). Anal. Calcd. for $C_{16}H_{15}ClFIN_2O_3$: C, 41.36; H, 3.25; N, 6.03; F, 4.09; Cl, 7.63; I, 27.31. Found: C, 41.41; H, 3.13; N, 5.84; F, 4.10; Cl, 7.62; I, 27.41.

EXAMPLE 31

5-Bromo-2-(2-chloro-4-iodo-phenylamino)-3,4-difluoro-N-(3-hydroxy-propoxy)-benzamide m.p. 120-121° C.; $^1$NMR (400 MHz; DMSO-$d_6$) δ 11.90 (bs, 1H), 8.91 (bs, 1H), 7.76 (bs, 2H), 7.47 (d, 1H, J=8.1), 6.67 (m, 1H), 4.48 (bs, 1H), 3.89 (bs, 2H), 3.47 (bs, 2H), 1.73 (m, 2H); MS(APCI+)=560.8/562.8. Anal. calcd/found for $C_{16}H_{13}BrClF_2IN_2O_3$: C, 34.22/34.45; H, 2.33/2.36; N, 4.99/4.91; F, 6.77/6.72.

EXAMPLE 32

3,4-Difluoro-2-(2-fluoro-4-iodo-phenylamino)-N-(3-hydroxy-propoxy)-benzamide m.p. 151.8-152.4° C.; $^1$H NMR (400 MHz, DMSO-$d_6$) δ 11.74 (1H, s), 8.71 (1H, s), 7.56 (1H, d, J=11.0 Hz), 7.20-7.30 (2H, m), 7.16-7.22 (1H, m), 6.62-6.68 (1H, m), 4.46 (1H, br s), 3.83 (2H, t, J=5.6 Hz), 3.46 (2H, t, J=4.6 Hz), 1.67-1.70 (2H, m). Anal. Calcd/Found for $C_{16}H_{14}F_3IN_2O_3$: C, 41.22/41.27; H, 3.03/2.87; N, 6.01/5.92; F, 12.23/11.97; I, 27.22/27.44.

EXAMPLE 33

3,4-Difluoro-2-(2-fluoro-4-iodo-phenylamino)-N-(4-hydroxy-butoxy)-benzamide m.p. 131.4-131.9° C.; $^1$H NMR (400 MHz, DMSO-$d_6$) δ 11.71 (1H, s), 8.68 (1H, s), 7.54 (1H, d, J=11.0 Hz), 7.20-7.36 (2H, m), 7.14-7.18 (1H, m), 6.60-6.66 (1H, m), 4.38 (1H, br s), 3.74 (2H, t, J=6.1 Hz), 3.36 (2H, t, J=4.2 Hz), 1.41-1.55 (4H, m). Anal. Calcd/Found for $C_{17}H_{16}F_3IN_2O_3$: C, 42.52/42.91; H, 3.36/3.27; N, 5.83/5.58; F, 11.87/11.61; I, 26.43/26.67.

EXAMPLE 34

5-Chloro-2-(2-chloro-4-iodo-phenylamino)-N-(2,3-dihydroxy-propoxy)-3,4-difluoro-benzamide Step A: To a stirring solution of 5-chloro-2-(2-chloro-4-iodo-phenylamino)-3,4-difluoro-benzoic acid pentafluorophenyl ester (5.80 g, 9.51 mmol) is freshly distilled tetrahydrofuran (40 mL) was added O-(2,2-dimethyl-[1,3]dioxolan-4-ylmethyl)-hydroxylamine (1.54 g, 10.5 mmol) and diisopropylethylamine (1.8 mL, 10.5 mmol). After 20 hours, the mixture was partitioned between ethyl acetate and water. The organic layer was washed twice with water and twice with saturated brine solution. The organic layer was collected, dried over $Na_2SO_4$, filtered and concentrated in vacuo. The residue was purified by crystallization in ethyl acetate/hexanes affording 5-chloro-2-(2-chloro-4-iodo-phenylamino)-N-(2,2-dimethyl-[1,3]dioxolan-4-ylmethoxy)-3,4-difluoro-benzamide as a white solid (3.7 g, 67.9%): $^1$H NMR (400 MHz; CDCl$_3$) δ 9.82 (bs, 1H), 8.10 (bs, 1H), 7.68 (s, 1H), 7.47 (bs, 1H), 7.40-7.43 (m, 1H), 6.44-6.47 (m, 1H), 4.40 (bs, 1H), 3.97-4.20 (m, 3H), 3.77 (t, 1H, J=8.0), 1.44 (s, 3H), 1.37 (s, 3H); MS (APCI+)=573.0/575.0.

Step B: To a stirring solution of 5-chloro-2-(2-chloro-4-iodo-phenylamino)-N-(2,2-dimethyl-[1,3]dioxolan-4-yl-methoxy)-3,4-difluoro-benzamide (3.7 g, 6.45 mmol) in methanol (20 mL) and water (2 mL) was added p-toluenesulfonic acid (0.12 g, 0.65 mmol). After 20 hours the reaction was concentrated in vacuo. The afforded residue was partitioned between ethyl acetate and water. The organic layer was washed twice with saturated NaHCO₃ solution and twice with saturated brine solution. The organic layers were collected, dried over Na₂SO₄, filtered and concentrated in vacuo. The residue was purified by crystallization with methanol/water and the solids were dried in a vacuum oven at 40° C. to afford 5-chloro-2-(2-chloro-4-iodo-phenylamino)-N-(2,3-dihydroxy-propoxy)-3,4-difluoro-benzamide: m.p.=152-154° C.; $^1$NMR (400 MHz, DMSO-d₆) δ 12.03 (s, 1H), 8.83 (s, 1H), 7.76 (s, 1H), 7.66 (d, 1H, J=6.8), 7.47 (d, 1H, J=8.5), 6.68 (t, 1H, J=6.6), 4.83 (bs, 1H), 4.60 (bs, 1H), 3.89-3.92 (m, 1H), 3.68-3.76 (m, 2H), 3.30 (2H, partially hidden by HDO); MS(APCI+)=533.0/535.0; Anal. calcd/found for C₁₆H₁₃Cl₂F₂IN₂O₄: C, 36.05/36.23; H, 2.46/2.40; N, 5.25/5.03; F, 7.13/7.14.

Examples 35-37 were prepared by the general procedure described in example 34.

EXAMPLE 35

5-Chloro-N-(2,3-dihydroxy-propoxy)-3,4-difluoro-2-(4-iodo-2-methyl-phenylamino)-benzamide m.p.=67-69° C.; $^1$H NMR (400 MHz, CDCl₃) δ 7.51 (s, 1H), 7.46 (d, 1H, J=6.3), 7.38 (d, 1H, J=8.5), 6.44 (dd, 1H, J=8.3, 4.9), 3.94-3.98 (m, 2H), 3.89 (m, 1H), 3.74 (A of abx, 1H, J=11.7, 3.9), 3.61 (B of abx, 1H, J=11.5, 4.9), 2.30 (s, 3H); MS(APCI+)=513.0/515.0. Anal. calcd/found for C₁₇H₁₆ClF₂IN₂O₄: C, 39.83/39.90; H, 3.15/3.23; N, 5.46/5.03; F, 7.41/7.20.

EXAMPLE 36

5-Chloro-N-(3,4-dihydroxy-butoxy)-3,4-difluoro-2-(4-iodo-2-methyl-phenylamino)-benzamide m.p.=135-138° C.; $^1$H NMR (400 MHz, DMSO-d₆) δ 11.86 (bs, 1H), 8.55 (bs, 1H), 7.85 (s, 1H), 7.60 (d, 1H, J=7.1), 7.51 (s, 1H), 7.35 (d, 1H, J=8.5), 6.53 (dd, 1H, J=8.3, 5.4), 4.51-4.52 (m, 2H), 3.86-3.88 (m, 2H), 3.53 (bs, 1H), 3.23-3.28 (cm, 1H), 2.20 (s, 3H), 1.73-1.77 (cm, 1H), 1.45-1.48 (cm, 1H); MS(APCI+)=527.0. Anal. calcd/found for C₁₈H₁₈ClF₂IN₂O₄: C, 41.05/41.12; H, 3.44/3.41; N, 5.32/5.13; F, 7.21/6.83.

EXAMPLE 37

5-Chloro-2-(2-chloro-4-iodo-phenylamino)-N-(3,4-dihydroxy-butoxy)-3,4-difluoro-benzamide m.p.=146-148° C.; $^1$H NMR (400 MHz, DMSO-d₆) δ 11.92 (s, 1H), 8.84 (s, 1H), 7.76 (s, 1H), 7.65 (d, 1H, J=7.1), 7.47 (d, 1H, J=8.8), 6.67 (dd, 1H, J=8.3, 6.3), 4.54-4.50 (m, 2H), 3.93 (t, 2H, J=6.3), 3.54 (t, 1H, J=4.2), 3.28-3.20 (m, 2H), 1.76 (cm, 1H), 1.52-1.47 (cm, 1H); MS (APCI+)=547.0/549.0. Anal. calcd/found for C₁₇H₁₅Cl₂F₂IN₂O₄: C, 37.32/37.26; H, 2.76/2.62; N, 5.12/4.99; F, 6.94/7.07.

EXAMPLE 38

N-(2,2-Dimethyl-[1.3]dioxolan-4-ylmethoxy)-3,4-difluoro-2-(2-fluoro-4-iodo-phenylamino)-benzamide To a stirring solution of 3,4-difluoro-2-(2-fluoro-4-iodo-phenylamino)-benzoic acid (4.52 g, 11.5 mmol) in freshly distilled tetrahydrofuran (20 mL) at −15° C. was added diphenylphosphinic chloride (2.85 mL, 14.95 mmol). The resultant reaction mixture was stirred for 30 minutes at −15° C. N-Methylmorpholine (1.26 mL, 11.5 mmol) was added and stirring was continued for 90 minutes at −15° C. The reaction was then charged with O-(2,2-dimethyl-[1,3]dioxolan-4-ylmethyl)-hydroxylamine (2.03 g, 13.8 mmol) and allowed to stir at −15° C. for 30 minutes. N-methylmorpholine (1.9 mL, 17.25 mmol) was added and the reaction was allowed to warm to room temperature. After 17 hours, the mixture was diluted with ethyl acetate and partitioned twice with saturated NaHCO₃ solution, then twice with water, and twice with saturated brine solution. Organic layers were collected, dried over sodium sulfate, filtered and concentrated in vacuo. The afforded residue was purified by silica column chromatography in 3:1 hexanes/ethyl acetate. The corresponding fractions were collected, dried in vacuo, and crystallized from ethyl acetate/hexanes affording N-(2,2-dimethyl-[1,3]dioxolan-4-ylmethoxy)-3,4-difluoro-2-(2-fluoro-4-iodo-phenylamino)-benzamide (4.12 g, 68.6%) as light brown solid: m.p.=114-115° C.; $^1$NMR (400 MHz, DMSO-d₆) δ 11.89 (s, 1H), 8.62 (s, 1H), 7.53-7.55 (m, 1H), 7.31-7.37 (m, 2H), 7.17 (dd, 1H, J=16.9, 9.3), 6.60-6.65 (m, 1H), 4.22 (t, 1H, J=6.1), 3.96 (t, 1H, J=8.3), 3.76-3.77 (m, 2H), 3.63 (t, 1H, J=4.9), 1.26 (s, 3H), 1.21 (s, 3H); MS(APCI+)=522.9; Anal. calcd/found for C₁₉H₁₈F₃IN₂O₄: C, 43.70/43.88; H, 3.47/3.43; N, 5.36/5.20; F, 10.91/10.87.

EXAMPLE 39

N-(2,3-Dihydroxy-propoxy)-3,4-difluoro-2-(2-fluoro-4-iodo-phenylamino)-benzamide (Form II of Compound A)

To a stirring solution of N-(2,2-dimethyl-[1,3]dioxolan-4-ylmethoxy)-3,4-difluoro-2-(2-fluoro-4-iodo-phenylamino)-benzamide (3.03 g, 5.81 mmol) in methanol (30 mL) and water (3 mL) at ambient temperature was added p-toluene sulfonic acid (0.11 g, 0.581 mmol). After 18 hours another 0.11 g of added p-toluene sulfonic acid and 2 mL of water was added. After an additional 24 hours the reaction mixture was concentrated in vacuo. The residue was partitioned between ethyl acetate and water. The organic layer was washed twice with saturated NaHCO₃ solution and twice with saturated brine solution. The organic layers were collected, dried over Na₂SO₄, filtered and concentrated in vacuo affording a light brown solid, which was crystallized from ethyl acetate/hexanes to afford N-(2,3-dihydroxy-propoxy)-3,4-difluoro-2-(2-fluoro-4-iodo-phenylamino)-benzamide as a white solid. m.p.=135.5-137.3° C.; $^1$NMR (400 MHz, DMSO-d₆) δ 11.87 (s, 1H), 8.69 (s, 1H), 7.54 (dd, 1H, J=10.9, 1.5), 7.32-7.38 (m, 2H), 7.17 (dd, 1H, J=16.8, 9.0), 6.61-6.66 (cm, 1H), 4.82 (bs, 1H), 4.58 (bs, 1H), 3.84-3.85 (m, 1H), 3.71-3.64 (cm, 2H), 3.33 (2H, partially hidden by HDO); MS(APCI+)=483.0; Anal. calcd/found for C₁₆H₁₄F₃IN₂O₄: C, 39.85/40.12; H, 2.93/2.84; N, 5.81/5.65; F, 11.82/11.47.

Alternatively, the crude white solid of N-(2,3-Dihydroxy-propoxy)-3,4-difluoro-2-(2-fluoro-4-iodo-phenylamino)-benzamide was suspended in heptane-CH₂Cl₂ (1:1). The ratio was 6 mL of the solvent per gram of solid. The suspension was stirred at ambient temperature for 30 min. The solid was filtered, and dried at a vacuum oven (20 mmHg), 45° C. for 18 hrs, to give white crystals, mp 131-132° C.

EXAMPLE 39A

N-(2,3-Dihydroxy-propoxy)-3,4-difluoro-2-(2-fluoro-4-iodo-phenylamino)-benzamide (Form I of Compound A)

To a stirring solution of N-(2,2-dimethyl-[1,3]dioxolan-4-ylmethoxy)-3,4-difluoro-2-(2-fluoro-4-iodo-phenylamino)-benzamide (0.907 g, 1.74 mmol) in methanol (10 mL) and water (1 mL) at ambient temperature was added p-toluene sulfonic acid (0.032 g, 0.17 mmol). After stirring for 18 hours the reaction mixture was concentrated in vacuo and the affording residue was partitioned between ethyl acetate and water. The organic layers were washed twice with water and once with saturated brine solution. Organic layers were collected, dried over $Na_2SO_4$, filtered and concentrated in vacuo affording a light brown solid, which was dissolved in ethanol and precipitated with water to afford N-(2,3-dihydroxy-propoxy)-3,4-difluoro-2-(2-fluoro-4-iodo-phenylamino)-benzamide as a white solid (0.387 g). m.p.=83-85° C.; $^1$NMR (400 MHz, DMSO-$d_6$) 11.87 (s, 1H), 8.69 (s, 1H), 7.56 (d, 1H, J=11.0), 7.33-7.39 (m, 2H), 7.19 (dd, 1H, J=16.6, 9.0), 6.62-6.68 (cm, 1H), 4.82 (d, 1H, J=4.2), 4.58 (t, 1H, J=5.5), 3.84-3.87 (m, 1H), 3.66-3.72 (m, 2H), 3.3 (2H, partially hidden by HDO); MS(APCI+)=483.0; Anal. calcd/found for $C_{16}H_{14}F_3IN_2O_4 \cdot 0.3H_2O$: C, 39.41/39.02; H, 3.02/2.93; N, 5.75, 5.81; F, 11.69/11.68.

Alternatively, the crude solid N-(2,3-Dihydroxy-propoxy)-3,4-difluoro-2-(2-fluoro-4-iodo-phenylamino)-benzamide was dissolved in minimum amount of boiling ethanol (95%). Water was added to this boiling solvent until slightly cloudy. The mixture was cooled to ambient temperature and then at 0° C. for 18 hrs. Solid formed was filtered and dried at a vacuum oven (20 mmHg), 45° C. for 18 hrs, mp 81-84° C.

Furthermore, the crude solid N-(2,3-Dihydroxy-propoxy)-3,4-difluoro-2-(2-fluoro-4-iodo-phenylamino)-benzamide was dissolved in minimum amount of boiling ethyl acetate, and heptane was added to this solution until slight cloudy. The mixture was cooled to ambient temperature and then at 0° C. for 18 hrs. Solid formed was filtered and dried at a vacuum oven (20 mmHg), 45° C. for 18 hrs, mp 86° C.

The compounds of examples 40-48 were prepared by the procedures described in Examples 38 and 39.

EXAMPLE 40

5-Bromo-N-(2,3-dihydroxy-propoxy)-3,4-difluoro-2-(2-fluoro-4-iodo-phenylamino)-benzamide m.p.=172-174° C.; $^1$H NMR (400 MHz, DMSO-$d_6$) δ 11.92 (s, 1H), 8.69 (s, 1H), 7.67 (d, 1H, J=6.8), 7.56 (d, 1H, J=10.7), 7.34 (d, 1H, J=8.3), 6.73 (cm, 1H), 4.81 (m, 1H), 4.58-4.57 (m, 1H), 3.86-3.84 (m, 1H), 3.70-3.67 (m, 2H), 3.30 (2H, partially under HDO); MS(APCI+)=561.0. Anal. calcd/found for $C_{16}H_{13}BrF_3IN_2O_4$: C, 34.25/34.27; H, 2.34/2.22; N, 4.99/4.75.

EXAMPLE 41

5-Chloro-N-(2,3-dihydroxy-propoxy)-3,4-difluoro-2-(2-fluoro-4-iodo-phenylamino)-benzamide m.p.=152-155° C.; $^1$H NMR (400 MHz, DMSO-$d_6$) δ 11.91 (s, 1H), 8.66 (s, 1H), 7.58-7.55 (m, 2H), 7.34 (d, 1H, J=8.1 Hz), 6.72 (cm, 1H), 4.81 (d, 1H, J=4.1 Hz), 4.58 (t, 1H, J=5.9 Hz), 3.87-3.84 (m, 1H), 3.70-3.68 (m, 2H), 3.33 (2H, partially under HDO); MS(APCI+)=517.0. Anal. calcd/found for $C_{16}H_{13}ClF_3IN_2O_4$: C, 37.20/36.88; H, 2.54/2.43; N, 5.42/5.14; F, 11.03/11.70.

EXAMPLE 42

N-(2,3-Dihydroxy-propoxy)-4-fluoro-2-(2-fluoro-4-iodo-phenylamino)-benzamide m.p.=173-175° C.; $^1$H NMR (400 MHz, DMSO-$d_6$) δ 11.86 (s, 1H), 9.59 (s, 1H), 7.69 (d, 1H, J=10.3), 7.58 (t, 1H, J=7.8), 7.49 (d, 1H, J=8.5), 7.27 (t, 1H, J=8.5), 6.82 (d, 1H, J=11.5), 6.69 (t, 1H, J=7.8), 3.94-3.92 (m, 1H), 3.78-3.71 (m, 2H), 3.4 (2H, under HDO); MS(APCI+)=465.0.

EXAMPLE 43

N-(2,3-Dihydroxy-propoxy)-3,4,5-trifluoro-2-(2-fluoro-4-iodo-phenylamino)-benzamide m.p.=157-160° C.; $^1$H NMR (400 MHz, DMSO-$d_6$) δ 11.82 (s, 1H), 8.32 (s, 1H), 7.53-7.48 (m, 2H), 7.29 (d, 1H J=8.3), 6.58-6.55 (m, 1H), 4.80 (d, 1H, J=3.0), 4.57 (t, 1H, J=5.9), 3.83-3.81 (m, 1H), 3.67-3.65 (m, 2H), 3.30 (2H, under HDO); MS(APCI+)=500.9. Anal. calcd/found for $C_{16}H_{13}F_4IN_2O_4$: C, 38.42/38.48; H, 2.62/2.54; N, 5.60/5.55; F, 15.19/14.96.

EXAMPLE 44

2-(4-Bromo-2-fluoro-phenylamino)-N-(2,3-dihydroxy-propoxy)-3,4-difluoro-benzamide Prepared in the manner of N-(2,3-dihydroxy-propoxy)-3,4-difluoro-2-(2-fluoro-4-iodo-phenylamino)-benzamide (Example 39): m.p. 110-117° C. (dec). Anal. Calcd/Found for $C_{16}H_{14}BrF_3BrN_2O_4$: C, 44.16/43.86; H, 3.24/2.97; N, 6.44/6.13; F, 13.10/12.76; Br, 18.36/18.64.

EXAMPLE 45

2-(4-Chloro-2-fluoro-phenylamino)-N-(2,3-dihydroxy-propoxy)-3,4-difluoro-benzamide m.p. 114.0-114.9° C.; $^1$H NMR (400 MHz, DMSO-$d_6$) δ 11.87 (1H, s), 8.74 (1H, s), 7.38 (1H, dd, J=11.3 Hz, 2.3 Hz), 7.36 (1H, m), 7.07-7.20 (2H, m), 6.84-6.90 (1H, m), 4.83 (1H, br s), 4.59 (1H, br s), 3.84-3.87 (1H, m), 3.65-3.72 (2H, m), 3.20-3.40 (2H, m). Anal Calcd/Found for $C_{16}H_{14}F_3ClN_2O_4$: C, 49.18/49.09; H, 3.61/3.56; N, 7.07/7.03; F, 14.59/14.45; Cl, 9.07/9.16.

EXAMPLE 46

N-(2,2-Dimethyl-[1,3]dioxan-5-yloxy)-3,4-difluoro-2-(2-fluoro-4-iodo-phenylamino)-benzamide m.p.=154-155° C.; $^1$H NMR (400 MHz, DMSO-$d_6$) δ 11.93 (s, 1H), 8.64 (s, 1H), 7.55 (dd, 1H, J=10.7, 1.7), 7.40 (t, 1H, J=7.1), 7.33 (d, 1H, J=8.3), 7.21-7.14 (m, 1H), 6.69-6.65 (m, 1H), 3.95 (A of AB, 2H, J=10.7), 3.80 (B of AB, 2H, J=12.2), 3.65 (bs, 1H), 1.33 (s, 3H), 1.25 (s, 3H); MS (APCI+)= 523.1; Anal. calc/found for $C_{19}H_{18}F_3IN_2O_4$: C, 43.70/43.76; H, 3.47/3.44; N, 5.36/5.21; F, 10.91/10.73.

EXAMPLE 47

3,4-Difluoro-2-(2-fluoro-4-iodo-phenylamino)-N-(2-hydroxy-1-hydroxymethyl-ethoxy)-benzamide m.p. 111-114° C.; $^1$H NMR (400 MHz, DMSO-d$_6$) δ 11.82 (bs, 1H), 8.64 (bs, 1H), 7.55 (dd, 1H, J=10.7, 1.9), 7.40 (t, 1H, J=7.3), 7.34-7.31 (m, 1H), 7.20 (dd, 1H, J=16.6, 9.3), 6.65-6.60 (m, 1H), 4.64 (bs, 2H), 3.75-3.72 (m, 1H), 3.48-3.44 (m, 4H); MS (APCI+)=482.9; Anal. calc/found for C$_{16}$H$_{14}$F$_3$IN$_2$O$_4$: C, 39.85/39.93; H, 2.93/2.93; N, 5.81/5.51; F, 11.82/11.72.

EXAMPLE 48

5-Chloro-3,4-difluoro-2-(2-fluoro-4-iodo-phenylamino)-N-(2-hydroxy-1-hydroxymethyl-ethoxy)-benzamide m.p. 173-175° C.; $^1$H NMR (400 MHz, DMSO-d$_6$) δ 11.87 (s, 1H), 8.56 (s, 1H), 7.61 (d, 1H, J-6.3), 7.55 (d, 1H, J=9.3), 7.32 (d, 1H, J=9.5), 6.69 (m, 1H), 4.61 (m, 2H), 3.73 (m, 1H), 3.48 (m, 4H); MS(APCI+)=516.9/518.9.

EXAMPLE 49

N-[(R)-2,3-Dihydroxy-propoxy]-3,4-difluoro-2-(2-fluoro-4-iodo-phenylamino)-benzamide (Form I of Compound B)

Step A: To a solution of 3,4-difluoro-2-(2-fluoro-4-iodo-phenylamino)-benzoic acid (39.3 g, 100.0 mmol) in dry tetrahydrofuran (500 mL, 0.2 M), under nitrogen atmosphere, was added (R)-O-(2,2-dimethyl-[1,3]dioxolan-4-ylmethyl)-hydroxylamine (14.7 g, 100.0 mmol), followed by N-methylmorpholine (27.5 mL, 0.25 mole). The orange-colored solution was cooled with an ice-water bath. Diphenylphosphinic chloride (22.9 mL, 0.12 mole) was added dropwise. Some solid formed. The mixture was warmed to ambient temperature and stirred for 18 hrs. Water was added to quench the reaction and the tetrahydrofuran was evaporated in vacuo. The remaining oil was dissolved in ethyl acetate (500 mL), washed with a mixture of saturated brine and saturated sodium bicarbonate (1:1) two times. The ethyl acetate was removed and the crude oily solid was purified by flash chromatography (silica gel, hexane-acetone/2:1) to give N-((R)-2,2-Dimethyl-[1,3]dioxolan-4-ylmethoxy)-3,4-difluoro-2-(2-fluoro-4-iodo-phenylamino)-benzamide as an off-white solid after drying in a vacuum oven at 40° C. for 20 hrs: 41.7 g (79.8%), m.p. 124-125° C. The impure fractions were combined and purified by a second column chromatography using the same condition to give a $2^{nd}$ batch of 6.4 g (12.3%), mp 124-125° C., total yield 48.1 g (92.1%). $^1$H NMR (d$^6$-DMSO): δ 11.9 (s, br, 1H), 8.7 (s, br, 1H), 7.6 (d, 1H, J=10.99 Hz), 7.4 (m, 2H), 7.2 (m, 1H), 6.7 (m, 1H), 4.2 (m, 1H), 4.0 (t, 1H, J1=8.3 Hz, J2=6.8 Hz), 3.8 (m, 2H), 3.7 (m, 1H), 1.3 (s, 3H), 1.2 (s, 3H); $^{19}$F NMR (d$^6$-DMSO): δ –128.0, –133.1, –144.3; MS: 523 (M$^+$+1).

Step B: N-((R)-2,2-Dimethyl-[1,3]dioxolan-4-ylmethoxy)-3,4-difluoro-2-(2-fluoro-4-iodo-phenylamino)-benzamide (22.3 g, 42.7 mmol) was suspended in methanol (223 mL, 10 mL/g), and a solution of pTsOH.H$_2$O (4.1 g, 21.35 mmol) in water (22.3 mL) was added. The mixture was stirred at ambient temperature for 18 hrs, during which all solids dissolved to give a colorless, clear solution. The solution was concentrated and extracted with ethyl acetate (2×300 mL). The organic solution was washed with sodium bicarbonate, dried over MgSO$_4$. After filtration, the filtrate was concentrated, and co-evaporated with heptane to give a foaming solid. To this solid was added hexane-CH$_2$Cl$_2$ (1:1, 100 mL) and the mixture was stirred for 30 min. A white solid formed, which was filtered, washed with hexane. The solid was recrystallized from hexane-AcOEt to give N-((R)-2,3-dihydroxy-propoxy)-3,4-difluoro-2-(2-fluoro-4-iodo-phenylamino)-benzamide as white crystals, 13.57 g (65.9%), after drying at 60° C. vacuum oven for 3 days. A second crop of 5.05 g was obtained from the mother liquor, after recrystallization from the same solvent system. The total yield was 18.62 g (90.4%): m.p. 89-90° C. (Form II of Compound B). The combined crystals were ground with a set of mortar and pestle to fine powder, and dried at 60° C. in a vacuum oven for 3 days: m.p. 117-118° C. (Form I of Compound B); [α]=–2.05° (c=1.12, methanol); Analysis: Calcd. For: C$_{16}$H$_{14}$F$_3$I$_1$N$_2$O$_4$: C, 39.85; H, 2.93; N, 5.81; F, 11.82; I, 26.32. Found: C, 39.95; H, 2.76; N, 5.72; F, 11.71; I, 26.53. $^1$NMR (400 MHz, DMSO-d$_6$) δ 11.87 (s, 1H), 8.69 (s, 1H), 7.54 (dd, 1H, J=10.9, 1.5), 7.32-7.38 (m, 2H), 7.17 (dd, 1H, J=16.8, 9.0), 6.61-6.66 (cm, 1H), 4.82 (bs, 1H), 4.58 (bs, 1H), 3.84-3.85 (m, 1H), 3.71-3.64 (cm, 2H), 3.33 (2H, partially hidden by HDO).

EXAMPLE 49A

N-[(R)-2,3-Dihydroxy-propoxy]-3,4-difluoro-2-(2-fluoro-4-iodo-phenylamino)-benzamide (Form In of Compound B)

Step A: To a solution of 3,4-difluoro-2-(2-fluoro-4-iodo-phenylamino)-benzoic acid (2.25 g, 5.10 mmol) in dry tetrahydrofuran under nitrogen atmosphere, at –15 C was added diphenylphosphinic chloride (1.26 mL, 6.63 mole) dropwise. After stirring 20 min., N-methyl morpholine (0.70 mL, 6.375 mmol) was added and the reaction stirred an additional 20 min. (R)-O-(2,2-dimethyl-[1,3]dioxolan-4-ylmethyl)-hydroxylamine (0.748 g, 5.1 mmol) was added and the reaction stirred for 1 hour, at which point N-methylmorpholine (0.7 mL, 6.37 mmol) was added. The mixture was warmed to ambient temperature and stirred for 12 h. The reaction was concentrated in vacuo and then diluted with EtOAc. The organic layer was washed with sat'd NaHCO$_3$ (2×), brine (1×), dried over Na$_2$SO$_4$, filtered and concentrated. The crude product was purified on SiO2 using 4:1 hexane/EtOAc as elutant to provide 1.82 g (68%) of a brownish red solid.

Step B: N-((R)-2,2-Dimethyl-[1,3]dioxolan-4-ylmethoxy)-3,4-difluoro-2-(2-fluoro-4-iodo-phenylamino)-benzamide (0.210 g, 0.40 mmol) was suspended in 10:1 methanol/H$_2$O and pTsOH.H$_2$O (0.008 g, 0.04 mmol) was added. The mixture was stirred at ambient temperature for 18 hrs, during which all solids dissolved to give a colorless, clear solution. The solution was diluted with EtOAc. The organic solution was washed with sodium bicarbonate (2×), brine (1×) and dried over Na$_2$SO$_4$. After filtration, the filtrate was concentrated, and recrystallized from EtOAc and heptane. This solid was washed with heptane-CH$_2$Cl$_2$ (1:1 and dried in vacuo at 60 C to give N-((R)-2,3-Dihydroxy-propoxy)-3,4-difluoro-2-(2-fluoro-4-iodo-phenylamino)-benzamide as a white solid, (0.136 g, 70%). Product shrinks at 90.8 C, melts at 115-117 C. Analysis shows C, 40.92; H, 3.16; N, 5.41; F, 11.30; I, 23.92 (6.75% EtOAc, 0.96% heptane).

EXAMPLE 50

N-[(S)-2,3-Dihydroxy-propoxy]-3,4-difluoro-2-(2-fluoro-4-iodo-phenylamino)-benzamide (Form I of Compound C)

Prepared from (S)-O-(2,2-dimethyl-[1,3]dioxolan-4-ylmethyl)-hydroxylamine and 3,4-difluoro-2-(2-fluoro-4-iodo-phenylamino)-benzoic acid by the procedure described above for N-[(R)-2,3-dihydroxy-propoxy]-3,4-difluoro-2-(2-fluoro-4-iodo-phenylamino)-benzamide: m.p. 116-118° C. (Form II of Compound C); and m.p. 116-118° C. (Form I of Compound C); [α]=+1.77° (c=1.13, methanol). Analysis: Calcd. For: $C_{16}H_{14}F_3I_1N_2O_4$: C, 39.85; H, 2.93; N, 5.81; F, 11.82; I, 26.32. Found: C, 40.01; H, 2.73; N, 5.84; F, 11.45; I, 26.42.

EXAMPLE 50A

N-[(S)-2,3-Dihydroxy-propoxy]-3,4-difluoro-2-(2-fluoro-4-iodo-phenylamino)-benzamide (Form II of Compound C)

Prepared from (S)-O-(2,2-dimethyl-[1,3]dioxolan-4-ylmethyl)-hydroxylamine and 3,4-difluoro-2-(2-fluoro-4-iodo-phenylamino)-benzoic acid by the alternative procedure described above for N-[(R)-2,3-Dihydroxy-propoxy]-3,4-difluoro-2-(2-fluoro-4-iodo-phenylamino)-benzamide: m.p. 118-119° C.

EXAMPLE 51

5-Chloro-2-(2-chloro-4-iodo-phenylamino)-N-[(R)-2,3-dihydroxy-propoxy]-3,4-difluoro-benzamide Prepared from (R)-O-(2,2-dimethyl-[1,3]dioxolan-4-ylmethyl)-hydroxylamine and 5-chloro-2-(2-chloro-4-iodo-phenylamino)-3,4-difluoro-benzoic acid by the procedure described for N-(2,3-dihydroxy-propoxy)-3,4-difluoro-2-(2-fluoro-4-iodo-phenylamino)-benzamide: m.p. 155-156° C.; [α]=−5.1° (c=3.5 mg/mL, ethanol); $^1$NMR (400 MHz, DMSO-$d_6$) δ 12.03 (s, 1H), 8.83 (s, 1H), 7.76 (s, 1H), 7.66 (d, 1H, J=6.8 Hz), 7.47 (d, 1H, J=8.5 Hz), 6.68 (t, 1H, J=6.6 Hz), 4.83 (bs, 1H), 4.60 (bs, 1H), 3.89-3.92 (m, 1H), 3.68-3.76 (m, 2H), 3.30 (2H, partially hidden by HDO); MS (APCI+)= 533.0/535.0; Anal. calcd/found for $C_{16}H_{13}Cl_2F_2IN_2O_4$: C, 36.05/36.04; H, 2.46/2.25; N, 5.25/5.10; F, 7.13/7.18; Cl, 13.30, 13.50; I, 23.80, 24.02.

EXAMPLE 52

5-Chloro-2-(2-chloro-4-iodo-phenylamino)-N-[(S)-2,3-dihydroxy-propoxy]-3,4-difluoro-benzamide Step A: A 1 L single necked round-bottomed flask equipped with a magnetic stirrer was charged with a solution of 5-chloro-2-(2-chloro-4-iodo-phenylamino)-3,4-difluoro-benzoic acid (59.6 g, 135 mmol) in dry tetrahydrofuran (300 mL). The solution was cooled to 0° C. in an ice-acetone bath. To this solution was added diisopropylethylamine (34.8 g, 270 mmol), (S)-O-(2,2-dimethyl-[1,3]dioxolan-4-ylmethyl)-hydroxylamine (29.7 g, 202 mmol), 1-hydroxybenzotriazole (30.93 g, 202 mmol), and benzotriazol-1-yloxy-tris(dimethylamino)phosphonium hexafluorophosphate (BOP) (89.32 g, 202 mmol). After 30 minutes, the cooling bath was removed, and the reaction was stirred at ambient temperature for 18 hrs. The solvent was evaporated in vacuo, and the residue was dissolved in diethyl ether. The organic solution was washed with 10% aqueous sodium hydroxide (3×500 mL) and brine, and dried ($MgSO_4$). The solution was concentrated to afford 5-chloro-2-(2-chloro-4-iodo-phenylamino)-N-((S)-2,2-dimethyl-[1,3]dioxolan-4-ylmethoxy)-3,4-difluoro-benzamide (69.9 g) as a pale yellow solid that was used directly in the next hydrolysis reaction.

Step B: A 3 L single necked round bottomed flask equipped with a magnetic stirrer was charged with a solution of 5-chloro-2-(2-chloro-4-iodo-phenylamino)-N-((S)-2,2-dimethyl-[1,3]dioxolan-4-ylmethoxy)-3,4-difluoro-benzamide (69.9 g, 122 mmol) in tetrahydrofuran (1.5 L). Aqueous 1N hydrochloric acid (500 mL) solution was added and the reaction mixture was stirred at ambient temperature for 18 hrs. The reaction mixture was concentrated and extracted with ethyl acetate (3×800 mL). The organic extracts were washed with saturated aqueous sodium bicarbonate (500 ml) and brine (500 ml), and dried ($MgSO_4$). The crude pale yellow solid was recrystallized from ethyl acetate/hexane and dried at 70° C. in vacuum oven to afford 5-Chloro-2-(2-chloro-4-iodo-phenylamino)-N-((S)-2,3-dihydroxy-propoxy)-3,4-difluoro-benzamide (35 g, 54%) as pale yellow crystals: m.p. 153-154° C.; [α]=+3.36° (c=1.04, methanol); $^1$H NMR ($d^6$-DMSO) δ 12.02 (s, 1H), 8.85 (s, 1H), 7.74 (s, 1H), 7.64 (d, 1H), 7.45 (d, 1H), 6.66 (t, 1H), 4.82 (s, 1H), 4.58 (s, 1H), 3.88 (m, 2H), 3.74 (m, 3H); $^{19}$F NMR ($d^6$-DMSO) δ −133.21 (s, 1F), −137.18 (s, 1F); MS (m/z): 534 (68), 532 (100), 483 (28), 481 (41), 440 (51). Anal. calcd/found for $C_{16}H_{13}Cl_2F_2IN_2O_4$: C, 36.05/36.36; H, 2.46/2.38; N, 5.25/5.30; F, 7.13/7.15; Cl, 13.30/13.76; I, 23.80/23.83.

EXAMPLE 53

5-Chloro-N-[(2(R),3-dihydroxy-propoxy]-3,4-difluoro-2-(2-fluoro-4-iodo-phenylamino) benzamide Prepared from from (R)-O-(2,2-dimethyl-[1,3]dioxolan-4-ylmethyl)-hydroxylamine and 5-dhloro-3,4-difluoro-2-(2-fluoro-4-iodo-phenylamino)-benzoic acid by the procedure described above for N-[(R)-2,3-dihydroxy-propoxy]-3,4-difluoro-2-(2-fluoro-4-iodo-phenylamino)-benzamide: m.p. 142-143° C. $^1$H NMR (400 MHz, DMSO-$d_6$) δ 11.91 (s, 1H), 8.66 (s, 1H), 7.58-7.55 (m, 2H), 7.34 (d, 1H, J=8.1 Hz), 6.72 (cm, 1H), 4.81 (d, 1H, J=4.1 Hz), 4.58 (t, 1H, J=5.9 Hz), 3.87-3.84 (m, 1H), 3.70-3.68 (m, 2H), 3.33 (2H, partially under HDO).

EXAMPLE 54

5-Chloro-N-[(2(S),3-dihydroxy-propoxy]-3,4-difluoro-2-(2-fluoro-4-iodo-phenylamino)-benzamide Prepared from from (S)-O-(2,2-dimethyl-[1,3]dioxolan-4-ylmethyl)-hydroxylamine and 5-dhloro-3,4-difluoro-2-(2-fluoro-4-iodo-phenylamino)-benzoic acid by the procedure described above for N-[(R)-2,3-dihydroxy-propoxy]-3,4-difluoro-2-(2-fluoro-4-iodo-phenylamino)-benzamide: m.p. 157-158° C.; [α]=+5.290 (c=1.02, methanol); $^1$H NMR (400 MHz, DMSO-$d_6$) δ 11.91 (s, 1H), 8.66 (s, 1H), 7.58-7.55 (m, 2H), 7.34 (d, 1H, J=8.1 Hz), 6.72 (cm, 1H), 4.81 (d, 1H, J=4.1 Hz), 4.58 (t, 1H, J=5.9 Hz), 3.87-3.84 (m, 1H), 3.70-3.68 (m, 2H), 3.33 (2H, partially under HDO). Anal. calcd/found for $C_{16}H_{13}ClF_3IN_2O_4$: C, 37.20/37.47; H, 2.54/2.57; N, 5.42/5.32; F, 11.03/11.09; Cl, 6.86/6.87; I, 24.56/24.80.

EXAMPLE 55

2-(4-Bromo-2-fluoro-phenylamino)-N-((R)-2,3-dihydroxy-propoxy)-3,4-difluoro-benzamide Prepared in the manner of N-[2,3-Dihydroxy-propoxy]-3,4-difluoro-2-(2-fluoro-4-iodo-phenylamino)-benzamide (Example 39) with the following exception: Organics were dried over sodium sulfate and concentrated to afford a white foam. This was heated to 100° C. under vacuum (0.5 mm) for 1 hr to afford a glass: m.p. 52° C. (shrink), 70° C. melt; [α]=−4.4°(c=6.8, ethanol); $^1$H NMR (400 MHz, CD$_3$OD) δ 7.40 [cm, 1H]; 7.29 [dd, J=11.0, 2.2 Hz, 1H]; 7.16 [d, J=8.5 Hz, 1H]; 6.98 [dd, J=16.4, 9 Hz, 1H]; 6.73 [cm, 1H]; 3.94 [cm, 1H]; 3.83 [cm, 2H]; 3.55 [cm, 2H]. Anal. Calcd/Found for C$_{16}$H$_{14}$BrF$_3$BrN$_2$O$_4$: C, 44.16/43.77; H, 3.24/3.36; N, 6.44/6.09; F, 13.10/12.64; Br, 18.36/18.24.

The compounds of examples 56-61 were prepared by the general procedure of example 1.

EXAMPLE 56

2-(2-Chloro-4-iodo-phenylamino)-3,4-difluoro-N-(2-vinyloxy-ethoxy)-benzamide Yield: 55%; m.p. 141.5-143.0° C.; $^1$H NMR (400 MHz, DMSO-d$_6$) δ 12.01 (s, 1H), 8.84 (s, 1H), 7.77 (d, J=1.7 Hz, 1H), 7.51-7.42 (m, 2H), 7.27 (ddd, J=9.0, 8.8, 7.8 Hz, 1H), 6.59 (dd, J=8.6, 6.4 Hz, 1H), 6.49 (dd, J=14.2, 6.6 Hz, 1H), 4.19 (d, J=14.1 Hz, 1H), 4.06 (br s, 2H), 3.98 (d, J=6.6 Hz, 1H), 3.87 (br s, 2H); $^{19}$F NMR (376 MHz, DMSO-d$_6$) δ −132.4, −141.4; MS (APCI+)=495.1; MS (APCI−)=493.0. Anal. Calcd/found for C$_{17}$H$_{14}$ClF$_2$N$_2$O$_3$ with 0.08 moles residual C$_6$H$_{14}$: C, 41.86/41.90; H, 3.04/2.91; N, 5.59/5.72.

EXAMPLE 57

2-(2-Chloro-4-iodo-phenylamino)-3,4,5-trifluoro-N-(2-vinyloxy-ethoxy)-benzamide Yield: 25%; m.p. 115-116° C.; $^1$H-NMR (400 MHz, DMSO-d$_6$) δ 11.96 (s, 1H), 8.42 (s, 1H), 7.73 (d, 1H, J=1.7 Hz), 7.59 (m, 1H), 7.44 (dd, 1H, J=8.6, 1.7 Hz), 6.54 (m, 1H), 6.47 (dd, 1H, J=14.2, 6.6 Hz), 4.15 (d, 1H, J=14.2 Hz), 4.02 (s, 2H), 3.96 (dd, 1H, J=6.9, 1.7 Hz), 3.83 (s, 2H); $^{19}$F-NMR (376 MHz; DMSO-d$_6$) δ −137.08 (d, 1F, J=20.2 Hz), −140.97 (s, 1F), −154.65 (s, 1F); MS (APCI+) 513.0 (M+1, 100); MS (APCI−) 511.0 (M−1, 65), 424.9 (100); IR (KBr) 1647 (C=O stretch), 1621, 1488 cm$^{-1}$. Anal. Calcd./found for C$_{17}$H$_{13}$ClF$_3$IN$_2$O$_3$: C, 39.83/40.04; H, 2.56/2.54; N, 5.46/5.32.

EXAMPLE 58

4-Fluoro-2-(2-fluoro-4-iodo-phenylamino)-N-(2-vinyloxy-ethoxy)-benzamide

Yield: 44%; m.p. 103.5-104° C.; $^1$H-NMR (400 MHz, DMSO-d$_6$) δ 11.90 (s, 1H), 9.62 (s, 1H), 7.69 (dd, 1H, J=10.5, 2.0 Hz), 7.60 (m, 1H), 7.49 (d, 1H, J=8.3 Hz), 7.27 (m, 1H), 6.84 (d, 1H, J=11.7 Hz), 6.70 (m, 1H), 6.52 (dd, 1H, J=14.4, 6.8 Hz), 4.20 (dd, 1H, J=14.4, 2.0 Hz), 4.09 (m, 2H), 3.98 (dd, 1H, J=6.8, 1.7 Hz), 3.90 (m, 2H); $^{19}$F-NMR (376 MHz; DMSO-d$_6$) δ −106.73 (s, 1F), −124.58 (s, 1F); MS (APCI+) 461.0 (M+1, 100); MS (APCI−) 459.0 (M−1, 100); IR (KBr) 1641 (C=O stretch), 1602 cm$^{-1}$. Anal. Calcd./found for C$_{17}$H$_{15}$F$_2$IN$_2$O$_3$: C, 44.37/44.42; H, 3.29/3.28; N, 6.09/5.89.

EXAMPLE 59

3,4-Difluoro-2-(2-fluoro-4-iodo-phenylamino)-N-(2-vinyloxy-ethoxy)-benzamide $^1$H-NMR (400 MHz; DMSO-d$_6$) δ 11.89 (s, 1H), 8.67 (s, 1H), 7.57 (dd, 11.0, 1.7 Hz, 1H), 7.41-7.32 (m, 2H), 7.20 (m, 1H), 6.66 (m, 1H), 6.46 (dd, J=14.2, 6.8 Hz, 1H), 4.17 (dd, J=14.2, 1.5 Hz, 1H), 4.00 (br s, 2H), 3.97 (dd, J=6.7, 1.8 Hz, 1H), 3.84 (br s, 2H); $^{19}$F-NMR (376 MHz; DMSO-d$_6$) δ −128.1(s, 1F), −133.1 (s, 1F), −144.3 (d, 17.7 Hz, 1F). Anal. Calcd./found for C$_{17}$H$_{14}$F$_3$IN$_2$O$_3$: C, 42.70/42.30; H, 2.95/2.92; N, 5.86/5.52.

EXAMPLE 60

5-Chloro-3,4-difluoro-2-(2-fluoro-4-iodo-phenylamino)-N-(2-vinyloxy-ethoxy)-benzamide Yield: 34%; m.p. 119-120° C.; $^1$H-NMR (400 MHz; DMSO-d$_6$) δ 11.96 (s, 1H), 8.64 (s, 1H), 7.59 (m, 2H), 7.35 (d, 1H, J=8.3 Hz), 6.71 (m, 1H), 6.48 (dd, 1H, J=14.4, 6.8 Hz), 4.17 (d, 1H, J=14.2 Hz), 3.98 (m, 3H), 3.84 (m, 2H); $^{19}$F-NMR (376 MHz; DMSO-d$_6$) δ −127.60 (s, 1F), −134.09 (d, 1F, J=15.2 Hz), −140.45 (d, 1F, J=17.7 Hz); MS (APCI$^-$) 511.0 (M−1, 100); IR (KBr) 1646 (C=O stretch), 1608 cm$^{-1}$. Anal. Calcd./found for C$_{17}$H$_{13}$ClF$_3$IN$_2$O$_3$: C, 39.83/39.78; H, 2.56/2.57; N, 5.46/5.36.

EXAMPLE 61

5-Bromo-3,4-difluoro-2-(2-fluoro-4-iodo-phenylamino)-N-(2-vinyloxy-ethoxy)-benzamide Yield: 39%; m.p. 128-130° C.; $^1$H-NMR (400 MHz; DMSO-d$_6$) δ 11.95 (s, 1H), 8.67 (s, 1H), 7.69 (d, 1H, J=6.4 Hz), 7.57 (dd, 1H, J=10.7, 1.7 Hz), 7.35 (d, 1H, J=8.1 Hz), 6.72 (m, 1H), 6.48 (dd, 1H, J=14.4, 6.6 Hz), 4.17 (d, 1H, J=14.2 Hz), 3.98 (m, 3H), 3.83 (s, 2H); $^{19}$F-NMR (376 MHz; DMSO-d$_6$) δ −126.37 (s, 1F), −127.54 (s, 1F), −140.31 (d, 1F, J=17.7 Hz); MS (APCI$^+$) 558.9 (100), 556.9 (M+1, 98); MS (APCI$^-$) 556.9 (31), 554.9 (M−1, 32), 468.9 (100); IR (KBr) 1644 (C=O stretch), 1607, 1515, 1490 cm$^{-1}$. Anal. Calcd./found for C$_7$H$_{13}$BrF$_3$IN$_2$O$_3$: C, 36.65/36.71; H, 2.35/2.23; N, 5.03/4.97.

The compounds of Examples 62-64 were prepared by the general procedure of example 12.

EXAMPLE 62

5-Bromo-2-(2-chloro-4-iodo-phenylamino)-3,4-difluoro-N-(2-hydroxy-1,1-dimethyl-ethoxy)-benzamide m.p.=179-181° C.; $^1$H NMR (400 MHz; DMSO-d$_6$) δ 11.36 (s, 1H), 8.48 (s, 1H), 7.76 (d, 1H, J=6.8), 7.72 (s, 1H), 7.43 (d, 1H, J=8.5), 6.59 (m, 1H), 4.55 (t, 1H, J=6.4), 3.20 (d, 2H, J=5.9), 1.09 (s, 6H); MS (APCI+)=574.9/576.9. Anal. calcd/found for C$_{17}$H$_{15}$BrClF$_2$IN$_2$O$_3$: C, 35.48/35.56; H, 2.63/2.53; N, 4.87/4.71; F, 6.60/6.68.

EXAMPLE 63

3,4-Difluoro-N-(2-hydroxy-1,1-dimethyl-ethoxy)-2-(4-iodo-2-methyl-phenylamino)-benzamide m.p.=175-176° C.; $^1$H NMR (400 MHz; DMSO-d$_6$) δ 11.29 (s, 1H), 8.15 (s, 1H), 7.46 (s, 1H), 7.41 (m, 1H), 7.32 (d, 1H, J=8.3), 7.32 (q, 1H, J=16.4, 8.8), 6.38 (m, 1H), 4.59 (bs, 1H), 3.15 (d, 2H, J=4.9), 2.17 (s, 3H), 1.08 (s, 6H); MS(APCI+)=477.0. Anal. calcd/found for $C_{18}H_{19}F_2IN_2O_3$ (0.05 eq CH$_2$Cl$_2$): C, 45.12/44.73; H, 4.01/3.96; N, 5.83/5.54; F, 7.91/7.71.

EXAMPLE 64

2-(2-Chloro-4-iodo-phenylamino)-3,4-difluoro-N-(2-hydroxy-2-methyl-propoxy)-benzamide Yield: 17%; m.p. 140-153° C.; $^1$H-NMR (400 MHz; DMSO-d$_6$) δ 11.94 (s, 1H), 8.82 (s, 1H), 7.76 (d, 1H, J=1.5 Hz), 7.48 (dd, 1H, J=8.5, 2.0 Hz), 7.42 (m, 1H), 7.25 (m, 1H), 6.57 (m, 1H), 4.58 (s, 1H), 3.63 (s, 2H), 1.12 (s, 6H); $^{19}$F-NMR (376 MHz; DMSO-d$_6$) δ −132.53 (s, 1F), −141.45 (d, 1F); MS (APCI$^+$) 496.9 (M+1, 100); MS (APCI$^-$) 495.0 (M−1, 48), 406.9 (100); IR (KBr) 1637 cm$^{-1}$ (C=O stretch). Anal. Calcd./found for $C_{17}H_{16}ClF_2IN_2O_3$ with 0.03 mole residual acetone: C, 41.18/41.57; H, 3.27/3.14; N, 5.62/5.31.

The compounds of examples 65-76 were prepared by the general procedure of example 38.

EXAMPLE 65

3,4-Difluoro-2-(2-fluoro-4-iodo-phenylamino)-N-(2-hydroxy-1,1-dimethyl-ethoxy)-benzamide m.p.=182-183° C.; $^1$H NMR (400 MHz, DMSO-d$_6$) δ 11.25 (s, 1H), 8.38 (s, 1H), 7.54 (d, 1H, J=11.0), 7.39 (m, 1H), 7.31 (d, 1H, J=8.1), 7.24 (dd, 1H, J=16.9, 9.5), 6.59-6.56 (m, 1H), 4.58, (m, 1H), 3.16 (d, 2H, J=6.3), 1.08 (s, 6H); MS(APCI+)=481.0. Anal. calcd/found for $C_{17}H_{16}F_3IN_2O_3$ (+0.47 $C_4H_8O_2$): C, 43.47/43.86; H, 3.82/3.40; N, 5.37/5.60.

EXAMPLE 66

5-Chloro-3,4-difluoro-2-(2-fluoro-4-iodo-phenylamino)-N-(2-hydroxy-1,1-dimethyl-ethoxy)-benzamide m.p.=178-180° C.; $^1$H NMR (400 MHz, DMSO-d$_6$) δ 11.31 (s, 1H), 8.41 (s, 1H), 7.64 (d, 1H, J=7.1), 7.56 (d, 1H, J=11.0), 7.33 (d, 1H, J=8.3), 6.69-6.65 (m, 1H), 4.57 (t, 1H, J=6.1), 3.19 (d, 2H, J=6.6), 1.10 (s, 6H); MS(APCI+)=514.9/516.9. Anal. calcd/found for $C_{17}H_{15}ClF_3IN_2O_3$: C, 39.67/39.99; H, 2.94/2.74; N, 5.44/5.31; F, 11.07/11.05.

EXAMPLE 67

3,4-Difluoro-2-(2-fluoro-4-iodo-phenylamino)-N-(2-hydroxy-2-methyl-propoxy)-benzamide m.p. 156.7-156.9° C.; $^1$H NMR (400 MHz, DMSO-d$_6$) δ 11.85 (1H, s), 8.70 (1H, s), 7.55 (1H, dd, J=10.8 Hz, 1.9 Hz), 7.33-7.37 (2H, m), 7.17 (1H, dd, J=16.7 Hz, 9.4 Hz), 6.62-6.67 (1H, m), 4.57 (1H, br s), 3.58 (2H, s), 1.09 (6H, s). Anal. Calcd/Found for $C_{17}H_{16}F_3IN_2O_3$: C, 42.52/42.48; H, 3.36/3.21; N, 5.83/5.67; F, 11.87/11.51; I, 26.43/26.38.

EXAMPLE 68

3,4-Difluoro-N-(2-hydroxy-3-methoxy-propoxy)-2-(4-iodo-2-methyl-phenylamino)-benzamide m.p. 136.2-136.5° C.; $^1$H NMR (400 MHz, DMSO-d$_6$) δ 11.90 (1H, s), 8.49 (1H, s), 7.50 (1H, d, J=1.7 Hz), 7.34-7.41 (2H, m), 7.14 (1H, dd, J=16.6 Hz, 9.3 Hz), 6.45 (1H, dd, J=8.4 Hz, 5.6 Hz), 4.97 (1H, s), 3.69-3.79 (3H, m), 3.25-3.31 (2H, m), 3.21 (3H, s), 2.21 (3H). Anal. Calcd/Found for $C_{18}H_{19}F_2IN_2O_4$: C, 43.92/44.14; H, 3.89/3.88; N, 5.69/5.59; F, 7.72/7.79; I, 25.78/25.89.

EXAMPLE 69

5-Bromo-2-(2-chloro-4-iodo-phenylamino)-3,4-difluoro-N-(2-hydroxy-3-methoxy-propoxy)-benzamide m.p. 139.5-140.1° C.; $^1$H NMR (400 MHz, DMSO-d$_6$) δ 12.03 (1H, s), 8.83 (1H, s), 7.50-7.76 (2H, m), 7.47 (1H, dd, J=8.6 Hz, 1.5 Hz), 6.65-6.69 (1H, m), 4.98 (1H, s), 3.70-3.90 (3H, m), 3.31 (2H, m), 3.22 (3H, s).

Anal. Calcd/Found for $C_{17}H_{15}BrClF_2IN_2O_4$: C, 34.52/34.92; H, 2.56/2.54; N, 4.74/4.67; F, 6.42/6.48; I, 21.45/21.12.

EXAMPLE 70

3,4-Difluoro-N-(1-hydroxymethyl-cyclopropyl-methoxy)-2-(4-iodo-2-methyl-phenylamino)-benzamide m.p. 165.4-165.6° C.; $^1$H NMR (400 MHz, DMSO-d$_6$) δ 11.74 (1H, s), 8.49 (1H, s), 7.47 (1H, d, J=10.5 Hz), 7.31-7.36 (2H, m), 7.11 (1H, dd, J=16.5 Hz, 9.4 Hz), 6.43 (1H, dd, J=8.3 Hz, 5.6 Hz), 4.55 (1H, br s), 3.67 (2H, s), 3.33 (2H, s), 2.17 (3H, s), 0.36 (4H, J=4.9 Hz). Anal. Calcd/Found for $C_{19}H_{19}F_2IN_2O_3$: C, 46.74/46.87; H, 3.92/3.93; N, 5.74/5.99; F, 7.78/7.64; I, 25.99/25.84.

EXAMPLE 71

5-Bromo-2-(2-chloro-4-iodo-phenylamino)-3,4-difluoro-N-(1-hydroxymethyl-cyclopropylmethoxy)-benzamide m.p. 152.6-153.9° C.; $^1$H NMR (400 MHz, DMSO-d$_6$) δ 11.88(1H, s), 8.81 (1H, s), 7.75 (1H, s), 7.69 (1H, d, J=6.6 Hz), 7.45 (1H, d, J=8.5 Hz), 6.63-6.67 (1H, m), 4.53 (1H, br s), 3.73 (2H, s), 3.33 (2H, s), 0.36 (4H, J=4.9 Hz). Anal. Calcd/Found for $C_{18}H_{15}BrClF_2IN_2O_3$: C, 36.79/37.21; H, 2.57/2.57; N, 4.77/4.64; F, 6.47/6.58; I, 21.60/21.78.

EXAMPLE 72

3,4-Difluoro-2-(4-iodo-2-methyl-phenylamino)-N-(3,3,3-trifluoro-2-hydroxy-propoxy) benzamide m.p. 175.2-175.5° C.; $^1$H NMR (400 MHz, DMSO-d$_6$) δ 12.00 (1H, s), 8.41 (1H, s), 7.47 (1H), 7.40 (1H, m), 7.33 (1H, d), 7.12 (1H, dd, J=16.6 Hz, 9.3 Hz), 6.54 (1H, br s), 6.44 (1H, dd, J=8.3 Hz, 5.3 Hz), 4.24 (1H, m), 3.83-3.98 (2H, m), 2.18 (3H, s). Anal. Calcd/Found for $C_{17}H_{14}F_5IN_2O_3$: C, 39.56/39.87; H, 2.73/2.66; N, 5.43/5.30; F, 18.40/18.32; I, 24.58/24.63.

EXAMPLE 73

5-Bromo-2-(2-chloro-4-iodo-phenylamino)-3,4-difluoro-N-(3,3,3-trifluoro-2-hydroxy-propoxy)-benzamide m.p. 186.9-187.3° C.; $^1$H NMR (400 MHz, DMSO-d$_6$) δ 12.16 (1H, s), 8.77 (1H, s), 7.80 (1H, dd, J=7.0 Hz, 1.5 Hz), 7.75 (1H, d, J=1.7 Hz), 7.47 (1H, dd, J=8.6 Hz, 1.9 Hz), 6.66 (1H, dd, J=8.5 Hz, 5.9 Hz), 6.55 (1H, br s), 4.31 (1H, m), 3.92-4.07 (2H, m). Anal. Calcd/Found for $C_{16}H_{10}BrClF_5IN_2O_3$: C, 31.22/31.52; H, 1.64/1.60; N, 4.55/4.46; F, 15.43/15.39; I, 20.62/20.87.

EXAMPLE 74

3,4-Difluoro-2-(2-fluoro-4-iodo-phenylamino)-N-[trans-(2-hydroxymethyl-cyclopropylmethoxy)]-benzamide m.p. 128.5-128.7° C.; $^1$H NMR (400 MHz, DMSO-d$_6$) δ 11.71(1H, s), 8.69 (1H, s), 7.54 (1H, dd, J=10.9 Hz, 1.8 Hz), 7.32-7.36 (2H, m), 7.17 (1H, dd, J=16.6 Hz, 9.3 Hz), 6.60-6.66 (1H, m), 4.43 (1H, t, J=5.6 Hz), 3.54-3.65 (2H, m), 3.14-3.34 (2H, m), 0.85-0.89 (2H, m), 0.34-0.41 (2H, m).

Anal. Calcd/Found for $C_{18}H_{16}F_3IN_2O_3$: C, 43.92/44.23; H, 3.28/3.23; N, 5.69/5.54; F, 11.58/11.47; I, 25.78/25.58.

EXAMPLE 75

5-Chloro-3,4-difluoro-2-(2-fluoro-4-iodo-phenylamino)-N-[trans-(2-hydroxymethyl-cyclopropylmethoxy)]-benzamide m.p. 152.5-153.1° C.; $^1$H NMR (400 MHz, DMSO-d$_6$) δ 11.76 (1H, s), 8.65 (1H, s), 7.56 (1H, m), 7.52-7.53 (1H, m), 7.32 (1H, d, J=8.5 Hz), 6.66-6.72 (1H, m), 4.44-4.47 (1H, m), 3.54-3.62 (2H, m), 3.12-3.42 (2H, m), 0.81-0.89 (2H, m), 0.32-0.40 (2H, m). Anal. Calcd/Found for $C_{18}H_{15}ClF_3IN_2O_3$: C, 41.05/41.00; H, 2.87/2.96; N, 5.31/5.13; F, 10.82/10.48; I, 24.09/24.33.

EXAMPLE 76

N-(2,3-Dihydroxy-3-methyl-butoxy)-3,4-difluoro-2-(2-fluoro-4-iodo-phenylamino)-benzamide m.p.=180-183° C.; $^1$H NMR (400 MHz, DMSO-d$_6$) δ 11.85 (s, 1H), 8.69 (bs, 1H), 7.56 (d, 1H, J=10.7), 7.40 (m, 1H), 7.35 (d, 1H, J=9.0), 7.20 (dd, 1H, J=16.6, 8.3), 6.65 (m, 1H), 4.87 (bs, 1H), 4.31 (s, 1H), 4.07 (d, 1H, J=9.8), 3.65 (t, 1H, J=9.8), 3.44-3.41 (m, 1H), 1.05 (s, 3H), 0.97 (s, 3H); MS(APCI+)=511.1. Anal. calcd/found for $C_{18}H_{18}F_3IN_2O_4$ (+0.22 eq $C_4H_8O_2$): C, 42.82/43.20; H, 3.76/3.61; N, 5.29/5.15.

EXAMPLE 77

2-(2-Chloro-4-iodo-phenylamino)-3,4-difluoro-N-(2-phenylamino-ethoxy)-benzamide

The title compound was prepared in the manner described for example 1. A white solid: m.p. 157.8° C.; $^1$H NMR (400 MHz, DMSO-d$_6$) δ 11.3 (s, 1H), 7.70 (m, 2H), 7.44 (dd, J=8.6 Hz, 1.95 Hz, 1H), 7.01 (t, J=8.1 Hz, 2H), 6.94 (t, J=9.2 Hz, 1H), 6.47 (m, 4H), 5.58 (br t, J=5.1 Hz, 1H), 3.91 (t, J=5.6 Hz, 2H), 3.19 (q, J=5.6 Hz, 2H); $^{19}$F NMR (376 MHz, DMSO-d$_6$) δ −139.77 (s, 1F), −143.39 (d, J=20.2 Hz, 1F).

EXAMPLE 78

3,4-Difluoro-2-(4-iodo-2-methyl-phenylamino)-N-(2-methylamino-ethoxy)-benzamide

Step A: To a solution of (2-aminooxy-ethyl)-methyl-carbamic acid tert-butyl ester (0.63 g, 3.31 mmol) and diisopropylethylamine (0.6 mL, 3.44 mmol) in dimethylformamide (10 mL) was added 3,4-Difluoro-2-(4-iodo-2-methyl-phenylamino)-benzoic acid pentafluorophenyl ester (1.66 g, 2.99 mmol). The resultant reaction mixture was stirred 5 h at ambient temperature and concentrated under reduced pressure. The residue was diluted with ether (100 mL), washed with water (2×25 mL) and brine (2×25 mL), dried over magnesium sulfate and concentrated in vacuo. The residue was purified by silica gel chromatography. Elution with dichloromethane afforded [2-({1-[3,4-difluoro-2-(4-iodo-2-methyl-phenylamino)-phenyl]-methanoyl}-aminooxy)-ethyl]-methyl-carbamic acid tert-butyl ester (1.05 g, 62%) as a white foam: $^1$H NMR (400 MHz, DMSO-d$_6$) δ 11.85 and 11.80 (br s, 1 H), 8.49 (br s, 1 H), 7.50 (s, 1 H), 7.39 (m, 1H), 7.35 (d, J=8.3 Hz, 1 H), 7.14 (m, 1 H), 6.46 (dd, J=7.8, 5.9 Hz, 1 H), 3.85 (br s, 2 H), 3.35 (br s, 2 H), 2.79 (br s, 3 H), 2.21 (s, 3 H), 1.36 and 1.33 (s, 9 H); $^{19}$F NMR (376 MHz, DMSO-d$_6$) δ −132.9, −143.3 (d, J=17.7 Hz); MS (APCI+)=562.1.

Step B: Trifluoroacetic acid (3.0 mL, 39 mmol) was added to a 0° C. solution of [2-({1-[3,4-difluoro-2-(4-iodo-2-methyl-phenylamino)-phenyl]-methanoyl}-aminooxy)-ethyl]-methyl-carbamic acid tert-butyl ester (0.75 g, 1.3 mmol) in dichlormethane (12 mL). The resultant solution was stirred 2.5 h at 0° C. and diluted with ether (50 mL). Water (20 mL) was added and, with vigorous stirring, the pH of the aqueous layer was adjusted to pH 8 with saturated aqueous sodium bicarbonate. The heterogeneous mixture was stirred 30 min and the precipitate was removed by filtration and washed with water-ethanol (2:1) and acetone. The solid (471 mg) was dried overnight in vacuo and was further triturated with hot methanol and dried at 70° C. under reduced pressure to afford 3,4-difluoro-2-(4-iodo-2-methyl-phenylamino)-N-(2-methylamino-ethoxy)-benzamide (272 mg) as a white powder: m.p. 183-185 (dec); $^1$H NMR (400 MHz, DMSO-d$_6$) δ 10.33 (s, 1 H), 7.69 (t, J=7.0 Hz, 1 H), 7.46 (d, J=1.7 Hz, 1 H), 7.33 (dd, J=8.6, 2.0 Hz, 1 H), 6.95 (app q, J=9.0 Hz, 1 H), 6.40 (t, J=7.8 Hz, 1 H), 3.87 (br t, J=4.4 Hz, 2 H), 2.82 (br s, 2 H), 2.47 (s, 3 H), 2.24 (s, 3 H); $^{19}$F NMR (376 MHz, DMSO-d$_6$) δ −137.7 (d, J=7.6 Hz), −143.3 (d, J=20.2 Hz). Anal Calcd./Found for $C_{17}H_{18}F_2IN_3O_2$+0.07 $C_4H_{10}O$: C, 44.50/44.61; H, 4.01/3.97; N, 9.01/8.72.

EXAMPLE 79

3,4-Difluoro-2-(2-fluoro-4-iodo-phenylamino)-N-(2-methylamino-ethoxy)-benzamide, hydrochloride salt Step A: A solution of 3,4-difluoro-2-(2-fluoro-4-iodo-phenylamino)-benzoic acid (3.11 g, 7.91 mmol) in tetrahydrofuran (20 mL) was cooled with a −40° C. bath and treated with N-methylmorpholine (0.87 mL, 7.9 mmol). Diphenylphosphinic chloride (2.00 mL, 10.5 mmol) was added dropwise over 5 min and the reaction mixture was stirred for 90 min, during which time the temperature of the cooling bath slowly warmed to 0° C. The reaction mixture was again cooled to −40° C. and (2-aminooxy-ethyl)-methyl-carbamic acid tert-butyl ester (2.00 g, 10.5 mmol) was added as a solution in tetrahydrofuran (6 mL). After an additional 10 min, N-methylmorpholine (1.33 mL, 12.1 mmol) was added. The temperature of the cooling bath was allowed to warm to ambient temperature over 4 h and the reaction mixture was further stirred overnight. The reaction was diluted with ethyl acetate (40 mL) and washed with saturated aqueous ammonium chloride (2×10 mL). The organics were dried over magnesium sulfate, concentrated and purified by silica gel chromatography. Elution with 35% ethyl acetate-hexanes afforded [2-({1-[3,4-difluoro-2-(2-fluoro-4-iodo-phenylamino)-phenyl]-methanoyl}-aminooxy)-ethyl]-methyl-carbamic acid tert-butyl ester (3.28 g, 73% yield) as an off-white foam: $^1$H NMR (400 MHz, DMSO-$d_6$) δ 11.84 and 11.75 (br s, 1 H total), 8.66 (br s, 1 H), 7.54 (dd, J=10.9, 1.6 Hz, 1 H), 7.36 (br t, J=8.8 Hz, 1 H), 7.33 (br d, J=8.8 Hz), 7.20 (m, 1 H), 6.64 (m, 1 H), 3.85 (t, J=5.2 Hz, 2 H), 3.34 (br s, 2 H), 2.81 and 2.79 (br s, 3 H total), 1.34 and 1.32 (s, 9 H total); $^{19}$F NMR (376 MHz, DMSO-$d_6$) δ −128.0 (d, J=32.9 Hz), −133.0, −144.2 (d, J=17.7 Hz); MS (APCI−)=564.1.

Step B: [2-({1-[3,4-Difluoro-2-(2-fluoro-4-iodo-phenylamino)-phenyl]-methanoyl}-aminooxy)-ethyl]-methyl-carbamic acid tert-butyl ester (3.28 g, 5.80 mmol) was dissolved in ethereal hydrogen chloride solution (20 mL, 1.0 M in diethyl ether). The resultant solution was stirred at ambient temperature for 48 h, during which precipitation of a white solid ensued. Hexanes (20 mL) was added and the reaction mixture was stirred vigorously for an additional 20 min. The reaction mixture was filtered, and the filter cake was broken up with a spatula. The solid was washed with hexanes (50 mL) and ether (20 mL) and was dried in vacuo to afford a free-flowing, tan-colored powder (2.46 g, 85% yield). Recrystallization from acetonitrile afforded colorless needles: m.p. 173-176° C.; $^1$H NMR (400 MHz, DMSO-$d_6$) δ 12.27 (s, 1 H), 8.76 (br s, 2 H), 8.64 (s, 1 H), 7.55 (dd, J=11.0, 1.9 Hz, 1 H), 7.47 (dd, J=7.1, 6.3 Hz, 1 H), 7.33 (d, J=8.3 Hz, 1 H), 7.23 (dt, J=7.6, 9.2 Hz, 1 H), 6.64 (td, J=8.8, 4.2 Hz, 1 H), 4.05 (t, 4.9 Hz, 2 H), 3.11 (br s, 2 H), 2.56 (t, J=4.6 Hz, 3 H); $^{19}$F NMR (376 MHz, DMSO-$d_6$) δ −128.2 (t, J=10.1 Hz), −132.5 (d, J=20.2 Hz), −144.0 (d, 20.2 Hz). Anal Calcd./Found for $C_{16}H_{16}F_3IN_3O_2Cl$: C, 38.31/38.20; H, 3.21/3.10; N, 8.38/8.34; F, 11.36/11.21; Cl, 7.07/7.05.

EXAMPLE 80

3,4-Difluoro-2-(4-iodo-2-methyl-phenylamino)-N-[2-(2,2,2-trifluoro-ethylamino)-ethoxy]-benzamide; hydrochloride Step A: Diethylazodicarboxylate (3.60 mL, 22.9 mmol) was added dropwise over 30 min to a solution comprised of 0-[2-(2,2,2-trifluoro-ethylamino)-ethyl]-hydroxylamine (3.19 g, 22.3 mmol, prepared as in J. Am. Chem. Soc. 1979, 101, 4300), triphenylphosphine (6.05 g, 23.1 mmol), and N-hydroxyphthalimide (3.65 g, 22.4 mmol). The resultant reaction mixture was stirred at ambient temperature. After 20 h, the reaction mixture was concentrated and the residue was dissolved in 60 mL of warm chloroform. Upon cooling, crystallization of diethyl 1,2-hydrazaine dicarboxylate ensued. The precipitate was filtered and the filtrate was concentrated and further diluted with ether. A single crystal of triphenylphosphine oxide was added, initiating copious precipitation. The resultant precipitate was removed by filtration and the filtrate was concentrated in vacuo and chromatographed on silica gel. Elution with hexanes-ethyl acetate (2:1) afforded 2-[2-(2,2,2-trifluoro-ethylamino)-ethoxy]-isoindole-1,3-dione (4.05 g, 63% yield) as a colorless oil: $^1$H NMR (400 MHz, CDCl$_3$) δ 7.84-7.73 (m, 4H), 4.30 (t, J=4.8 Hz, 2H), 3.26 (q, J=9.5 Hz, 2H), 3.00 (t, J=4.9 Hz, 2H), 2.33 (br s, 1H); MS (APCI+)=289.0.

Step B: Dichloromethane (5 mL) was added to 2-[2-(2,2,2-trifluoro-ethylamino)-ethoxy]-isoindole-1,3-dione (0.46 g, 1.6 mmol) and the resultant solution was cooled to 0° C. Methylhydrazine (0.086 mL, 1.62 mmol) was added and the resultant solution was stirred at ambient temperature for 1 h. Ether (20 mL) was added and the precipitate was filtered and the filtrate was concentrated in vacuo. Dimethylformamide (5 mL) was added and the resultant solution was treated sequentially with 3,4-difluoro-2-(4-iodo-2-methyl-phenylamino)-benzoic acid pentafluorophenyl ester (0.847 g, 1.51 mmol) and diisopropylethylamine (0.60 mL, 3.4 mmol). The resultant reaction mixture was stirred overnight, diluted with ethyl acetate and washed with water (4×) and saturated brine, dried over magnesium sulfate and concentrated in vacuo. Purification by silica gel chromatography (hexanes-ethyl acetate, 1:1) afforded 3,4-difluoro-2-(4-iodo-2-methyl-phenylamino)-N-[2-(2,2,2-trifluoro-ethylamino)-ethoxy]-benzamide (0.70 g, 83% yield) as a waxy foam: $^1$H NMR (400 MHz, Acetone-$d_6$) δ 10.98 (br s, 1H), 8.69 (br s, 1H), 7.52 (br s, 2H), 7.39 (dd, J=8.6 Hz, 2.0 Hz, 1H), 7.00 (m, 1H), 6.55 (dd, J=8.6 Hz, 6.4 Hz, 1H), 3.27 (q, J=10.0 Hz, 2H), 2.90 (br t, J=4.9 Hz, 2H), 2.82 (br s, 2H), 2.30 (s, 3H); $^{19}$F NMR (376 MHz, Acetone-$d_6$) δ −73.1 (t, J=10.0 Hz, 3F), −133.8 (s, 1F), −143.2 (s, 1F); MS (APCI+)=530.0.

Step C: The hydrochloride salt was prepared by treatment of a solution of 3,4-difluoro-2-(4-iodo-2-methyl-phenylamino)-N-[2-(2,2,2-trifluoro-ethylamino)-ethoxy]-benzamide (375 mg, 0.708 mmol) in ether (5 mL) with ethereal hydrogen chloride (2 mL, 1.0 M in ether) and precipitation by addition of hexanes (50 mL). The resultant solid was dried in vacuo at 75° C. overnight to afford a straw-colored powder: $^1$H NMR (400 MHz, Acetone-$d_6$) δ 12.35 (br s, 1H), 8.84 (br s, 1H), 7.73 (br s, 1H), 7.54 (s, 1H), 7.40 (dd, J=8.4 Hz, 1.9 Hz, 1H), 7.00 (apparent q, J=8.4 Hz, 1H), 6.58 (dd, J=8.4 Hz, 6.40 Hz, 1H), 4.43 (br s, 2H), 4.17 (br q, 2H), 3.59 (br s, 2H), 2.30 (s, 3H); $^{19}$F NMR (376 MHz, Acetone-$d_6$) δ −68.39 (s, 3F), −133.07 (s, 1F), −143.20 (s, 1F). Anal Calcd./Found for $C_{18}H_{17}F_5IN_3O_2$+0.86 HCl: C, 38.57/38.77; H, 3.21/3.04; N, 7.49/7.19; Cl, 5.44/5.66.

EXAMPLE 81

2-(2-Chloro-4-iodo-phenylamino)-4-fluoro-N-(2-hydroxy-ethoxy)-N-methyl-benzamide A solution of 2-(2-chloro-4-iodo-phenylamino)-4-fluoro-N-(2-hydroxy-ethoxy)-benzamide (0.460 g, 1.02 mmol) in dimethylformamide (10 mL) was sequentially treated with potassium carbonate (0.61 g, 4.4 mmol) and iodomethane (0.075 mL, 1.2 mmol). The resultant reaction mixture was stirred 1 h at ambient temperature, was diluted with excess water and was extracted with ethyl acetate. The organic extracts were washed with brine, dried over magnesium sulfate and concentrated in vacuo. Chromatography on silica gel afforded a white solid (200 mg). Further purification by chromatography on C-18 reverse phase silica gel (30% water-acetonitrile) afforded 2-(2-chloro-4-iodo-phenylamino)-4-fluoro-N-(2-hydroxy-ethoxy)-N-methyl-benzamide (139 mg, 29% yield) as a white foam: $^1$H NMR (400 MHz, Acetone-$d_6$) δ 8.45 (s, 1H), 7.79 (d, J=2.0 Hz, 1H), 7.69 (dd, J=8.8, 6.6 Hz, 1H), 7.60 (dd, J=8.5, 2.0 Hz, 1H), 7.28 (d, J=8.5 Hz, 1H), 7.09 (dd, J=11.4, 2.3 Hz, 1H), 6.77 (td, J=8.6, 2.5 Hz, 1H), 3.90 (t, J=2H), 3.85 (br m, OH), 3.58 (t, J=4.5 Hz, 2H), 3.38 (s, 3H); $^{19}$F-NMR (376 MHz, Acetone-d$_6$) δ −109.8 (dd, J=10.1, 7.6 Hz); MS (APCI+)=465.0.

EXAMPLE 82

Acetic acid 2-({1-[3,4,5-trifluoro-2-(4-iodo-2-methyl-phenylamino)-phenyl]-methanoyl}-aminooxy)-ethyl ester To a 0° C. solution of 3,4,5-trifluoro-N-(2-hydroxyethoxy)-2-(4-iodo-2-methyl-phenylamino)-benzamide (0.25 g, 0.536 mmol) in THF (10.72 mL) was added triethylamine (0.113 mL, 0.804 mmol). After 5 min, acetyl chloride (0.039 mL, 0.536 mmol) was added to the cold solution, which immediately produced a precipate. After stirring for 50 min between 0-5° C., the reaction mixture was partitioned between water (20 mL) and ethyl acetate (20 mL). The aqueous layer was extracted with ethyl acetate (20 mL). The organic layers were combined and dried over anhydrous magnesium sulfate. The resultant mixture was filtered and the filter cake was thoroughly rinsed with ethyl acetate. The filtrate was concentrated in vacuo to obtain a yellow oil (0.1755 g). Chromatographed crude oil using a gradient of hexanes and ethyl acetate. Combined fractions and removed the solvent in vacuo to obtain a solid. The solid was recrystalized in a mixture of hexanes/acetone to afford 0.0221 g (8%) of a solid; $^1$H NMR (400 MHz, Acetone-d$_6$): δ 10.15 (br s, 1H), 8.49 (br s, 1H), 7.88 (t, J=0.9 Hz, 1H), 7.56 (s, 1H), 7.43 (d, J=8.3 Hz, 1H), 6.69 (dd, J=8.55, 5.86 Hz, 1H), 4.53 (br s, 2H), 4.19 (br s, 2H), 2.33 (s, 3H), 1.81 (br s, 3H). $^{19}$F NMR (375 MHz, Acetone-d$_6$): δ −139.52 (br t, 1F), −146.62 (br q, 1F), −153.43 (br s, 1F). Anal. Calcd/Found for C$_{18}$H$_{16}$F$_3$IN$_2$O$_4$: C, 42.54/40.87; H, 3.17/2.98; N, 5.51/5.17.

EXAMPLE 83

[3,4-Difluoro-2-(2-fluoro-4-iodo-phenylamino)-phenyl]-(4-hydroxy-isoxazolidin-2-yl)-methanone To a stirring solution of 3,4-difluoro-2-(2-fluoro-4-iodo-phenylamino)-benzoic acid pentafluorophenyl ester (171 mg, 0.306 mmol) and 4-hydroxytetrahydroisoxazol-2-ium chloride (BIONET, 58 mg, 0.46 mmol) in dimethylformamide (2 mL) was added 4-methylmorpholine (0.1 mL, 0.91 mmol). The resultant reaction mixture was stirred at ambient temperature for 3 h. Ethyl acetate (50 mL) was added the mixture was washed with water (3×10 mL) and saturated brine solution (10 mL). The extracts were dried over magnesium sulfate and concentrated in vacuo. Chromatography (10% methanol-dichloromethane) afforded a tan-colored oil that solidified upon standing. Recrystallization from acetone-ether afforded [3,4-Difluoro-2-(2-fluoro-4-iodo-phenylamino)-phenyl]-(4-hydroxy-isoxazolidin-2-yl)-methanone (61 mg, 43% yield) as a white powder:

m.p. 122-124° C.; $^1$H NMR (400 MHz, Acetone-d$_6$) δ 7.97 (br s, 1 H), 7.51-7.45 (m, 2 H), 7.38 (ddd, J=8.6, 1.7, 1.2 Hz, 1 H), 7.12 (m, 1H), 6.68 (td, J=8.8, 5.2 Hz, 1H), 4.82 (m, 1 H), 4.71 (br d, J=4.2 Hz, OH), 3.98 (dd, J=8.8, 4.2 Hz, 1H), 3.96-3.88 (m, 2 H), 3.75 (dd, J=11.8, 0.9 Hz, 1 H); $^{19}$F-NMR (376 MHz, Acetone-d$_6$) δ −30.5, −135.4, −144.4. Anal Calcd/Found C$_{16}$H$_{12}$F$_3$IN$_2$O$_3$: C, 41.40/41.52; H, 2.61/2.53; N, 6.03/6.05.

EXAMPLE 84

5-Bromo-N-(2,3-dihydroxy-propoxy)-3,4-difluoro-2-(2-fluoro-phenylamino)-benzamide A solution of 5-bromo-N-(2,3-dihydroxy-propoxy)-3,4-difluoro-2-(2-fluoro-4-iodo-phenylamino)-benzamide (0.240 g, 0.429 mmol) and triethylamine (0.2 g, 1.98 mmol) in tetrahydrofuran (16 mL) was hydrogenated over Raney Nickel (0.12 g, pre-rinsed with tetrahydrofuran) at 10 psig at room temperature for a total of 7 hours. The catalyst was removed by filtration and the filtrate was concentrated in vacuo. The afforded residue was partitioned between ethyl acetate and water. The organics were washed twice with water, twice with saturated brine, collected, dried over sodium sulfate, filtered and concentrated in vacuo. HPLC purification was performed using a YMC 30×100 mm 5u (C18) column in 0-100% acetonitrile (3.0% n-propanol)/100-0% water (3.0% n-propanol) at 30 mL/min. The desired fractions were collected, concentrated and dried in a vacuum oven overnight at 50° C. to afford 5-bromo-N-(2,3-dihydroxy-propoxy)-3,4-difluoro-2-(2-fluoro-phenylamino)-benzamide as a white solid (0.054 g, 30%): m.p.=143.5-144.5° C.; $^1$NMR (400 MHz, DMSO-d$_6$) δ 11.95 (bs, 1H), 8.74 (bs, 1H), 7.68 (d, 1H, J=6.1 Hz), 7.17 (t, 1H, J=9.8 Hz), 7.01-7.04 (m, 1H), 6.94 (m, 2H), 4.81 (m, 1H), 4.57 (m, 1H), 3.86 (m, 1H), 3.69-3.71 (m, 2H), 3.3, (2H, under HDO); MS(APCI+)= 435.0/437.0.

EXAMPLE 85

N-(2,3-Dihydroxy-propoxy)-3,4-difluoro-2-(2-fluoro-phenylamino)-benzamide

A solution of N-(2,3-dihydroxy-propoxy)-3,4-difluoro-2-(2-fluoro-4-iodo-phenylamino)-benzamide (0.260 g, 0.539 mmol) and triethylamine (2.0 mL, 14.3 mmol) in tetrahydrofuran (14 mL) was hydrogenated over Raney Nickel (0.2 g wet) at 50 psig at room temperature for 20 hours. The catalyst was removed by filtration and the filtrate was concentrated in vacuo. The afforded residue was partitioned between ethyl acetate and water. The organics were washed twice with saturated sodium bicarbonate solution, twice with water, collected, dried over sodium sulfate, filtered and concentrated in vacuo. HPLC purification was performed using a YMC 30×100 mm 5u (C18) column in 0-100% acetonitrile (3.0% n-propanol)/100-0% water (3.0% n-propanol) at 30 ml/min. The desired fractions were collected and concentrated. The afforded residue was extracted with ethyl acetate/water. Organic layers were washed with saturated NaCl solution, collected and dried in vacuo to afford N-(2,3-dihydroxy-propoxy)-3,4-difluoro-2-(2-fluoro-phenylamino)-benzamide as a white solid (0.061 g, 31%): m.p.=113-115° C.; $^1$NMR (400 MHz; DMSO-d$_6$) δ 11.90 (s, 1H), 8.73 (s, 1H), 7.37 (m, 1H), 7.10-7.19 (m, 2H), 7.02 (t, 1H, J=7.4 Hz), 6.84-6.93 (m, 2H), 4.82 (m, 1H), 4.57-4.58 (m, 1H), 3.86-3.88 (m, 1H), 3.67-3.73 (m, 2H), 3.3 (2H, under HDO); MS(APCI+)=357.1; Anal. calcd/found for C$_{16}$H$_{15}$F$_3$N$_2$O$_4$: C, 53.94/53.97; H, 4.24/4.37; N, 7.86/7.83.

EXAMPLES 86-97

Examples 86 to 97 were prepared utilizing combinatorial synthetic methods, as detailed below, by the combination of the respective alkoxyamine and pentafluorophenyl ester, prepared as described above. General Procedure:

Step A: An array of 2-dram vials was charged with the appropriate pentafluorophenyl ester diarylamine (0.12 mmol)

as a solid and diluted with 2 mL of N,N-dimethylformamide. Using a bulk dispenser, each reaction was charged with 0.2 grams of polymer-supported morpholine resin (commercially available from Novabiochem or prepared by the method of Booth and Hodges: *J. Am. Chem. Soc.,* 1997, 119, 4842). Solutions were prepared of the hydroxylamine acetonides in N,N-dimethylformamide (0.8M, 1.6 mL) and dispensed (0.1 mmol, 0.2 mL) into the corresponding reaction vial. The reactions were sealed with teflon coated caps and were allowed to shake on an orbital shaker for 5 days at ambient temperature. The 14 reactions were charged with 0.2 grams of polymer-supported tris(2-aminoethyl)amine [Novabiochem; see also: Booth, R. J.; Hodges, J. C. *J. Am. Chem. Soc.,* 1997, 119, 4842.], 0.1 grams of polymer-supported methylisocyanate [Novabiochem; see also: Booth, R. J.; Hodges, J. C. *J. Am. Chem. Soc.,* 1997, 119, 4842.], and 1 mL of dichloromethane. The reaction vessels were resealed and allowed to shake an additional 6 hours at ambient temperature. The reactions were filtered through a Specdisk 3A filter and rinsed with 6 mL of a 10% methanol/dichloromethane solution and concentrated via a nitrogen stream.

Step B: The resulting acetonide benzamides were charged with 2 mL of methanol, 0.05 mL of deionized water, approximately 2 milligrams of p-toluenesulfonic acid, and 0.1 grams of glycerol resin. Reactions were sealed with teflon coated caps and allowed to shake for 17 hours. The reactions were filtered through a Specdisk 3A filter and washed with 6 mL of 50% methanol in dichloromethane and concentrated via a nitrogen stream. Purification was performed on all samples using a SQ1600 Combi-Flash column eluting with acetonitrile/water (0.05% trifluoroacetic acid). LC/MS was performed using CPI 120SE C18 column (4.6×50 μm) eluting with acetonitrile/water (0.05% trifluoroacetic acid).

| Example No. | Compound | Formula | Exact Mass Found |
|---|---|---|---|
| 86 | 2-(2-Chloro-4-iodo-phenylamino)-N-(2,3-dihydroxy-propoxy)-3,4-difluoro-benzamide | $C_{16}H_{14}ClF_2IN_2O_4$ | 499 (APCI+) |
| 87 | 2-(2-Chloro-4-iodo-phenylamino)-N-(2,3-dihydroxy-propoxy)-3,4,5-trifluoro-benzamide | $C_{16}H_{13}ClF_3IN_2O_4$ | 517 (APCI+) |
| 88 | 5-Bromo-2-(2-chloro-4-iodo-phenylamino)-N-(2,3-dihydroxy-propoxy)-3,4-difluoro-benzamide | $C_{16}H_{13}BrClF_2IN_2O_4$ | 577/579 (APCI+) |
| 89 | N-(2,3-Dihydroxy-propoxy)-3,4-difluoro-2-(4-iodo-2-methyl-phenylamino)-benzamide | $C_{17}H_{17}F_2IN_2O_4$ | 479 (APCI+) |
| 90 | N-(2,3-Dihydroxy-propoxy)-3,4,5-trifluoro-2-(4-iodo-2-methyl-phenylamino)-benzamide | $C_{17}H_{16}F_3IN_2O_4$ | 495 (APCI−) |
| 91 | 5-Bromo-N-(2,3-dihydroxy-propoxy)-3,4-difluoro-2-(4-iodo-2-methyl-phenylamino)-benzamide | $C_{17}H_{16}BrF_2IN_2O_4$ | 557/559 (APCI+) |
| 92 | 2-(2-Chloro-4-iodo-phenylamino)-N-(3,4-dihydroxy-butoxy)-3,4-difluoro-benzamide | $C_{17}H_{16}ClF_2IN_2O_4$ | 513 (APCI+) |
| 93 | 2-(2-Chloro-4-iodo-phenylamino)-N-(3,4-dihydroxy-butoxy)-3,4,5-trifluoro-benzamide | $C_{17}H_{15}ClF_3IN_2O_4$ | 531 (APCI+) |
| 94 | 5-Bromo-2-(2-chloro-4-iodo-phenylamino)-N-(3,4-dihydroxy-butoxy)-3,4-difluoro-benzamide | $C_{17}H_{15}BrClF_2IN_2O_4$ | 591/593 (APCI+) |
| 95 | N-(3,4-Dihydroxy-butoxy)-3,4-difluoro-2-(4-iodo-2-methyl-phenylamino)-benzamide | $C_{18}H_{19}F_2IN_2O_4$ | 493 (APCI+) |
| 96 | N-(3,4-Dihydroxy-butoxy)-3,4,5-trifluoro-2-(4-iodo-2-methyl-phenylamino)-benzamide | $C_{18}H_{18}F_3IN_2O_4$ | 511 (APCI+) |
| 97 | 5-Bromo-N-(3,4-dihydroxy-butoxy)-3,4-difluoro-2-(4-iodo-2-methyl-phenylamino)-benzamide | $C_{18}H_{18}BrF_2IN_2O_4$ | 571/573 (APCI+) |

EXAMPLES 98-235

Examples 98-235 were prepared utilizing combinatorial synthetic methods, as detailed below, by the combination of the respective alkoxyamine and pentafluorophenyl ester, prepared as described above. General Procedure: Two-dram vials were each charged with 100-110 mg of polymer-supported morpholine (3.55 mmol N/g) employing a bulk resin dispenser. [Polymer-supported morpholinomethyl resin is commercially available (Novabiochem) or may be prepared by the method of Booth and Hodges: *J. Am. Chem. Soc.*, 1997, 119, 4842.] The appropriate vials were treated sequentially with a 0.08 M stock solution of the alkoxyamine in DMF (0.6 mL, 0.048 mmol) and a 0.12 M stock solution of the pentafluorophenyl ester in DMF (0.48 mL, 0.0576 mmol, 1.2 eq).

The vials were sealed with Teflon-lined caps and agitated on an orbital shaker at ambient temperature. After 48 h, the reaction mixtures were treated with polymer-supported tris (2-aminoethyl)amine (100 mg, 4.28 mmol/g) [Novabiochem; see also: Booth, R. J.; Hodges, J. C. *J. Am. Chem. Soc.*, 1997, 119, 4842.] and dichloromethane (1.0 mL). The vials were capped again and shaken an additional 6 h. The solids were removed by filtration though a Speckdisc 3A filter and washed with 10% methanol-dichloromethane solution (3×2 mL). The filtrates were concentrated under a stream of nitrogen and purified by HPLC using a SQ1600 Combiflash column eluting with acetonitrile/water (0.05% trifluoroacetic acid). LC/MS was performed using CPI 120SE C18 column (0.0046×0.050 mm) eluting with acetonitrile/water (0.05% trifluoroacetic acid).

| Example No. | Compound | Formula | Exact Mass (APCI+) |
|---|---|---|---|
| 98 | 5-Bromo-2-(2-chloro-4-iodo-phenylamino)-3,4-difluoro-N-(3-hydroxy-propoxy)-benzamide | $C_{16}H_{13}BrClF_2IN_2O_3$ | 561/563 (M + 1) |
| 99 | 2-(2-Chloro-4-iodo-phenylamino)-3,4-difluoro-N-(3-hydroxy-propoxy)-benzamide | $C_{16}H_{14}ClF_2IN_2O_3$ | 483 (M + 1) |
| 100 | 3,4,5-Trifluoro-N-(3-hydroxy-propoxy)-2-(4-iodo-2-methyl-phenylamino)-benzamide | $C_{17}H_{16}F_3IN_2O_3$ | 481 (M + 1) |
| 101 | 2-(2-Chloro-4-iodo-phenylamino)-3,4,5-trifluoro-N-(3-hydroxy-propoxy)-benzamide | $C_{16}H_{13}ClF_3IN_2O_3$ | 501 (M + 1) |
| 102 | 5-Bromo-3,4-difluoro-N-(3-hydroxy-propoxy)-2-(4-iodo-2-methyl-phenylamino)-benzamide | $C_{17}H_{16}BrF_2IN_2O_3$ | 541/543 (M + 1) |
| 103 | 3,4-Difluoro-N-(3-hydroxy-propoxy)-2-(4-iodo-2-methyl-phenylamino)-benzamide | $C_{17}H_{17}F_2IN_2O_3$ | 463 (M + 1) |
| 104 | 2-(2-Chloro-4-iodo-phenylamino)-3,4-difluoro-N-(2-hydroxy-butoxy)-benzamide | $C_{17}H_{16}ClF_2IN_2O_3$ | 496.9 (M + 1) |
| 105 | 2-(2-Chloro-4-iodo-phenylamino)-3,4,5-trifluoro-N-(2-hydroxy-butoxy)-benzamide | $C_{17}H_{15}ClF_3IN_2O_3$ | 514.9 (M + 1) |
| 106 | 3,4,5-Trifluoro-N-(2-hydroxy-butoxy)-2-(4-iodo-2-methyl-phenylamino)-benzamide | $C_{18}H_{18}F_3IN_2O_3$ | 494.9 (M + 1) |
| 107 | 5-Bromo-2-(2-chloro-4-iodo-phenylamino)-3,4-difluoro-N-(2-hydroxy-butoxy)-benzamide | $C_{17}H_{15}BrClF_2IN_2O_3$ | 574.8/576.8 (M + 1) |
| 108 | 5-Bromo-3,4-difluoro-N-(2-hydroxy-butoxy)-2-(4-iodo-2-methyl-phenylamino)-benzamide | $C_{18}H_{18}BrF_2IN_2O_3$ | 554.9/556.9 (M + 1) |
| 109 | 3,4-Difluoro-N-(2-hydroxy-butoxy)-2-(4-iodo-2-methyl-phenylamino)-benzamide | $C_{18}H_{19}F_2IN_2O_3$ | 476.9 (M + 1) |
| 110 | 5-Chloro-2-(2-chloro-4-iodo-phenylamino)-3,4-difluoro-N-(2-hydroxy-butoxy)-benzamide | $C_{17}H_{15}Cl_2F_2IN_2O_3$ | 530.8 (M + 1) |
| 111 | 5-Chloro-3,4-difluoro-N-(2-hydroxy-butoxy)-2-(4-iodo-2-methyl-phenylamino)-benzamide | $C_{18}H_{18}ClF_2IN_2O_3$ | 510.9 (M + 1) |
| 112 | 3,4-Difluoro-2-(2-fluoro-4-iodo-phenylamino)-N-(2-hydroxy-butoxy)-benzamide | $C_{17}H_{16}F_3IN_2O_3$ | 481.1 (M + 1) |
| 113 | 5-Bromo-3,4-difluoro-2-(2-fluoro-4-iodo-phenylamino)-N-(2-hydroxy-butoxy)-benzamide | $C_{17}H_{15}BrF_3IN_2O_3$ | 559.0/561.0 (M + 1) |
| 114 | 5-Chloro-3,4-difluoro-2-(2-fluoro-4-iodo-phenylamino)-N-(2-hydroxy-butoxy)-benzamide | $C_{17}H_{15}ClF_3IN_2O_3$ | 515.1 (M + 1) |
| 115 | 4,5-Difluoro-2-(2-fluoro-4-iodo-phenylamino)-N-(2-hydroxy-butoxy)-benzamide | $C_{17}H_{16}F_3IN_2O_3$ | 481.1 (M + 1) |

-continued

| Example No. | Compound | Formula | Exact Mass (APCI+) |
|---|---|---|---|
| 116 | 5-Chloro-2-(2,4-difluoro-phenylamino)-3,4-difluoro-N-(2-hydroxy-butoxy)-benzamide | $C_{17}H_{15}ClF_4N_2O_3$ | 407.4 (M + 1) |
| 117 | 2-(2,4-Difluoro-phenylamino)-3,4-difluoro-N-(2-hydroxy-butoxy)-benzamide | $C_{17}H_{16}F_4N_2O_3$ | 373.5 (M + 1) |
| 118 | 2-(4-Bromo-2-fluoro-phenylamino)-3,4-difluoro-N-(2-hydroxy-butoxy)-benzamide | $C_{17}H_{16}BrF_3N_2O_3$ | 433.3/435.3 (M + 1) |
| 119 | 5-Chloro-3,4-difluoro-N-(2-hydroxy-1-methyl-ethoxy)-2-(4-iodo-2-methyl-phenylamino)-benzamide | $C_{17}H_{16}ClF_2IN_2O_3$ | 496.9 (M + 1) |
| 120 | 2-(2-Chloro-4-iodo-phenylamino)-3,4-difluoro-N-(2-hydroxy-1-methyl-ethoxy)-benzamide | $C_{16}H_{14}ClF_2IN_2O_3$ | 482.9 (M + 1) |
| 121 | 2-(2-Chloro-4-iodo-phenylamino)-3,4,5-trifluoro-N-(2-hydroxy-1-methyl-ethoxy)-benzamide | $C_{16}H_{13}ClF_3IN_2O_3$ | 500.9 (M + 1) |
| 122 | 3,4,5-Trifluoro-N-(2-hydroxy-1-methyl-ethoxy)-2-(4-iodo-2-methyl-phenylamino)-benzamide | $C_{17}H_{16}F_3IN_2O_3$ | 480.9 (M + 1) |
| 123 | 5-Bromo-2-(2-chloro-4-iodo-phenylamino)-3,4-difluoro-N-(2-hydroxy-1-methyl-ethoxy)-benzamide | $C_{16}H_{13}BrClF_2IN_2O_3$ | 560.8/562.8 (M + 1) |
| 124 | 5-Bromo-3,4-difluoro-N-(2-hydroxy-1-methyl-ethoxy)-2-(4-iodo-2-methyl-phenylamino)-benzamide | $C_{17}H_{16}BrF_2IN_2O_3$ | 540.8/542.8 (M + 1) |
| 125 | 2-(4-Chloro-2-fluoro-phenylamino)-3,4-difluoro-N-(2-hydroxy-1-methyl-ethoxy)-benzamide | $C_{16}H_{14}ClF_3N_2O_3$ | 375.0 (M + 1) |
| 126 | 3,4-Difluoro-N-(2-hydroxy-1-methyl-ethoxy)-2-(4-iodo-2-methyl-phenylamino)-benzamide | $C_{17}H_{17}F_2IN_2O_3$ | 462.9 (M + 1) |
| 127 | 5-Chloro-2-(2-chloro-4-iodo-phenylamino)-3,4-difluoro-N-(2-hydroxy-1-methyl-ethoxy)-benzamide | $C_{16}H_{13}Cl_2F_2IN_2O_3$ | 516.8 (M + 1) |
| 128 | 3,4-Difluoro-2-(2-fluoro-4-iodo-phenylamino)-N-(2-hydroxy-1-methyl-ethoxy)-benzamide | $C_{16}H_{14}F_3IN_2O_3$ | 466.9 (M + 1) |
| 129 | 5-Bromo-3,4-difluoro-2-(2-fluoro-4-iodo-phenylamino)-N-(2-hydroxy-1-methyl-ethoxy)-benzamide | $C_{16}H_{13}BrF_3IN_2O_3$ | 545.0/547.0 (M + 1) |
| 130 | 5-Chloro-3,4-difluoro-2-(2-fluoro-4-iodo-phenylamino)-N-(2-hydroxy-1-methyl-ethoxy)-benzamide | $C_{16}H_{13}ClF_3IN_2O_3$ | 500.9 (M + 1) |
| 131 | 4,5-Difluoro-2-(2-fluoro-4-iodo-phenylamino)-N-(2-hydroxy-1-methyl-ethoxy)-benzamide | $C_{16}H_{14}F_3IN_2O_3$ | 466.9 (M + 1) |
| 132 | 5-Chloro-2-(2,4-difluoro-phenylamino)-3,4-difluoro-N-(2-hydroxy-1-methyl-ethoxy)-benzamide | $C_{16}H_{13}ClF_4N_2O_3$ | 393.4 (M + 1) |
| 133 | 2-(2,4-Difluoro-phenylamino)-3,4-difluoro-N-(2-hydroxy-1-methyl-ethoxy)-benzamide | $C_{16}H_{14}F_4N_2O_3$ | 359.4 (M + 1) |
| 134 | 2-(2-Chloro-4-iodo-phenylamino)-3,4-difluoro-N-(2-methoxy-ethoxy)-benzamide | $C_{16}H_{14}ClF_2IN_2O_3$ | 482.9 (M + 1) |
| 135 | 2-(2-Chloro-4-iodo-phenylamino)-3,4,5-trifluoro-N-(2-methoxy-ethoxy)-benzamide | $C_{16}H_{13}ClF_3IN_2O_3$ | 500.9 (M + 1) |
| 136 | 3,4-Difluoro-2-(4-iodo-2-methyl-phenylamino)-N-(2-methoxy-ethoxy)-benzamide | $C_{17}H_{17}F_2IN_2O_3$ | 462.9 (M + 1) |
| 137 | 5-Bromo-3,4-difluoro-2-(4-iodo-2-methyl-phenylamino)-N-(2-methoxy-ethoxy)-benzamide | $C_{17}H_{16}BrF_2IN_2O_3$ | 540.8/542.8 (M + 1) |

-continued

| Example No. | Compound | Formula | Exact Mass (APCI+) |
|---|---|---|---|
| 138 | 3,4,5-Trifluoro-2-(4-iodo-2-methyl-phenylamino)-N-(2-methoxy-ethoxy)-benzamide | $C_{17}H_{16}F_3IN_2O_3$ | 480.9 (M + 1) |
| 139 | 5-Bromo-2-(2-chloro-4-iodo-phenylamino)-3,4-difluoro-N-(2-methoxy-ethoxy)-benzamide | $C_{16}H_{13}BrClF_2IN_2O_3$ | 560.8/562.8 (M + 1) |
| 140 | 5-Chloro-2-(2-chloro-4-iodo-phenylamino)-3,4-difluoro-N-(2-methoxy-ethoxy)-benzamide | $C_{16}H_{13}Cl_2F_2IN_2O_3$ | 516.8 (M + 1) |
| 141 | 5-Chloro-3,4-difluoro-2-(4-iodo-2-methyl-phenylamino)-N-(2-methoxy-ethoxy)-benzamide | $C_{17}H_{16}ClF_2IN_2O_3$ | 496.9 (M + 1) |
| 142 | 5-Chloro-3,4-difluoro-2-(2-fluoro-4-iodo-phenylamino)-N-(2-methoxy-ethoxy)-benzamide | $C_{16}H_{13}ClF_3IN_2O_3$ | 501.1 (M + 1) |
| 143 | 2-(2-Chloro-4-iodo-phenylamino)-3,4-difluoro-N-(2-hydroxy-3-morpholin-4-yl-propoxy)-benzamide | $C_{20}H_{21}ClF_2IN_3O_4$ | 568.0 (M + 1) |
| 144 | 5-Bromo-2-(2-chloro-4-iodo-phenylamino)-3,4-difluoro-N-(2-hydroxy-3-morpholin-4-yl-propoxy)-benzamide | $C_{20}H_{20}BrClF_2IN_3O_4$ | 645.9/647.9 (M + 1) |
| 145 | 2-(2-Chloro-4-iodo-phenylamino)-3,4,5-trifluoro-N-(2-hydroxy-3-morpholin-4-yl-propoxy)-benzamide | $C_{20}H_{20}ClF_3IN_3O_4$ | 585.9 (M + 1) |
| 146 | 3,4,5-Trifluoro-N-(2-hydroxy-3-morpholin-4-yl-propoxy)-2-(4-iodo-2-methyl-phenylamino)-benzamide | $C_{21}H_{23}F_3IN_3O_4$ | 566.0 (M + 1) |
| 147 | 5-Bromo-3,4-difluoro-N-(2-hydroxy-3-morpholin-4-yl-propoxy)-2-(4-iodo-2-methyl-phenylamino)-benzamide | $C_{21}H_{23}BrF_2IN_3O_4$ | 625.9/627.9 (M + 1) |
| 148 | 3,4-Difluoro-N-(2-hydroxy-3-morpholin-4-yl-propoxy)-2-(4-iodo-2-methyl-phenylamino)-benzamide | $C_{21}H_{24}F_2IN_3O_4$ | 548.0 (M + 1) |
| 149 | 5-Chloro-2-(2-chloro-4-iodo-phenylamino)-3,4-difluoro-N-(2-hydroxy-3-morpholin-4-yl-propoxy)-benzamide | $C_{20}H_{20}Cl_2F_2IN_3O_4$ | 601.9 (M + 1) |
| 150 | 5-Chloro-3,4-difluoro-N-(2-hydroxy-3-morpholin-4-yl-propoxy)-2-(4-iodo-2-methyl-phenylamino)-benzamide | $C_{21}H_{23}ClF_2IN_3O_4$ | 582.0 (M + 1) |
| 151 | 3,4-Difluoro-2-(2-fluoro-4-iodo-phenylamino)-N-(2-hydroxy-3-morpholin-4-yl-propoxy)-benzamide | $C_{20}H_{21}F_3IN_3O_4$ | 551.9 (M + 1) |
| 152 | 5-Chloro-3,4-difluoro-2-(2-fluoro-4-iodo-phenylamino)-N-(2-hydroxy-3-morpholin-4-yl-propoxy)-benzamide | $C_{20}H_{20}ClF_3IN_3O_4$ | 585.8 (M + 1) |
| 153 | 4,5-Difluoro-2-(2-fluoro-4-iodo-phenylamino)-N-(2-hydroxy-3-morpholin-4-yl-propoxy)-benzamide | $C_{20}H_{21}F_3IN_3O_4$ | 551.9 (M + 1) |
| 154 | 5-Chloro-2-(2,4-difluoro-phenylamino)-3,4-difluoro-N-(2-hydroxy-3-morpholin-4-yl-propoxy)-benzamide | $C_{20}H_{20}ClF_4N_3O_4$ | 478.4 (M + 1) |
| 155 | 2-(4-Chloro-2-fluoro-phenylamino)-3,4-difluoro-N-(2-hydroxy-3-morpholin-4-yl-propoxy)-benzamide | $C_{20}H_{21}ClF_3N_3O_4$ | 460.0 (M + 1) |
| 156 | 2-(2-Chloro-4-iodo-phenylamino)-3,4-difluoro-N-(2-hydroxy-propoxy)-benzamide | $C_{16}H_{14}ClF_2IN_2O_3$ | 482.9 (M + 1) |
| 157 | 3,4,5-Trifluoro-N-(2-hydroxy-propoxy)-2-(4-iodo-2-methyl-phenylamino)-benzamide | $C_{17}H_{16}F_3IN_2O_3$ | 480.9 (M + 1) |
| 158 | 5-Bromo-2-(2-chloro-4-iodo-phenylamino)-3,4-difluoro-N-(2-hydroxy-propoxy)-benzamide | $C_{16}H_{13}BrClF_2IN_2O_3$ | 560.8/562.8 (M + 1) |

-continued

| Example No. | Compound | Formula | Exact Mass (APCI+) |
|---|---|---|---|
| 159 | 5-Bromo-3,4-difluoro-N-(2-hydroxy-propoxy)-2-(4-iodo-2-methyl-phenylamino)-benzamide | $C_{17}H_{16}BrF_2IN_2O_3$ | 540.8/542.8 (M + 1) |
| 160 | 2-(2-Chloro-4-iodo-phenylamino)-3,4,5-trifluoro-N-(2-hydroxy-propoxy)-benzamide | $C_{16}H_{13}ClF_3IN_2O_3$ | 500.8 (M + 1) |
| 161 | 5-Chloro-2-(2-chloro-4-iodo-phenylamino)-3,4-difluoro-N-(2-hydroxy-propoxy)-benzamide | $C_{16}H_{13}Cl_2F_2IN_2O_3$ | 516.8 (M + 1) |
| 162 | 3,4-Difluoro-N-(2-hydroxy-propoxy)-2-(4-iodo-2-methyl-phenylamino)-benzamide | $C_{17}H_{17}F_2IN_2O_3$ | 462.9 (M + 1) |
| 163 | 5-Chloro-3,4-difluoro-N-(2-hydroxy-propoxy)-2-(4-iodo-2-methyl-phenylamino)-benzamide | $C_{17}H_{16}ClF_2IN_2O_3$ | 496.9 (M + 1) |
| 164 | 3,4-Difluoro-2-(2-fluoro-4-iodo-phenylamino)-N-(2-hydroxy-propoxy)-benzamide | $C_{16}H_{14}F_3IN_2O_3$ | 466.9 (M + 1) |
| 165 | 5-Chloro-3,4-difluoro-2-(2-fluoro-4-iodo-phenylamino)-N-(2-hydroxy-propoxy)-benzamide | $C_{16}H_{13}ClF_3IN_2O_3$ | 500.8 (M + 1) |
| 166 | 5-Chloro-2-(2,4-difluoro-phenylamino)-3,4-difluoro-N-(2-hydroxy-propoxy)-benzamide | $C_{16}H_{13}ClF_4N_2O_3$ | 393.1 (M + 1) |
| 167 | 2-(2,4-Difluoro-phenylamino)-3,4-difluoro-N-(2-hydroxy-propoxy)-benzamide | $C_{16}H_{14}F_4N_2O_3$ | 359.4 (M + 1) |
| 168 | 2-(4-Chloro-2-fluoro-phenylamino)-3,4-difluoro-N-(2-hydroxy-propoxy)-benzamide | $C_{16}H_{14}ClF_3N_2O_3$ | 375.1 (M + 1) |
| 169 | 4,5-Difluoro-2-(2-fluoro-4-iodo-phenylamino)-N-(2-hydroxy-propoxy)-benzamide | $C_{16}H_{14}F_3IN_2O_3$ | 466.9 (M + 1) |
| 170 | 2-(2-Chloro-4-iodo-phenylamino)-3,4,5-trifluoro-N-(2-hydroxy-2-methyl-propoxy)-benzamide | $C_{17}H_{15}ClF_3IN_2O_3$ | 514.9 (M + 1) |
| 171 | 3,4,5-Trifluoro-N-(2-hydroxy-2-methyl-propoxy)-2-(4-iodo-2-methyl-phenylamino)-benzamide | $C_{18}H_{18}F_3IN_2O_3$ | 494.9 (M + 1) |
| 172 | 5-Bromo-3,4-difluoro-N-(2-hydroxy-2-methyl-propoxy)-2-(4-iodo-2-methyl-phenylamino)-benzamide | $C_{18}H_{18}BrF_2IN_2O_3$ | 554.9/556.9 (M + 1) |
| 173 | 5-Bromo-2-(2-chloro-4-iodo-phenylamino)-3,4-difluoro-N-(2-hydroxy-2-methyl-propoxy)-benzamide | $C_{17}H_{15}BrClF_2IN_2O_3$ | 574.8/576.8 (M + 1) |
| 174 | 3,4-Difluoro-N-(2-hydroxy-2-methyl-propoxy)-2-(4-iodo-2-methyl-phenylamino)-benzamide | $C_{18}H_{19}F_2IN_2O_3$ | 477.0 (M + 1) |
| 175 | 5-Chloro-2-(2-chloro-4-iodo-phenylamino)-3,4-difluoro-N-(2-hydroxy-2-methyl-propoxy)-benzamide | $C_{17}H_{15}Cl_2F_2IN_2O_3$ | 530.9 (M + 1) |
| 176 | 5-Chloro-3,4-difluoro-N-(2-hydroxy-2-methyl-propoxy)-2-(4-iodo-2-methyl-phenylamino)-benzamide | $C_{18}H_{18}ClF_2IN_2O_3$ | 510.9 (M + 1) |
| 177 | 3,4-Difluoro-2-(2-fluoro-4-iodo-phenylamino)-N-(2-hydroxy-2-methyl-propoxy)-benzamide | $C_{17}H_{16}F_3IN_2O_3$ | 481.1 (M + 1) |
| 178 | 5-Bromo-3,4-difluoro-2-(2-fluoro-4-iodo-phenylamino)-N-(2-hydroxy-2-methyl-propoxy)-benzamide | $C_{17}H_{15}BrF_3IN_2O_3$ | 559.0/561.0 (M + 1) |
| 179 | 5-Chloro-3,4-difluoro-2-(2-fluoro-4-iodo-phenylamino)-N-(2-hydroxy-2-methyl-propoxy)-benzamide | $C_{17}H_{15}ClF_3IN_2O_3$ | 515.1 (M + 1) |
| 180 | 5-Chloro-2-(2,4-difluoro-phenylamino)-3,4-difluoro-N-(2-hydroxy-2-methyl-propoxy)-benzamide | $C_{17}H_{15}ClF_4N_2O_3$ | 407.4 (M + 1) |
| 181 | 2-(2,4-Difluoro-phenylamino)-3,4-difluoro-N-(2-hydroxy-2-methyl-propoxy)-benzamide | $C_{17}H_{16}F_4N_2O_3$ | 373.5 (M + 1) |

| Example No. | Compound | Formula | Exact Mass (APCI+) |
|---|---|---|---|
| 182 | 2-(4-Bromo-2-fluoro-phenylamino)-3,4-difluoro-N-(2-hydroxy-2-methyl-propoxy)-benzamide | $C_{17}H_{16}BrF_3N_2O_3$ | 433.3/435.3 (M + 1) |
| 183 | Chloro-4-iodo-phenylamino)-3,4-difluoro-N-(2-hydroxy-3-phenoxy-propoxy)-benzamide | $C_{22}H_{18}ClF_2IN_2O_4$ | 575.0 (M + 1) |
| 184 | 2-(2-Chloro-4-iodo-phenylamino)-3,4,5-trifluoro-N-(2-hydroxy-3-phenoxy-propoxy)-benzamide | $C_{22}H_{17}ClF_3IN_2O_4$ | 592.9 (M + 1) |
| 185 | 3,4,5-Trifluoro-N-(2-hydroxy-3-phenoxy-propoxy)-2-(4-iodo-2-methyl-phenylamino)-benzamide | $C_{23}H_{20}F_3IN_2O_4$ | 573.0 (M + 1) |
| 186 | 5-Bromo-2-(2-chloro-4-iodo-phenylamino)-3,4-difluoro-N-(2-hydroxy-3-phenoxy-propoxy)-benzamide | $C_{22}H_{17}BrClF_2INO_4$ | 652.8/654.8 (M + 1) |
| 187 | 5-Bromo-3,4-difluoro-N-(2-hydroxy-3-phenoxy-propoxy)-2-(4-iodo-2-methyl-phenylamino)-benzamide | $C_{23}H_{20}BrF_2IN_2O_4$ | 632.9/634.9 (M + 1) |
| 188 | 3,4-Difluoro-N-(2-hydroxy-3-phenoxy-propoxy)-2-(4-iodo-2-methyl-phenylamino)-benzamide | $C_{23}H_{21}F_2IN_2O_4$ | 555.0 (M + 1) |
| 189 | 5-Chloro-2-(2-chloro-4-iodo-phenylamino)-3,4-difluoro-N-(2-hydroxy-3-phenoxy-propoxy)-benzamide | $C_{22}H_{17}Cl_2F_2IN_2O_4$ | 608.9 (M + 1) |
| 190 | 5-Chloro-3,4-difluoro-N-(2-hydroxy-3-phenoxy-propoxy)-2-(4-iodo-2-methyl-phenylamino)-benzamide | $C_{23}H_{20}ClF_2IN_2O_4$ | 588.9 (M + 1) |
| 191 | 3,4-Difluoro-2-(2-fluoro-4-iodo-phenylamino)-N-(2-hydroxy-3-phenoxy-propoxy)-benzamide | $C_{22}H_{18}F_3IN_2O_4$ | 558.9 (M + 1) |
| 192 | 5-Chloro-3,4-difluoro-2-(2-fluoro-4-iodo-phenylamino)-N-(2-hydroxy-3-phenoxy-propoxy)-benzamide | $C_{22}H_{17}ClF_3IN_2O_4$ | 592.8 (M + 1) |
| 193 | 4,5-Difluoro-2-(2-fluoro-4-iodo-phenylamino)-N-(2-hydroxy-3-phenoxy-propoxy)-benzamide | $C_{22}H_{18}F_3IN_2O_4$ | 558.9 (M + 1) |
| 194 | 5-Chloro-2-(2,4-difluoro-phenylamino)-3,4-difluoro-N-(2-hydroxy-3-phenoxy-propoxy)-benzamide | $C_{22}H_{17}ClF_4N_2O_4$ | 485.4 (M + 1) |
| 195 | 2-(2,4-Difluoro-phenylamino)-3,4-difluoro-N-(2-hydroxy-3-phenoxy-propoxy)-benzamide | $C_{22}H_{18}F_4N_2O_4$ | 451.5 (M + 1) |
| 196 | 2-(4-Chloro-2-fluoro-phenylamino)-3,4-difluoro-N-(2-hydroxy-3-phenoxy-propoxy)-benzamide | $C_{22}H_{18}ClF_3N_2O_4$ | 467.0 (M + 1) |
| 197 | 3,4-Difluoro-N-(3-hydroxy-2,2-dimethyl-propoxy)-2-(4-iodo-2-methyl-phenylamino)-benzamide | $C_{19}H_{21}F_2IN_2O_3$ | 491.0 (M + 1) |
| 198 | 2-(2-Chloro-4-iodo-phenylamino)-3,4,5-trifluoro-N-(3-hydroxy-2,2-dimethyl-propoxy)-benzamide | $C_{18}H_{17}ClF_3IN_2O_3$ | 528.9 (M + 1) |
| 199 | 3,4,5-Trifluoro-N-(3-hydroxy-2,2-dimethyl-propoxy)-2-(4-iodo-2-methyl-phenylamino)-benzamide | $C_{19}H_{20}F_3IN_2O_3$ | 508.9 (M + 1) |
| 200 | 5-Chloro-2-(2-chloro-4-iodo-phenylamino)-3,4-difluoro-N-(3-hydroxy-2,2-dimethyl-propoxy)-benzamide | $C_{18}H_{17}Cl_2F_2IN_2O_3$ | 544.9 (M + 1) |
| 201 | 5-Chloro-3,4-difluoro-N-(3-hydroxy-2,2-dimethyl-propoxy)-2-(4-iodo-2-methyl-phenylamino)-benzamide | $C_{19}H_{20}ClF_2IN_2O_3$ | 524.9 (M + 1) |
| 202 | 3,4-Difluoro-2-(2-fluoro-4-iodo-phenylamino)-N-(3-hydroxy-2,2-dimethyl-propoxy)-benzamide | $C_{18}H_{18}F_3IN_2O_3$ | 495.1 (M + 1) |

-continued

| Example No. | Compound | Formula | Exact Mass (APCI+) |
|---|---|---|---|
| 203 | 5-Chloro-2-(2,4-difluoro-phenylamino)-3,4-difluoro-N-(3-hydroxy-2,2-dimethyl-propoxy)-benzamide | $C_{18}H_{17}ClF_4N_2O_3$ | 421.4 (M + 1) |
| 204 | 3,4-Difluoro-2-(4-iodo-2-methyl-phenylamino)-N-[2-(2-methoxy-ethoxy)-ethoxy]-benzamide | $C_{19}H_{21}F_2IN_2O_4$ | 507 (M + 1) |
| 205 | 3,4,5-Trifluoro-2-(4-iodo-2-methyl-phenylamino)-N-[2-(2-methoxy-ethoxy)-ethoxy]-benzamide | $C_{19}H_{20}F_3IN_2O_4$ | 525 (M + 1) |
| 206 | 5-Bromo-3,4-difluoro-2-(4-iodo-2-methyl-phenylamino)-N-[2-(2-methoxy-ethoxy)-ethoxy]-benzamide | $C_{19}H_{20}BrF_2IN_2O_4$ | 585/587 (M + 1) |
| 207 | 2-(2-Chloro-4-iodo-phenylamino)-3,4-difluoro-N-[2-(2-methoxy-ethoxy)-ethoxy]-benzamide | $C_{18}H_{18}ClF_2IN_2O_4$ | 527 (M + 1) |
| 208 | 2-(2-Chloro-4-iodo-phenylamino)-3,4,5-trifluoro-N-[2-(2-methoxy-ethoxy)-ethoxy]-benzamide | $C_{18}H_{17}ClF_3IN_2O_4$ | 545 (M + 1) |
| 209 | 5-Bromo-2-(2-chloro-4-iodo-phenylamino)-3,4-difluoro-N-[2-(2-methoxy-ethoxy)-ethoxy]-benzamide | $C_{18}H_{17}BrClF_2IN_2O_4$ | 605/607 (M + 1) |
| 210 | 3,4,5-Trifluoro-2-(2-fluoro-4-iodo-phenylamino)-N-(3,3,3-trifluoro-2-hydroxy-propoxy)-benzamide | $C_{16}H_{10}F_7IN_2O_3$ | 539.1 (M + 1) |
| 211 | 5-Chloro-2-(2,4-difluoro-phenylamino)-3,4-difluoro-N-(3,3,3-trifluoro-2-hydroxy-propoxy)-benzamide | $C_{16}H_{10}ClF_7N_2O_3$ | 447.4 (M + 1) |
| 212 | 2-(2,4-Difluoro-phenylamino)-3,4-difluoro-N-(3,3,3-trifluoro-2-hydroxy-propoxy)-benzamide | $C_{16}H_{11}F_7N_2O_3$ | 413.4 (M + 1) |
| 213 | 2-(4-Chloro-2-fluoro-phenylamino)-3,4-difluoro-N-(3,3,3-trifluoro-2-hydroxy-propoxy)-benzamide | $C_{16}H_{11}ClF_6N_2O_3$ | 429.0 (M + 1) |
| 214 | 5-Chloro-2-(2,4-difluoro-phenylamino)-3,4-difluoro-N-(2-hydroxymethyl-cyclopropylmethoxy)-benzamide | $C_{18}H_{15}ClF_4N_2O_3$ | 419.4 (M + 1) |
| 215 | 2-(2,4-Difluoro-phenylamino)-3,4-difluoro-N-(2-hydroxymethyl-cyclopropylmethoxy)-benzamide | $C_{18}H_{16}F_4N_2O_3$ | 385.4 (M + 1) |
| 216 | 2-(4-Chloro-2-fluoro-phenylamino)-3,4-difluoro-N-(2-hydroxymethyl-cyclopropylmethoxy)-benzamide | $C_{18}H_{16}ClF_3N_2O_3$ | 401.0 (M + 1) |
| 217 | 4,5-Difluoro-2-(2-fluoro-4-iodo-phenylamino)-N-(2-hydroxymethyl-cyclopropylmethoxy)-benzamide | $C_{18}H_{16}F_3IN_2O_3$ | 492.9 (M + 1) |
| 218 | 3,4-Difluoro-2-(2-fluoro-4-iodo-phenylamino)-N-(1-hydroxymethyl-cyclopropylmethoxy)-benzamide | $C_{18}H_{16}F_3IN_2O_3$ | 493.5 (M + 1) |
| 219 | 3,4,5-Trifluoro-2-(2-fluoro-4-iodo-phenylamino)-N-(1-hydroxymethyl-cyclopropylmethoxy)-benzamide | $C_{18}H_{15}F_4IN_2O_3$ | 511.1 (M + 1) |
| 220 | 5-Bromo-3,4-difluoro-2-(2-fluoro-4-iodo-phenylamino)-N-(1-hydroxymethyl-cyclopropylmethoxy)-benzamide | $C_{18}H_{15}BrF_3IN_2O_3$ | 571.0/573.0 (M + 1) |
| 221 | 4,5-Difluoro-2-(2-fluoro-4-iodo-phenylamino)-N-(1-hydroxymethyl-cyclopropylmethoxy)-benzamide | $C_{18}H_{16}F_3IN_2O_3$ | 493.1 (M + 1) |
| 222 | 2-(2,4-Difluoro-phenylamino)-3,4-difluoro-N-(1-hydroxymethyl-cyclopropylmethoxy)-benzamide | $C_{18}H_{16}F_4N_2O_3$ | 385.4 (M + 1) |

-continued

| Example No. | Compound | Formula | Exact Mass (APCI+) |
|---|---|---|---|
| 223 | 2-(4-Bromo-2-fluoro-phenylamino)-3,4-difluoro-N-(1-hydroxymethyl-cyclopropylmethoxy)-benzamide | $C_{18}H_{16}BrF_3N_2O_3$ | 445.3/447.3 (M + 1) |
| 224 | 2-(4-Chloro-2-fluoro-phenylamino)-3,4-difluoro-N-(1-hydroxymethyl-cyclopropylmethoxy)-benzamide | $C_{18}H_{16}ClF_3N_2O_3$ | 401.4 (M + 1) |
| 225 | 5-Chloro-2-(2,4-difluoro-phenylamino)-3,4-difluoro-N-(1-hydroxymethyl-cyclopropylmethoxy)-benzamide | $C_{18}H_{15}ClF_4N_2O_3$ | 419.1 (M + 1) |
| 226 | 2-(2,4-Difluoro-phenylamino)-3,4-difluoro-N-(2-hydroxy-3-methoxy-propoxy)-benzamide | $C_{17}H_{16}F_4N_2O_4$ | 389.4 (M + 1) |
| 227 | 5-Chloro-2-(2,4-difluoro-phenylamino)-3,4-difluoro-N-(2-hydroxy-3-methoxy-propoxy)-benzamide | $C_{17}H_{15}ClF_4N_2O_4$ | 423.4 (M + 1) |
| 228 | 2-(4-Bromo-2-fluoro-phenylamino)-3,4-difluoro-N-(2-hydroxy-3-methoxy-propoxy)-benzamide | $C_{17}H_{16}BrF_3N_2O_4$ | 449.3/451.3 (M + 1) |
| 229 | 2-(4-Chloro-2-fluoro-phenylamino)-3,4-difluoro-N-(2-hydroxy-3-methoxy-propoxy)-benzamide | $C_{17}H_{16}ClF_3N_2O_4$ | 405.4 (M + 1) |
| 230 | 3,4,5-Trifluoro-2-(4-iodo-2-methyl-phenylamino)-N-(2-phenylamino-ethoxy)-benzamide | $C_{22}H_{19}F_3IN_3O_2$ | 542.0 (M + 1) |
| 231 | 5-Bromo-3,4-difluoro-2-(4-iodo-2-methyl-phenylamino)-N-(2-phenylamino-ethoxy)-benzamide | $C_{22}H_{19}BrF_2IN_3O_2$ | 574.0/576.0 (M + 1) |
| 232 | 2-(2-Chloro-4-iodo-phenylamino)-3,4-difluoro-N-(2-phenylamino-ethoxy)-benzamide | $C_{21}H_{17}ClF_2IN_3O_2$ | 544.0 (M + 1) |
| 233 | 2-(2-Chloro-4-iodo-phenylamino)-3,4,5-trifluoro-N-(2-phenylamino-ethoxy)-benzamide | $C_{21}H_{16}ClF_3IN_3O_2$ | 562.0 (M + 1) |
| 234 | 3,4-Difluoro-2-(4-iodo-2-methyl-phenylamino)-N-(2-phenylamino-ethoxy)-benzamide | $C_{22}H_{20}F_2IN_3O_2$ | 524.0 (M + 1) |
| 235 | 5-Bromo-2-(2-chloro-4-iodo-phenylamino)-3,4-difluoro-N-(2-phenylamino-ethoxy)-benzamide | $C_{21}H_{16}BrClF_2IN_3O_2$ | 622.0/624.0 (M + 1) |

EXAMPLE 236

3,4-Difluoro-2-(2-fluoro-4-iodo-phenylamino)-N-((S)-3-hydroxy-2-methylamino-propoxy)-benzamide Step A: N-Boc-O-Benzyl-L-Serine (8.86 g, 30.0 mmol) was dissolved in tetrahydrofuran (94 mL) and the resultant solution was cooled with a 0° C. ice bath. Methyl iodide (15.0 mL, 241 mmol) was added in one portion. After 5 min, sodium hydride (60% dispersion in mineral oil, 3.6 g, 90 mmol) was added in three portions during 10 min. The resultant reaction mixture was stirred under nitrogen for 76 h while the cooling bath temperature was maintained at 0° C. The reaction mixture was diluted with cold (0-5° C.) ethyl acetate (150 mL) and water (1.5 mL) was added dropwise over 10 min. The cooling bath temp was allowed to slowly warm to ambient temperature overnight. The reaction mixture was concentrated to a viscous oil on a rotary evaporator without heating. The residue was partitioned between ether (100 mL) and water (300 mL). The ethereal layer was further washed with saturated aqueous sodium bicarbonate (150 mL). The combined aqueous portions were acidified to pH 3 using aqueous citric acid (2 M) and were extracted with ethyl acetate (3×150 mL). The combined extracts were washed with water (2×150 mL) and 5% aqueous sodium thiosulfate (150 mL), dried over magnesium sulfate and concentrated on a rotary evaporator (without heating) to afford (S)-3-Benzyloxy-2-(tert-butoxycarbonyl-methyl-amino)-propionic acid as viscous, colorless oil (8.98 g).

Step B: The acid prepared in Step A (8.95 g, 28.9 mmol) was dissolved in methanol (50 mL) and dichloromethane (50 mL). The resultant solution was cooled to 0° C. Trimethylsilyldiazomethane (2.0 M in hexane, 26 mL) was added dropwise over 1 h and the resultant reaction mixture was stirred an additional h at 0° C. An additional portion of trimethylsilyldiazomethane (2.0 M in hexane, 3 mL) was added and the reaction was stirred an additional 30 min at 0° C. The reaction mixture was concentrated in vacuo, taking care not to heat the solution above 20° C. The residual liquid was dissolved in tetrahydrofuran-methanol (3:1, 200 mL) and the resultant solution was cooled to 0° C. A solution of lithium borohydride (2.0 M in tetrahydrofuran, 20 mL) was added dropwise over 30 min. The reaction mixture was stirred and additional 1 h at 0° C. and 1 h at ambient temperature. An additional portion of lithoum borohydride solution (20 mL) was added and the reaction mixture was stirred overnight. Water (30 mL)

was cautiously added with vigorous stirring. After gas evolution had subsided, 50% aqueous sodium hydroxide (1 mL) was added and the stirring was continued for 20 min. The reaction mixture was concentrated in vacuo to about ¼ volume and was diluted with ethyl acetate (300 mL) and washed with water (50 mL), saturated aqueous ammonium chloride (50 mL) and saturated brine (50 mL). The extracts were dried over magnesium sulfate and concentrated in vacuo. Chromatography of the residual oil (40% ethyl acetate in hexanes) on silica gel provided the product ((R)-1-Benzyloxymethyl-2-hydroxy-ethyl)-methyl-carbamic acid tert-butyl ester (6.02 g, 68% from N-Boc-O-Benzyl serine) as a colorless oil: $^1$H NMR (400 MHz, CDCl3) δ 7.39-7.28 (m, 5 H), 4.55 (AB-quartet, J=8.0 Hz, Δν=16.4 Hz, 2 H), 4.13 (br s, 1 H), 3.85-3.55 (cm, 4 H), 2.86 (s, 3 H), 1.45 (s, 9 H); [α]D=+77 (methanol, c=1 mg/mL); MS (APCI+) 296.2 (M+1, 10%), 222.1 (M+1-$C_4H_{10}O$, 60%), 196.1 (M+1-$C_5H_8O_2$, 100%).

Step C, D: According to the procedure of Preparation 74, ((R)-1-Benzyloxymethyl-2-hydroxy-ethyl)-methyl-carbamic acid tert-butyl ester can be converted to ((S)-2-Aminooxy-1-benzyloxymethyl-ethyl)-methyl-carbamic acid tert-butyl ester.

Step E: [(S)-1-Benzyloxymethyl-2-({1-[3,4-difluoro-2-(2-fluoro-4-iodo-phenylamino)-phenyl]-methanoyl}-aminooxy)-ethyl]-methyl-carbamic acid tert-butyl ester can be prepared from to ((S)-2-Aminooxy-1-benzyloxymethyl-ethyl)-methyl-carbamic acid tert-butyl ester and 3,4-Difluoro-2-(2-fluoro-4-iodo-phenylamino)-benzoic acid by the procedure of Example 80, Step A.

Step F: Treatment of the product of Step E with iodotrimethylsilane followed by a workup with aqueous hydrochloric acid will provide 3,4-Difluoro-2-(2-fluoro-4-iodo-phenylamino)-N-((S)-3-hydroxy-2-methylamino-propoxy)-benzamide, which may be isolated as a pharmaceutically acceptable salt.

EXAMPLE 237

3,4-Difluoro-2-(2-fluoro-4-iodo-phenylamino)-N-((R)-3-hydroxy-2-methylamino-propoxy)-benzamide Step A: Treatment of ((R)-1-Benzyloxymethyl-2-hydroxy-ethyl)-methyl-carbamic acid tert-butyl ester with tert-butyldimethylsilyl chloride and imidazole in dimethylformamide will afford [(S)-1-Benzyloxymethyl-2-(tert-butyl-dimethyl-silanyloxy)-ethyl]-methyl-carbamic acid tert-butyl ester.

Step B: Exposure of the compound prepared in Step A to a pressurized atmosphere of hydrogen in the presence of activated palladium on charcoal will provide [(S)-2-(tert-Butyl-dimethyl-silanyloxy)-1-hydroxymethyl-ethyl]-methyl-carbamic acid tert-butyl ester.

Step C, D: The compound of step B can be converted to [(S)-1-Aminooxymethyl-2-(tert-butyl-dimethyl-silanyloxy)-ethyl]-methyl-carbamic acid tert-butyl ester by the general procedure of Preparation 74.

Step E: [(S)-2-(tert-Butyl-dimethyl-silanyloxy)-1-({1-[3,4-difluoro-2-(2-fluoro-4-iodo-phenylamino)-phenyl]-methanoyl}-aminooxymethyl)-ethyl]-methyl-carbamic acid tert-butyl ester can be prepared by the procedure of Example 80, Step A.

Step F: Treatment of the product of Step E with iodotrimethylsilane followed by a workup with tetrabutylammonium fluoride will provide 3,4-Difluoro-2-(2-fluoro-4-iodo-phenylamino)-N-((R)-3-hydroxy-2-methylamino-propoxy)-benzamide, which may be isolated as a pharmaceutically acceptable salt.

EXAMPLE 238

(S)- and (R)-5-Chloro-3,4-Difluoro-2-(2-fluoro-4-iodo-phenylamino)-N-(3-hydroxy-2-methylamino-propoxy)-benzamide (S)- and (R)-5-Chloro-3,4-difluoro-2-(2-fluoro-4-iodo-phenylamino)-N-(3-hydroxy-2-methylamino-propoxy)-benzamide may be prepared from 5-Chloro-3,4-difluoro-2-(2-fluoro-4-iodo-phenylamino)-benzoic acid by analogy to examples 236 and 237 respectively.

EXAMPLE 239

(S)- and (R)-5-Chloro-2-(2-chloro-4-iodo-phenylamino)-3,4-difluoro-N-(3-hydroxy-2-methylamino-propoxy)-benzamide (S)- and (R)-5-Chloro-2-(2-chloro-4-iodo-phenylamino)-3,4-difluoro-N-(3-hydroxy-2-methylamino-propoxy)-benzamide may be prepared from 5-chloro-2-(2-chloro-4-iodo-phenylamino)-3,4-difluoro-benzoic acid by analogy to examples 236 and 237 respectively.

EXAMPLE 240

3,4-Difluoro-2-(2-fluoro-4-iodo-phenylamino)-N-(2-hydroxy-3-methylamino-propoxy)-benzamide Step A: N-(tert-butoxycarbonyl)-N-methyl-2,3-epoxypropylamine (available by the literature procedure: Edwards, M. L.; Snyder, R. D.; Stemerick, D. M. *J. Med. Chem.* 1991, 34, 2414) can be converted to (3-aminooxy-2-hydroxy-propyl)-methyl-carbamic acid tert-butyl ester by the general procedure of example 56.

Step B, C: 3,4-difluoro-2-(2-fluoro-4-iodo-phenylamino)-N-(2-hydroxy-3-methylamino-propoxy)-benzamide can be prepared from (3-aminooxy-2-hydroxy-propyl)-methyl-carbamic acid tert-butyl ester and 3,4-difluoro-2-(2-fluoro-4-iodo-phenylamino)-benzoic acid by the general procedure of example 236, steps E and F.

EXAMPLE 241

Cellular Assay for Measuring MEK Inhibition

The evaluation of the compounds as MEK inhibitors was performed in an assay that measures their ability to inhibit phosphorylation of MAP kinase (ERK) in murine colon 26 (C26) carcinoma cells. Since ERK1 and ERK2 represent the only known substrates for MEK, measurement of inhibition of ERK phosphorylation in cells provides direct readout of cellular MEK inhibition by the compounds of the invention. Briefly, the assay involves treating exponentially growing C26 cells with varying concentrations of the test compound (or vehicle control) for one hour at 37° C. Cells are then rinsed free of compound/vehicle and lysed in a solution containing 70 mM NaCl, 50 mM glycerol phosphate, 10 mM HEPES, pH 7.4, 1% Triton X-100, 1 mM $Na_3VO_4$, 100 μM PMSF, 10 μM leupeptin and 10 μM pepstatin. Supernatants are then subjected to gel electrophoresis and Western blotting using a primary antibody recognizing dually phosphorylated ERK1 and ERK2. To evaluate total MAPK levels, blots were subsequently 'stripped' and re-probed with a 1:1 mixture of polyclonal antibodies recognizing unphosphorylated ERK1 and ERK2.

The inhibition data generated by the above protocol is disclosed in Table 1. If several concentrations of inhibitor were tested, IC$_{50}$ values (the concentration which gives 50% inhibition) were determined graphically from the dose response curve for % inhibition. Otherwise, percent inhibitions at measured concentrations are reported.

Table 8. Cellular Inhibition of ERK Phosphorylation by Compounds of the Invention

TABLE 8

| Compound of Example No. | IC$_{50}$ (μM) | % Inhibition @ 0.1 μM | % Inhibition @ 1 μM | % Inhibition @ 10 μM |
| --- | --- | --- | --- | --- |
| 1 | 0.008 | | | |
| 2 | 0.003 | | | |
| 3 | 0.004 | | | |
| 4 | 0.002 | | | |
| 5 | 0.003 | | | |
| 6 | 0.005 | | | |
| 7 | 0.005 | | | |
| 8 | 0.0003 | | | |
| 9 | 0.00007 | | | |
| 10 | 0.0003 | | | |
| 11 | 0.002 | | | |
| 12 | 0.022 | | | |
| 13 | 0.002 | | | |
| 14 | 0.002 | | | |
| 15 | 0.001 | | | |
| 16 | 0.02 | | | |
| 17 | 0.045 | | | |
| 18 | 0.002 | | | |
| 19 | 0.001 | | | |
| 20 | 0.003 | | | |
| 21 | 0.0018 | | | |
| 22 | 0.0077 | | | |
| 23 | 0.032 | | | |
| 24 | 0.026 | | | |
| 25 | 0.052 | | | |
| 26 | 0.24 | | | |
| 27 | 0.12 | | | |
| 28 | 0.12 | | | |
| 29 | 0.047 | | | |
| 30 | 0.13 | | | |
| 32 | 0.0044 | | | |
| 33 | 0.005 | | | |
| 34 | 0.001 | | | |
| 35 | 0.006 | | | |
| 36 | 0.053 | | | |
| 37 | 0.03 | | | |
| 38 | >1.00 | | | |
| 39 | 0.0004 | | | |
| 40 | 0.0014 | | | |
| 41 | 0.00073 | | | |
| 42 | 0.0027 | | | |
| 43 | 0.0018 | | | |
| 44 | 0.003 | | | |
| 45 | 0.019 | | | |
| 46 | 0.582 | | | |
| 47 | 0.001 | | | |
| 48 | 0.0016 | | | |
| 49 | 0.00033 | | | |
| 50 | 0.00083 | | | |
| 51 | 0.0038 | | | |
| 52 | 0.0078 | | | |
| 53 | 0.0012 | | | |
| 54 | 0.0012 | | | |
| 55 | 0.0045 | | | |
| 58 | 0.06 | | | |
| 61 | 0.15 | | | |
| 62 | 0.018 | | | |
| 63 | 0.047 | | | |
| 64 | 0.013 | | | |
| 65 | 0.014 | | | |
| 66 | 0.002 | | | |
| 67 | 0.006 | | | |
| 68 | 0.024 | | | |
| 69 | 0.06 | | | |
| 70 | 0.2 | | | |
| 71 | 0.12 | | | |
| 72 | 0.019 | | | |
| 73 | 0.08 | | | |
| 74 | 0.018 | | | |
| 75 | 0.042 | | | |
| 76 | 0.006 | | | |
| 77 | 0.24 | | | |
| 78 | 0.23 | | | |
| 79 | 0.02 | | | |
| 80 | 0.49 | | | |
| 81 | 0.134 | | | |
| 82 | >1 | | | |
| 83 | 0.041 | | | |
| 85 | 0.054 | | | |
| 86 | 0.019 | | | |
| 87 | 0.025 | | | |
| 88 | 0.11 | | | |
| 89 | 0.012 | | | |
| 90 | 0.04 | | | |
| 91 | | 89.4 | 98.9 | |
| 92 | | 51.8 | 92.4 | |
| 93 | | 4 | 79.1 | |
| 94 | 0.28 | | | |
| 95 | 0.19 | | | |
| 96 | | 35 | 87.1 | |
| 97 | | 30.1 | 91.9 | |
| 98 | 0.011 | | | |
| 99 | 0.018 | | | |
| 100 | 0.058 | | | |
| 101 | 0.225 | | | |
| 102 | 0.275 | | | |
| 103 | 0.487 | | | |
| 104 | 0.024 | | | |
| 105 | | 3.3 | 71.3 | |
| 106 | | 13.2 | 81.6 | |
| 107 | 0.076 | | | |
| 108 | | 74 | 94.6 | |
| 109 | 0.038 | | | |
| 111 | | 78 | 93.4 | |
| 112 | | 95.2 | 95.5 | |
| 113 | | 89.9 | 94.6 | |
| 114 | | 90.5 | 97.3 | |
| 115 | | 94.8 | 98.5 | |
| 116 | | | 62.8 | 75.8 |
| 117 | | 0 | 66.7 | 86.9 |
| 118 | | 74.6 | 95.6 | |
| 119 | | 87.4 | 97.9 | |
| 120 | 0.014 | | | |
| 121 | | 46.9 | 85.5 | |
| 122 | | 49.6 | 87.3 | |
| 123 | 0.021 | | | |
| 124 | | 78 | 96.9 | |
| 125 | | 9.1 | 89 | |
| 126 | 0.026 | | | |
| 127 | 0.025 | | | |
| 128 | 0.009 | | | |
| 129 | | 100 | 100 | |
| 130 | 0.004 | | | |
| 131 | | 78.7 | 91.3 | |
| 132 | | | 45.7 | 80.6 |
| 133 | | 0 | 26.4 | |
| 134 | 0.37 | | | |
| 135 | | 0 | 41.4 | |
| 136 | 0.25 | | | |
| 137 | 0.1 | | | |
| 138 | | 0 | 19.6 | |
| 139 | 0.36 | | | |
| 140 | 0.45 | | | |
| 141 | | 38 | 92.7 | |
| 142 | | 31 | 91.4 | |
| 143 | 0.6 | | | |
| 145 | 0.1 | | | |
| 146 | | 0 | 40.5 | |
| 147 | 0.1 | | | |
| 148 | 0.23 | | | |
| 149 | 0.17 | | | |
| 150 | | | 49 | 99.9 |

TABLE 8-continued

| Compound of Example No. | IC$_{50}$ (μM) | % Inhibition @ 0.1 μM | % Inhibition @ 1 μM | % Inhibition @ 10 μM |
|---|---|---|---|---|
| 151 | 0.041 | | | |
| 152 | | 59.2 | 90.3 | |
| 153 | | 13.9 | 89.5 | |
| 154 | | | 8.9 | 51 |
| 155 | | 0 | 30.9 | |
| 156 | 0.011 | | | |
| 157 | | 50.7 | 91.5 | |
| 159 | | 88.4 | 100 | |
| 160 | | 71.9 | 96.8 | |
| 161 | 0.015 | | | |
| 162 | 0.00785 | | | |
| 163 | | 88.9 | 95.1 | |
| 164 | 0.003 | | | |
| 165 | 0.004 | | | |
| 166 | | 0 | 31.9 | 88.7 |
| 167 | | | 80.5 | 89.2 |
| 168 | | 48.8 | 89.5 | |
| 169 | 0.014 | | | |
| 170 | | 19 | 85.7 | |
| 171 | | 35.6 | 94.6 | |
| 172 | | 41.9 | 92.9 | |
| 173 | 0.3 | | | |
| 174 | 0.1 | | | |
| 175 | 0.18 | | | |
| 176 | | 14.1 | 87.7 | |
| 177 | | 91.6 | 95.7 | |
| 178 | | 61.8 | 94.9 | |
| 179 | | 90.4 | 99.3 | |
| 180 | | | 34 | 58.6 |
| 181 | | | 0 | 65.1 |
| 182 | | 13.1 | 81.9 | |
| 183 | 0.053 | | | |
| 184 | | 16.1 | 82.5 | |
| 185 | | 6.2 | 71.9 | |
| 186 | 0.034 | | | |
| 187 | | 13.8 | 83.3 | |
| 188 | 0.044 | | | |
| 190 | | 51.5 | 94.6 | |
| 191 | 0.006 | | | |
| 192 | 0.007 | | | |
| 193 | 0.01 | | | |
| 194 | | 0 | 0 | |
| 195 | | | 26.7 | 82.6 |
| 196 | | 10.2 | 82.8 | |
| 197 | 0.051 | | | |
| 198 | | 0 | 43.5 | |
| 199 | 0.1 | | | |
| 200 | 0.3 | | | |
| 201 | 0.1 | | | |
| 202 | | 59.7 | 94.6 | |
| 203 | | | 0 | 37.4 |
| 206 | 0.14 | | | |
| 207 | 0.212 | | | |
| 208 | 1.029 | | | |
| 210 | | 79.7 | 99.2 | |
| 211 | | | 35 | 71.9 |
| 212 | | | 20.1 | 85.1 |
| 213 | | 6.2 | 78.7 | |
| 214 | | | 15.4 | 38.2 |
| 215 | | | 11.7 | 84.8 |
| 216 | | 41.2 | 87.6 | |
| 217 | | 26.9 | 93.1 | |
| 218 | | 87 | 96.9 | |
| 219 | | 65.3 | 96.2 | |
| 220 | | 35.4 | 88.8 | |
| 221 | | 46 | 92.4 | |
| 222 | | | 9.6 | 55.6 |
| 223 | | 5.2 | 56.7 | |
| 224 | | 0 | 18.1 | |
| 225 | | 0 | 8.7 | 36.9 |
| 226 | | | 41.5 | 84.1 |
| 227 | | | 24.2 | 63 |
| 228 | | 48.6 | 92.4 | |
| 229 | | 9.8 | 76.5 | |
| 230 | 0.051 | | | |
| 231 | 0.067 | | | |
| 232 | 0.022 | | | |
| 233 | 0.033 | | | |
| 234 | 0.054 | | | |
| 235 | 0.062 | | | |

EXAMPLE 242

Carrageenan-Induced Footpad Edema (CFE) Rat Model

Male outbred Wistar rats (135-150 g, Charles River Labs) were dosed orally with 10 ml/kg vehicle or test compound one hour prior to administration of a sonicated suspension of carrageenan (1 mg/0.1 ml saline). Carrageenan was injected into the subplantar region of the right hind paw. Paw volume was determined by mercury plethysmography immediately after injection and again five hours after carrageenan injection. Percent inhibition of edema was determined, and the ID40 calculated by linear regression. Differences in swelling compared to control animals were assessed by a 1-way ANOVA, followed by Dunnett's test.

EXAMPLE 243

Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 μg type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

EXAMPLE 244

SCW-Induced Monoarticular Arthritis

Arthritis is induced as described by Schwab, et al., *Infection and Immunity*, 59:4436-4442 (1991) with minor modifications. Rats receive 6 μg sonicated SCW [in 10 μl Dulbecco's PBS (DPBS)] by an intraarticular injection into the right tibiotalar joint on day 0. On day 21, the DTH is initiated with 100 μg of SCW (250 μl) administered i.v. For oral compound studies, compounds are suspended in vehicle (0.5% hydroxypropyl-methylcellulose/0.2% Tween 80), sonicated, and administered twice daily (10 ml/kg volume) beginning 1 hr prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on day 21, and comparing them with volumes at subsequent time points such as day 22, 23, 24, and 25. Paw volume is determined by mercury plethysmography.

EXAMPLE 245

Mouse Ear-Heart Transplant Model

Fey, T. A. et al. describe methods for transplanting split-heart neonatal cardiac grafts into the ear pinna of mice and rats (J. Pharm. and Toxic. Meth. 39:9-17 (1998)). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (day 0) through day 13 or until grafts have been rejected. Rats are dosed once, twice, or three times daily from day 0 through day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10-20-fold magnification with a stereoscopic dissecting microscope without anesthesia. Recipients whose grafts are not visibly beating may be anesthetized and evaluated for the presence of electrical activity using Grass E-2 platinum subdermal pin microelectrodes placed either in the pinna or directly into the graft and a tachograph. Implants can be examined 1-4 times a day for 10, 20, 30 or more days. The ability of a test compound to ameliorate symptoms of transplant rejection can be compared with a control compound such as cyclosporine, tacrolimus, or orally-administered lefluonomide.

EXAMPLE 246

The analgesic activity of the compounds of the present invention was assessed by a test with rats. Rats weighing from 175 to 200 g were injected with carrageenan (2% in 0.9% sodium chloride aqueous solution, 100 µL injection volume) into the footpad of one hind limb. The rats were placed on a glass plate with illumination from a halogen lamp placed directly under the injected paw. The time (in seconds) from beginning illumination until the hindlimb was withdrawn from the glass was measured and scored as Paw Withdrawal Latency (PWL). Drug substances were given by oral gavage injection 2½ hours after carrageenan injection to the footpad. PWL was measured prior to carrageenan injection, just prior to drug injection, and 1, 2 (and sometimes 3) hours after drug injection.

Carrageenan (a polysaccharide extracted from seaweed) causes a sterile inflammation when injected under the skin. Injection into the rat footpad causes little or no spontaneous pain-related behavior but induces hyperalgesia (pain-related behavioral responses of greater intensity than expected) to peripheral thermal or mechanical stimuli. This hyperalgesia is maximal 2 to 3 hours after injection. Treatment of rats with various analgesic drugs reduces hyperalgesia measured in this way and is a conventional test for detection of analgesic activity in rats. (Hargreaves K, Dubner R, Brown F, Flores C, Joris J. A new and sensitive method for measuring thermal nociception in cutaneous hyperalgesia. Pain 1988; 32:77-88 and Kayser V, Guilbaud G. Local and remote modifications of nociceptive sensitivity during carrageenan-induced inflammation in the rat. Pain 1987; 28:99-108). Untreated rats had a PWL of approximately 10 seconds. Carrageenan injection reduced PWL to approximately 3 seconds for at least 4 hours, indicating thermal hyperalgesia. Inhibition of the carrageenan thermal hyperalgesia response was determined by the difference between reduced PWL prior to drug and subsequent to drug treatment, and was expressed as percent inhibition of the response. Administration of MEK inhibitors dose-dependently reduced thermal hyperalgesia (Table 9).

In Table 9, doses were given by oral gavage (PO) and inhibition of the response was measured 1 hour (1 hr), 2 hours (2 hr) or in some cases, 3 hours (3 hr) after drug administration. Inhibition indicates and analgesic effect.

TABLE 9

Administration of MEK Inhibitors to Rats Reduces Thermal Hyperalgesia from Intraplantar Carrageenan.

| EXAMPLE NO. | DOSE (PO) | % Inhibition (1 hr) | % Inhibition (2 hr) | % Inhibition (3 hr) |
|---|---|---|---|---|
| 9 | 30 | 103.0 | 114.4 | 65.2 |
|   | 10 | 57.2 | 80.0 | 50.8 |
|   | 3 | 38.1 | 44.3 | 26.1 |
| 34 | 10 | 39.6 | 61.5 |   |
| 41 | 10 | 26.7 | 61.0 |   |
| 55 | 10 | 36.8 | 60 | 22 |
| 54 | 10 | 49 | 52.9 | 29.6 |

What is claimed is:
1. A compound of formula

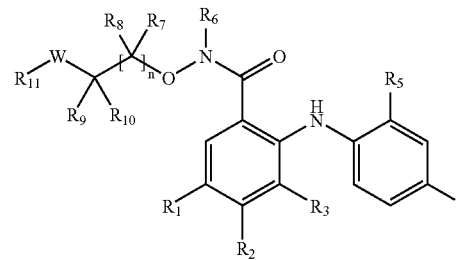

I or a pharmaceutically acceptable salt, wherein
$R_1$ is hydrogen, halogen, or nitro;
$R_2$ is hydrogen or fluorine;
$R_3$ is hydrogen or fluorine;
$R_4$ is hydrogen, iodine, bromine, chlorine, or fluorine;
$R_5$ is hydrogen, halogen, hydroxy, $C_{1-8}$ alkyl, $C_{1-8}$ alkoxy, trifluoromethyl, or cyano;
n is 1 to 5;
$R_6$, $R_7$, $R_8$, $R_9$, and $R_{10}$ are independently hydrogen, $C_{1-8}$ alkyl, $C_{3-8}$ cycloalkyl, $C_{1-8}$ alkoxy, perhalo($C_{1-3}$) alkyl, hydroxy($C_{1-8}$)alkyl, ($C_{1-5}$)alkoxy($C_{1-5}$)alkyl,

[(C$_{1-4}$)alkyl]$_2$aminomethyl, or aryloxy(C$_{1-5}$)alkyl, wherein R$_7$ and R$_8$ are independently selected for n>1;

Ra and Rb are independently hydrogen or C$_{1-4}$ alkyl;

W is O or NRa;

R$_{11}$ is hydrogen, C$_{1-8}$ alkyl, C$_{2-6}$ alkenyl, C$_{3-8}$ cycloalkyl, hydroxy(C$_{1-8}$)alkyl, (C$_{1-5}$)alkoxy(C$_{1-5}$)alkyl, phenyl, (C$_{1-8}$)alkylcarbonyl, (phenyl)carbonyl, (phenyl)(C$_{1-3}$ alkyl)carbonyl, or trifluoro(C$_{1-6}$)alkyl;

wherein the above alkyl, alkoxy, cycloalkyl, and phenyl groups can be optionally substituted with between 1 and 5 substituents independently selected from the group consisting of hydroxy, amino, monoalkylamino, dialkylamino, halogen, cyano, (C$_{1-3}$)alkoxy, COOR, OCORa, CONRaRb, NRaCORb, SO, SO$_2$, SO$_4$, and SO$_2$NRaRb;

provided that when R$_{11}$ is phenyl and n is 1, W cannot be O;

further provided that the compound is not

5-Bromo-N-(2-diethylamino-ethoxy)-3,4-difluoro-(4-iodo-2-methyl-phenylamino)-benzamide;

5-Bromo-N-(2-dimethylamino-propoxy)-3,4-difluoro-2-(4-iodo-2-methyl-phenylamino)-benzamide; or 5-Bromo-2-(2-chloro-4-iodo-phenylamino)-N-(2-dimethylamino-ethoxy)-3,4-difluoro-benzamide.

2. The compound of claim 1 wherein R$_1$ is hydrogen or halogen.

3. The compound of claim 2 wherein halogen is fluorine, bromine or chlorine.

4. The compound of claim 1 wherein R$_2$ is fluorine.

5. The compound of claim 1 wherein R$_3$ is fluorine.

6. The compound of claim 1 wherein R$_4$ is iodine.

7. The compound of claim 1 wherein R$_5$ is fluorine, chlorine, or methyl.

8. The compound of claim 1 wherein n is 1 or 2.

9. The compound of claim 1 wherein R$_6$, R$_7$, R$_8$, R$_9$, R$_{10}$, and R$_{11}$ are hydrogen.

10. The compound of claim 1 wherein R$_6$, R$_7$, R$_8$, R$_9$, and R$_{10}$ are hydrogen.

11. The compound of claim 1 wherein R$_6$, R$_7$, R$_9$, R$_{10}$, and R$_{11}$ are hydrogen.

12. The compound of claim 1 wherein W is oxygen.

13. The compound of claim 1 wherein W is NRa and Ra is hydrogen.

14. The compound of claim 1 wherein R$_{11}$ is methyl or phenyl.

15. A compound of claim 1 wherein the compound is of formula

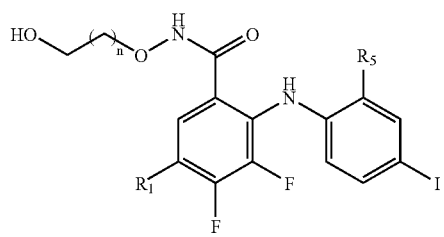

II wherein

R$_1$ is hydrogen or halogen;

R$_5$ is fluorine, chlorine, or methyl; and n is 1 or 2.

16. A compound of claim 1 wherein the compound is of formula

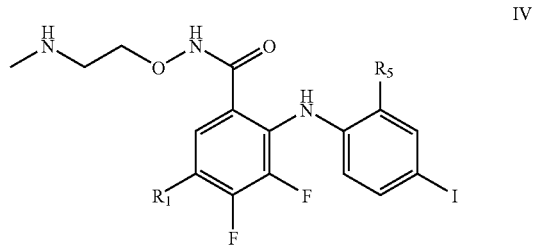

IV wherein

R$_1$ is hydrogen or halogen; and

R$_5$ is fluorine, chlorine, or methyl.

17. A compound of claim 1 wherein the compound is of formula

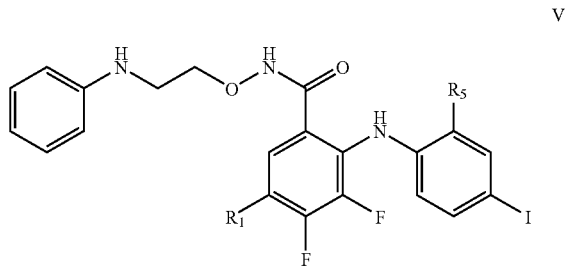

V wherein

R$_1$ is hydrogen or halogen; and

R$_5$ is fluorine, chlorine, or methyl.

18. A pharmaceutical composition comprising a compound of claim 1 and a pharmaceutically acceptable carrier.

19. A compound which is selected from the group consisting of 3,4-Difluoro-2-(2-fluoro-4-iodo-phenylamino)-N-(2-hydroxy-ethoxy)-benzamide;

3,4-Difluoro-2-(2-fluoro-4-iodo-phenylamino)-N-(2-methylamino-ethoxy)-benzamide; hydrochloride;

3,4-Difluoro-2-(2-fluoro-4-iodo-phenylamino)-N-(2-hydroxy-1-hydroxymethyl-ethoxy)-benzamide; and 5-Chloro-3,4-difluoro-2-(2-fluoro-4-iodo-phenylamino)-N-(2-hydroxy-1-hydroxymethyl-ethoxy)-benzamide.

20. A compound which is selected from the group consisting of 3,4,5-Trifluoro-N-(2-hydroxy-ethoxy)-2-(4-iodo-2-methyl-phenylamino)-benzamide;

3,4-Difluoro-N-(2-hydroxy-ethoxy)-2-(4-iodo-2-methyl-phenylamino)-benzamide;

2-(2-Chloro-4-iodo-phenylamino)-3,4-difluoro-N-(2-hydroxy-ethoxy)-benzamide;

2-(2-Chloro-4-iodo-phenylamino)-4-fluoro-N-(2-hydroxy-ethoxy)-benzamide;

4-Fluoro-N-(2-hydroxy-ethoxy)-2-(4-iodo-2methyl-phenylamino)-benzamide;

2-(2-Chloro-4-iodo-phenylamino)-3,4,5-difluoro-N-(2-hydroxy-ethoxy)-benzamide;

5Chloro-3,4-difluoro-N-(2-hydroxy-ethoxy)-2)4-iodo-phenylamino)-benzamide;

4-Fluoro-2-(2-fluoro-4-iodo-phenylamino)-N-(2-hydroxy-ethoxy)-benzamide;

3,4-Difluoro-2-(2-fluoro-4-iodo-phenylamino)-N-(2-hydroxy-ethoxy-benzamide;
5-Chloro-3,4-difluoro-2)2-fluoro-4-iodo-phenylamino)-N-(2)-hydroxy-ethoxy-benzamide;
5-Bromo-3,4-difluoro-2-(2-fluoro-4-iodo-phenylamino)-N-(2hydroxy-ethoxy)-benzamide;
4,5-Difluoro-N-(2-hydroxy-ethoxy)-2-(4-iodo-2-methyl-phenylamino)-benzamide;
5-Bromo-3,4-difluoro-N-(2-hydroxy-ethoxy)-2-(4-iodo-2methyl-phenylamino)-benzamide;
5-Bromo-2-(2-chloro-4-iodo-phenylamino)-3,4-difluoro-N-(2-hydroxy-ethoxy)-benzamide;
5-Chloro-3,4-difluoro-N-(2-hydroxy-ethoxy)-2-(4-iodo-2-methyl-phenylamino)-benzamide;
5-Bromo-4-fluoro-N-(2-hydroxy-ethoxy-)-2-(4-iodo-2-methyl-phenylamino)-benzamide;
2-(2-Chloro-4-iodo-phenylamino)-4,5-difluoro-N-(2-hydroxy-ethoxy-benzamide;
4,5-Difluoro-2-(2-fluoro-4-iodo-phenylamino)-N-(2-hydroxy-ethoxy-benzamide;
5-Bromo-4-fluoro-2-(2-fluoro-4-iodo-phenylamino)-N-(2-hydroxy-ethoxy)-benzamide;
5-Chloro-2-(2-chloro-4-iodo-phenylamino)-3,4-difluoro-N-(2-hydroxy-ethoxy)-benzamide;
3,4,5-Trifluoro-2-(2-fluoro-4-iodo-phenylamino)-N-(2-hydroxy-ethoxy)-benzamide;
2-(4-Bromo-2-fluoro-phenylamino)-3,4-difluoro-N-(2-hydroxy-ethoxy)-benzamide;
2-(4-Bromo-2-fluoro-phenylamino)-4,5-difluoro-N-(2hydroxy-ethoxy-benzamide;
2-(4-Chloro-2-fluoro-phenylamino)-3,4-difluoro-N-(2-hydroxy-ethoxy)-benzamide;
3,4-Difluoro-2-(2-fluoro-phenylamino)-N-(2hydroxy-ethoxy-benzamide;
5-Chloro-2-(2,4-difluoro-phenylamino)-3,4-difluoro-N-(2-hydroxy-ethoxy)-benzamide;
2-2,4-Difluoro-phenylamino)-3,4-difluoro-N-(2-hydroxy-ethoxy)-benzamide;
4-Difluoro-N-(3-hydroxy-propoxy)2-(4-iodo-2-methyl-phenylamino)-benzamide;
5-Chloro-3,4-difluoro-N-(3-hydroxy-propoxy)-2-(4-iodo-2methyl-phenylamino)-benzamide;
2-(2-Chloro-4-iodo-phenylamino)-4-fluoro-N-(3-hydroxy-propoxy)-benzamide;
5-Bromo-2-(2-chloro-4-iodo-phenylamino)-3,4-difluoro-N-(3-hydroxy-propoxy)-benzamide;
3,4-Difluoro-2-(2fluoro-4-iodo-phenylamino)-N-(3-hydroxy-propoxy)-benzamide;
3,4-Difluoro-2-(2fluoro-4-iodo-phenylamino)-N-(4-hydroxy-butoxy)-benzamide;
3,4-Difluoro-2-(2-fluoro-4-iodo-phenylamino)-N-(2hydroxy-1-hydroxymethyl-ethoxy)-benzamide;
5-Chloro-3,4-difluoro-2-(2-fluoro-4-iodo-phenylamino)-N-(2-hydroxy-1-hydroxymethyl-ethoxy)-benzamide;
2-(2-Chloro-4-iodo-phenylamino)-3,4-difluoro-N-(2-vinyloxy-ethoxy)-benzamide;
2-(2-Chloro-4-iodo-phenylamino)-3,4,5-trifluoro-N-(2-vinyloxy-ethoxy)-benzamide;
4-Fluoro-2-(2-fluoro-4-iodo-phenylamino)-N-(2-vinyloxy-ethoxy-benzamide;
3,4-Difluoro-2-(2-fluoro-4-iodo-phenylamino)-N-(2-vinyloxy-ethoxy)-benzamide;
5-Chloro-3,4-difluoro-2-(2-fluoro-4-iodo-phenylamino)-N-(2-vinyloxy-ethoxy)-benzamide;
5-Bromo-3,4-difluoro-2-(2-fluoro-4-iodo-phenylamino)-N-(2-vinyloxy-ethoxy)-benzamide;
5-Bromo-2-(2-chloro-4-iodo-phenylamino)-3,4-difluoro-N-(2-hydroxy-1,1-dimethyl-ethoxy)-benzamide;
3,4-Difluoro-N-(2-hydroxy-1,1-dimethyl-ethoxy)-2-(4-iodo-2-methyl-phenylamino)-benzamide;
3,4-Difluoro-2-(2-fluoro-4-iodo-phenylamino)-N-(2-hydroxy-1,1-dimethyl-ethoxy)-benzamide;
5-Chloro-3,4-difluoro-2-(2fluoro-4-iodo-phenylamino)-N-(2-hydroxy-1,1-dimethyl-ethoxy)-benzamide;
2-(2-Chloro-4-iodo-phenylamino)-3,4-difluoro-N-(2-phenylamino-ethoxy)-benzamide;
3,4-Difluoro-2-(4-iodo-2-methyl-phenylamino)-N-(2-methylamino-ethoxy)-benzamide;
3,4-Difluoro-2-(2-fluoro-4-iodo-phenylamino)-N-(2-methylamino-ethoxy)-benzamide; hydrochloride;
3,4-Difluoro-2-(4-iodo-2-methyl-phenylamino)-N-[2-(2,2,2-trifluoro-bethylamino)-ethoxy]-benzamide; hydrochloride;
2-(2-Chloro-4-iodo-phenylamino)-4-fluoro-N-(2-hydroxy-ethoxy)-N-methyl-benzamide;
5-Bromo-N-(2,3-hydroxy-propoxy)-3,4-difluoro-2-(2-fluoro-phenylamino)-benzamide;
5-Bromo-2-(2-chloro-4-iodo-phenylamino)-3,4-difluoro-N-(3-hydroxy-propoxy)-benzamide;
2-(2-Chloro-4-iodo-phenylamino)-3,4-difluoro-N-(3-hydroxy-propoxy)-benzamide;
3,4,5-Trifluoro-N-(3-hydroxy-propoxy)-2-(4-iodo-2-methyl-phenylamino)-benzamide;
2-(2-Chloro-4-iodo-phenylamino)-3,4,5-difluoro-N-(3-hydroxy-propoxy)-benzamide;
5-Bromo-3,4-difluoro-N-(3-hydroxy-propoxy)-2-(4-iodo-2-methyl-phenylamino)-benzamide;
3,4-Difluoro-N-(3-hydroxy-propoxy)-2-(4-iodo-2-methyl-phenylamino)-benzamide;
5-Chloro-3,4-difluoro-N-(2-hydroxy-1-methyl-ethoxy)-2-(4-iodo-2-methyl-phenylamino)-benzamide;
2-(2-Chloro-4-iodo-phenylamino)-3,4-difluoro-N-(2-hydroxy-1-methyl-ethoxy)-benzamide;
2-(2-Chloro-4-iodo-phenylamino)-3,4,5-trifluoro-N-(2-hydroxy-1-methyl-ethoxy)-benzamide;
3,4,5-Trifluoro-N-(2-hydroxy-1-methyl-ethoxy)-2-(4-iodo-2-methyl-phenylamino)-benzamide;
5-Bromo-2-(2-chloro-4-iodo-phenylamino)-3,4-difluoro-N-(2-hydroxy-1-methyl-ethoxy)-benzamide;
5-Bromo-3,4-difluoro-N-(2-hydroxy-1-methyl-ethoxy)-2-(4-iodo-2-methyl-phenylamino)-benzamide;
2-(4-Chloro-2-fluoro-phenylamino)-3,4-difluoro-N-(2-hydroxy-1-methyl-ethoxy)-benzamide;
3,4-Difluoro-N-(2-hydroxy-1-methyl-ethoxy)-2-(4-iodo-2-methyl-phenylamino)-benzamide;
5-Chloro-2-(2-chloro-4-iodo-phenylamino)-3,4-difluoro-N-(2-hydroxy-1-methyl-ethoxy)-benzamide;
3,4-Difluoro-2-(2-fluoro-4-iodo-phenylamino)-N-(2-hydroxy-1-methyl-ethoxy)-benzamide;
5-Bromo-3,4-difluoro-2-(2-fluoro-4-iodo-phenylamino)-N-(2-hydroxy-1-methyl-ethoxy)-benzamide;
5-Chloro-3,4-difluoro-2-(2-fluoro-4-iodo-phenylamino)-N-(2-hydroxy-1-methyl-ethoxy)-benzamide;
4,5-Difluoro-2-(2-fluoro-4-iodo-phenylamino)-N-(2-hydroxy-1-methyl-ethoxy)-benzamide;
5-Chloro-2-(2,4-difluoro-phenylamino)-3,4-difluoro-N-(2-hydroxy-1-methyl-ethoxy)-benzamide;
2-(2,4-Difluoro-phenylamino)-3,4-difluoro-N-(2-hydroxy-1-methyl-ethoxy)-benzamide;
2-(2-Chloro-4-iodo-phenylamino)-3,4-difluoro-N-(2-methoxy-ethoxy)-benzamide;
2-(2-Chloro-4-iodo-phenylamino)-3,4,5-trifluoro-N-(2-methoxy-ethoxy)-benzamide;

3,4-Difluoro-2-(4-iodo-2-methyl-phenylamino)-N-(2-methoxy-ethoxy)-benzamide;
5-Bromo-3,4-difluoro-2-(4-iodo-2-methyl-phenylamino)-N-(2-methoxy-ethoxy)-benzamide;
3,4,5-Trifluoro-2-(4-iodo-2-methyl -phenylamino)-N-(2-methoxy-ethoxy)-benzamide;
5-Bromo-2-(2-chloro-4-iodo-phenylamino)-3,4-difluoro-N-(2-methoxy-ethoxy)-benzamide;
5-Chloro-2-(2-chloro-4-iodo-phenylamino)-3,4-difluoro-N-(2-methoxy-ethoxy)-benzamide;
5Chloro-3,4-difluoro-2-(4-iodo-2-methyl-phenylamino)-N-(2-methoxy-ethoxy)-benzamide;
5Chloro-3,4-difluoro-2-(2-fluoro-4-iodo-phenylamino-N-(2-methoxy-ethoxy)-benzamide;
3,4-Difluoro-N-(3-hydroxy-2,2-dimethyl-propoxy)-2-(4-iodo-2-methyl-phenylamino)benzamide;
2-(2-Chloro-4-iodo-phenylamino)-3,4,5-trifluoro-N-(3-hydroxy-2,2-dimethyl-propoxy-benzamide;
3,4,5-Trifluoro-N-(3-hydroxy-2,2-dimethyl-propoxy)-2-(4-iodo-2-methyl-phenylamino)-benzamide;
5-Chloro-2-(2chloro-4-iodo-phenylamino)-3,4-difluoro-N-(3-hydroxy-2,2-dimethyl-propoxy)-benzamide;
5-Chloro-3,4-difluoro-N-)3-hydroxy-2,2-dimethyl-propoxy)-2-(4-iodo-2-methyl-phenylamino)-benzamide;
3,4-Difluoro-2-(2-fluoro-4-iodo-phenylamino)-N-(3-hydroxy-2,2-dimethyl-propoxy)-benzamide;
5-Chloro-2-(2,4-difluoro-phenylamino)-3,4-difluoro-N-(3-hydroxy-2,2-dimethyl-propoxy)-benzamide;
3,4-Difluoro-2-(4-iodo-2-methyl-phenylamino)-N-[2-(2-methoxy-ethoxy)-ethoxy]-benzamide;
3,4,5-Trifluoro-2-(4-iodo-2-methyl-phenylamino)-N-[2-(2-methoxy-ethoxy)-ethoxy]-benzamide;
5-Bromo-3,4-difluoro-2-(4-iodo-2-methyl-phenylamino)-N-[2-(2-methoxy-ethoxy)-ethoxy]-benzamide;
2-(2-Chloro-4-iodo-phenylamino)-3,4-difluoro-N-[2-(2-methoxy-ethoxy)-ethoxy]-benzamide;
2-(2-Chloro-4-iodo-phenylamino)-3,4,5-trifluoro-N-[2-(2-methoxy-ethoxy)-ethoxy]-benzamide;
5-Bromo-2-(2-chloro-4-iodo-phenylamino)-3,4-difluoro-N-[2-(2-methoxy-ethoxy)-ethoxy]-benzamide;
3,4,5-Trifluoro-2-(4-iodo-2-methyl-phenylamino)-N-(2-phenylamino-ethoxy)-benzamide;
5-Bromo-3,4-difluoro-2-(4-iodo-2-methyl-phenylamino)-N-(2-phenylamino-ethoxy)-benzamide;
2-(2-Chloro-4-iodo-phenylamino)-3,4-difluoro-N-(2-phenylamino-ethoxy)-benzamide;
2-(2-Chloro-4-iodo-phenylamino)-3,4,5-trifluoro-N-(2-phenylamino-ethoxy)-benzamide;
3,4-Difluoro-2-(4-iodo-2-methyl-phenylamino)-N-(2-phenylamino-ethoxy)-benzamide;
5-Bromo-2-(2-chloro-4-iodo-phenylamino)-3,4-difluoro-N-(2-phenylamino-ethoxy)-benzamide;
3,4-Difluoro-2-(2-fluoro-4-iodo-phenylamino)-N-((S)-(3-hydroxy-2-methylamino-propoxy)-benzamide;
3,4-Difluoro-2-(2fluoro-4-iodo-phenylamino)-N-((R)-(3-hydroxy-2-methylamino-propoxy)-benzamide;
(S)-5-Chloro-3,4-Difluoro-2-(2-fluoro-4-iodo-phenylamino)-N-(3-hydroxy-2-methylamino-propoxy)-benzamide;
(R)-5-Chloro-3,4-Difluoro-2-(2-fluoro-4-iodo-phenylamino)-N-(3-hydroxy-2-methylamino-propoxy)-benzamide;
(S)-5-Chloro-2-(2-chloro-4-iodo-phenylamino)-3,4-difluoro-N-(3-hydroxy-2-methylamino-propoxy)-benzamide;
(R)-5-Chloro-2-(2-chloro-4-iodo-phenylamino)-3,4-difluoro-N-(3-hydroxy-2-methyl-amino-propoxy)-benzamide; and
3,4-Difluoro-2-(2-fluoro-4-iodo-phenylamino)-N-(2-hydroxy-3-methylamino-propoxy)-benzamide.

21. A compound of claim 20 which is 4-fluoro-N-(2-hydroxy-ethoxy)-2-(4-iodo-2-methyl-phenylamino)-benzamide.

\* \* \* \* \*